US012410170B2

(12) United States Patent
Beatty et al.

(10) Patent No.: US 12,410,170 B2
(45) Date of Patent: Sep. 9, 2025

(54) 2,3,5-TRISUBSTITUTED PYRAZOLO[1,5-A]PYRIMIDINE COMPOUNDS

(71) Applicant: Arcus Biosciences, Inc., Hayward, CA (US)

(72) Inventors: Joel Worley Beatty, San Mateo, CA (US); Samuel Lawrie Drew, Millbrae, CA (US); Jeremy Thomas Andre Fournier, Fremont, CA (US); Jenna Leigh Jeffrey, Oakland, CA (US); Kenneth Victor Lawson, San Francisco, CA (US); Manmohan Reddy Leleti, Dublin, CA (US); Artur Karenovich Mailyan, Hayward, CA (US); Guillaume Mata, Berkeley, CA (US); Dillon Harding Miles, Berkeley, CA (US); Jay Patrick Powers, Pacifica, CA (US); Ehesan Ui Sharif, Menlo Park, CA (US); Rhiannon Thomas-Tran, San Jose, CA (US); Xuelei Yan, Foster City, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 916 days.

(21) Appl. No.: 17/615,550

(22) PCT Filed: Jun. 3, 2020

(86) PCT No.: PCT/US2020/035920
§ 371 (c)(1),
(2) Date: Nov. 30, 2021

(87) PCT Pub. No.: WO2020/247496
PCT Pub. Date: Dec. 10, 2020

(65) Prior Publication Data
US 2023/0024302 A1    Jan. 26, 2023

Related U.S. Application Data

(60) Provisional application No. 62/857,148, filed on Jun. 4, 2019.

(51) Int. Cl.
*C07D 487/04* (2006.01)
*A61K 45/06* (2006.01)
*A61N 5/06* (2006.01)

(52) U.S. Cl.
CPC .......... *C07D 487/04* (2013.01); *A61K 45/06* (2013.01); *A61N 5/06* (2013.01); *A61N 2005/0636* (2013.01)

(58) Field of Classification Search
CPC .......... A61K 45/06; A61N 2005/0636; A61N 5/06; A61P 35/00; C07D 487/04; C07D 519/00
See application file for complete search history.

(56) References Cited

U.S. PATENT DOCUMENTS

| 10,023,576 | B2 | 7/2018 | Bhide et al. |
| 10,065,963 | B2 | 9/2018 | Shvartsbart et al. |
| 10,112,926 | B2 | 10/2018 | Bellenie et al. |
| 10,301,304 | B2 | 5/2019 | Boyd et al. |
| 10,329,299 | B2 | 6/2019 | Castro et al. |
| 2010/0311729 | A1 | 12/2010 | Capraro et al. |
| 2017/0088553 | A1 | 3/2017 | Grenier et al. |
| 2017/0319558 | A1 | 11/2017 | Vakkalanka et al. |
| 2018/0009816 | A1 | 1/2018 | Buesking et al. |
| 2018/0055852 | A1 | 3/2018 | Kutok et al. |
| 2018/0258105 | A1 | 9/2018 | Li et al. |
| 2019/0135833 | A1 | 5/2019 | Evans et al. |
| 2019/0152975 | A1 | 5/2019 | Douty et al. |

FOREIGN PATENT DOCUMENTS

| CN | 101678026 A | 3/2010 |
| CN | 105793255 A | 7/2016 |
| CN | 108017641 A | 5/2018 |
| EP | 1841763 | 6/2010 |
| JP | 2016536283 A | 11/2016 |
| JP | 2018529682 A | 10/2018 |
| TW | 200900404 A | 1/2009 |
| WO | WO-2006051270 | 5/2006 |
| WO | WO-2007082956 | 7/2007 |
| WO | WO-2008025821 | 3/2008 |
| WO | WO-2009068482 | 6/2009 |
| WO | WO-2010001126 | 1/2010 |
| WO | WO-2010039740 | 4/2010 |

(Continued)

OTHER PUBLICATIONS

Nurnberg et. al. ("Function, Regulation, and Biological Roles of PI3Kγ Variants", Biomolecules, 9, 427 (Year: 2019).*
Kunnumakkara et. al. ("Cancer drug development: The missing links", Experimental Biology and Medicine, 244:663-689 (Year: 2019).*
International Search Report and Written Opinion for International Application No. PCT/US2020/035920 dated Aug. 19, 2020. 7 pages.
Come J. H., et al., "Design and Synthesis of a Novel Series of Orally Bioavailable, CNS-Penetrant, Isoform Selective Phosphoinositide 3-Kinase [gamma] (PI3K[gamma]) Inhibitors with Potential for the Treatment of Multiple Sclerosis (MS)," Journal of Medicinal Chemistry, vol. 61, No. 12, May 30, 2018, pp. 5245-5256.
Extended European Search Report for Application No. 20818646.0, dated May 9, 2023, 8 Pages.
Office Action for Japanese Patent Application No. 2021-572048, mailed Jun. 4, 2024, 6 pages.

(Continued)

*Primary Examiner* — Jeffrey H Murray
*Assistant Examiner* — Daniel John Burkett
(74) *Attorney, Agent, or Firm* — DLA Piper LLP (US)

(57) ABSTRACT

Compounds that inhibit PI3Kγ, and compositions containing the compound(s) and methods for synthesizing the compounds, are described herein. Also described are the use of such compounds and compositions for the treatment of a diverse array of diseases, disorders, and conditions, including cancer- and immune-related disorders that are mediated, at least in part, by PI3Kγ.

13 Claims, No Drawings

(56) References Cited

FOREIGN PATENT DOCUMENTS

| WO | WO-2010051042 | 5/2010 |
| WO | WO-2011022439 | 2/2011 |
| WO | WO-2011087776 | 7/2011 |
| WO | WO-2015048318 | 4/2015 |
| WO | WO-2015051244 A1 | 4/2015 |
| WO | WO-2015143012 A1 | 9/2015 |
| WO | WO-2015162459 | 10/2015 |
| WO | WO-2015162461 | 10/2015 |
| WO | WO-2016035032 | 3/2016 |
| WO | WO-2017048702 A1 | 3/2017 |
| WO | WO-2017153527 | 9/2017 |
| WO | WO-2017161116 | 9/2017 |
| WO | WO-2017214269 | 12/2017 |
| WO | WO-2018055040 | 3/2018 |

OTHER PUBLICATIONS

Pemberton N., et al., "Discovery of Highly Isoform Selective Orally Bioavailable Phosphoinositide 3-Kinase (PI3K)-[gamma] Inhibitors," Journal of Medicinal Chemistry, vol. 61, No. 12, May 31, 2018, pp. 5435-5441.

* cited by examiner

2,3,5-TRISUBSTITUTED PYRAZOLO[1,5-A]PYRIMIDINE COMPOUNDS

CROSS-REFERENCES TO RELATED APPLICATIONS

This application is a U.S. National Stage Application under 35 U.S.C. § 371 of International Application No. PCT/US2020/035920, filed Jun. 3, 2020, which application claims priority benefit under 35 U.S.C. § 119(e) from U.S. Provisional No. 62/857,148, filed Jun. 4, 2019, which are hereby incorporated by reference in their entireties for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Phosphatidylinositol 3-kinases (PI3Ks) are a family of lipid kinases that phosphorylate the 3-OH of the inositol ring of phosphoinositides. These enzymes play a key role in critical cellular processes including cell growth, proliferation, differentiation, motility, and intracellular trafficking. Deregulation of the phosphoinositide 3-kinase (PI3K) pathway has been implicated in numerous pathologies such as cancer, diabetes, thrombosis, rheumatoid arthritis, and asthma. To date, the eight known family members are subdivided into three classes, I, II, and III, with class I further subdivided into IA (PI3Kα, β, and δ) and IB (PI3Kγ), based on their regulatory proteins and signaling pathways [J. Med. Chem. 2019, 62, 10, 4815-4850]. The class I PI3Ks play an important role in immune regulation, though the four isoforms differ in terms of function and tissue distribution. Expression of the PI3Kα and PI3Kβ isoforms are ubiquitous, while the expression of the PI3Kδ and PI3Kγ isoforms is primarily in leukocytes [J. Med. Chem. 2012, 55, 20, 8559-8581]. PI3Kα is essential for angiogenesis and insulin signaling whereas inhibition of PI3Kδ and PI3Kγ has been shown to result in a heightened immune response against cancer.

The expression profile for PI3Kγ has now expanded to include structural populations such as cardiomyocytes, fibroblasts, and smooth muscle cells. Cardiac PI3Kγ has been shown to regulate phosphodiesterases in the sarcoplasmic reticulum, a potential protective mechanism against catecholamine-induced ventricular arrythmias. Increased PI3Kγ expression in fibroblasts and basal cells has been implicated in idiopathic pulmonary fibrosis. Unlike in hematopoietic cells, PI3Kγ activity in nonhematopoietic cells appears to play an important role in the development of obesity and insulin resistance as observed in knockout mice.

In view of the significant correlations between PI3Kγ in cancer, inflammatory and immunomodulatory conditions, there is a need in the art for PI3Kγ inhibitors. The present invention addresses this need and provides related advantages as well.

BRIEF SUMMARY OF THE INVENTION

The present invention relates to compounds that inhibit the activity of phosphoinositide 3-kinase (γ isoform). The compounds are represented by Formula (I):

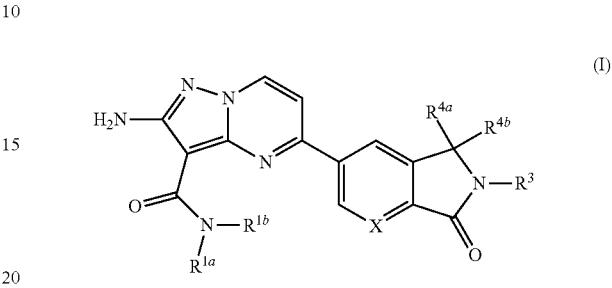

or a pharmaceutically acceptable salt, hydrate, or solvate thereof, wherein X, $R^{1a}$, $R^{1b}$, $R^3$, $R^{4a}$ and $R^{4b}$ are as defined hereinbelow.

In a related aspect, provided herein are methods for treating or preventing cancer in a subject (e.g., a human) comprising administering to the subject a therapeutically effective amount of at least one PI3Kγ inhibitor described herein. In some embodiments, provided herein are methods of treating or preventing a cancer in a subject by administering to the subject at least one of the compounds described herein in an amount effective to reverse, slow or stop the progression of PI3Kγ-mediated dysregulation.

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell lung carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma. Cancers that are candidates for treatment with the compounds and compositions of the present invention are discussed further hereafter.

In certain embodiments, provided herein are methods for treating or preventing an infective disorder (e.g., a viral infection) in a subject (e.g., a human) comprising administering to the subject a therapeutically effective amount of at least one PI3Kγ inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, provided herein are methods for treating or preventing an immune-related disease, disorder or condition in a subject (e.g., a human), comprising administering to the subject a therapeutically effective amount of at least one PI3Kγ inhibitor described herein. Examples of immune-related diseases, disorders and conditions are described hereafter.

In still other embodiments, provided herein are methods for treating or preventing inflammation in a subject (e.g., a human), comprising administering to the subject a therapeutically effective amount of at least one PI3Kγ inhibitor described herein. Examples of inflammatory diseases, disorders and conditions are described hereafter.

Other diseases, disorders and conditions that can be treated or prevented, in whole or in part, by modulation of PI3Kγ activity are candidate indications for the PI3Kγ inhibitor compounds as provided herein.

Also provided herein is the use of the described PI3Kγ inhibitors in combination with one or more additional agents. The one or more additional agents may have some PI3Kγ modulating activity; alternatively, they may function through distinct mechanisms of action. In some embodiments, such agents comprise radiation (e.g., localized radiation therapy or total body radiation therapy) and/or other treatment modalities of a non-pharmacological nature. When combination therapy is utilized, the compound(s) described herein and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In particular embodiments, provided herein are methods wherein the PI3Kγ inhibitors described herein are used in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD-1 (programmed cell death protein 1); PD-L1 (PD-1 ligand); BTLA (B and T lymphocyte attenuator); CTLA-4 (cytotoxic T-lymphocyte associated antigen 4); TIM-3 (T-cell membrane protein 3); LAG-3 (lymphocyte activation gene 3); TIGIT (T cell immunoreceptor with Ig and ITIM domains); and Killer Inhibitory Receptors. Immune checkpoint inhibitors, and combination therapy therewith, are discussed in detail elsewhere herein.

In other embodiments, provided herein are methods for treating cancer in a subject, comprising administering to the subject a therapeutically effective amount of at least one PI3Kγ inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the phosphoinositide 3-kinase (γ isoform) (PI3Kγ) inhibitors in combination with other agents known in the art (e.g., arsenic trioxide) and other chemotherapeutic agents developed in the future.

In some embodiments, provided herein are methods of treating cancer in which a therapeutically effective amount of an PI3Kγ inhibitor described herein is administered in combination with at least one chemotherapeutic agent, resulting in a cancer survival rate greater than the cancer survival rate observed by administering either alone. In further embodiments drawn to methods of treating cancer, the administration of a therapeutically effective amount of an PI3Kγ inhibitor described herein in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one PI3Kγ inhibitor described herein and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an PI3Kγ inhibitor in conjunction with at least one chemotherapeutic agent and/or radiation therapy, wherein the resulting rejection of tumor cells is greater than that obtained by administering either the PI3Kγ inhibitor, the chemotherapeutic agent or the radiation therapy alone.

In further embodiments, the present invention provides methods for treating cancer in a subject, comprising administering to the subject a therapeutically effective amount of at least one PI3Kγ inhibitor and at least one immunomodulator other than an PI3Kγ inhibitors. In particular embodiments, the at least one immunomodulator is selected from the group consisting of CD40L, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, anti-IL-10 and indoleamine 2,3-dioxygenase 1 (IDO1). Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one PI3Kγ inhibitor described herein and a therapeutically effective amount of an anti-infective agent(s).

In some embodiments of the present invention, the additional therapeutic agent is a cytokine, including, for example granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the compounds described herein to treat (either alone or as a component of combination therapy) infection is discussed further hereafter.

In additional embodiments, treatment of an infective disorder is effected through the co-administration of a vaccine in combination with administration of a therapeutically effective amount of an PI3Kγ inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-C SF). In particular embodiments, the vaccine includes one or more immunogenic peptides and/or dendritic cells.

In certain embodiments drawn to treatment of an infection by administering an PI3Kγ inhibitor and at least one additional therapeutic agent, a symptom of infection observed after administering both the PI3Kγ inhibitor and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

BRIEF DESCRIPTION OF THE DRAWINGS

NOT APPLICABLE

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Provided herein, for example, are compounds and compositions for inhibition of phosphoinositide 3-kinase (γ isoform) (PI3Kγ), and pharmaceutical compositions comprising the same. Also provided herein are, for example, methods of treating or preventing a disease, disorder or condition, or a symptom thereof, mediated by inhibition of phosphoinositide 3-kinase (γ isoform) (PI3Kγ).

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. When two moieties are linked to the alkylene they can be linked to the same atom or different atoms of the alkylene group. For instance, a straight chain alkylene can be the bivalent radical of $-(CH_2)_n-$, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, often referred to as $X^1$ or $X^2$ groups in the present application, can be substituted or unsubstituted. When a group comprising $X^1$ or $X^2$ is optionally substituted, it is understood that the optional substitutions may be on the alkylene portion of the moiety. Similarly, the term alkylene, as used herein, encompasses substitutions unless noted otherwise.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. In some embodiments, the cycloalkyl compounds of the present disclosure are monocyclic $C_{3-6}$ cycloalkyl moieties.

The term "heterocycloalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The heterocycloalkyl may be a monocyclic, a bicyclic or a polycyclic ring system, and may have one or two double bonds connecting ring vertices. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "haloalkyl" refers to an alkyl group having the indicated number of carbon atoms, which is substituted with one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$.

The term "alkoxy" refers to an —OR radical where R is an alkyl group having the indicated number of carbon atoms as defined above, e.g., methoxy, ethoxy, propoxy, or 2-propoxy, n-, iso-, or tert-butoxy.

The term "alkoxyalkyl" refers to a linear or branched monovalent hydrocarbon radical having the indicated number of carbon atoms and which is substituted with one alkoxy group, as defined above, e.g., 2-methoxyethyl, 1-, 2-, or 3-methoxypropyl, 2-ethoxyethyl, and the like.

The term "haloalkoxy" refers to an —OR radical where R is haloalkyl as defined above e.g., —OCF3, —OCHF2, and the like.

The term "haloalkoxyalkyl" refers to an alkyl radical that is substituted with haloalkoxy, each as defined above, e.g., trifluoromethoxyethyl, and the like.

The term "hydroxyalkyl" refers to a linear or branched monovalent hydrocarbon radical having the indicated number of carbon atoms which is substituted with one to three hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

The term "hydroxyalkoxy" refers to an —OR radical where R is hydroxyalkyl as defined above e.g., hydroxyethyloxy, hydroxypropyloxy, and the like.

As used herein, a wavy line, "⁓", that intersects a single, double or triple bond in any chemical structure depicted herein, represent the point of attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl. The term is also meant to include fused cycloalkylphenyl and heterocycloalkylphenyl ring systems such as, for example, indane, tetrahydronaphthalene, chromane and isochromane rings. As a substituent group, the point of attachment to the remainder of the molecule, for a fused ring system can be through a carbon atom on the aromatic portion, a carbon atom on the cycloalkyl portion, or an atom on the heterocycloalkyl portion.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, and alkynyl) can be a variety of groups selected from: halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy, oxo, cycloalkyl and heterocycloalkyl in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Optional substituents for the cycloalkyl and heterocycloalkyl radicals can be a variety of groups selected from: alkyl optionally substituted with C(O)OR', halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy and oxo. R', R" and R''' each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-6 carbon atoms.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CR$^f$R$^g$)$_r$-B-, wherein A and B are independently —CH$_2$—, —O—, —NH—, —S—, —S(O)—, —S(O)$_2$—, —S(O)$_2$NR'— or a single bond, r is an integer of from 1 to 3, and R$^f$ and R$^g$ are each independently H of halogen. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention may be present, under particular conditions, as polymorphs. Polymorphism refers to the ability of a solid material to exist in more than one crystal structure form or phase, wherein the molecules in the crystal lattice have different arrangements or conformations. If such types of differences exist due to packing it is referred to as "packing polymorphism", and if they exist due to differences in conformation it is referred to as "conformational polymorphism". Different polymorphs of the same compound often display different physical properties, including packing properties, spectroscopic properties, thermodynamic properties, solubility, and melting point; kinetic properties such as rate of dissolution and stability; and mechanical properties such as hardness and tensile strength.

Polymorphs can be classified as one of two types according to their stability with respect to different ranges of temperature and pressure. In a monotropic system, only one polymorph (i.e., monotrope) is stable, and it exhibits lower free energy content and solubility at all temperatures and pressure below melting point. In an enantiotropic system, one polymorph is stable at a certain temperature and pressure, while the other polymorph(s) is stable at various temperatures and pressure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium (3H), iodine-125 ($^{125}$I) or carbon-14 ($^{14}$C), or non-radioactive isotopes, such as deuterium ($^{2}$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of PI3Kγ, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of PI3Kγ or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an PI3Kγ inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an PI3Kγ inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of PI3Kγ, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

Compounds that are selective may be particularly useful in the treatment of certain disorders or may offer a reduced likelihood of undesired side effects. In one embodiment, compounds of the present disclosure are selective over other PI3K isoforms. In still another embodiment, the compounds of the present disclosure are selective over other kinases and targets in the PI3K/mTOR/Akt pathway. Specific examples include PI3Kα, PI3Kβ, and PI3Kδ as well as mTOR, Ak5, PIP5K and PDPK1. Selectivity may be determined, for example, by comparing the inhibition of a compound as described herein against PI3Kγ against the inhibition of a compound as described herein against another target. In one embodiment, the selective inhibition of PI3Kγ is at least 1000 times greater, 500 times greater, or 100 times greater, or 20 times greater than inhibition of another target or isoform.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

Phosphoinosotide-3-Kinase γ and Inhibition Thereof

As set forth above, although a precise understanding of the underlying mechanism of action by which the compounds of the present invention effect their activity is not required to practice the invention, the compounds (or a subset thereof) are believed to exert their effect through inhibition of phosphoinositide 3-kinase (γ isoform).

Compounds of the Invention

In one particular aspect, provided herein are compounds having Formula (I):

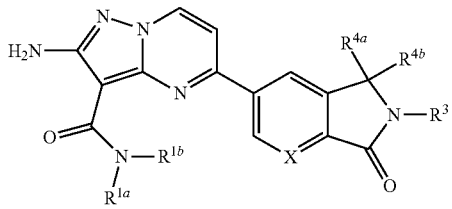

(I)

or a pharmaceutically acceptable salt, hydrate, or solvate thereof, wherein,

X is $C(R^2)$ or N;

$R^{1a}$ and $R^{1b}$ are each a member independently selected from the group consisting of H, $C_{1-6}$ alkyl, $C_{3-6}$ alkenyl, $C_{3-6}$ alkynyl, $C_{1-6}$ haloalkyl, $C_{1-6}$ hydroxyalkyl, $-Y^1$, $-X^1-C(O)_2R^a$, $-X^1-OR^a$, $-X^1-NR^aR^b$, $-X^1-CONR^aR^b$, $-X^1-N(R^a)SO_2R^a$, $-X^1-SO_2R^a$, $-X-SO_2NR^aR^b$, $-X^1-SO_3R^a$, $-X_1-CN$, $-X^1-Y^1$ and $-X^1-Y^1-Y^{1a}$ wherein each $X^1$ is a bond or $C_{1-6}$ alkylene and is optionally further substituted with from 1 to 3 substituents independently selected from the group consisting of OH, $SO_2NH_2$, $CONH_2$, $C(O)NHOH$, $PO_3H_2$, $COO-C_{1-8}$alkyl and $CO_2H$, and each $Y^1$ and $Y^{1a}$ is independently selected from the group consisting of $C_{3-10}$ cycloalkyl, 4- to 8-membered heterocycloalkyl, 5- to 6-membered heteroaryl, and aryl, wherein each heterocycloalkyl and heteroaryl have 1 to 3 heteroatom ring vertices selected from O, N and S; and each $Y^1$ and $Y^{1a}$ is optionally further substituted with one to four substituents independently selected from the group consisting of halogen, oxo, CN, OH, $C_{1-4}$ alkyl, $C_{1-4}$haloalkyl, $C_{1-4}$ hydroxyalkyl, $C_{1-4}$ alkoxy, $C_{1-4}$haloalkoxy, $C_{1-4}$ hydroxyalkoxy, $NH_2$, $NH(C_{1-4}$ alkyl), $N(C_{1-4}$ alkyl)$_2$, $SO_2NH_2$, $CONH_2$, $C(O)NHOH$, $PO_3H_2$, $CO-C_{1-8}$alkyl, $COO-C_{1-8}$alkyl, and $CO_2H$;

or $R^{1a}$ and $R^{1b}$, are optionally combined to form a 4- to 8-membered ring or spirocyclic ring, optionally substituted with from one to four members independently selected from the group consisting of halogen, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO-C_{1-8}$alkyl and $CO_2H$;

$R^2$ is a member selected from the group consisting of halogen, CN, $C_{1-6}$ alkyl, $C_{2-6}$ alkenyl, $C_{2-6}$ alkynyl, $C_{1-6}$ haloalkyl, $C_{1-6}$ hydroxyalkyl, $-Y^2$, $-X^2-C(O)_2R^a$, $-X^2-OR^a$, $-X^2-NR^aR^b$, $-X^2-CONR^aR^b$, $-X^2-SO_2R^a$, $-X^2-N(R^a)SO_2R^a$, $-X^2-SO_2NR^aR^b$, $-X^2-SO_3R^a$, $-O-X^2-Y^2$ and $-X^2-Y^2$ wherein each $X^2$ is a bond or $C_{1-6}$ alkylene and is optionally further substituted with from 1 to 3 substituents independently selected from the group consisting of OH, $SO_2NH_2$, $CONH_2$, $C(O)NHOH$, $PO_3H_2$, $COO-C_{1-8}$ alkyl and $CO_2H$, and each $Y^2$ is selected from the group consisting of $C_{3-6}$ cycloalkyl, 4- to 8-membered heterocycloalkyl, and 5- to 6-membered heteroaryl, wherein each heterocycloalkyl and heteroaryl have 1 to 3 heteroatom ring vertices selected from O, N and S; and each $Y^2$ is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO-C_{1-8}$alkyl, and $CO_2H$;

$R^3$ is a member selected from the group consisting of $C_{1-6}$ alkyl, $C_{3-6}$ cycloalkyl, $C_{3-6}$ cycloalkyl$C_{1-3}$ alkyl, $C_{1-6}$ hydroxyalkyl, $C_{1-6}$ haloalkyl and $-X^3-Y^3$ wherein each $X^3$ is a bond, $C_{1-6}$ alkylene or $C_{1-6}$ haloalkylene and is optionally further substituted with OH, $SO_2NH_2$, $CONH_2$, $C(O)NHOH$, $PO_3H_2$, $COO-C_{1-8}$ alkyl or $CO_2H$, and each $Y^3$ is selected from the group consisting of $C_{3-6}$ cycloalkyl, 4- to 8-membered heterocycloalkyl, and 5- to 6-membered heteroaryl, wherein each heterocycloalkyl and heteroaryl have 1 to 3 heteroatom ring vertices selected from O, N and S; and each $Y^3$ is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO-C_{1-8}$alkyl, and $CO_2H$;

$R^{4a}$ and $R^{4b}$ are each a member independently selected from the group consisting of H, halogen, $C_{1-6}$ alkyl, $C_{2-6}$ alkenyl, $C_{2-6}$ alkynyl, $C_{1-6}$ haloalkyl, and $C_{1-6}$ hydroxyalkyl;

each $R^a$ is independently selected from the group consisting of H, $C_{1-6}$ alkyl, $C_{1-6}$ haloalkyl, $C_{1-6}$ hydroxyalkyl, $C_{1-6}$ alkylene-$CO_2H$, $C_{1-6}$ alkylene-$SO_3H$, $C_{3-6}$ cycloalkyl, $C_{3-6}$ cycloalkyl$C_{1-3}$ alkyl, $C_{1-3}$ alkyl$C_{3-6}$ cycloalkyl, phenyl and 3- to 7-membered heterocycloalkyl having from one to three heteroatom ring vertices selected from O, N and S; and each $R^a$ is optionally further substituted with one or two members independently selected from halogen, OH, $C_{1-4}$ alkoxy, $SO_2NH_2$, $CONH_2$, $C(O)NHOH$, $PO_3H_2$, $COO-C_{1-8}$alkyl and $CO_2H$;

each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$, each of which is optionally further substituted with one or two members independently selected from OH, $SO_2NH_2$, $CONH_2$, $C(O)NHOH$, $PO_3H_2$, $COO-C_{1-8}$alkyl and $CO_2H$;

and $R^a$ and $R^b$, when attached to the same nitrogen atom, are optionally combined to form a 4- to 8-membered ring or spirocyclic ring, optionally substituted with from one to four members independently selected from the group consisting of halogen, OH, $SO_2NH_2$, $CONH_2$, $C(O)NHOH$, $PO_3H_2$, $COO-C_{1-8}$alkyl and $CO_2H$.

In some embodiments, a compound of Formula (I) is provided, or a pharmaceutically acceptable salt, hydrate, or solvate thereof, wherein:

X is $C(R^2)$ or N;

$R^{1a}$ and $R^{1b}$ are each a member independently selected from the group consisting of H, $C_{1-6}$ alkyl, $C_{3-6}$ alkenyl, $C_{3-6}$ alkynyl, $C_{1-6}$ haloalkyl, $C_{1-6}$ hydroxyalkyl, $-Y^1$, $-X^1-C(O)_2R^a$, $-X^1-OR^a$, $-X^1-NR^aR^b$, $-X^1-CONR^aR^b$, $-X^1-N(R^a)SO_2R^a$, $-X^1-SO_2R^a$, $-X^1-SO_2NR^aR^b$, $-X^1-SO_3R^a$, $-X^1-CN$, $-X^1-Y^1$ and $-X^1-Y^1-Y^{1a}$ wherein each $X^1$ is a bond or $C_{1-6}$ alkylene and is optionally further substituted with OH, $SO_2NH_2$, $CONH_2$, $C(O)NHOH$, $PO_3H_2$, $COO-C_{1-8}$alkyl or $CO_2H$, and each $Y^1$ and $Y^{1a}$ is independently selected from the group consisting of $C_{3-10}$ cycloalkyl, 4- to 8-membered heterocycloalkyl, 5- to 6-membered heteroaryl, and aryl, each of which is optionally further substituted with one to four substituents independently selected from the group consisting of halogen, oxo, CN, OH, $C_{1-4}$ alkyl, $C_{1-4}$haloalkyl, $C_{1-4}$ hydroxyalkyl, $C_{1-4}$ alkoxy, $C_{1-4}$haloalkoxy, $C_{1-4}$ hydroxyalkoxy, $NH_2$, $NH(C_{1-4}$ alkyl), $N(C_{1-4}$ alkyl)$_2$, $SO_2NH_2$, $CONH_2$, $C(O)NHOH$, $PO_3H_2$, $CO$—$C_{1-8}$alkyl, $COO$—$C_{1-8}$alkyl, and $CO_2H$;

or $R^{1a}$ and $R^{1b}$, are optionally combined to form a 4- to 8-membered ring or spirocyclic ring, optionally substituted with from one to four members independently selected from the group consisting of halogen, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO$—$C_{1-8}$alkyl and $CO_2H$;

$R^2$ is a member selected from the group consisting of halogen, CN, $C_{1-6}$ alkyl, $C_{2-6}$ alkenyl, $C_{2-6}$ alkynyl, $C_{1-6}$ haloalkyl, $C_{1-6}$ hydroxyalkyl, —$Y^2$, —$X^2$—$C(O)_2R^a$, —$X^2$—$OR^a$, —$X^2$—$NR^aR^b$, —$X^2$—$CONR^aR^b$, —$X^2$—$SO_2R^a$, —$X^2$—$N(R^a)SO_2R^a$, —$X^2$—$SO_2NR^aR^b$, —$X^2$—$SO_3R^a$, —$O$—$X^2$—$Y^2$ and —$X^2$—$Y^2$ wherein each $X^2$ is a bond or $C_{1-6}$ alkylene and is optionally further substituted with OH, $SO_2NH_2$, $CONH_2$, $C(O)NHOH$, $PO_3H_2$, $COO$—$C_{1-8}$ alkyl or $CO_2H$, and each $Y^2$ is selected from the group consisting of $C_{3-6}$ cycloalkyl, 4- to 8-membered heterocycloalkyl, and 5- to 6-membered heteroaryl, each of which is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO$—$C_{1-8}$alkyl, and $CO_2H$;

$R^3$ is a member selected from the group consisting of $C_{1-6}$ alkyl, $C_{3-6}$ cycloalkyl, $C_{3-6}$ cycloalkyl$C_{1-3}$ alkyl, $C_{1-6}$ hydroxyalkyl, $C_{1-6}$ haloalkyl and —$X^3$—$Y^3$ wherein each $X^3$ is a bond, $C_{1-6}$ alkylene or $C_{1-6}$ haloalkylene and is optionally further substituted with OH, $SO_2NH_2$, $CONH_2$, $C(O)NHOH$, $PO_3H_2$, $COO$—$C_{1-8}$ alkyl or $CO_2H$, and each $Y^3$ is selected from the group consisting of $C_{3-6}$ cycloalkyl, 4- to 8-membered heterocycloalkyl, and 5- to 6-membered heteroaryl, each of which is optionally further substituted with one to four substituents independently selected from the group consisting of halogen, oxo, OH, $C_{1-4}$ alkyl, $C_{1-4}$haloalkyl, $C_{1-4}$ hydroxyalkyl, $C_{1-4}$ alkoxy, $C_{1-4}$haloalkoxy, $C_{1-4}$ hydroxyalkoxy, $SO_2NH_2$, $CONH_2$, $C(O)NHOH$, $PO_3H_2$, $COO$—$C_{1-8}$alkyl, and $CO_2H$;

$R^{4a}$ and $R^{4b}$ are each a member independently selected from the group consisting of H, halogen, $C_{1-6}$ alkyl, $C_{2-6}$ alkenyl, $C_{2-6}$ alkynyl, $C_{1-6}$ haloalkyl, and $C_{1-6}$ hydroxyalkyl;

each $R^a$ is independently selected from the group consisting of H, $C_{1-6}$ alkyl, $C_{1-6}$ haloalkyl, $C_{1-6}$ hydroxyalkyl, $C_{1-6}$ alkylene-$CO_2H$, $C_{1-6}$ alkylene-$SO_3H$, $C_{3-6}$ cycloalkyl, $C_{3-6}$ cycloalkyl$C_{1-3}$ alkyl, phenyl and 3- to 7-membered heterocycloalkyl, each of which is optionally further substituted with one or two members independently selected from OH, $SO_2NH_2$, $CONH_2$, $C(O)NHOH$, $PO_3H_2$, $COO$—$C_{1-8}$alkyl and $CO_2H$;

each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$, each of which is optionally further substituted with one or two members independently selected from OH, $SO_2NH_2$, $CONH_2$, $C(O)NHOH$, $PO_3H_2$, $COO$—$C_{1-8}$alkyl and $CO_2H$;

and $R^a$ and $R^b$, when attached to the same nitrogen atom, are optionally combined to form a 4- to 8-membered ring or spirocyclic ring, optionally substituted with from one to four members independently selected from the group consisting of halogen, OH, $SO_2NH_2$, $CONH_2$, $C(O)NHOH$, $PO_3H_2$, $COO$—$C_{1-8}$alkyl and $CO_2H$.

In some selected embodiments, the compound of Formula (I) is a compound wherein X is $C(R^2)$.

In some selected embodiments, the compound of Formula (I) is a compound wherein X is N.

In some selected embodiments, the compound of Formula (I) is represented by Formula (Ia):

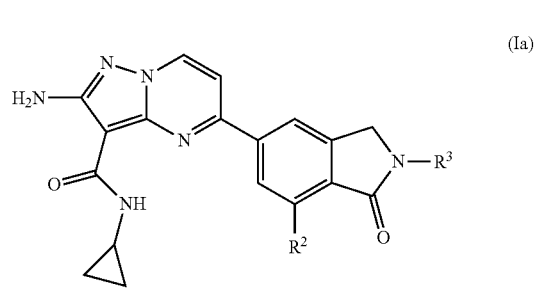

(Ia)

or a pharmaceutically acceptable salt, hydrate, or solvate thereof.

In some selected embodiments, the compound of Formula (I) is represented by Formula (Ib):

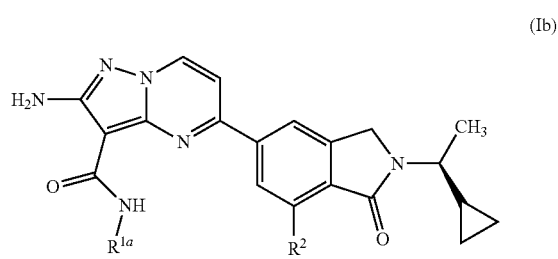

(Ib)

or a pharmaceutically acceptable salt, hydrate, or solvate thereof.

In some selected embodiments, the compound of Formula (I) is represented by Formula

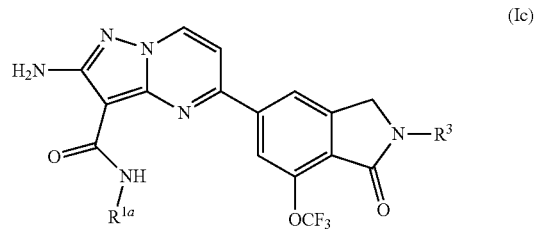

(Ic)

or a pharmaceutically acceptable salt, hydrate, or solvate thereof.

In some selected embodiments, the compound of Formula (I) is represented by Formula (Id):

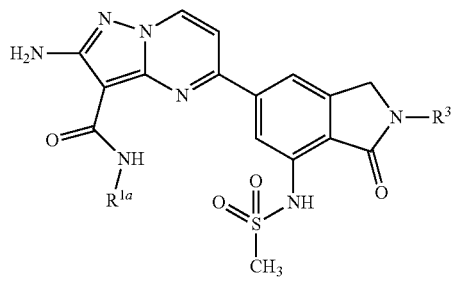

(Id)

or a pharmaceutically acceptable salt, hydrate, or solvate thereof.

In some selected embodiments, the compound of Formula (I) is represented by Formula (Ie):

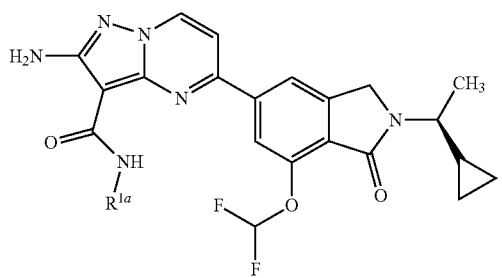

(Ie)

or a pharmaceutically acceptable salt, hydrate, or solvate thereof.

In some selected embodiments, the compound of Formula (I) is represented by Formula (If):

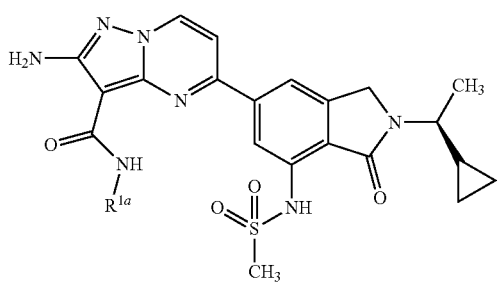

(If)

or a pharmaceutically acceptable salt, hydrate, or solvate thereof.

In some selected embodiments, the compound of Formula (I) is represented by Formula

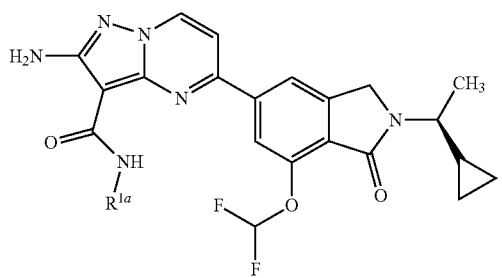

(Ig)

or a pharmaceutically acceptable salt, hydrate, or solvate thereof.

In some selected embodiments, the compound of Formula (I) is represented by Formula (Ih):

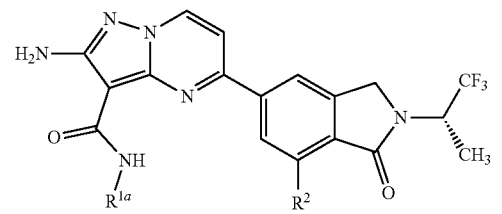

(Ih)

or a pharmaceutically acceptable salt, hydrate, or solvate thereof.

In some selected embodiments, the compound of Formula (I) is represented by Formula (Ii):

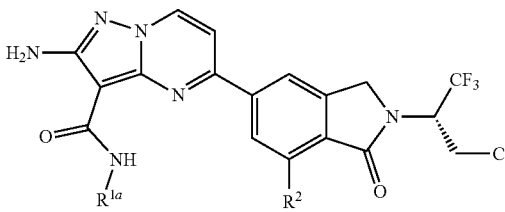

(Ii)

or a pharmaceutically acceptable salt, hydrate, or solvate thereof.

In some selected embodiments, compounds of Formula (I), (Ia), and (Ib) are provided wherein $N(R^{1a})(R^{1b})$ is selected from the group consisting of:

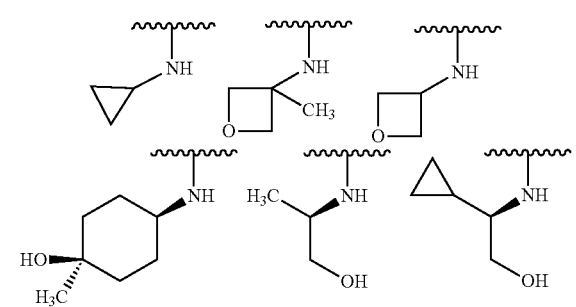

-continued
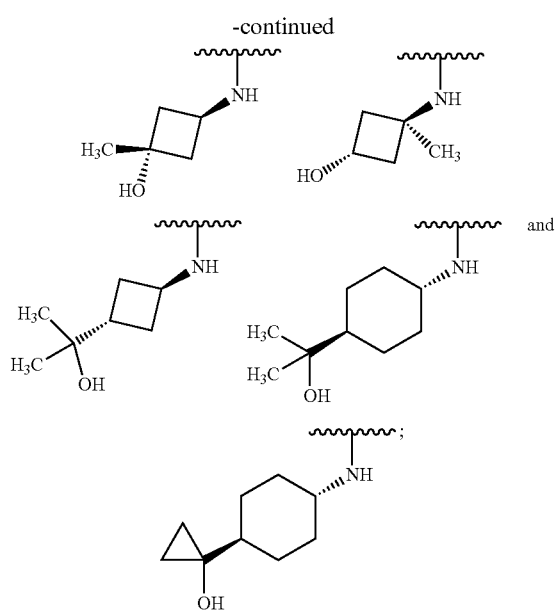
and stereoisomers thereof.
In some selected embodiments, compounds provided herein are selected from the group consisting of:
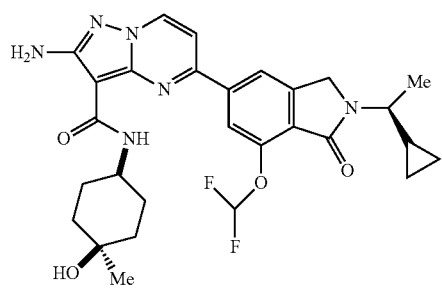
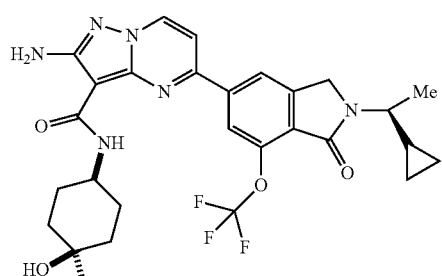
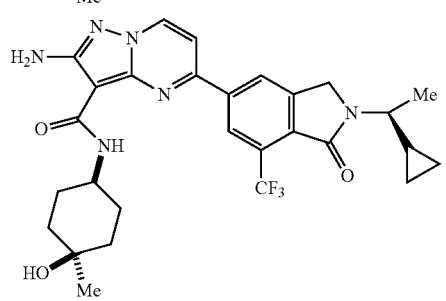
-continued
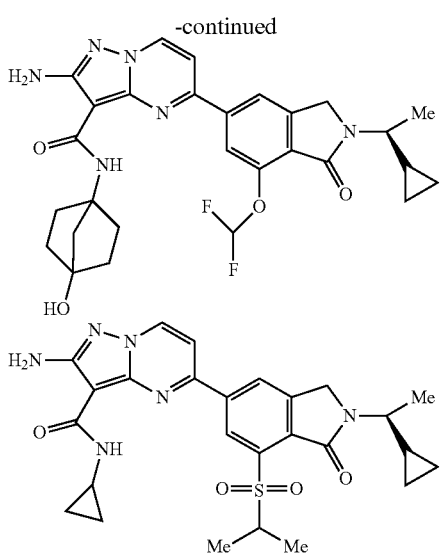
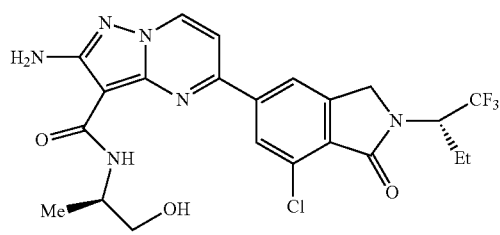
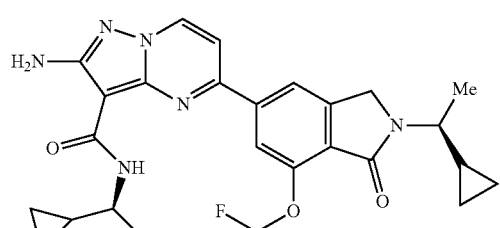
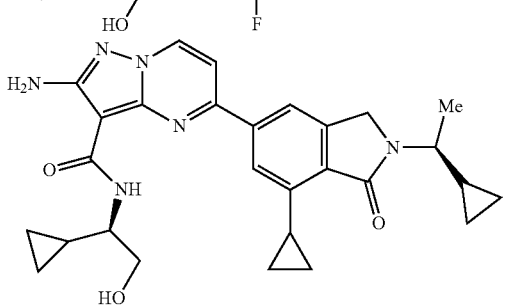

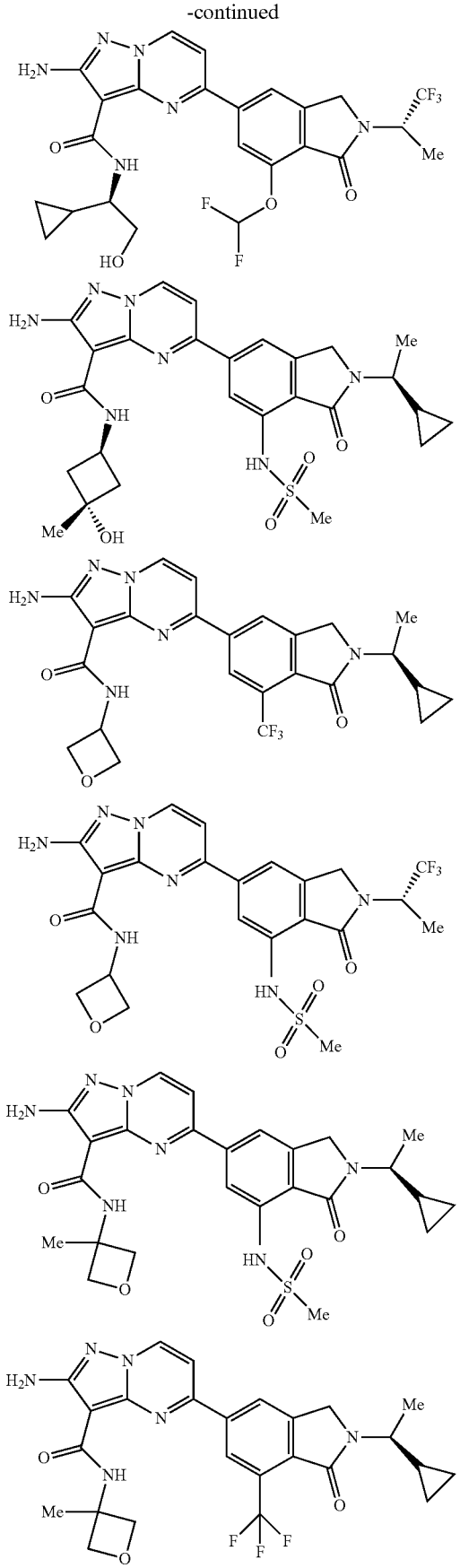

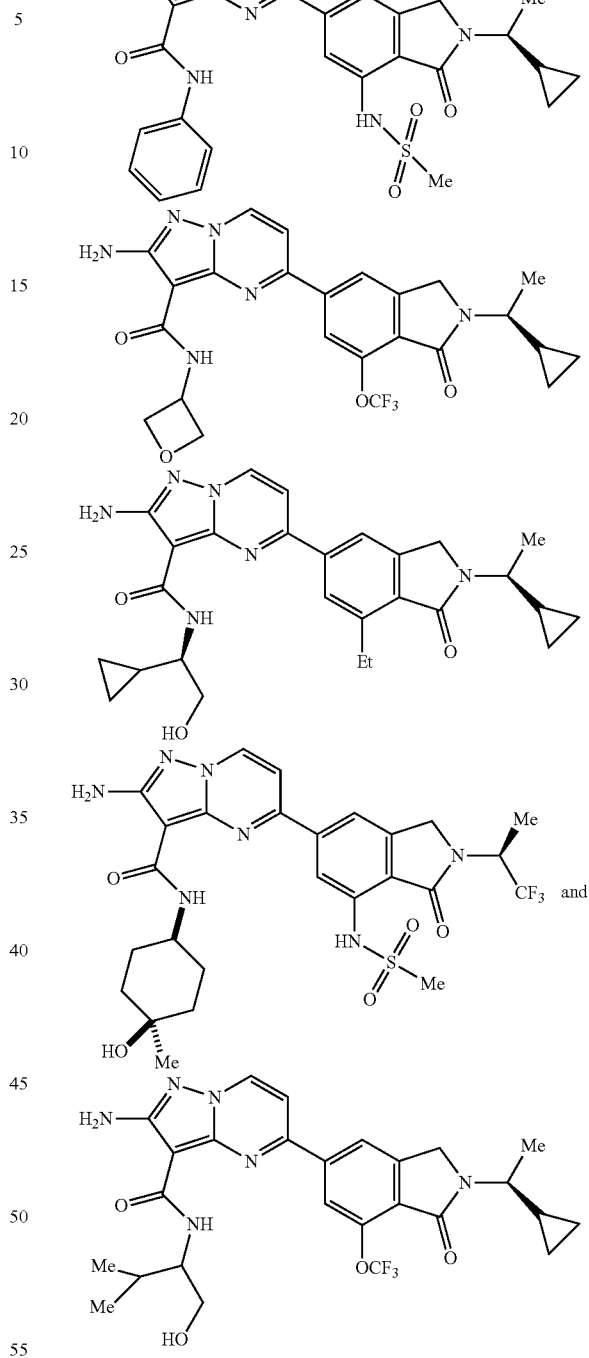

In some selected embodiments, compounds of Formula (I), (Ib), (Ic), (Id), (Ie), (If), (Ig), (Ih) and (Ii) are provided wherein $R^{1a}$ and $R^{1b}$ are each a member independently selected from the group consisting of H, $C_{1-3}$ alkyl, $C_{1-3}$haloalkyl, $C_{1-3}$ hydroxyalkyl, —$Y^1$, —$X^1$—$C(O)_2R^a$, —$X^1$—OR a, $X^1$—$NR^aR^b$, —$X^1$—$CONR^aR^b$, —$X^1$—$N(R^a)SO_2R^a$, —$X^1$—$SO_2R^a$, —$X^1$—$SO_2NR^aR^b$, —$X^1$—$SO_3R^a$, —$X^1$—CN, —$X^1$—$Y^1$ and —$X^1$—$Y^1$—$Y^{1a}$ wherein each $X^1$ is a bond or $C_{1-3}$ alkylene and is optionally further substituted with OH, $SO_2NH_2$, $CONH_2$, C(O)NHOH, $PO_3H_2$, COO—$C_{1-8}$alkyl or $CO_2H$, and each $Y^1$ and $Y^{1a}$ is selected from the group consisting of $C_{3-6}$ cycloalkyl, 4- to 6-membered heterocycloalkyl, 5- to 6-membered heteroaryl, and aryl, and each $Y^1$ and $Y^{1a}$ is optionally further substituted with one to four substituents independently selected from the group consisting of halogen, oxo, CN, OH, $C_{1-4}$ alkyl, $C_{1-4}$haloalkyl, $C_{1-4}$ hydroxyalkyl, $C_{1-4}$ alkoxy, $C_{1-4}$ haloalkoxy, $C_{1-4}$ hydroxyalkoxy, $NH_2$, $NH(C_{1-4}$ alkyl), $N(C_{1-4}$ alkyl$)_2$, $SO_2NH_2$, $CONH_2$, $C(O)NHOH$, $PO_3H_2$, $CO$—$C_{1-8}$ alkyl, $COO$—$C_{1-8}$ alkyl, and $CO_2H$.

In some selected embodiments, compounds of Formula (I), (Ia), (Ib), (Ih) and (Ii) are provided wherein $R^2$ is a member selected from Cl, $CH_3$, $CH_2CH_3$, $CH(CH_3)_2OH$, $OCH_3$, and $NHSO_2CH_3$. In still other embodiments, $R^2$ is a member selected from $OCF_3$ or $OCF_2H$.

In some selected embodiments, compounds of Formula (I), (Ia), (Ic), (Id) and (Ie) are provided wherein $R^3$ is a member selected from the group consisting of:

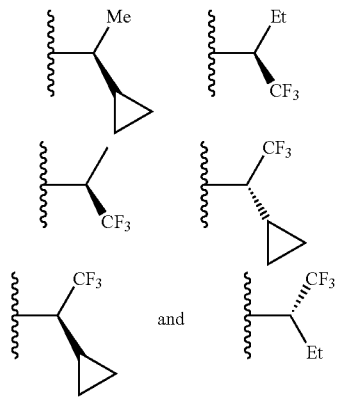

In some selected embodiments, compounds of Formula (I) are provided wherein $R^{4a}$ and $R^{4b}$ are each members independently selected from the group consisting of H, halogen, $C_{1-3}$ alkyl, $C_{1-3}$haloalkyl, and $C_{1-3}$ hydroxyalkyl.

In still other embodiments, including any of the selected embodiments above, each $R^a$ is independently selected from the group consisting of H, $C_{1-3}$ alkyl, $C_{1-3}$ haloalkyl, $C_{1-3}$ hydroxyalkyl, $C_{1-3}$ alkylene-$CO_2H$, $C_{1-3}$ alkylene-$SO_3H$, $C_{3-6}$ cycloalkyl, $C_{3-6}$ cycloalkyl$C_{1-3}$ alkyl, phenyl and 3- to 7-membered heterocycloalkyl, each of which is optionally further substituted with one or two members independently selected from OH, $SO_2NH_2$, $CONH_2$, $C(O)NHOH$, $PO_3H_2$, $COO$—$C_{1-8}$alkyl and $CO_2H$; and each $R^b$ is independently selected from the group consisting of H, $C_{1-3}$ alkyl, $C_{3-6}$ cycloalkyl, $C_{1-3}$ haloalkyl, $C_{1-3}$ hydroxyalkyl, $C_{1-3}$ alkylene-$CO_2H$, and $C_{1-3}$ alkylene-$SO_3H$.

In some selected embodiments, any one compound of Tables 1 to 7, is provided.

Identification of PI3Kγ inhibitors Possessing Desirable Characteristics

The present invention is drawn, in part, to the identification of inhibitors of PI3Kγ with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may be the "best-of-class" of current inhibitors) are indicative of the potential viability of such candidates.

Methods of Synthesis

General Methods for the Preparation of Compounds of the Claims

Those skilled in the art will recognize that there are a variety of methods available to prepare molecules represented in the claims. In general, useful methods for constructing compounds represented in the claims consist of three parts, which may be done in any order: modification of the functional groups present in fragments a-c, connection of the a and b fragments, and connection of the b and c fragments. Retrosynthetic disconnection of the compounds of the invention into fragments a-c useful for construction of the compounds is shown below:

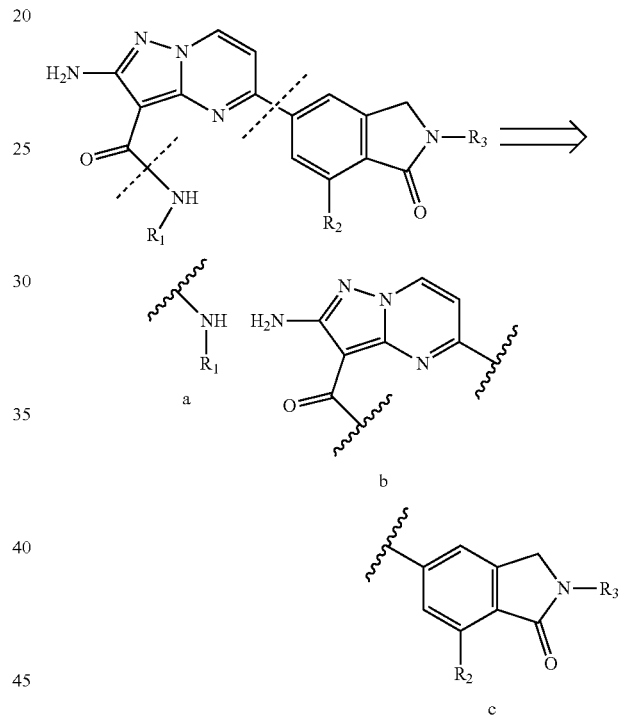

Several methods for the preparation of claimed compounds are exemplary (eq. 1-4). Equation 1 demonstrates one method of synthesizing an appropriately functionalized fragment c. In the case of eq. 1, readily available 4-halo-2-methylbenzoic acid methyl esters are converted to isoindolinones via radical benzylic bromination (e.g., using NBS) followed by cyclization with an appropriately functionalized primary amine. In the case of eq. 1, X may be chosen from an appropriate group such as Cl, Br, or I.

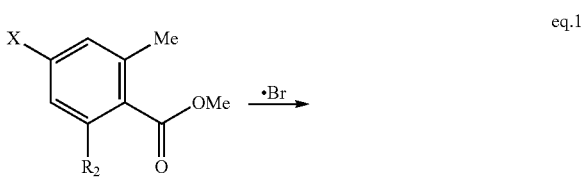

eq.1

-continued

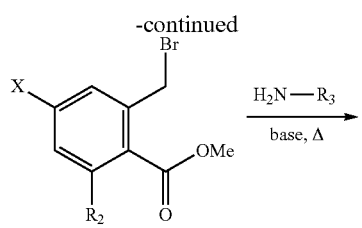

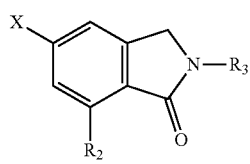

Alternatively, a wide variety of methods are known in the art for the formation of isoindolinones (see for instance "Synthesis of Isoindolinones" in https://www.organic-chemistry.org/synthesis/heterocycles/benzo-fused/isoindolinones.shtm).

Equation 2 demonstrates one method of forming the bond between fragments b and c via a Suzuki reaction. In the case of eq. 2, Z may be chosen from an appropriate group such as Cl or Br, and $-B(OR)_2$ is a boronic acid or ester and the coupling is mediated by a transition metal catalyst, preferably palladium with an appropriate ligand.

eq.2

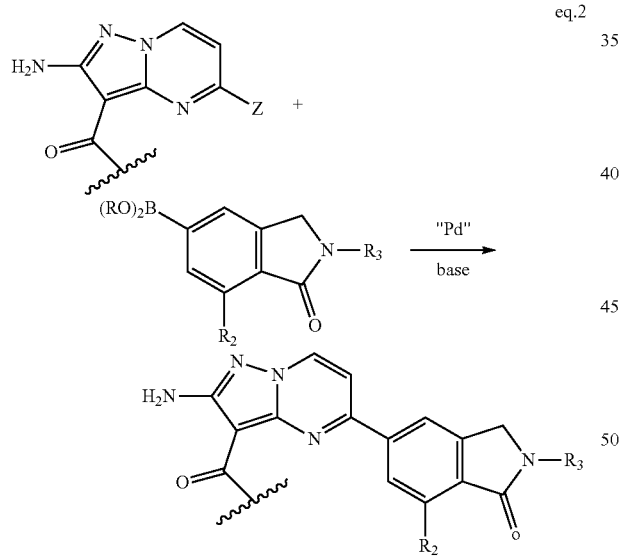

The coupling may be assisted by the use of an organic or inorganic base, and a wide variety of conditions are known in the art to facilitate the Suzuki coupling. The functionalization of the coupling partners may also be reversed as exemplified in eq. 3. Those skilled in the art will recognize that there are other possible combinations which will also result in the desired product. Formation of the bond between the b and c fragments may take place before or after formation of the connection between the a and b fragments, and the groups may be further modified before or after connection of the b and c fragments.

eq.3

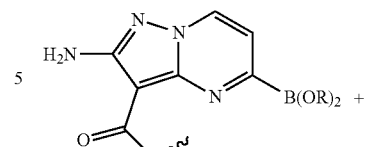

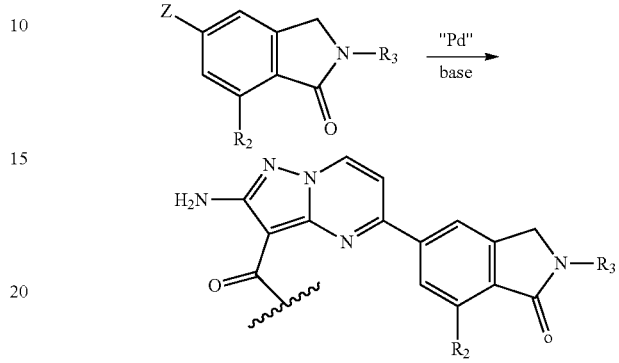

Equation 4 demonstrates one method of forming the bond between fragments a and b. In the case of eq. 4, readily available primary amines are coupled with the carboxylic acid derivative of fragment b (or an activated analog thereof) in the presence of suitable amide coupling reagents, e.g., EDC, HOBt, HATU, or a variety of other reagents (see "Synthesis of amides" in https://www.organic-chemistry.org/synthesis/C1N/amides.shtm). One skilled in the art will understand that there are a wide variety of methods available to effect this transformation.

eq. 4

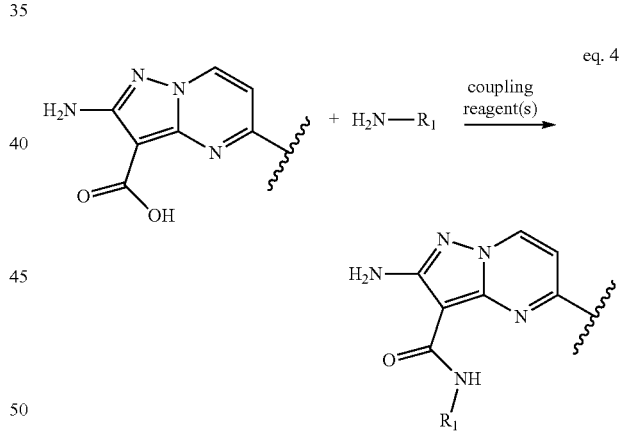

For the most efficient preparation of any particular compound of the invention, one skilled in the art will recognize that the timing and the order of connection of the fragments and modification of the functionality present in any of the fragments may vary in the preparation of any given compound. A variety of the methods described above have been used to prepare compounds of the invention, some of which are exemplified in the examples.

Prodrugs and Other Means of Drug Delivery and/or Half-Life Extension

In some aspects of the present invention, compounds described herein are administered in prodrug form.

In order to effect extension of therapeutic activity, drug molecules may be engineered to utilize carriers for delivery. Such carriers are either used in a non-covalent fashion, with the drug moiety physicochemically formulated into a solvent-carrier mixture, or by permanent covalent attachment of a carrier reagent to one of the drug moiety's functional groups (see generally WO 2015/0202317).

Several non-covalent approaches are favored. By way of example, but not limitation, in certain embodiments depot formulations comprising non-covalent drug encapsulation into polymeric carriers are employed. In such formulations, the drug molecule is combined with carrier material and processed such that the drug molecule becomes distributed inside the bulk carrier. Examples include microparticle polymer-drug aggregates (e.g., Degradex® Microspheres (Phosphorex, Inc.)), which are administered as an injectable suspension; polymer-drug molecule aggregates formulated as gels (e.g., Lupron Depot® (AbbVie Inc.)), which are administered as a single bolus injection; and liposomal formulations (e.g., DepoCyt® (Pacira Pharmaceuticals)), where the carrier may be a polymeric or non-polymeric entity capable of solubilizing the drug. In these formulations, release of the drug molecule may occur when the carrier swells or physically deteriorates. In other instances, chemical degradation allows diffusion of the drug into the biological environment; such chemical degradation processes may be autohydrolytic or enzyme-catalyzed. Among other limitations, non-covalent drug encapsulation requires prevention of uncontrolled release of the drug, and dependence of the release mechanism of the drug upon biodegradation may cause interpatient variability.

In particular embodiments, drug molecules, including both small molecules and large molecules, are conjugated to a carrier through permanent covalent bonds. Certain small molecule therapeutics that exhibit low solubility in aqueous fluids may be solubilized by conjugation to hydrophilic polymers, examples of which are described elsewhere herein. Regarding large molecule proteins, half-life extension may be achieved by, for example, permanent covalent modification with a palmitoyl moiety, and by permanent covalent modification with another protein that itself has an extended half-life (e.g., Albuferon®). In general, drug molecules show decreased biological activity when a carrier is covalently conjugated to the drug.

In certain instances, limitations associated with either drug molecules comprising non-covalent polymer mixtures or permanent covalent attachment may be successfully addressed by employing a prodrug approach for chemical conjugation of the drug to the polymer carrier. In this context, therapeutic agents that are inactive or less active than the drug moiety itself are predictably transformed into active molecular entities. The reduced biological activity of the prodrug as compared to the released drug is advantageous if a slow or controlled release of the drug is desired. In such instances, release of the drug occurs over time, thereby reducing the necessity of repeated and frequent administration of the drug. A prodrug approach may also be advantageous when the drug moiety itself is not absorbed, or has less than optimal absorption, in the gastrointestinal tract; in these instances, the prodrug facilitates absorption of the drug moiety and is then cleaved off at some later time (e.g., via first-pass metabolism). The biologically active drug molecule is typically linked to the polymeric carrier moiety by a temporary bond formed between the carrier moiety and a hydroxy, amino or carboxy group of the drug molecule.

The approaches described above are associated with several limitations. Prodrug activation may occur by enzymatic or non-enzymatic cleavage of the temporary bond between the carrier and the drug molecule, or a sequential combination of both (e.g., an enzymatic step followed by a non-enzymatic modification). In an enzyme-free in vitro environment (e.g., an aqueous buffer solution), a temporary bond such as an ester or amide may undergo hydrolysis, but the corresponding rate of hydrolysis may be such that it is outside the therapeutically useful range. In contrast, in an in vivo environment, esterases or amidases are typically present, and the esterases and amidases may cause significant catalytic acceleration of the kinetics of hydrolysis from two-fold up to several orders of magnitude (see, e.g., Greenwald et al., (1999) J Med Chem 42(18):3857-67).

As described herein, prodrugs may be classified as i) bioprecursors and ii) carrier-linked prodrugs. Bioprecursors do not contain a carrier group and are activated by the metabolic creation of a functional group. In contrast, in carrier-linked prodrugs the active substance is conjugated to a carrier moiety via a temporary linkage at a functional group of the bioactive entity. Preferred functional groups are hydroxyl or amino groups. Both the attachment chemistry and hydrolysis conditions depend on the type of functional group employed. The carrier may be biologically inert (e.g., PEG) or may have targeting properties (e.g., an antibody). Cleavage of the carrier moiety of a carrier-linked prodrug results in the bioactive entity of interest, and the nature of the deprotected functional group of the bioactive entity often contributes to its bioactivity.

The patent and scientific literature describe many macromolecular prodrugs where the temporary linkage is a labile ester bond. In these cases, the functional group of the bioactive entity is either a hydroxyl group or a carboxylic acid (see, e.g. Cheng et al. (2003) Bioconjugate Chem 14:1007-17). In addition, it is often advantageous for biomacromolecules and certain small molecule drugs to link the carrier to an amino group(s) of the bioactive entity (e.g., the N-terminus or lysine amino groups of proteins). During preparation of the prodrug, the amino groups may be more chemoselectively addressed due to their greater nucleophilicity compared to hydroxylic or phenolic groups. This is especially relevant for proteins and peptides containing a great variety of different reactive functionalities, where non-selective conjugation reactions lead to undesired product mixtures requiring extensive characterization or purification, thus decreasing reaction yield and therapeutic efficiency of the active moiety.

In general, amide bonds are more stable against hydrolysis than ester bonds, and the rate of cleavage of the amide bond may be too slow for therapeutic utility in a carrier-linked prodrug. As a result, it may be advantageous to add structural chemical components in order to effect control over the cleavability of the prodrug amide bond. These additional cleavage-controlling chemical components that are provided neither by the carrier entity nor by the drug are generally referred to as "linkers". Prodrug linkers can have a major effect on the rate of hydrolysis of temporary bond, and variation of the chemical nature of the linkers often results in particular properties. Prodrug activation of amine-containing biologically active moieties by specific enzymes for targeted release requires that the structure of the linker display a structural motif recognized as a substrate by a corresponding endogenous enzyme. In these cases, the cleavage of the temporary bond occurs in a one-step process which is catalyzed by the enzyme. For example, the enzymatic release of cytarabin is effected by the protease plasmin, which concentration is relatively high in various kinds of tumor mass.

Interpatient variability is a major drawback of predominant enzymatic cleavage. Enzyme levels may differ significantly between subjects resulting in biological variation of prodrug activation by the enzymatic cleavage. Enzyme levels may also vary depending on the site of administration (e.g., for subcutaneous injection, certain areas of the body yield more predictable therapeutic effects than others). In addition, it is difficult to establish an in vivo-in vitro correlation of the pharmacokinetic properties for enzyme-dependent carrier-linked prodrugs.

Other carrier prodrugs employing temporary linkages to amino groups in the drug moiety are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino group of the drug molecule through a second temporary linkage (e.g., a carbamate). The stability or susceptibility to hydrolysis of the second temporary linkage is dependent on the presence or absence of the masking group. In the presence of the masking group, the second temporary linkage is highly stable and unlikely to release the drug molecule with therapeutically useful kinetics, whereas in the absence of the masking group this linkage becomes highly labile, resulting in rapid cleavage and release of the drug moiety.

The cleavage of the first temporary linkage is the rate-limiting step in the cascade mechanism. The first step may induce a molecular rearrangement of the activating group (e.g., a 1,6-elimination as described in Greenwald et al. (1999) J Med Chem 42:3657-67), and the rearrangement renders the second temporary linkage much more labile such that its cleavage is induced. Ideally, the cleavage rate of the first temporary linkage is identical to the desired release rate for the drug molecule in a given therapeutic scenario. In addition, it is desirable that the cleavage of the second temporary linkage be substantially instantaneous after its lability has been induced by cleavage of the first temporary bond.

Another embodiment comprises polymeric amino-containing prodrugs based on trimethyl lock lactonization (see, e.g., Greenwald et al. (2000) J Med Chem 43(3):457-87). In this prodrug system, substituted o-hydroxyphenyl-dimethylpropionic acid is linked to PEG by an ester, carbonate, or carbamate group as a first temporary linkage and to an amino group of a drug molecule by means of an amide bond as a second temporary linkage. The rate-determining step in drug release is the enzymatic cleavage of the first linkage, which is followed by fast amide cleavage by lactonization, releasing an aromatic lactone side product. The primary disadvantage of the prodrug systems described by Greenwald et al. is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

In certain embodiments of cascade prodrugs comprising aromatic activating groups based on 1,6-elimination, the masking group is structurally separate from the carrier. This may be effected by employing a stable bond between the polymer carrier and the activating group, wherein the stable bond does not participate in the cascade cleavage mechanism. If the carrier is not serving as a masking group and the activating group is coupled to the carrier by means of a stable bond, release of potentially toxic side products (such as the activating group) is avoided. The stable attachment of the activating group and the polymer also suppresses the release of drug-linker intermediates with undefined pharmacology.

A first example of the approach described in the preceding paragraph comprises a polymeric prodrug system based on a mandelic acid activating group (see, e.g., Shabat et al. (2004) Chem Eur J 10:2626-34). In this approach the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released; the activating group is still connected to the polyacrylamide polymer after drug release. A similar prodrug system is based on a mandelic acid activating group and an enzymatically cleavable ester-linked masking group (see, e.g., Lee et al. (2004) Angew Chem 116:1707-10).

When the aforementioned linkers are used, the 1,6-elimination step still generates a highly reactive aromatic intermediate. Even if the aromatic moiety remains permanently attached to the polymeric carrier, side reactions with potentially toxic by-products or immunogenic effects may result. Thus, it is advantageous to generate linker technologies for forming polymeric prodrugs of amine-containing active agents using aliphatic prodrug linkers that are not enzyme-dependent and do not generate reactive aromatic intermediates during cleavage. One such example uses PEG5000-maleic anhydride for the reversible modification of amino groups in tissue-type plasminogen activator and urokinase (see, e.g. (1987) Garman et al. FEBS Lett 223(2):361-65). Regeneration of functional enzyme from PEG-uPA conjugate upon incubation at pH 7.4 buffer by cleavage of the maleamic acid linkage follows first order kinetics with a half-life of roughly 6 hours. A disadvantage of the maleamic acid linkage is the lack of stability of the conjugate at lower pH values.

A further approach comprises a PEG cascade prodrug system based on N,N-bis-(2-hydroxyethyl)glycine amide (bicine) linker (see e.g. (2004) J Med Chem 47:726-34). In this system, two PEG carrier molecules are linked via temporary bonds to a bicine molecule coupled to an amino group of the drug molecule. The first steps in prodrug activation involves the enzymatic cleavage of the first temporary linkages connecting both PEG carrier molecules with the hydroxy groups of the bicine activating group. Different linkages between PEG and bicine result in different prodrug activation kinetics. The second step in prodrug activation involves the cleavage of the second temporary linkage connecting the bicine activating group to the amino group of the drug molecule. A disadvantage of this system is the slow hydrolysis rate of this second temporary bicine amide linkage, which results in the release of a bicine-modified prodrug intermediate that may show different pharmacokinetic, immunogenic, toxicity and pharmacodynamic properties as compared to the native parent drug molecule.

In particular embodiments, dipeptides are utilized for prodrug development for targeting or targeted transport as they are substrates for enzymes or biotransport systems. The non-enzymatic route for dipeptide prodrug formation, that is, the ability to undergo intramolecular cyclization to form the corresponding diketopiperazine (DKP) and release the active drug, is not well defined.

In some embodiments, dipeptides are attached to a drug moiety via ester bonds, as was described for dipeptide esters of the drug paracetamol (Gomes et al. (2005) Bio & Med Chem Lett). In this case, the cyclization reaction consists of a nucleophilic attack of the N-terminal amine of the peptide on the ester carbon atom to form a tetrahedral intermediate, which is followed by a proton transfer from the amine to the leaving group oxyanion with simultaneous formation of a peptide bond to give the cyclic DKP product and free drug. This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al. (Molecules 12 (2007) 2484-2506). Susceptibility of dipeptide-based prodrugs to peptidases may be addressed by incorporating at least one non-natural amino acid in the dipeptide motif. However, endogenous enzymes capable of cleaving ester bonds are not limited to peptidases, and the enzyme-dependence of such prodrug cleavage still gives rise to unpredictable in vivo performance.

In some embodiments, enzyme-dependence is intentionally engineered into DKP prodrugs, such as where dipeptide ester prodrugs are formylated at the amino terminus of the dipeptide, and enzymatic deformylation is used to initiate diketopiperazine formation and subsequent cleavage of the ester-dipeptide bond, followed by release of the drug molecule (see, e.g., U.S. Pat. No. 7,163,923). By way of further example, an octapeptide is attached by an ester linkage to the 4-hydroxyl group of vinblastine and undergoes ester bond cleavage by DKP formation after specific enzymatic removal of the N-terminal hexapeptide (see Brady et al. (2002) J Med Chem 45:4706-15).

The scope of the DKP formation reaction has also been extended to amide prodrugs. By way of example, U.S. Pat. No. 5,952,294 describes prodrug activation using diketopiperazine formation for dipeptidyl amide prodrugs of cytarabine. In this case, the temporary linkage is formed between the carbonyl of a dipeptide and the aromatic amino group of cytarabine. However, it is unlikely that a slow-release effect can be achieved for such conjugates as there is no carrier or other half-life extending moiety or functionality present.

Dipeptide prodrugs comprising bioactive peptides such as GLP-1 capable of releasing the peptide through diketopiperazine formation of the dipeptidic extension have also been described (see, e.g., WO 2009/099763). The bioactive peptide moiety may include an additional PEG chain on one of its amino acid side chain residues to achieve extended circulation of the bioactive peptide. However, this approach is associated with several significant disadvantages. First, the PEG chain has to be linked to the peptide without compromising its bioactivity, which can be difficult to achieve for many peptide-based bioactive agents. Second, as the pegylated peptide itself is bioactive, the dipeptidic promoiety has an effect on the peptide's bioactivity and may negatively affect its receptor binding properties.

Specific exemplary technologies that may be used with the compounds of the present invention include those developed by ProLynx (San Francisco, CA) and Ascendis Pharma (Palo Alto, CA). The ProLynx technology platform utilizes sets of novel linkers that are pre-programmed to cleave at different rates to allow the controlled, predictable and sustained release of small molecules and peptides from circulating semi-solid macromolecular conjugates. The technology allows for maintenance of desired steady-state serum levels of therapeutic agents for weeks to months.

The Ascendis technology platform combines the benefits of prodrug and sustained release technologies to enhance the properties of small molecules and peptides. While in circulation, proprietary prodrugs release the unmodified active parent therapeutic agent at predetermined rates governed by physiological pH and temperature conditions. Because the therapeutic agent is released in its unmodified form, it retains its original mechanism of action.

Modifications to Enhance Inhibitor Characteristics

It is frequently beneficial, and sometimes imperative, to improve one or more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Other known modifications include deuteration to improve pharmacokinetics, pharmacodynamics and toxicity profiles. Due to the greater atomic mass of deuterium, cleavage of the carbon-deuterium bond requires more energy than the carbon-hydrogen bond. Because these stronger bonds are more difficult to break, the rate of drug metabolism is slower as compared to non-deuterated forms, which allows for less frequent dosing and may further reduce toxicities. (Charles Schmidt, Nature Biotechnology, 2017, 35(6): 493-494; Harbeson, S. and Tung, R., Medchem News, 2014(2): 8-22).

Therapeutic and Prophylactic Uses

The present invention contemplates the use of the PI3Kγ inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the diseases, disorders and/or conditions described herein are mediated, at least in part, by PI3Kγ.

In some embodiments, the PI3Kγ inhibitors described herein are administered in an amount effective to reverse or stop the progression of PI3Kγ-mediated dysregulation.

Oncology-related Disorders. Studies exploring immune responses in tumors have identified PI3Kγ as a central node within the signaling cascade. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T-cell responses leading to decreased cancer development and spread.

Without being bound to any particular theory, a PI3Kγ inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer may be metastatic or at risk of becoming metastatic, or may occur in a diffuse tissue, including cancers of the blood or bone marrow (e.g., leukemia).

In some embodiments, the present invention provides methods for treating a proliferative condition, cancer, tumor, or precancerous condition with a PI3Kγ inhibitor and at least one additional therapeutic or diagnostic agent, examples of which are set forth elsewhere herein.

Immune- and Inflammatory-related Disorders. Inability to resolve an immune response can lead to autoimmune disease, inflammatory conditions and allergic conditions. Autoimmune disease results from a breakdown in tolerance leading to an immune response directed against host cells, causing conditions such as multiple sclerosis, systemic lupus erythematosus, rheumatoid arthritis, psoriasis and autoimmune (type I) diabetes. Chronic inflammatory conditions such as chronic obstructive pulmonary disease (COPD), atherosclerosis and inflammatory bowel disease arise from failure to resolve an ongoing immune response. Uncontrolled inflammation is also a risk factor for the development of cancer, and has been shown to contribute to tumor growth and metastasis. Allergic conditions such as asthma or anaphylaxis are caused by an inappropriate immune response directed against a normally harmless antigen [Curr Opin Pharmacol. 2015 August; 23: 82-91.]. As such, as used herein, terms such as "immune disease", "immune condition", "immune disorder", "inflammatory disease", "inflammatory condition", "inflammatory disorder" and the like are meant to broadly encompass any immune-related condition that can be treated by the PI3Kγ inhibitors described herein such that some therapeutic benefit is obtained.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

In particular embodiments of the present disclosure, the PI3Kγ inhibitors are used to increase or enhance an immune response to an antigen by providing adjuvant activity. In a particular embodiment, at least one antigen or vaccine is administered to a subject in combination with at least one PI3Kγ inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one PI3Kγ inhibitor of the present invention.

In some embodiments, a PI3Kγ inhibitor described herein can be combined with an immunosuppressive agent to reduce the number of immune effector cells.

Some of the aforementioned diseases, disorders and conditions for which a PI3Kγ inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 10% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL® (etanercept), REMICADE® (infliximab), HUMIRA® (adalimumab) and KINERET® (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate- to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL® (etanercept), REMICADE® (infliximab) and HUMIRA® (adalimumab)), and T-cell inhibitors such as AMEVIVE® (alefacept) and RAPTIVA® (efalizumab). Though several of these agents are effective to some extent in certain patient populations, none have been shown to effectively treat all patients.

Other Disorders. Embodiments of the present invention contemplate the administration of the PI3Kγ inhibitors described herein to a subject for the treatment or prevention of any other disorder that may benefit from at least some level of PI3Kγ inhibition. Such diseases, disorders and conditions include, for example, cardiovascular (e.g., cardiac ischemia) and metabolic (e.g., diabetes, insulin resistance, obesity) disorders.

Pharmaceutical Compositions

The PI3Kγ inhibitors of the present invention may be in the form of compositions suitable for administration to a subject. In general, such compositions are "pharmaceutical compositions" comprising an PI3Kγ inhibitor(s) and one or more pharmaceutically acceptable or physiologically acceptable diluents, carriers or excipients. In certain embodiments, the PI3Kγ inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of PI3Kγ function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a PI3Kγ inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a PI3Kγ inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the PI3Kγ inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the PI3Kγ inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The PI3Kγ inhibitors contemplated by the present invention may be in the form of any other suitable pharmaceutical composition (e.g., sprays for nasal or inhalation use) currently known or developed in the future.

Routes of Administration

The present invention contemplates the administration of PI3Kγ inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the PI3Kγ inhibitors disclosed herein over a defined period of time.

Particular embodiments of the present invention contemplate oral administration.

Combination Therapy

The present invention contemplates the use of PI3Kγ inhibitors alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the PI3Kγ inhibitors are administered or applied sequentially, e.g., where one agent is administered prior to one or more other agents. In other embodiments, the PI3Kγ inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The PI3Kγ inhibitors of the present invention may be used in combination with at least one other (active) agent in any manner appropriate under the circumstances. In one embodiment, treatment with the at least one active agent and at least one PI3Kγ inhibitor of the present invention is maintained over a period of time. In another embodiment, treatment with the at least one active agent is reduced or discontinued (e.g., when the subject is stable), while treatment with a PI3Kγ inhibitor of the present invention is maintained at a constant dosing regimen. In a further embodiment, treatment with the at least one active agent is reduced or discontinued (e.g., when the subject is stable), while treatment with a PI3Kγ inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the PI3Kγ inhibitor of the present invention is increased (e.g., higher dose, more frequent dosing or longer treatment regimen). In yet another embodiment, treatment with the at least one active agent is maintained and treatment with the PI3Kγ inhibitor of the present invention is reduced or discontinued (e.g., lower dose, less frequent dosing or shorter treatment regimen). In yet another embodiment, treatment with the at least one active agent and treatment with the PI3Kγ inhibitor of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with a PI3Kγ inhibitor and at least one additional therapeutic or diagnostic agent. In some embodiments, the additional therapeutic or diagnostic agent is radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present invention provides methods for tumor suppression of tumor growth comprising administration of a PI3Kγ inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC®); (ii) epidermal growth factor (EGF) receptor inhibitors, including kinase inhibitors and antibodies; (iii) her-2/neu receptor inhibitors (e.g., HERCEPTIN®); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with the PI3Kγ inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, poialidomide, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; arginase inhibitors (see WO 2019/173188 A1 and PCT/US2019/061657) and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as abiraterone, enzalutamide, flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with a PI3Kγ inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present invention contemplates the use of the compounds described herein in combination with agents that modulate the level of adenosine. Such therapeutic agents may act on the ectonucleotides that catalyze the conversion of ATP to adenosince, including ectonucleoside triphosphate diphosphohydrolase 1 (ENTPD1, also known as CD39 or Cluster of Differentiation 39), which hydrolyzes ATP to ADP and ADP to AMP, and 5'-nucleotidase, ecto (NT5E or 5NT, also known as CD73 or Cluster of Differentiation 73), which converts AMP to adenosine. The enzymatic activities of CD39 and CD73 play strategic roles in calibrating the duration, magnitude, and chemical nature of purinergic signals delivered to various cells (e.g., immune cells). In one embodiment, the present invention contemplates combination with CD73 inhibitors such as those described in WO 2017/120508, WO 2018/094148, WO 2018/067424, and WO 2020/046813.

Alternatively, such therapeutic agents can be adenosine 2 receptor ($A_2R$) antagonists. Adenosine can bind to and active four different G-protein coupled receptors: $A_1R$, $A_{2a}R$, $A_{2b}R$, and $A_3R$. The binding of adenosine to the $A_{2a}R$ receptor, which is expressed on T cells, natural killer cells and myeloid cells such as dendritic cells, leads to increased intracellular levels of cyclic AMP and the impairment of maturation and/or activation of such cells. This process significantly impairs the activation of the immune system against cancer cells. In addition, $A_{2a}R$ has been implicated in selectively enhancing anti-inflammatory cytokines, promoting the upregulation of PD-1 and CTLA-4, promoting the generation of LAG-3 and Foxp3+ regulatory T cells, and mediating the inhibition of regulatory T cells. PD-1, CTLA-4 and other immune checkpoints which are discussed further herein. In one embodiment, the adenosine receptor agonist may be a dual adenosine receptor. Exemplary adenosine receptor agonists are described in WO/2018/136700, WO 2018/204661, or WO 2020/023846.

In certain embodiments, the present invention contemplates the use of the compounds described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present invention contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

Immune Checkpoint Inhibitors. The present invention contemplates the use of the inhibitors of PI3Kγ function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints which results in the amplification of antigen-specific T cell responses has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD-1 (programmed cell death protein 1); PD-L1 (PD1 ligand); BTLA (B and T lymphocyte attenuator); CTLA-4 (cytotoxic T-lymphocyte associated antigen 4); TIM-3 (T-cell membrane protein 3); LAG-3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-Si, B7x and VCTN1)). [See Pardoll, (April 2012) Nature Rev. Cancer 12:252-64].

The present invention contemplates the use of the inhibitors of PI3Kγ function described herein in combination with inhibitors of the aforementioned immune-checkpoint receptors and ligands, as well as yet-to-be-described immune-checkpoint receptors and ligands. Certain modulators of immune checkpoints are currently approved, and many others are in development. When it was approved for the treatment of melanoma in 2011, the fully humanized CTLA-4 monoclonal antibody ipilimumab (YERVOY®; Bristol-Myers Squibb) became the first immune checkpoint inhibitor to receive regulatory approval in the US. Fusion proteins comprising CTLA-4 and an antibody (CTLA-4-Ig; abatcept (ORENCIA®; Bristol-Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD1 antibodies include nivolumab (OPDIVO; Bristol-Myers Squibb) and pembrolizumab (KEYTRUDA®; Merck) for various cancers, including squamous cell carcinoma, classical Hodgkin lymphoma and urothelial carcinoma. Approved anti-PD-L1 antibodies include avelumab (BAVENCIO®, EMD Serono & Pfizer), atezolizumab (TECENTRIQ®; Roche/Genentech), and durvalumab (IMFINZI®; AstraZeneca) for certain cancers, including urothelial carcinoma. While there are no approved therapeutics targeting TIGIT or its ligands CD155 and CD112, those in development include BMS-986207 (Bristol-Myers Squibb), MTIG7192A/RG6058 (Roche/Genentech), and OMP-31M32 (OncoMed).

In one aspect of the present invention, the claimed PI3Kγ inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), B7-H6, and B7-H7 (HHLA2). Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD3OL, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the disclosed PI3Kγ inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the PI3Kγ inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-IR antagonists such as CSF-IR antagonist antibodies including RG7155 (WO11/70024, WO11/107553, WO/131407, WO13/87699, WO13/119716, WO13/132044) or FPA-008 (WO11/140249; WO13169264; WO14/036357).

In another aspect, the disclosed PI3Kγ inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO2012/145493) or zimberelimab The immuno-oncology agent may also include pidilizumab (CT-011). Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, TECENTRIC® (atezolizumab; MPDL3280A; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with a PI3Kγ inhibitor and at least one additional therapeutic or diagnostic agent.

Examples of therapeutic agents useful in combination therapy for the treatment of hypercholesterolemia (and atherosclerosis as well) include statins (e.g., CRESTOR®, LESCOL®, LIPITOR®, MEVACOR®, PRAVACOL®, and ZOCOR®), which inhibit the enzymatic synthesis of cholesterol; bile acid resins (e.g., COLESTID®, LO-CHOLEST®, PREVALITE®, QUESTRAN®, and WELCHOL®), which sequester cholesterol and prevent its absorption; ezetimibe (ZETIA®), which blocks cholesterol absorption; fibric acid (e.g., TRICOR), which reduces triglycerides and may modestly increase HDL; niacin (e.g., NIACOR®), which modestly lowers LDL cholesterol and triglycerides; and/or a combination of the aforementioned (e.g., VYTORIN® (ezetimibe with simvastatin)). Alternative cholesterol treatments that may be candidates for use in combination with the PI3Kγ inhibitors described herein include various supplements and herbs (e.g., garlic, policosanol, and guggul).

The present invention encompasses pharmaceutically acceptable salts, acids or derivatives of any of the above.

Immune- and Inflammatory-related Disorders. The present invention provides methods for treating and/or preventing immune-related diseases, disorders and conditions; and diseases, disorders and conditions having an inflammatory component; with a PI3Kγ inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE®, anti-TNF antibody fragments (e.g., CDP870), and soluble p55 or p75 TNF receptors, derivatives thereof, p75TNFRIgG (ENBREL®) or p55TNFRIgG (LENERCEPT®), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the PI3Kγ inhibitors described herein include interferon-131a (AVONEX®); interferon-131b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Dosing

The PI3Kγ inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the PI3Kγ inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the PI3Kγ inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired PI3Kγ inhibitor is contained in a "unit dosage form". The phrase "unit dosage form" refers to physically discrete units, each unit containing a predetermined amount of the PI3Kγ inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound described herein, and pharmaceutical compositions thereof. The kits are generally in the form of a physical structure housing various components, as described below, and may be utilized, for example, in practicing the methods described above.

A kit can include one or more of the compounds disclosed herein (provided in, e.g., a sterile container), which may be in the form of a pharmaceutical composition suitable for administration to a subject. The compounds described herein can be provided in a form that is ready for use (e.g., a tablet or capsule) or in a form requiring, for example, reconstitution or dilution (e.g., a powder) prior to administration. When the compounds described herein are in a form that needs to be reconstituted or diluted by a user, the kit may also include diluents (e.g., sterile water), buffers, pharmaceutically acceptable excipients, and the like, packaged with or separately from the compounds described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; rt=room temperature; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

The literature is replete with assays and other experimental techniques that can serve as a basis for evaluation of the compounds described herein.

EXAMPLES

Example 1: 2-Amino-5-{2-[(1S)-1-cyclopropylethyl]-7-methyl-1-oxo-2,3-dihydro-1H-isoindol-5-yl}-N-[trans-3-hydroxycyclobutyl]pyrazolo[1,5-a]pyrimidine-3-carboxamide

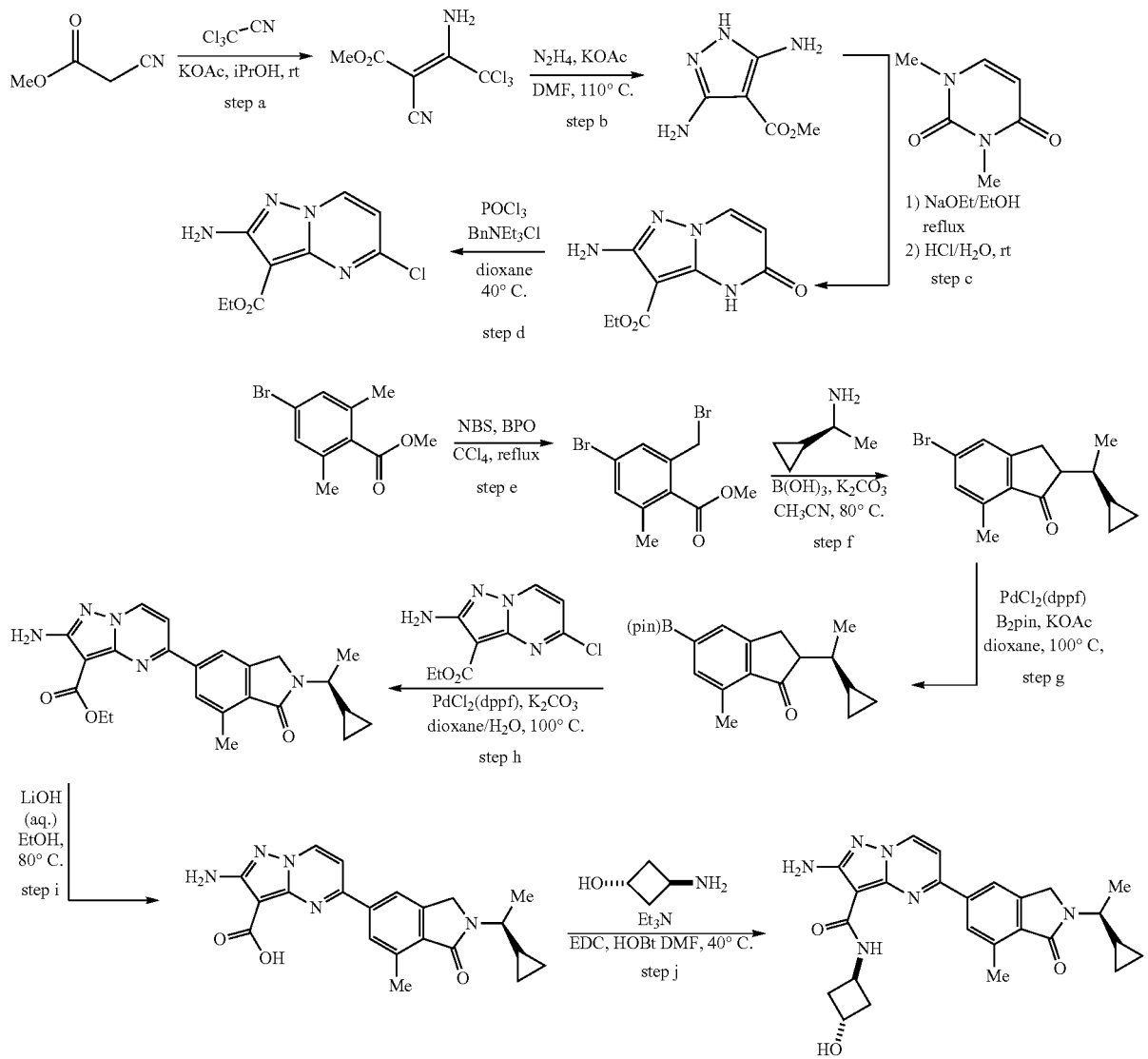

Step a: To a mixture of methyl cyanoacetate (44.1 mL, 500 mmol), KOAc (85.9 g, 875 mmol), and i-PrOH (500 mL) was added trichloroacetonitrile (50.1 mL, 500 mmol). The reaction mixture was stirred at rt for 14 h. $H_2O$ (675 mL) was added and the formed solids were collected by filtration, washed with $H_2O$ (500 mL), and dried in vacuo to afford the desired product as a white solid (93.8 g; 77%).

Step b: To a mixture of the product of Step a (93.8 g, 385 mmol), KOAc (56.7 g, 578 mmol), and DMF (385 mL) at 0° C. was added hydrazine monohydrate (28.0 mL, 578 mmol) dropwise. The mixture was stirred at rt for 1 h and then at 110° C. for 15 h. The mixture was cooled, and solids were removed by filtration, washing the cake with DMF (100 mL). The filtrate was concentrated to a thick film. The residue was recrystallized with $H_2O$ (720 mL) and the collected solids were washed with $H_2O$ (500 mL). The solids were dried in vacuo to afford the desired product as a light brown solid (37.6 g, 63%).

Step c: To a mixture of the product of Step b (31.2 g, 200 mmol), 1,3-dimethyluracil (28.0 g, 200 mmol) and EtOH (700 mL) at rt was added NaOEt (299 mL, 800 mmol, 21% by wt. in EtOH). The reaction mixture was stirred at reflux for 14 h and then allowed to cool. Solids were collected by filtration, washed with EtOH, and dried in vacuo to afford the sodium salt of the desired product as a brown solid (44.8 g; 92%; ~9:1 mixture of the ethyl and methyl esters). To a mixture of the sodium salt of the desired product (37.5 g, 154 mmol) and $H_2O$ (375 mL) at rt was added 2 M $HCl_{(aq)}$ (76.8 mL, 154 mL) at a rate of 60 mL/min. The mixture was stirred at rt for 15 mins. (pH of aq. phase should be ~4). The precipitated solids were collected by filtration, washed with $H_2O$, and dried in vacuo to afford the neutral form of the desired product as a brown solid (28.2 g, 83%).

Step d: To a mixture of the product of Step c (26.0 g, 117 mmol), benzyltriethylammonium chloride (26.6 g, 117 mmol), and dioxane (234 mL) at rt was added $POCl_3$ (32.7 mL, 351 mmol). The reaction mixture was stirred at 40° C. for 14 h and then allowed to cool. The mixture was poured into $H_2O$ (1.17 L) at rt with stirring. Solid $NaHCO_3$ (147 g) was added cautiously until pH is neutral. EtOAc (1 L) was added and the mixture was filtered to remove any suspended solids. The phases were separated and the aq. phase was extracted with EtOAc (1 L). The combined organic phases were dried over $Na_2SO_4$ and concentrated to afford the desired product (2-amino-5-chloropyrazolo[1,5-a]pyrimidine-3-carboxylic acid ethyl ester) as a light brown solid (24.9 g; 89%).

Step e: A mixture of methyl 4-bromo-2,6-dimethylbenzoate (24.7 g, 102 mmol), NBS (20.8 g, 117 mmol), BPO (3.28 g, 10.2 mmol, 75 wt. % in $H_2O$), and $CCl_4$ (406 mL) was stirred at reflux for 20 h. Upon cooling, $H_2O$ (100 mL) and brine (100 mL) were added. The organic phase was dried over $Na_2SO_4$, concentrated, and taken crude into the next step.

Step f: A mixture of the crude product of Step e (102 mmol), (S)-1-cyclopropylethylamine (13.0 g, 153 mmol), $B(OH)_3$ (6.30 g, 102 mmol), $K_2CO_3$ (42.3 g, 306 mmol), and $CH_3CN$ (406 mL) was stirred at 60° C. for 2 h. The mixture was cooled, the solids were removed by filtration, and the organic phase was concentrated. The crude material was purified by column chromatography ($SiO_2$, 0 to 20% EtOAc in hexanes) to afford the desired product as an off-white solid (15.8 g; 53%).

Step g: To a mixture of the product of Step f (15.8 g, 53.8 mmol), $B_2pin_2$ (13.7 g, 53.8 mmol), $PdCl_2(dppf)$ (1.97 g, 2.69 mmol), and KOAc (10.6 g, 108 mmol) under $N_2$ was added degassed dioxane (269 mL). The reaction mixture was stirred at 100° C. for 2 h. Upon cooling, MTBE (250 mL) was added, the solids were removed by filtration, and the organic phase was concentrated. The crude material was purified by column chromatography ($SiO_2$, 0 to 30% EtOAc in hexanes) to afford the desired product as an off-white solid (15.8 g; 86%).

Step h: To a mixture of the product of Step g (4.80 g, 20.0 mmol), the product of Step d (6.83 g, 20.0 mmol), $PdCl_2$ (dppf) (732 mg, 1.00 mmol), and $K_2CO_3$ (5.53 g, 40.0 mmol) under $N_2$ was added a degassed mixture of 4:1 dioxane:$H_2O$ (100 mL). The reaction mixture was stirred at 100° C. for 1 h. Upon cooling, brine (20 mL) and 19:1 $CH_2Cl_2$:MeOH (500 mL) were added. The organic phase was dried over $Na_2SO_4$, concentrated, and purified twice by column chromatography ($SiO_2$, 0 to 10% MeOH in $CH_2Cl_2$) and (0 to 50% acetone in $CH_2Cl_2$) to afford the desired product as a yellow solid (4.02 g; 48%).

Step i: To a mixture of the product of Step h (4.02 g, 9.58 mmol) and EtOH (48 mL) at rt was added LiOH (9.58 mL, 28.8 mmol, 3 M in $H_2O$). The reaction mixture was stirred at 80° C. for 1 h. The mixture was cooled and EtOH was removed under reduced pressure. $H_2O$ (200 mL) was added and the mixture was acidified to pH 2-3 with 2 M $HCl_{(aq)}$ (~14 mL). The solids were collected by filtration, washed with $H_2O$, and dried in vacuo to afford the desired product as a yellow solid (3.49 g; 93%).

Step j: To a mixture of the product of Step i (78 mg, 0.20 mmol), trans-3-aminocyclobutanol hydrochloride (27 mg, 0.22 mmol), HOBt hydrate (34 mg, 0.22 mmol), $Et_3N$ (138 μL, 1.00 mmol), and DMF (1 mL) at rt was added EDCI·HCl (58 mg, 0.30 mmol). The reaction mixture was stirred at 40° C. for 2 h and $H_2O$ (20 mL) was added. The formed solids were collected by filtration and washed with $H_2O$. The crude material was purified by column chromatography ($SiO_2$, 0 to 10% MeOH in $CH_2Cl_2$) to afford the desired product as a yellow solid (70 mg; 76%). $^1H$ NMR (400 MHz, DMSO-$d_6$) δ 9.01 (d, J=7.1 Hz, 1H), 8.20 (s, 1H), 8.12 (d, J=6.9 Hz, 1H), 8.10 (s, 1H), 7.64 (d, J=7.2 Hz, 1H), 6.54 (s, 2H), 5.18 (d, J=5.4 Hz, 1H), 4.59 (s, 2H), 4.50-4.39 (m, 2H), 3.59 (dq, J=9.3, 6.8 Hz, 1H), 2.72 (s, 3H), 2.37-2.23 (m, 4H), 1.31 (d, J=6.8 Hz, 3H), 1.23-1.11 (m, 1H), 0.64-0.54 (m, 1H), 0.48-0.34 (m, 2H), 0.30-0.22 (m, 1H). ESI MS [M+H]$^+$ for $C_{25}H_{29}N_6O_3$, calcd 461.2, found 461.1.

Example 2: 2-Amino-5-{2-[(1S)-1-cyclopropylethyl]-7-methyl-1-oxo-2,3-dihydro-1H-isoindol-5-yl}-N-[cis-4-hydroxy-4-methylcyclohexyl]pyrazolo[1,5-a]pyrimidine-3-carboxamide

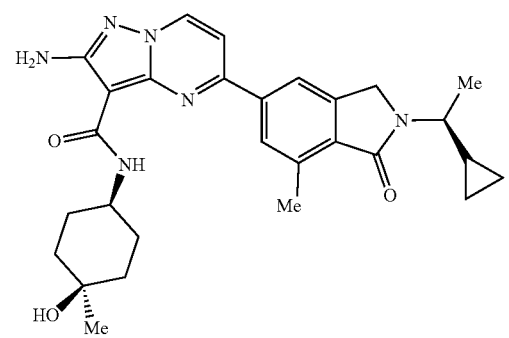 [SMILES: Cc1cc(-c2ccn3nc(N)c(C(=O)N[C@H]4CC[C@@](C)(O)CC4)c3n2)cc2c1C(=O)N([C@@H](C)C1CC1)C2]

The title compound was prepared in a similar manner to example 1. $^1H$ NMR (400 MHz, DMSO-$d_6$) δ 9.01 (d, J=7.1 Hz, 1H), 8.18 (s, 1H), 8.08 (s, 1H), 7.92 (d, J=7.6 Hz, 1H), 7.63 (d, J=7.2 Hz, 1H), 6.55 (s, 2H), 4.58 (s, 2H), 4.20 (s, 1H), 3.86-3.74 (m, 1H), 3.59 (dq, J=8.6, 6.8 Hz, 1H), 2.72 (s, 3H), 1.86-1.69 (m, 4H), 1.69-1.58 (m, 2H), 1.51-1.40 (m, 2H), 1.31 (d, J=6.8 Hz, 3H), 1.22-1.11 (m, 4H), 0.64-0.54 (m, 1H), 0.48-0.35 (m, 2H), 0.30-0.21 (m, 1H). ESI MS [M+H]$^+$ for $C_{28}H_{35}N_6O_3$, calcd 503.3, found 503.2.

Example 3: 2-Amino-5-{2-[(1S)-1-cyclopropyl-ethyl]-7-methyl-1-oxo-2,3-dihydro-1H-isoindol-5-yl}-N-[(1S,3S)-3-hydroxycyclopentyl]pyrazolo[1,5-a]pyrimidine-3-carboxamide

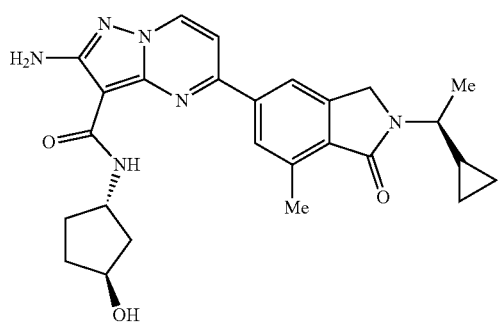 [SMILES: Cc1cc(-c2ccn3nc(N)c(C(=O)N[C@H]4CC[C@H](O)C4)c3n2)cc2c1C(=O)N([C@@H](C)C1CC1)C2]

The title compound was prepared in a similar manner to example 1. $^1$H NMR (400 MHz, DMSO-d$_6$) δ 9.00 (d, J=7.1 Hz, 1H), 8.16 (s, 1H), 8.06 (s, 1H), 7.94 (d, J=7.4 Hz, 1H), 7.62 (d, J=7.2 Hz, 1H), 6.55 (s, 2H), 4.65 (d, J=3.8 Hz, 1H), 4.58 (s, 2H), 4.46 (h, J=6.9 Hz, 1H), 4.37-4.30 (m, 1H), 3.59 (dq, J=9.1, 6.8 Hz, 1H), 2.71 (s, 3H), 2.27-2.15 (m, 1H), 2.07-1.95 (m, 2H), 1.75 (dt, J=12.9, 6.2 Hz, 1H), 1.64-1.48 (m, 2H), 1.31 (d, J=6.8 Hz, 3H), 1.22-1.12 (m, 1H), 0.63-0.55 (m, 1H), 0.47-0.35 (m, 2H), 0.30-0.22 (m, 1H). ESI MS [M+H]$^+$ for $C_{26}H_{31}N_6O_3$, calcd 475.2, found 475.1.

Example 4: 2-Amino-5-{2-[(1S)-1-cyclopropyl-ethyl]-7-methyl-1-oxo-2,3-dihydro-1H-isoindol-5-yl}-N-{trans-3-hydroxycyclobutyl]methyl}pyrazolo[1,5-a]pyrimidine-3-carboxamide

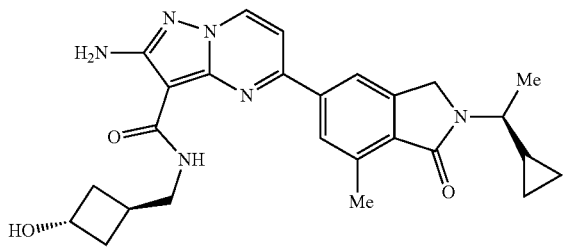 [SMILES: Cc1cc(-c2ccn3nc(N)c(C(=O)NC[C@H]4C[C@H](O)C4)c3n2)cc2c1C(=O)N([C@@H](C)C1CC1)C2]

The title compound was prepared in a similar manner to example 1. $^1$H NMR (400 MHz, DMSO-d$_6$) δ 9.00 (d, J=7.1 Hz, 1H), 8.20 (s, 1H), 8.07 (s, 1H), 7.90 (t, J=5.7 Hz, 1H), 7.62 (d, J=7.2 Hz, 1H), 6.57 (s, 2H), 5.01 (d, J=6.3 Hz, 1H), 4.58 (s, 2H), 4.30 (h, J=6.8 Hz, 1H), 3.59 (dq, J=9.4, 6.8 Hz, 1H), 3.46 (dd, J=7.4, 5.7 Hz, 2H), 2.72 (s, 3H), 2.45-2.32 (m, 1H), 2.19-2.09 (m, 2H), 2.07-1.97 (m, 2H), 1.31 (d, J=6.8 Hz, 3H), 1.22-1.11 (m, 1H), 0.63-0.55 (m, 1H), 0.47-0.35 (m, 2H), 0.30-0.22 (m, 1H). ESI MS [M+H]$^+$ for $C_{26}H_{31}N_6O_3$, calcd 475.2, found 475.2.

Example 5: 2-Amino-5-{2-[(1S)-1-cyclopropyl-ethyl]-7-methyl-1-oxo-2,3-dihydro-1H-isoindol-5-yl}-N-[(1R,3R)-3-hydroxycyclopentyl]pyrazolo[1,5-a]pyrimidine-3-carboxamide

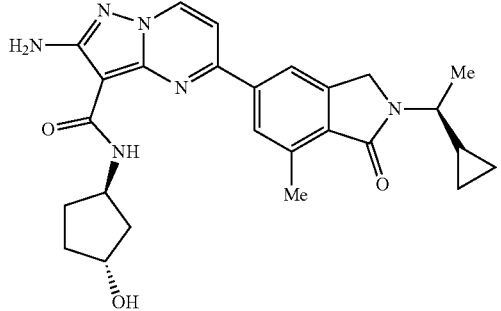 [SMILES: Cc1cc(-c2ccn3nc(N)c(C(=O)N[C@@H]4CC[C@@H](O)C4)c3n2)cc2c1C(=O)N([C@@H](C)C1CC1)C2]

The title compound was prepared in a similar manner to example 1. $^1$H NMR (400 MHz, DMSO-d$_6$) δ 9.00 (d, J=7.1 Hz, 1H), 8.17 (s, 1H), 8.06 (s, 1H), 7.94 (d, J=7.4 Hz, 1H), 7.62 (d, J=7.2 Hz, 1H), 6.55 (s, 2H), 4.65 (d, J=3.8 Hz, 1H), 4.59 (s, 2H), 4.46 (h, J=6.9 Hz, 1H), 4.33 (tq, J=6.9, 3.5 Hz, 1H), 3.59 (dq, J=9.1, 6.8 Hz, 1H), 2.72 (s, 3H), 2.27-2.15 (m, 1H), 2.07-1.95 (m, 2H), 1.75 (dt, J=12.9, 6.2 Hz, 1H), 1.64-1.49 (m, 2H), 1.31 (d, J=6.8 Hz, 3H), 1.23-1.12 (m, 1H), 0.63-0.54 (m, 1H), 0.47-0.35 (m, 2H), 0.30-0.21 (m, 1H). ESI MS [M+H]$^+$ for $C_{26}H_{31}N_6O_3$, calcd 475.2, found 475.1.

Example 6: 2-Amino-5-{2-[(1S)-1-cyclopropyl-ethyl]-7-methyl-1-oxo-2,3-dihydro-1H-isoindol-5-yl}-N-[trans-3-hydroxy-3-methylcyclobutyl]pyrazolo[1,5-a]pyrimidine-3-carboxamide

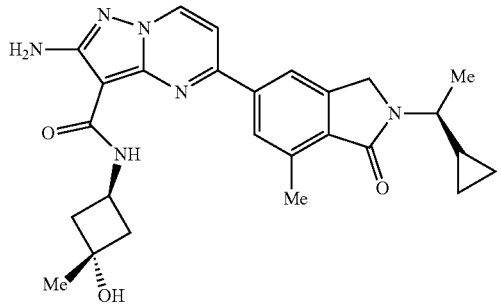 [SMILES: Cc1cc(-c2ccn3nc(N)c(C(=O)N[C@H]4C[C@](C)(O)C4)c3n2)cc2c1C(=O)N([C@@H](C)C1CC1)C2]

The title compound was prepared in a similar manner to example 1. $^1$H NMR (400 MHz, DMSO-d$_6$) δ 9.01 (d, J=7.1 Hz, 1H), 8.20 (s, 1H), 8.12 (s, 1H), 8.11 (s, 1H), 7.63 (d, J=7.2 Hz, 1H), 6.55 (s, 2H), 5.01 (s, 1H), 4.58 (s, 2H), 4.54-4.43 (m, 1H), 3.60 (dq, J=9.1, 6.8 Hz, 1H), 2.73 (s, 3H), 2.50-2.45 (m, 2H), 2.06-1.98 (m, 2H), 1.39 (s, 3H), 1.31 (d, J=6.8 Hz, 3H), 1.22-1.11 (m, 1H), 0.62-0.54 (m, 1H), 0.47-0.35 (m, 2H), 0.30-0.21 (m, 1H). ESI MS [M+H]$^+$ for $C_{26}H_{31}N_6O_3$, calcd 475.2, found 475.2.

Example 7: 2-Amino-5-{2-[(1S)-1-cyclopropyl-ethyl]-7-methyl-1-oxo-2,3-dihydro-1H-isoindol-5-yl}-N-[trans-4-hydroxy-4-methylcyclohexyl]pyrazolo[1,5-a]pyrimidine-3-carboxamide

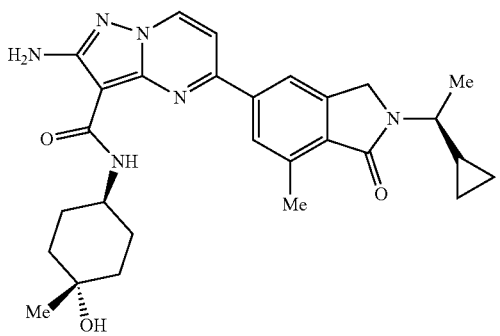 [SMILES: Cc1cc(-c2ccn3nc(N)c(C(=O)N[C@H]4CC[C@](C)(O)CC4)c3n2)cc2c1C(=O)N([C@@H](C)C1CC1)C2]

The title compound was prepared in a similar manner to example 1. $^1$H NMR (400 MHz, DMSO-d$_6$) δ 9.01 (d, J=7.1 Hz, 1H), 8.14 (s, 1H), 8.02 (s, 1H), 7.99 (d, J=7.5 Hz, 1H), 7.58 (d, J=7.1 Hz, 1H), 6.58 (s, 2H), 4.57 (s, 2H), 4.25 (s, 1H), 4.08-3.98 (m, 1H), 3.60 (dq, J=9.3, 6.8 Hz, 1H), 2.71 (s, 3H), 2.03-1.89 (m, 2H), 1.65-1.46 (m, 6H), 1.30 (d, J=6.8 Hz, 3H), 1.20-1.12 (m, 1H), 1.10 (s, 3H), 0.64-0.55 (m, 1H), 0.48-0.35 (m, 2H), 0.30-0.20 (m, 1H). ESI MS [M+H]$^+$ for C$_{28}$H$_{35}$N$_6$O$_3$, calcd 503.3, found 503.2.

Example 8: 2-Amino-5-{2-[(1S)-1-cyclopropyl-ethyl]-7-methyl-1-oxo-2,3-dihydro-1H-isoindol-5-yl}-N-[(1R,2R)-2-hydroxycyclopentyl]pyrazolo[1,5-a]pyrimidine-3-carboxamide

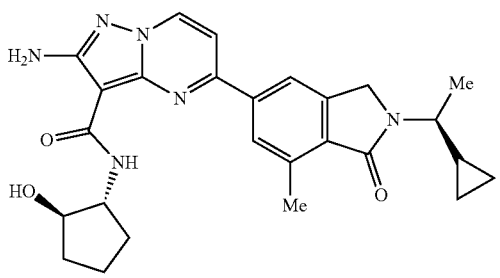 [SMILES: Cc1cc(-c2ccn3nc(N)c(C(=O)N[C@@H]4CCC[C@H]4O)c3n2)cc2c1C(=O)N([C@@H](C)C1CC1)C2]

The title compound was prepared in a similar manner to example 1. $^1$H NMR (400 MHz, CDCl$_3$) δ 8.54 (d, J=7.1 Hz, 1H), 8.18 (d, J=3.9 Hz, 1H), 7.88 (s, 2H), 7.29 (d, J=7.1 Hz, 1H), 5.77 (s, 2H), 4.64-4.41 (m, 2H), 4.21-4.02 (m, 2H), 3.83-3.72 (m, 1H), 2.82 (s, 3H), 2.42-2.27 (m, 1H), 2.24-2.10 (m, 1H), 2.04-1.62 (m, 4H), 1.39 (d, J=6.8 Hz, 3H), 1.12-0.97 (m, 1H), 0.73-0.60 (m, 1H), 0.53-0.32 (m, 3H). ESI MS [M+H]$^+$ for C$_{26}$H$_{31}$N$_6$O$_3$; calcd 475.2, found 475.2.

Example 9: 2-Amino-5-{2-[(1S)-1-cyclopropyl-ethyl]-7-methyl-1-oxo-2,3-dihydro-1H-isoindol-5-yl}-N-[(1S,3R)-3-hydroxycyclohexyl]pyrazolo[1,5-a]pyrimidine-3-carboxamide

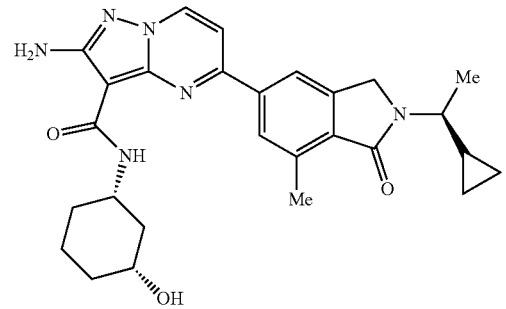 [SMILES: Cc1cc(-c2ccn3nc(N)c(C(=O)N[C@H]4CCC[C@@H](O)C4)c3n2)cc2c1C(=O)N([C@@H](C)C1CC1)C2]

The title compound was prepared in a similar manner to example 1. $^1$H NMR (400 MHz, DMSO-d$_6$) δ 8.97 (d, J=7.1 Hz, 1H), 8.21 (s, 1H), 8.11-8.08 (m, 1H), 8.03 (d, J=7.8 Hz, 1H), 7.60 (d, J=7.2 Hz, 1H), 4.56 (s, 2H), 3.89 (m, 1H), 3.64-3.52 (m, 2H), 2.69 (s, 3H), 2.14 (d, J=11.9 Hz, 1H), 1.90 (d, J=11.7 Hz, 1H), 1.82-1.72 (s, 2H), 1.37-1.18 (m, 8H), 1.14 (m, 1H), 0.56 (m, 1H), 0.44-0.33 (m, 2H), 0.23 (m, 1H). ESI MS [M+H]$^+$ for C$_{27}$H$_{33}$N$_6$O$_3$, calcd 489.2, found 489.2.

Example 10: 2-Amino-5-{2-[(1S)-1-cyclopropyl-ethyl]-7-methyl-1-oxo-2,3-dihydro-1H-isoindol-5-yl}-N-[(3R)-5-oxopyrrolidin-3-yl]pyrazolo[1,5-a]pyrimidine-3-carboxamide

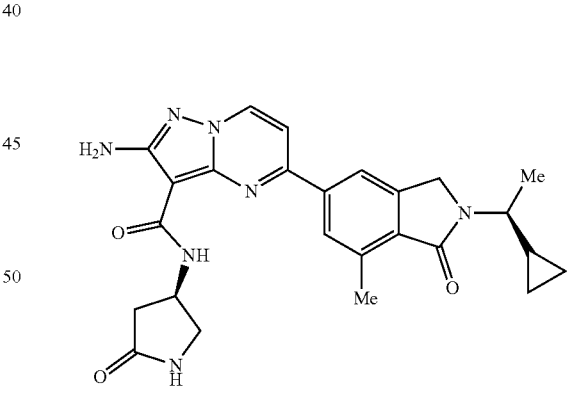

The title compound was prepared in a similar manner to example 1. $^1$H NMR (400 MHz, DMSO-d$_6$) δ 8.99 (d, J=7.1 Hz, 1H), 8.24 (d, J=7.3 Hz, 1H), 8.16 (m, 1H), 8.04 (m, 1H), 7.77 (s, 1H), 7.64 (d, J=7.2 Hz, 1H), 6.53 (s, 2H), 4.66-4.57 (m, 3H), 3.65 (dd, J=10.1, 6.1 Hz, 1H), 3.56 (m, 1H), 3.22 (m, 1H), 2.74-2.65 (m, 4H), 2.18 (dd, J=16.7, 3.7 Hz, 1H), 1.28 (d, J=6.8 Hz, 3H), 1.11 (m, 1H), 0.56 (m, 1H), 0.44-0.34 (m, 2H), 0.22 (m, 1H). ESI MS [M+H]$^+$ for C$_{25}$H$_{28}$N$_7$O$_3$, calcd 474.2, found 474.2.

Example 11: 2-Amino-5-{2-[(1S)-1-cyclopropyl-ethyl]-7-methyl-1-oxo-2,3-dihydro-1H-isoindol-5-yl}-N-[(1R,3R)-3-hydroxycyclohexyl]pyrazolo[1,5-a]pyrimidine-3-carboxamide

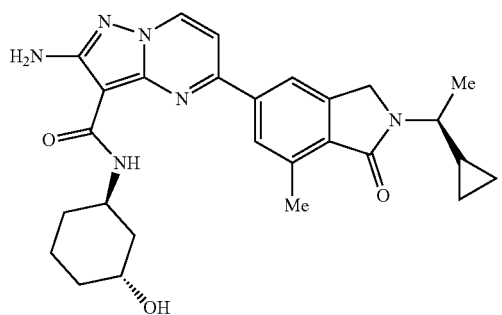 [SMILES: Cc1cc(-c2ccn3nc(N)c(C(=O)N[C@@H]4CCC[C@@H](O)C4)c3n2)cc2c1C(=O)N([C@@H](C)C1CC1)C2]

The title compound was prepared in a similar manner to example 1. $^1$H NMR (400 MHz, DMSO-d$_6$) δ 8.99 (d, J=7.1 Hz, 1H), 8.12 (s, 1H), 8.01 (m, 1H), 7.94 (d, J=8.1 Hz, 1H), 7.58 (d, J=7.2 Hz, 1H), 4.57 (s, 2H), 4.31 (s, 1H), 3.85 (s, 1H), 3.56 (m, 2H), 2.69 (s, 3H), 1.83-1.60 (m, 5H), 1.59-1.47 (m, 2H), 1.35 (m, 1H), 1.28 (d, J=6.8 Hz, 3H), 1.13 (m, 1H), 0.56 (m, 1H), 0.45-0.33 (m, 2H), 0.23 (m, 1H). ESI MS [M+H]$^+$ for C$_{27}$H$_{33}$N$_6$O$_3$, calcd 489.2, found 489.2.

Example 12: 2-Amino-5-{2-[(1S)-1-cyclopropyl-ethyl]-7-methyl-1-oxo-2,3-dihydro-1H-isoindol-5-yl}-N-[trans-3-(hydroxymethyl)cyclobutyl]pyrazolo[1,5-a]pyrimidine-3-carboxamide

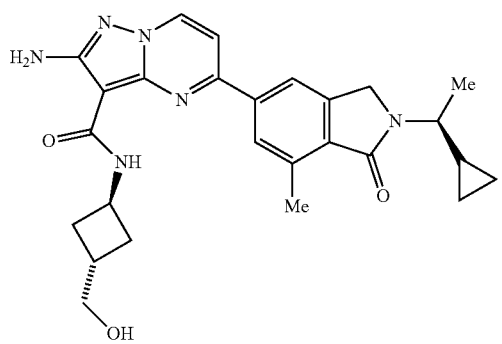 [SMILES: Cc1cc(-c2ccn3nc(N)c(C(=O)N[C@H]4C[C@H](CO)C4)c3n2)cc2c1C(=O)N([C@@H](C)C1CC1)C2]

The title compound was prepared in a similar manner to example 1. $^1$H NMR (400 MHz, DMSO-d$_6$) δ 9.01 (d, J=7.1 Hz, 1H), 8.22 (s, 1H), 8.15 (d, J=7.5 Hz, 1H), 8.12 (s, 1H), 7.65 (d, J=7.1 Hz, 1H), 6.55 (s, 2H), 4.66 (t, J=5.3 Hz, 1H), 4.60 (s, 2H), 4.54-4.42 (m, 1H), 3.64-3.54 (m, 1H), 3.51 (dd, J=6.8, 5.3 Hz, 2H), 2.73 (s, 3H), 2.47-2.34 (m, 1H), 2.30-2.18 (m, 2H), 2.16-2.02 (m, 2H), 1.31 (d, J=6.8 Hz, 3H), 1.26-1.09 (m, 1H), 0.66-0.53 (m, 1H), 0.50-0.32 (m, 2H), 0.30-0.19 (m, 1H). ESI MS [M+H]$^+$ for C$_{26}$H$_{31}$N$_6$O$_3$, calcd 475.2, found 475.2.

Example 13: 2-Amino-5-{2-[(1S)-1-cyclopropyl-ethyl]-7-methyl-1-oxo-2,3-dihydro-1H-isoindol-5-yl}-N-[trans-3-hydroxy-1-methylcyclobutyl]pyra-zolo[1,5-a]pyrimidine-3-carboxamide

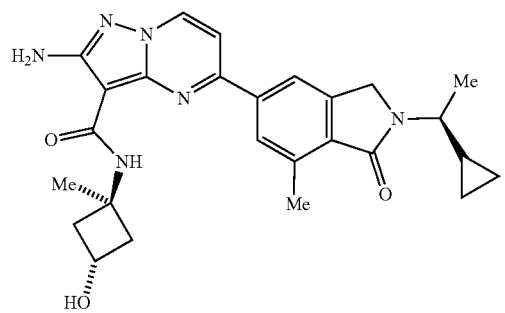 [SMILES: Cc1cc(-c2ccn3nc(N)c(C(=O)N[C@]4(C)C[C@@H](O)C4)c3n2)cc2c1C(=O)N([C@@H](C)C1CC1)C2]

The title compound was prepared in a similar manner to example 1. $^1$H NMR (400 MHz, DMSO-d$_6$) δ 9.01 (d, J=7.1, 0.7 Hz, 1H), 8.19 (s, 1H), 8.09 (s, 1H), 8.00 (s, 1H), 7.64 (d, J=7.2, 0.8 Hz, 1H), 6.56 (s, 2H), 5.09 (d, J=5.9 Hz, 1H), 4.59 (s, 2H), 4.29 (q, J=6.6 Hz, 1H), 3.65-3.53 (m, 1H), 2.76-2.64 (m, 5H), 2.05-1.94 (m, 2H), 1.58 (s, 3H), 1.31 (d, J=6.8 Hz, 3H), 1.23-1.09 (m, 1H), 0.65-0.52 (m, 1H), 0.51-0.33 (m, 2H), 0.31-0.18 (m, 1H). ESI MS [M+H]$^+$ for C$_{26}$H$_{31}$N$_6$O$_3$, calcd 475.2, found 475.2.

Example 14: 2-Amino-5-{2-[(1S)-1-cyclopropyl-ethyl]-7-methyl-1-oxo-2,3-dihydro-1H-isoindol-5-yl}-N-[trans-3-(2-hydroxypropan-2-yl)cyclobutyl]pyrazolo[1,5-a]pyrimidine-3-carboxamide

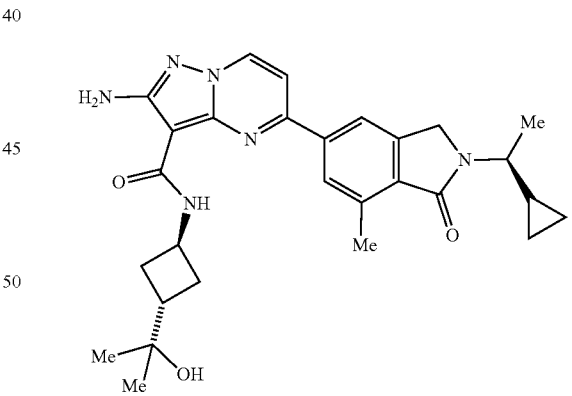

The title compound was prepared in a similar manner to example 1. $^1$H NMR (400 MHz, DMSO-d$_6$) δ 9.02 (d, J=7.2 Hz, 1H), 8.27-8.16 (m, 2H), 8.12 (s, 1H), 7.65 (d, J=7.2 Hz, 1H), 6.55 (s, 2H), 4.59 (s, 2H), 4.29 (s, 2H), 3.71-3.51 (m, 1H), 2.72 (d, J=0.7 Hz, 3H), 2.49-2.36 (m, 3H), 2.00-1.84 (m, 2H), 1.30 (d, J=6.8 Hz, 3H), 1.21-1.10 (m, 1H), 1.07 (s, 6H), 0.67-0.52 (m, 1H), 0.49-0.32 (m, 2H), 0.29-0.17 (m, 1H). ESI MS [M+H]$^+$ for C$_{28}$H$_{35}$N$_6$O$_3$, calcd 503.3, found 503.2.

Example 15: m-[(5-{2-[(S)-1-Cyclopropylethyl]-7-methyl-5-isoindolinoyl}-2-amino-1,4,7a-triaza-3-indenyl)carbonylamino]benzoic acid

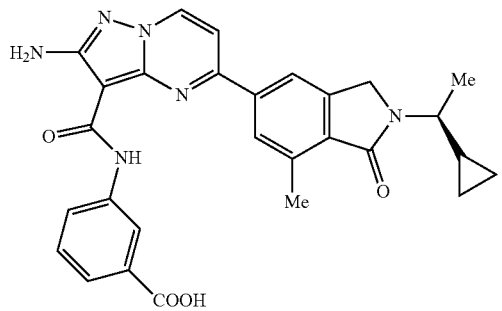 [SMILES: Cc1cc(-c2ccn3nc(N)c(C(=O)Nc4cccc(C(=O)O)c4)c3n2)cc2c1C(=O)N([C@@H](C)C1CC1)C2]

The title compound was prepared in a similar manner to example 1. $^1$H NMR (400 MHz, DMSO-$d_6$) δ 13.07 (s, 1H), 10.21 (s, 1H), 9.08 (d, J=7.1 Hz, 1H), 8.30 (s, 1H), 8.17 (dq, J=1.3, 10.2 Hz, 2H), 7.72 (d, J=7.2 Hz, 1H), 7.66 (dt, J=1.3, 7.7 Hz, 1H), 7.55-7.48 (m, 1H), 6.69 (s, 2H), 4.62 (s, 2H), 3.58 (dd, J=6.8, 9.2 Hz, 1H), 2.76 (s, 3H), 1.31 (d, J=6.8 Hz, 3H), 1.20-1.10 (m, 1H), 0.63-0.53 (m, 1H), 0.46-0.34 (m, 2H), 0.29-0.21 (m, 1H). ESI MS [M+H]$^+$ for $C_{28}H_{26}N_6O_4$, calcd 511.2, found 511.2.

Example 16: 2-Amino-5-{2-[(1S)-1-cyclopropyl-ethyl]-7-methyl-1-oxo-2,3-dihydro-1H-isoindol-5-yl}-N-[1-(2-hydroxyethyl)-1H-pyrazol-4-yl]pyrazolo[1,5-a]pyrimidine-3-carboxamide

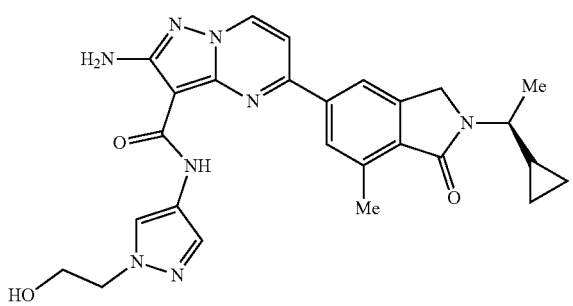 [SMILES: Cc1cc(-c2ccn3nc(N)c(C(=O)Nc4cnn(CCO)c4)c3n2)cc2c1C(=O)N([C@@H](C)C1CC1)C2]

The title compound was prepared in a similar manner to example 1. $^1$H NMR (400 MHz, DMSO-$d_6$) δ 9.68 (s, 1H), 9.05 (d, J=7.1 Hz, 1H), 8.28 (s, 1H), 8.15 (s, 1H), 8.10 (d, J=0.6 Hz, 1H), 7.69 (d, J=7.2 Hz, 1H), 7.65 (d, J=0.7 Hz, 1H), 6.64 (s, 2H), 4.94-4.90 (m, 1H), 4.64 (s, 2H), 4.15 (t, J=5.6 Hz, 2H), 3.75 (q, J=5.5 Hz, 2H), 3.60 (dq, J=9.2, 6.8 Hz, 1H), 2.75 (s, 3H), 1.32 (d, J=6.8 Hz, 3H), 1.24-1.13 (m, 1H), 0.64-0.55 (m, 1H), 0.48-0.36 (m, 2H), 0.30-0.22 (m, 1H). ESI MS [M+H]$^+$ for $C_{26}H_{29}N_8O_3$, calcd 501.2, found 501.1.

Example 17: 2-Amino-5-{2-[(1S)-1-cyclopropyl-ethyl]-7-methyl-1-oxo-2,3-dihydro-1H-isoindol-5-yl}-N-[1-(2-hydroxy-2-methylpropyl)-1H-pyrazol-4-yl]pyrazolo[1,5-a]pyrimidine-3-carboxamide

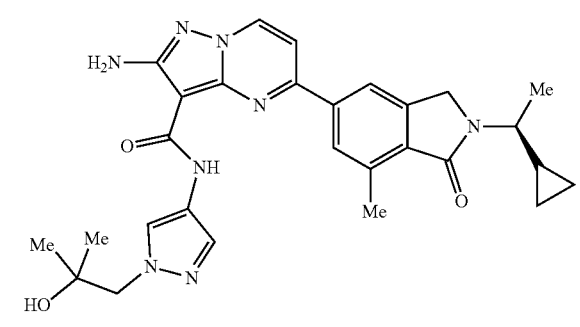 [SMILES: Cc1cc(-c2ccn3nc(N)c(C(=O)Nc4cnn(CC(C)(C)O)c4)c3n2)cc2c1C(=O)N([C@@H](C)C1CC1)C2]

The title compound was prepared in a similar manner to example 1. $^1$H NMR (400 MHz, DMSO-$d_6$) δ 9.71 (s, 1H), 9.05 (d, J=7.1 Hz, 1H), 8.28 (s, 1H), 8.15 (s, 1H), 8.11 (d, J=0.7 Hz, 1H), 7.69 (d, J=7.2 Hz, 1H), 7.63 (d, J=0.7 Hz, 1H), 6.64 (s, 2H), 4.72 (s, 1H), 4.64 (s, 2H), 4.02 (s, 2H), 3.60 (dq, J=9.4, 6.8 Hz, 1H), 2.75 (s, 3H), 1.32 (d, J=6.8 Hz, 3H), 1.24-1.12 (m, 1H), 1.09 (s, 6H), 0.64-0.55 (m, 1H), 0.48-0.35 (m, 2H), 0.31-0.21 (m, 1H). ESI MS [M+H]$^+$ for $C_{28}H_{33}N_8O_3$, calcd 529.3, found 529.2.

Example 18: 2-Amino-5-{2-[(1S)-1-cyclopropyl-ethyl]-7-methyl-1-oxo-2,3-dihydro-1H-isoindol-5-yl}-N-(1-methyl-1H-pyrazol-4-yl)pyrazolo[1,5-a]pyrimidine-3-carboxamide

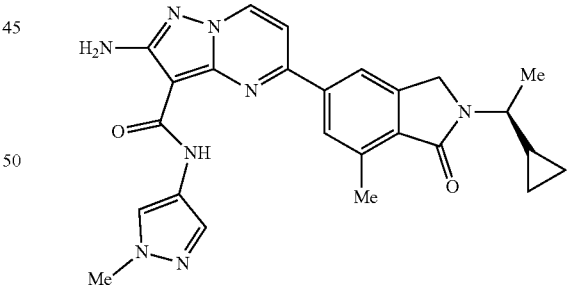

The title compound was prepared in a similar manner to example 1. $^1$H NMR (400 MHz, DMSO-$d_6$) δ 9.64 (s, 1H), 9.05 (d, J=7.1 Hz, 1H), 8.28 (s, 1H), 8.15 (s, 1H), 8.06 (s, 1H), 7.69 (d, J=7.2 Hz, 1H), 7.63 (s, 1H), 6.65 (s, 2H), 4.65 (s, 2H), 3.85 (s, 3H), 3.60 (dq, J=9.3, 6.8 Hz, 1H), 2.75 (s, 3H), 1.32 (d, J=6.8 Hz, 3H), 1.22-1.13 (m, 1H), 0.64-0.55 (m, 1H), 0.48-0.36 (m, 2H), 0.30-0.22 (m, 1H). ESI MS [M+H]$^+$ for $C_{25}H_{27}N_8O_2$, calcd 471.2, found 471.2.

Example 19: 2-Amino-5-{2-[(1S)-1-cyclopropyl-ethyl]-7-methyl-1-oxo-2,3-dihydro-1H-isoindol-5-yl}-N-(1,5-dimethyl-1H-pyrazol-4-yl)pyrazolo[1,5-a]pyrimidine-3-carboxamide

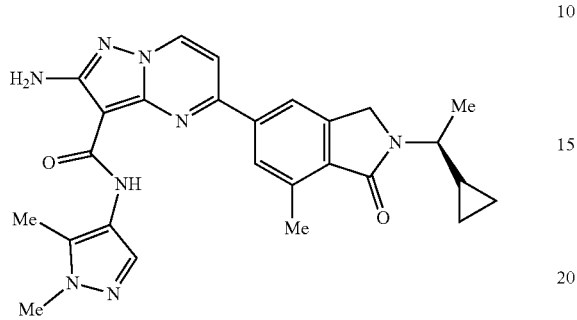

The title compound was prepared in a similar manner to example 1. $^1$H NMR (400 MHz, DMSO-$d_6$) δ 9.32 (s, 1H), 9.07 (d, J=7.1 Hz, 1H), 8.23 (s, 1H), 8.12 (s, 1H), 7.80 (s, 1H), 7.65 (d, J=7.1 Hz, 1H), 6.66 (s, 2H), 4.58 (s, 2H), 3.76 (s, 3H), 3.64-3.51 (m, 1H), 2.72 (s, 3H), 2.36 (s, 3H), 1.31 (d, J=6.8 Hz, 3H), 1.21-1.11 (m, 1H), 0.63-0.52 (m, 1H), 0.47-0.34 (m, 2H), 0.30-0.20 (m, 1H). ESI MS [M+H]$^+$ for $C_{26}H_{29}N_8O_2$; calcd 485.2, found 485.2.

Example 20: 2-Amino-N-cyclopropyl-5-{2-[(1S)-1-cyclopropylethyl]-1-oxo-7-(trifluoromethoxy)-2,3-dihydro-1H-isoindol-5-yl}pyrazolo[1,5-a]pyrimidine-3-carboxamide

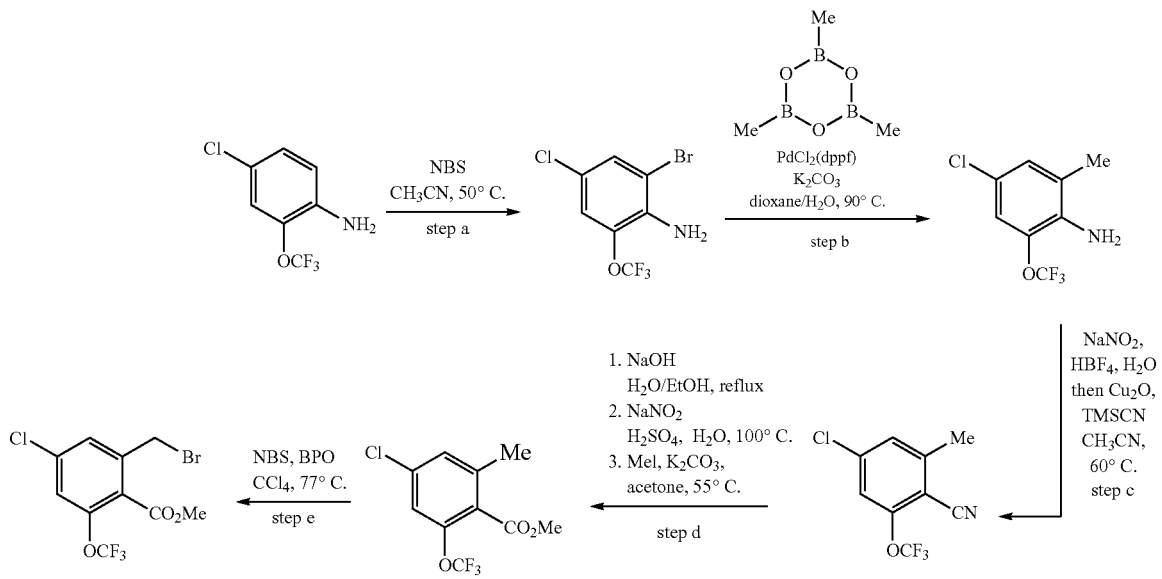

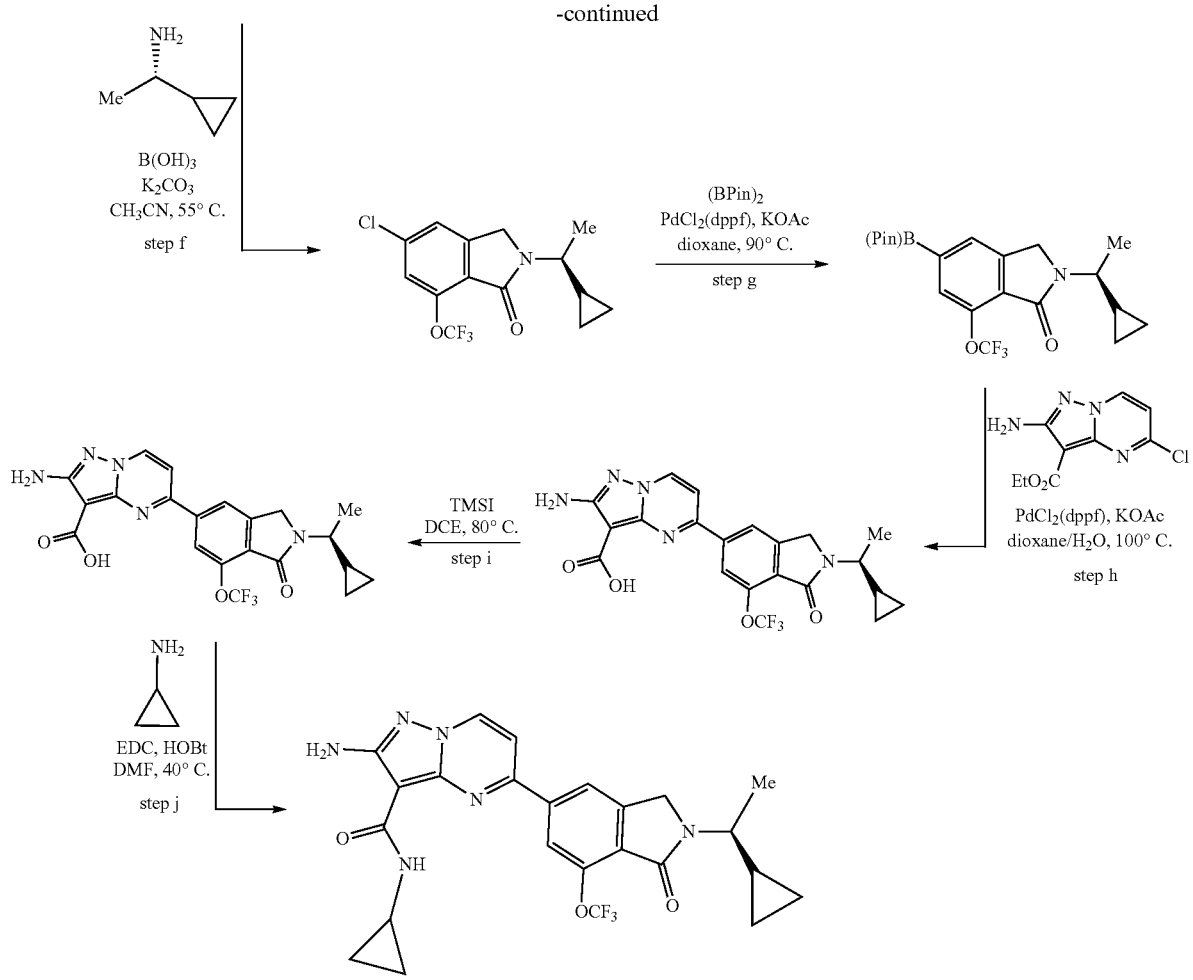

Step a: A solution of 4-chloro-2-(trifluoromethoxy)aniline (25.0 g, 118 mmol) and NBS (21.0 g, 118 mmol) in CH$_3$CN (600 mL) was stirred at 50° C. for 1.5 h. Then the reaction mixture was cooled to rt and concentrated to 50 mL volume under reduced pressure. The residual material was dissolved in EtOAc (400 mL) and was sequentially washed with sat. aq. Na$_2$S$_2$O$_3$ (200 mL) and brine (200 mL). The organic phase was separated and dried over Na$_2$SO$_4$. After all solvent was removed under reduced pressure, the residue was purified by column chromatography (SiO$_2$, hexanes/EtOAc gradient) to afford 2-bromo-4-chloro-6-(trifluoromethoxy)aniline as a yellowish liquid (30.8 g, 94% yield). $^1$H NMR (400 MHz, CDCl$_3$) δ 7.36 (d, J=2.2 Hz, 1H), 7.13 (dq, J=2.9, 1.5 Hz, 1H), 4.30 (br. s, 2H).

Step b: 2-Bromo-4-chloro-6-(trifluoromethoxy)aniline (30.8 g, 106 mmol), trimethylboroxine (14.9 mL, 106 mmol) and K$_2$CO$_3$ (44 g, 318 mmol) were mixed together in dioxane (500 mL) and H$_2$O (50 mL). The resulting mixture was degassed under vacuum and backfilled with N$_2$. Then PdCl$_2$(dppf) (2.6 g, 3.2 mmol) was added and the reaction mixture was maintained at 90° C. overnight. After complete conversion of the starting material was observed by TLC, the mixture was cooled to rt and concentrated to 100 mL volume. The residue was partitioned between EtOAc (500 mL) and H$_2$O (300 mL), the organic phase was separated and the aq. solution was extracted with EtOAc (2×150 mL). The combined organic phase was washed with brine, dried over Na$_2$SO$_4$ and concentrated to dryness. The residue was purified by column chromatography (SiO$_2$, hexanes/EtOAc gradient) to provide 20.7 g of an inseparable mixture of 4-chloro-2-methyl-6-(trifluoromethoxy)aniline and an unknown impurity (2:1 ratio, respectively). This material was used for the next step without additional purification.

Step c: A solution of HBF$_4$ (aq.) (40 mL, 48 wt. %) was added at rt to a mixture of the product from Step b (28.8 g) and H$_2$O (100 mL) in a round-bottom flask equipped with mechanical stirrer. The resulting suspension was cooled to 0° C. and solid NaNO$_2$ (9.7 g, 140 mmol) was added in small portions while maintaining the temperature below 5° C. After the addition was complete, the mixture was stirred at 0° C. for 0.5 h, then the precipitate was collected by filtration [Note: additional H$_2$O washes should be avoided since the product is partially soluble in H$_2$O]. The precipitated diazonium salt was washed with MTBE (5×100 mL) and dried under vacuum for 0.5 h. The solid thus obtained was dissolved in CH$_3$CN (500 mL) and then TMSCN (32.0 mL, 255 mmol) and Cu$_2$O (4.4 g, 102 mmol) were added sequentially. The reaction mixture was stirred at 60° C. until N$_2$ formation completely ceased and complete consumption of the starting material was observed by $^1$H NMR. The reaction mixture was filtered, and the filtrate was concentrated to dryness. The resulting crude product was dissolved in EtOAc and the solution was passed through a plug of SiO$_2$. The solvent was removed under reduced pressure to afford 4-chloro-2-methyl-6-(trifluoromethoxy)benzonitrile as a red oil (15.1 g, 49% yield). $^1$H NMR (400 MHz, CDCl$_3$) δ 7.31-7.25 (m, 1H), 7.26-7.19 (m, 1H), 2.57 (t, J=0.7 Hz, 3H).

Step d: A solution of 4-chloro-2-methyl-6-(trifluoromethoxy)benzonitrile (3.25 g, 13.8 mmol) and NaOH (2.2 g, 55.2 mmol) in 1:1 EtOH/H$_2$O (50 mL) was refluxed for 4 h. The solution was then cooled to rt and neutralized to acidic pH with 1 M aq. HCl. The product was extracted with EtOAc (3×70 mL). The combined organic phase was washed with brine (150 ml), dried over Na$_2$SO$_4$ and concentrated to dryness under reduced pressure. The crude product was purified by column chromatography (SiO$_2$, hexanes/EtOAc gradient) to produce 4-chloro-2-methyl-6-(trifluoromethoxy)benzamide (2.67 g, 76% yield) as beige solid. $^1$H NMR (400 MHz, CDCl$_3$) δ 7.31-7.25 (m, 1H), 7.26-7.19 (m, 1H), 2.57 (t, J=0.7 Hz, 3H). The solid thus obtained was suspended in 1:1 H$_2$SO$_4$/H$_2$O (80 mL) and cooled to 0° C. Then, a solution of NaNO$_2$ (2.7 g, 39.4 mmol) in H$_2$O (10 mL) was added in portions over 10 min. After the addition was complete, the mixture was stirred at 100° C. for 1.5 h. Once complete consumption of the starting material was observed, the mixture was cooled to rt and diluted with CH$_2$Cl$_2$ (70 mL). The organic phase was separated, and the aq. solution was additionally extracted with CH$_2$Cl$_2$ (2×70 mL). The combined organic solution was washed with H$_2$O, dried (Na$_2$SO$_4$) and concentrated to dryness under reduced pressure, providing the crude 4-chloro-2-methyl-6-(trifluoromethoxy)benzoic acid. This material was dissolved in acetone. Then K$_2$CO$_3$ (11.0 g, 80 mmol) and MeI (3.5 mL, 56 mmol) were added at rt and the heterogenous mixture was stirred at 55° C. for 2 h. Upon completion (TLC monitoring), the mixture was cooled to rt and concentrated to dryness. The residue was partitioned between EtOAc (60 ml) and H$_2$O (60 mL), the organic phase was separated and the aq. solution was additionally extracted with EtOAc (2×50 mL). The combined organic extracts were dried (Na$_2$SO$_4$) and concentrated to dryness. The crude product was purified by column chromatography to afford methyl 4-chloro-2-methyl-6-(trifluoromethoxy)benzoate as a yellowish oil (3.73 g, 88% yield). $^1$H NMR (400 MHz, CDCl$_3$) δ 7.20-7.14 (m, 1H), 7.18-7.12 (m, 1H), 3.92 (s, 3H), 2.35 (t, J=0.6 Hz, 3H).

Step e. A mixture of methyl 4-chloro-2-methyl-6-(trifluoromethoxy)benzoate (3.7 g, 13.8 mmol), NBS (2.8 g, 15.8 mmol) and BPO (0.45 g, 0.14 mmol, contains 25 wt. % of H$_2$O) was refluxed in CCl$_4$ (55 mL) under N$_2$ overnight. Then the mixture was cooled to rt and concentrated to dryness. The residue was dissolved in EtOAc (70 mL) and washed with H$_2$O (2×50 mL). The organic phase was dried over Na$_2$SO$_4$ and concentrated to dryness to produce a mixture of the starting material, the desired product and dibrominated byproduct in a 1:3:1 ratio, respectively ($^1$H NMR analysis). This mixture was used for the next step without additional purification.

Step f. The crude product from Step e was dissolved in CH$_3$CN (55 mL) followed by the addition of (S)-1-cyclopropylethylamine (1.4 g, 16.5 mmol), K$_2$CO$_3$ (5.7 g, 41.4 mmol) and B(OH)$_3$ (0.85 g, 13.8 mmol). The mixture was stirred at 55° C. for 2 h. The mixture was cooled to rt and diluted with EtOAc (150 mL) and H$_2$O (150 mL). The organic phase was separated and the aq. solution was extracted with EtOAc (2×70 mL). The combined organic extracts were dried over Na$_2$SO$_4$ and concentrated to dryness. The residue was purified by column chromatography to produce (S)-5-chloro-2-(1-cyclopropylethyl)-7-(trifluoromethoxy)isoindolin-1-one as a white solid (2.45 g, 56% yield).

Step g. A mixture of the product of Step f (1.0 g, 3.1 mmol), B$_2$pin$_2$ (0.87 g, 3.4 mmol), and KOAc (1.07 g, 10.9 mmol) in dioxane (16 mL) was degassed under vacuum and backfilled with N$_2$. Then P(Cy)$_3$ Pd G2 (185.0 mg, 0.31 mmol) was added and the reaction mixture was heated to 90° C. and maintained at that temperature for 1 h. Once complete consumption of the starting material was observed by LCMS analysis the mixture was cooled and concentrated under reduced pressure. The residue was partitioned between EtOAc (50 mL) and H$_2$O (30 mL), the organic phase was separated and the aq. phase was extracted with EtOAc (2×35 mL). The combined organic phase was dried over Na$_2$SO$_4$ and concentrated under reduced pressure to produce the desired boronic acid pinacol ester, which was used in the next step without additional purification. ESI MS [M+H]$^+$ for C$_{14}$H$_{14}$F$_3$NO$_2$, calcd 285.1, found 285.2.

Step h. The product of Step g was dissolved in dioxane (31 mL). To this solution was added 2-amino-5-chloropyrazolo[1,5-a]pyrimidine-3-carboxylic acid ethyl ester (0.75 g, 3.1 mmol), followed by 12.4 mL of 1 M aq. Na$_2$CO$_3$ and PdCl$_2$(dppf) (227 mg, 0.31 mmol). The resulting mixture was refluxed for 1 h, then cooled to rt and diluted with EtOAc (150 mL) and H$_2$O (100 mL). The organic phase was separated and the aq. phase was extracted with EtOAc (3×50 mL). The combined organic phase was dried over Na$_2$SO$_4$ and the solvent was removed under reduced pressure. The crude material was purified by column chromatography (SiO$_2$, EtOAc) to produce the desired product as a dark brown solid (1.2 g, 82% yield). $^1$H NMR (400 MHz, DMSO-d$_6$) δ 8.97 (d, J=7.1 Hz, 1H), 8.43 (s, 1H), 8.31 (s, 1H), 7.72 (d, J=7.2 Hz, 1H), 6.53 (s, 2H), 4.65 (s, 2H), 4.25 (q, J=7.1 Hz, 2H), 3.66-3.49 (m, 1H), 1.35 (t, J=7.1 Hz, 3H), 1.29 (d, J=6.8 Hz, 3H), 1.21-1.07 (m, 1H), 0.60-0.50 (m, 1H), 0.47-0.31 (m, 2H), 0.31-0.20 (m, 1H).

Step i. A mixture of the product (1.0 g, 2.0 mmol) from the previous step and TMSI (2.3 mL, 16.0 mmol) in DCE (10 mL) was placed in a sealed vial under N$_2$ and was stirred in the dark at 80° C. overnight. Then the mixture was cooled to rt, diluted with DCE and poured into 100 ml of 5% aq. NaHSO$_3$. The organic phase was separated and the aq. phase was additionally extracted with 10% i-PrOH in CH$_2$Cl$_2$ (4×70 mL). The combined organic phase was dried over Na$_2$SO$_4$ and the solvent was removed under reduced pressure. The crude material was purified by column chromatography (SiO$_2$, CH$_2$Cl$_2$/MeOH gradient) to produce the desired carboxylic acid as a yellow solid (0.94 g, 67% yield). $^1$H NMR (400 MHz, DMSO-d$_6$) δ 12.15 (br. s, 1H), 8.98 (d, J=7.1 Hz, 1H), 8.47 (s, 1H), 8.25 (s, 1H), 7.73 (d, J=7.1 Hz, 1H), 6.53 (br. s, 2H), 4.68 (s, 2H), 3.74-3.27 (m, 1H), 1.28 (d, J=6.8 Hz, 3H), 1.18-1.10 (m, 1H), 0.64-0.50 (m, 1H), 0.46-0.31 (m, 2H), 0.30-0.18 (m, 1H).

Step j. Performed similarly to example 1. $^1$H NMR (400 MHz, DMSO-d$_6$) δ 9.06 (d, J=7.1 Hz, 1H), 8.43 (d, J=1.3 Hz, 1H), 8.20-8.17 (m, 1H), 7.77 (d, J=3.8 Hz, 1H), 7.69 (d, J=7.1 Hz, 1H), 6.64 (s, 2H), 4.70 (s, 2H), 3.59 (dq, J=9.3, 6.8 Hz, 1H), 2.87 (tt, J=7.5, 3.8 Hz, 1H), 1.32 (d, J=6.9 Hz, 3H), 1.24-1.13 (m, 1H), 0.83-0.77 (m, 2H), 0.65-0.54 (m, 3H), 0.49-0.36 (m, 2H), 0.31-0.23 (m, 1H). ESI MS [M+H]$^+$ for C$_{24}$H$_{24}$F$_3$N$_6$O$_3$, calcd 501.2, found 501.1.

Example 21: 2-Amino-5-{2-[(1S)-1-cyclopropyl-ethyl]-1-oxo-7-(trifluoromethoxy)-2,3-dihydro-1H-isoindol-5-yl}-N-(oxetan-3-yl)pyrazolo[1,5-a]pyrimidine-3-carboxamide

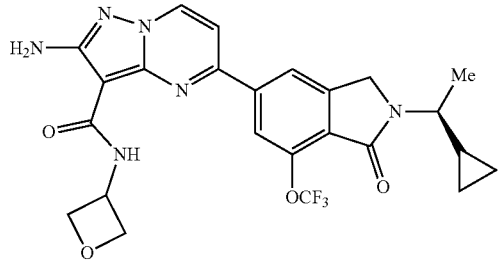 [SMILES: C[C@@H](C1CC1)N1Cc2cc(-c3ccn4nc(N)c(C(=O)NC5COC5)c4n3)cc(OC(F)(F)F)c2C1=O]

The title compound was prepared in a similar manner to example 20. $^1$H NMR (400 MHz, DMSO-$d_6$) δ 9.09 (d, J=7.1 Hz, 1H), 8.51 (d, J=1.2 Hz, 1H), 8.32 (t, J=1.4 Hz, 1H), 8.24 (d, J=6.6 Hz, 1H), 7.73 (d, J=7.1 Hz, 1H), 6.63 (s, 2H), 5.07 (dt, J=7.1, 6.3 Hz, 1H), 4.86 (dd, J=7.4, 6.7 Hz, 2H), 4.71 (s, 2H), 4.59 (t, J=6.6 Hz, 2H), 3.59 (dq, J=9.3, 6.9 Hz, 1H), 1.33 (d, J=6.8 Hz, 3H), 1.24-1.14 (m, 1H), 0.64-0.56 (m, 1H), 0.48-0.36 (m, 2H), 0.31-0.24 (m, 1H). ESI MS [M+H]$^+$ for $C_{24}H_{24}F_3N_6O_4$, calcd 517.2, found 517.1.

Example 22: 2-Amino-5-{2-[(1S)-1-cyclopropyl-ethyl]-1-oxo-7-(trifluoromethoxy)-2,3-dihydro-1H-isoindol-5-yl}-N-[(2R)-1-hydroxypropan-2-yl]pyrazolo[1,5-a]pyrimidine-3-carboxamide

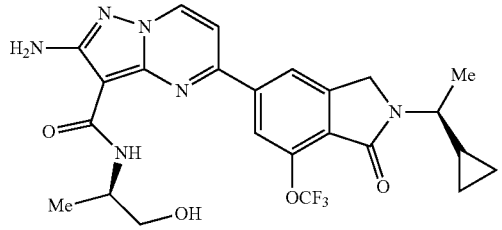 [SMILES: C[C@H](CO)NC(=O)c1c(N)nn2ccc(-c3cc4c(c(OC(F)(F)F)c3)C(=O)N([C@@H](C)C3CC3)C4)nc12]

The title compound was prepared in a similar manner to example 20. $^1$H NMR (400 MHz, DMSO-$d_6$) δ 9.03 (d, J=7.1 Hz, 1H), 8.58 (s, 1H), 8.23 (s, 1H), 8.08 (d, J=8.0 Hz, 1H), 7.72 (d, J=7.2 Hz, 1H), 6.60 (s, 2H), 4.66 (s, 2H), 4.06 (m, 1H), 3.60-3.47 (m, 4H), 1.30 (d, J=6.8 Hz, 3H), 1.20 (d, J=6.7 Hz, 3H), 1.14 (m, 1H), 0.57 (m, 1H), 0.45-0.33 (m, 2H), 0.24 (m, 1H). ESI MS [M+H]$^+$ for $C_{24}H_{26}F_3N_6O_4$, calcd 519.2, found 519.2.

Example 23: 2-Amino-5-{2-[(1S)-1-cyclopropyl-ethyl]-1-oxo-7-(trifluoromethoxy)-2,3-dihydro-1H-isoindol-5-yl}-N-[cis-3-hydroxy-3-methylcy-clobutyl]pyrazolo[1,5-a]pyrimidine-3-carboxamide

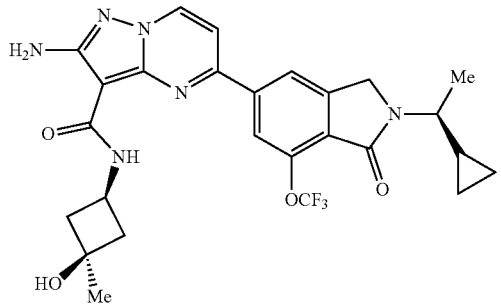 [SMILES: C[C@@H](C1CC1)N1Cc2cc(-c3ccn4nc(N)c(C(=O)N[C@H]5C[C@@](C)(O)C5)c4n3)cc(OC(F)(F)F)c2C1=O]

The title compound was prepared in a similar manner to example 20. $^1$H NMR (400 MHz, DMSO-$d_6$) δ 9.05 (d, J=7.1 Hz, 1H), 8.45 (m, 1H), 8.20 (s, 1H), 7.84 (d, J=7.2 Hz, 1H), 7.69 (d, J=7.2 Hz, 1H), 6.60 (s, 2H), 4.68 (s, 2H), 4.07-3.97 (m, 2H), 3.57 (dd, J=9.3, 6.8 Hz, 1H), 2.46-2.38 (m, 2H), 2.00 (t, J=9.9 Hz, 2H), 1.33-1.24 (m, 6H), 1.15 (m, 1H), 0.57 (m, 1H), 0.45-0.34 (m, 2H), 0.25 (m, 1H). ESI MS [M+H]$^+$ for $C_{26}H_{28}F_3N_6O_4$, calcd 545.2, found 545.2.

Example 24: 2-Amino-5-{2-[(1S)-1-cyclopropyl-ethyl]-1-oxo-7-(trifluoromethoxy)-2,3-dihydro-1H-isoindol-5-yl}-N-[cis-4-hydroxy-4-methylcyclo-hexyl]pyrazolo[1,5-a]pyrimidine-3-carboxamide

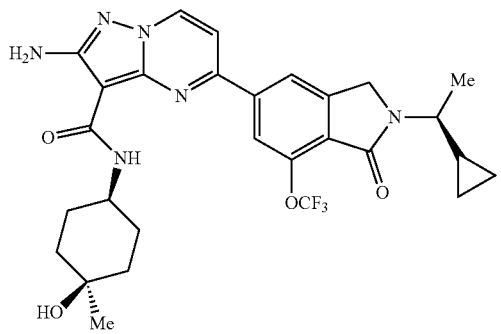 [SMILES: C[C@@H](C1CC1)N1Cc2cc(-c3ccn4nc(N)c(C(=O)N[C@H]5CC[C@@](C)(O)CC5)c4n3)cc(OC(F)(F)F)c2C1=O]

The title compound was prepared in a similar manner to example 20. $^1$H NMR (400 MHz, DMSO-$d_6$) δ 9.07 (d, J=7.1 Hz, 1H), 8.44 (d, J=1.2 Hz, 1H), 8.16 (t, J=1.4 Hz, 1H), 7.69 (d, J=7.2 Hz, 1H), 7.65 (d, J=7.4 Hz, 1H), 6.64 (s, 2H), 4.69 (s, 2H), 4.10 (s, 1H), 3.82-3.70 (m, 1H), 3.59 (dq, J=9.1, 6.7 Hz, 1H), 1.82-1.72 (m, 2H), 1.72-1.66 (m, 2H), 1.66-1.56 (m, 2H), 1.43 (td, J=12.8, 4.2 Hz, 2H), 1.32 (d, J=6.9 Hz, 3H), 1.23-1.16 (m, 1H), 1.15 (s, 3H), 0.64-0.55 (m, 1H), 0.49-0.35 (m, 2H), 0.31-0.23 (m, 1H). ESI MS [M+H]$^+$ for $C_{28}H_{32}F_3N_6O_4$, calcd 573.2, found 573.1.

Example 25: 2-Amino-5-{2-[(1S)-1-cyclopropyl-ethyl]-1-oxo-7-(trifluoromethoxy)-2,3-dihydro-1H-isoindol-5-yl}-N-[(2R)-1-hydroxy-3-methylbutan-2-yl]pyrazolo[1,5-a]pyrimidine-3-carboxamide

Example 26: 2-Amino-N-[(1R)-1-cyclopropyl-2-hydroxyethyl]-5-{2-[(1S)-1-cyclopropylethyl]-1-oxo-7-(trifluoromethoxy)-2,3-dihydro-1H-isoindol-5-yl}pyrazolo[1,5-a]pyrimidine-3-carboxamide

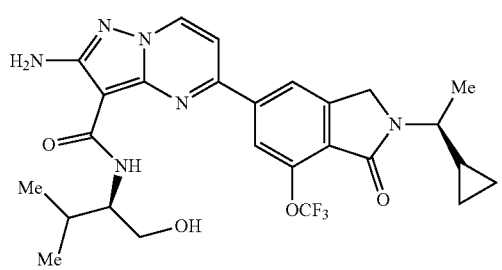 [SMILES: CC(C)[C@H](CO)NC(=O)c1c(N)nn2ccc(-c3cc4c(c(OC(F)(F)F)c3)C(=O)N([C@@H](C)C3CC3)C4)nc12]

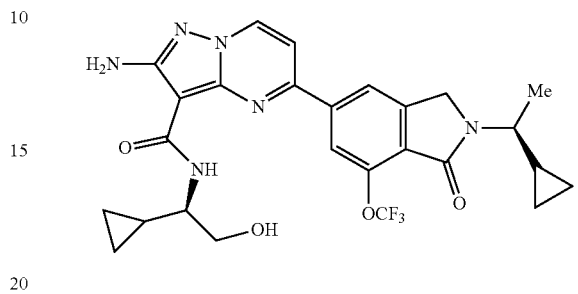

The title compound was prepared in a similar manner to example 20. $^1$H NMR (400 MHz, DMSO-d$_6$) δ 9.04 (d, J=7.1 Hz, 1H), 8.52 (d, J=1.3 Hz, 1H), 8.23-8.15 (m, 1H), 7.97 (d, J=9.3 Hz, 1H), 7.69 (d, J=7.1 Hz, 1H), 6.61 (s, 2H), 4.60 (s, 2H), 3.86 (dq, J=10.2, 4.9 Hz, 1H), 3.63 (d, J=6.6 Hz, 1H), 3.58-3.54 (m, 1H), 3.48 (dd, J=10.9, 5.0 Hz, 1H), 2.00 (h, J=6.8 Hz, 1H), 1.30 (d, J=6.8 Hz, 3H), 1.19-1.06 (m, 1H), 0.94 (dd, J=6.8, 0.9 Hz, 6H), 0.62-0.50 (m, 1H), 0.47-0.33 (m, 2H), 0.30-0.16 (m, 1H). ESI MS [M+H]$^+$ for C$_{26}$H$_{30}$F$_3$N$_6$O$_4$, calcd 547.2, found 547.2.

The title compound was prepared in a similar manner to example 20. $^1$H NMR (400 MHz, DMSO-d$_6$) δ 9.04 (d, J=7.1 Hz, 1H), 8.61 (d, J=1.3 Hz, 1H), 8.26-8.21 (m, 2H), 7.72 (d, J=7.2 Hz, 1H), 6.59 (s, 2H), 4.66 (s, 2H), 3.68 (dd, J=10.5, 3.5 Hz, 1H), 3.62-3.52 (m, 2H), 3.52-3.44 (m, 1H), 1.30 (d, J=6.8 Hz, 3H), 1.19-1.09 (m, 2H), 0.60-0.53 (m, 1H), 0.46-0.34 (m, 5H), 0.30-0.21 (m, 2H). ESI MS [M+H]$^+$ for C$_{26}$H$_{28}$F$_3$N$_6$O$_4$, calcd 545.2, found 545.2.

Example 27: 2-Amino-N-[(2R)-1-hydroxypropan-2-yl]-5-[1-oxo-7-(trifluoromethoxy)-2-[(2S)-1,1,1-trifluoropropan-2-yl]-2,3-dihydro-1H-isoindol-5-yl]pyrazolo[1,5-a]pyrimidine-3-carboxamide

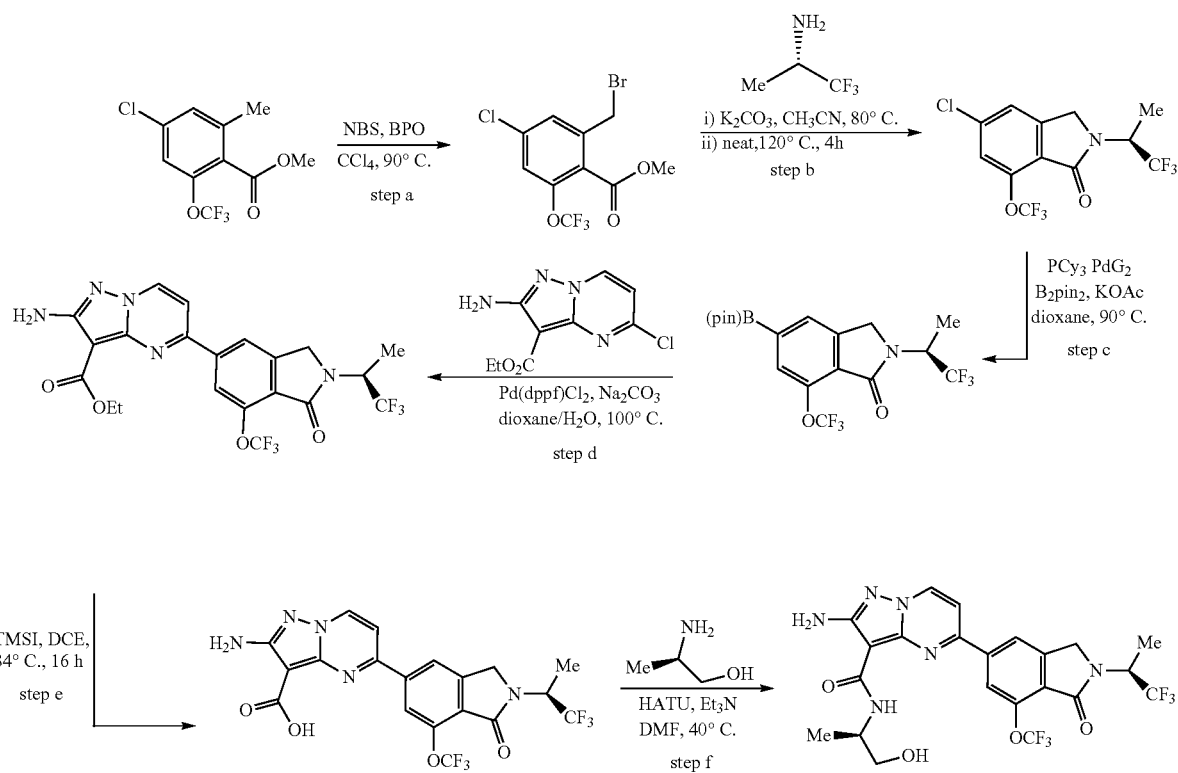

Steps a and b: Step a was performed in a similar manner to Example 1 Step e. The product of Step a (500 mg, 1.44 mmol, 1.0 equiv.) was dissolved in CH$_3$CN (5.8 mL) and (S)-trifluoro-2-propylamine (179 mg, 1.58 mmol, 1.1 equiv.), K$_2$CO$_3$ (597 mg, 4.32 mmol, 3.0 equiv.) were added sequentially. The reaction mixture was stirred at 80° C. for 16 h, then partitioned between H$_2$O and EtOAc. The organic layer was separated and washed with sat. aq. NaHCO$_3$, dried over Na$_2$SO$_4$ and concentrated. The residue was then heated at 120° C. neat for 4 h. Purification by column chromatography (gradient 12% EtOAc in hexanes) afforded the desired compound as a yellow solid (152 mg, 30%).

Steps c, d, e, and f. Performed in a similar manner to example 20 to provide the title compound. $^1$H NMR (400 MHz, DMSO-d$_6$) δ 9.05 (d, J=7.1 Hz, 1H), 8.61 (d, J=1.3 Hz, 1H), 8.28 (s, 1H), 8.10 (d, J=8.0 Hz, 1H), 7.72 (d, J=7.2 Hz, 1H), 6.61 (s, 2H), 5.04 (p, J=7.6 Hz, 1H), 4.76 (d, J=17.8 Hz, 1H), 4.55 (d, J=17.7 Hz, 1H), 4.10-4.01 (m, 1H), 3.54-3.50 (m, 2H), 1.51 (d, J=7.1 Hz, 3H), 1.20 (d, J=6.6 Hz, 3H). ESI MS [M+H]$^+$ for C$_{22}$H$_{21}$F$_6$N$_6$O$_4$, calcd 547.2, found 547.2.

Example 28: 2-Amino-5-{2-[(1S)-1-cyclopropyl-ethyl]-1-oxo-7-(trifluoromethoxy)-2,3-dihydro-1H-isoindol-5-yl}-N-[(3R)-5-oxopyrrolidin-3-yl]pyrazolo[1,5-a]pyrimidine-3-carboxamide

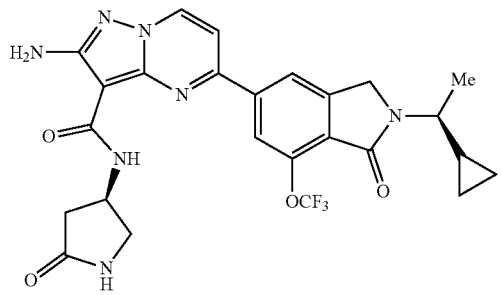 [SMILES: C[C@@H](C1CC1)N1Cc2cc(-c3ccn4nc(N)c(C(=O)N[C@H]5CNC(=O)C5)c4n3)cc(OC(F)(F)F)c2C1=O]

The title compound was prepared in a similar manner to example 20. $^1$H NMR (400 MHz, DMSO-d$_6$) δ 9.04 (d, J=7.1 Hz, 1H), 8.39 (m, 1H), 8.20 (m, 1H), 8.06 (d, J=7.4 Hz, 1H), 7.76 (s, 1H), 7.70 (d, J=7.2 Hz, 1H), 4.70 (d, J=2.0 Hz, 2H), 4.63 (m, 1H), 3.69-3.50 (m, 2H), 3.19 (dd, J=9.8, 4.4 Hz, 1H), 2.63 (dd, J=16.6, 7.9 Hz, 1H), 2.21 (dd, J=16.5, 5.3 Hz, 1H), 1.30 (d, J=6.8 Hz, 3H), 1.13 (m, 1H), 0.58 (m, 1H), 0.45-0.33 (m, 2H), 0.25 (m, 1H). ESI MS [M+H]$^+$ for C$_{25}$H$_{25}$F$_3$N$_7$O$_4$, calcd 544.2, found 544.2.

Example 29: 2-Amino-5-{2-[(1S)-1-cyclopropyl-ethyl]-1-oxo-7-(trifluoromethoxy)-2,3-dihydro-1H-isoindol-5-yl}-N-[(1S,3R)-3-hydroxycyclohexyl]pyrazolo[1,5-a]pyrimidine-3-carboxamide

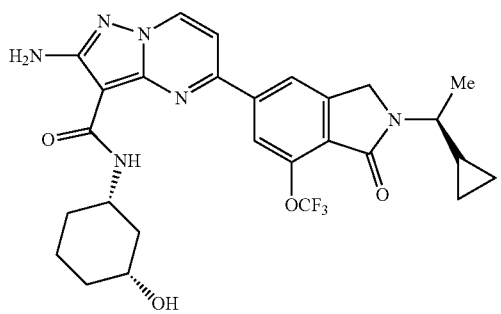 [SMILES: C[C@@H](C1CC1)N1Cc2cc(-c3ccn4nc(N)c(C(=O)N[C@H]5CCC[C@@H](O)C5)c4n3)cc(OC(F)(F)F)c2C1=O]

The title compound was prepared in a similar manner to example 20. $^1$H NMR (400 MHz, DMSO-d$_6$) δ 9.03 (d, J=7.1 Hz, 1H), 8.47 (d, J=1.3 Hz, 1H), 8.19 (t, J=1.5 Hz, 1H), 7.82 (d, J=8.1 Hz, 1H), 7.66 (d, J=7.2 Hz, 1H), 6.61 (s, 2H), 4.66 (s, 2H), 3.98-3.84 (m, 1H), 3.62-3.52 (m, 2H), 2.14-2.06 (m, 1H), 1.87-1.70 (m, 3H), 1.35-1.27 (m, 1H), 1.29 (d, J=6.8 Hz, 3H), 1.26-1.09 (m, 4H), 0.60-0.51 (m, 1H), 0.45-0.33 (m, 2H), 0.28-0.21 (m, 1H). ESI MS [M+H]$^+$ for C$_{27}$H$_{30}$F$_3$N$_6$O$_4$, calcd 559.2, found 559.2.

Example 30: 2-Amino-5-(2-((S)-1-cyclopropyl-ethyl)-1-oxo-7-(trifluoromethoxy)isoindolin-5-yl)-N-(trans-4-(1-hydroxycyclopropyl)cyclohexyl)pyrazolo[1,5-a]pyrimidine-3-carboxamide

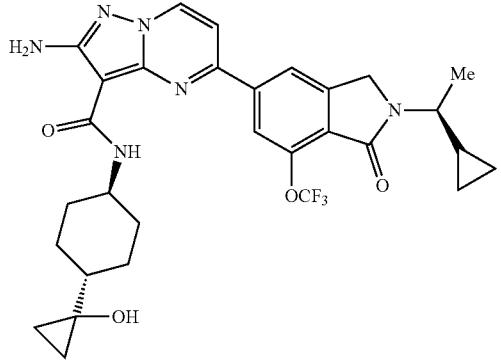 [SMILES: C[C@@H](C1CC1)N1Cc2cc(-c3ccn4nc(N)c(C(=O)N[C@H]5CC[C@H](C6(O)CC6)CC5)c4n3)cc(OC(F)(F)F)c2C1=O]

The title compound was prepared in a similar manner to example 20. $^1$H NMR (400 MHz, CDCl$_3$) δ 8.51 (d, J=7.1 Hz, 1H), 8.04 (s, 1H), 7.92 (s, 1H), 7.62 (d, J=7.9 Hz, 1H), 7.19 (d, J=7.1 Hz, 1H), 5.77 (br. s, 2H), 4.64 (d, J=17.5 Hz, 1H), 4.53 (d, J=17.5 Hz, 1H), 4.07-3.87 (m, 1H), 3.84-3.64 (m, 1H), 2.32-2.17 (m, 2H), 1.96-1.82 (m, 2H), 1.61-1.43 (m, 2H), 1.38 (d, J=6.8 Hz, 3H), 1.37-1.22 (m, 2H), 1.12-0.97 (m, 2H), 0.78-0.71 (m, 2H), 0.70-0.61 (m, 1H), 0.52-0.38 (m, 5H). $^{19}$F NMR (376 MHz, CDCl$_3$) δ −57.34. ESI MS [M+H]$^+$ for C$_{30}$H$_{34}$F$_3$N$_6$O$_4$, calcd 599.3, found 599.1.

Example 31: 2-Amino-5-{2-[(1S)-1-cyclopropyl-ethyl]-1-oxo-7-(trifluoromethoxy)-2,3-dihydro-1H-isoindol-5-yl}-N-[trans-4-aminocyclohexyl]pyrazolo[1,5-a]pyrimidine-3-carboxamide

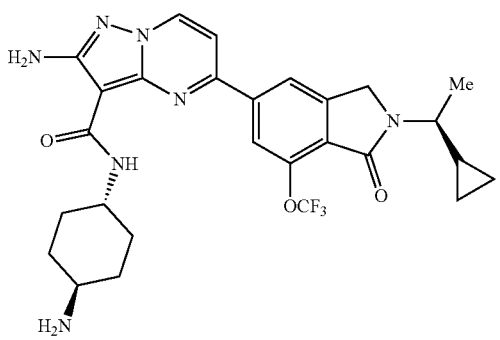 [SMILES: C[C@@H](C1CC1)N1Cc2cc(-c3ccn4nc(N)c(C(=O)N[C@H]5CC[C@H](N)CC5)c4n3)cc(OC(F)(F)F)c2C1=O]

The title compound was prepared in a similar manner to example 20. $^1$H NMR (400 MHz, DMSO-$d_6$) δ 9.06 (d, J=7.1 Hz, 1H), 8.41 (s, 1H), 8.15 (m, 1H), 7.83 (d, J=4.7 Hz, 2H), 7.67 (d, J=7.2 Hz, 1H), 7.62 (d, J=7.5 Hz, 1H), 6.61 (s, 2H), 4.65 (s, 2H), 3.73 (m, 1H), 3.55 (m, 1H), 2.99 (m, 1H), 2.10 (d, J=11.4 Hz, 2H), 1.98 (d, J=11.7 Hz, 2H), 1.52-1.32 (m, 4H), 1.30 (d, J=6.8 Hz, 3H), 1.14 (m, 1H), 0.57 (m, 1H), 0.44-0.35 (m, 2H), 0.24 (m, 1H). ESI MS [M+H]$^+$ for $C_{27}H_{31}F_3N_7O_3$, calcd 558.2, found 558.2.

Example 32: 2-Amino-5-{2-[(1S)-1-cyclopropyl-ethyl]-1-oxo-7-(trifluoromethoxy)-2,3-dihydro-1H-isoindol-5-yl}-N-[(3S)-2-oxopyrrolidin-3-yl]pyrazolo[1,5-a]pyrimidine-3-carboxamide

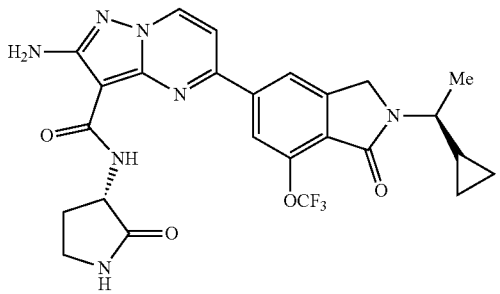 [SMILES: C[C@@H](C1CC1)N1Cc2cc(-c3ccn4nc(N)c(C(=O)N[C@H]5CCNC5=O)c4n3)cc(OC(F)(F)F)c2C1=O]

The title compound was prepared in a similar manner to example 20. $^1$H NMR (400 MHz, DMSO-$d_6$) δ 9.05 (d, J=7.1 Hz, 1H), 8.63 (s, 1H), 8.29 (s, 1H), 8.26 (d, J=5.2 Hz, 1H), 8.05 (m, 1H), 7.73 (d, J=7.2 Hz, 1H), 6.60 (s, 2H), 4.65 (s, 2H), 4.37 (ddd, J=10.9, 8.1, 5.2 Hz, 1H), 3.57 (m, 1H), 3.29-3.22 (m, 2H), 2.63 (m, 1H), 1.90 (m, 1H), 1.29 (d, J=6.8 Hz, 3H), 1.13 (m, 1H), 0.57 (m, 1H), 0.45-0.34 (m, 2H), 0.24 (m, 1H). ESI MS [M+H]$^+$ for $C_{25}H_{25}F_3N_7O_4$, calcd 544.2, found 544.2.

Example 33: 2-Amino-N-[(1R,3S)-3-aminocyclo-hexyl]-5-{2-[(1S)-1-cyclopropylethyl]-1-oxo-7-(trifluoromethoxy)-2,3-dihydro-1H-isoindol-5-yl}pyrazolo[1,5-a]pyrimidine-3-carboxamide

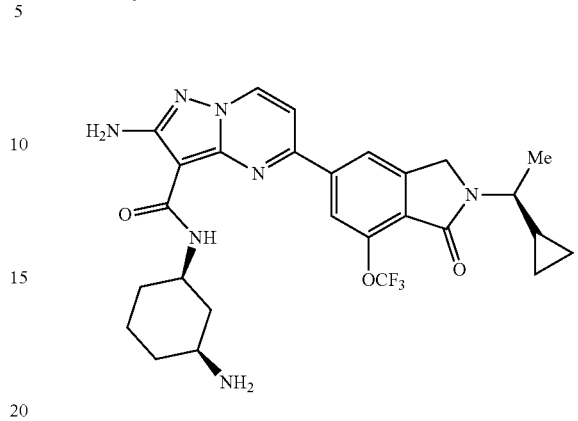

The title compound was prepared in a similar manner to example 20. $^1$H NMR (400 MHz, DMSO-$d_6$) δ 9.05 (d, J=7.1 Hz, 1H), 8.39 (m, 1H), 8.20-8.14 (m, 3H), 7.68 (dd, J=7.4, 5.3 Hz, 2H), 4.73 (s, 2H), 3.85 (m, 1H), 3.55 (m, 1H), 3.14 (s, 1H), 2.39 (d, J=11.6 Hz, 1H), 2.02-1.91 (m, 2H), 1.80 (d, J=12.9 Hz, 1H), 1.51-1.10 (m, 8H), 0.56 (m, 1H), 0.44-0.34 (m, 2H), 0.23 (m, 1H). ESI MS [M+H]$^+$ for $C_{27}H_{31}F_3N_7O_3$, calcd 558.2, found 558.2.

Example 34: 2-Amino-5-{2-[(1S)-1-cyclopropyl-ethyl]-1-oxo-7-(trifluoromethoxy)-2,3-dihydro-1H-isoindol-5-yl}-N-[(1R,3S)-3-(dimethylamino)cyclo-hexyl]pyrazolo[1,5-a]pyrimidine-3-carboxamide

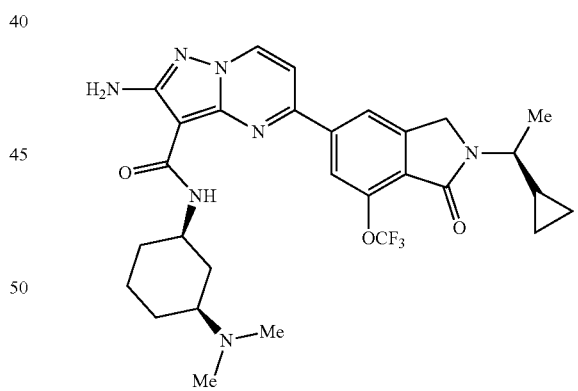

The title compound was prepared in a similar manner to example 20. $^1$H NMR (400 MHz, DMSO-$d_6$) δ 10.74 (s, 1H), 9.06 (d, J=7.1 Hz, 1H), 8.43 (s, 1H), 8.18 (s, 1H), 7.76-7.67 (m, 2H), 4.71 (s, 1H), 3.90 (m, 1H), 3.55 (m, 1H), 3.33 (t, J=11.5 Hz, 1H), 2.69 (d, J=5.0 Hz, 6H), 2.06 (m, 1H), 1.99 (d, J=12.4 Hz, 1H), 1.87 (m, 1H), 1.55-1.32 (m, 4H), 1.29 (d, J=6.8 Hz, 3H), 1.27-1.10 (m, 2H), 0.56 (m, 1H), 0.45-0.34 (m, 2H), 0.24 (m, 1H). ESI MS [M+H]$^+$ for $C_{29}H_{35}F_3N_7O_3$, calcd 586.3, found 586.2.

Example 35: 2-Amino-5-{2-[(1S)-1-cyclopropyl-ethyl]-1-oxo-7-(trifluoromethoxy)-2,3-dihydro-1H-isoindol-5-yl}-N-[(1R,2R)-2-hydroxycyclopentyl]pyrazolo[1,5-a]pyrimidine-3-carboxamide

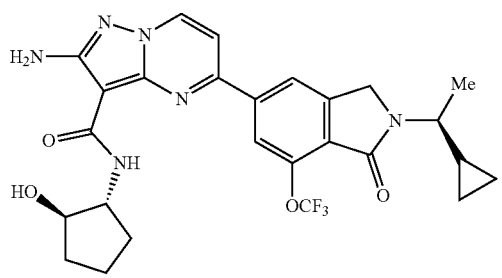

The title compound was prepared in a similar manner to example 20. ¹H NMR (400 MHz, DMSO-d$_6$) δ 9.08 (d, J=7.1 Hz, 1H), 8.43 (d, J=1.3 Hz, 1H), 8.17-8.12 (m, 1H), 7.74-7.68 (m, 2H), 6.64 (s, 2H), 4.69 (s, 2H), 4.11-4.02 (m, 1H), 4.00-3.95 (m, 1H), 3.63-3.53 (m, 1H), 2.20-2.10 (m, 1H), 1.94-1.83 (m, 1H), 1.84-1.65 (m, 2H), 1.62-1.45 (m, 2H), 1.32 (d, J=6.8 Hz, 3H), 1.23-1.13 (m, 1H), 0.63-0.55 (m, 1H), 0.47-0.36 (m, 2H), 0.31-0.23 (m, 1H). ESI MS [M+H]⁺ for C$_{26}$H$_{28}$F$_3$N$_6$O$_4$, calcd 545.2, found 545.2.

Example 36: 2-Amino-5-{2-[(1S)-1-cyclopropyl-ethyl]-1-oxo-7-(trifluoromethoxy)-2,3-dihydro-1H-isoindol-5-yl}-N-[(1S,3S)-3-hydroxycyclopentyl]pyrazolo[1,5-a]pyrimidine-3-carboxamide

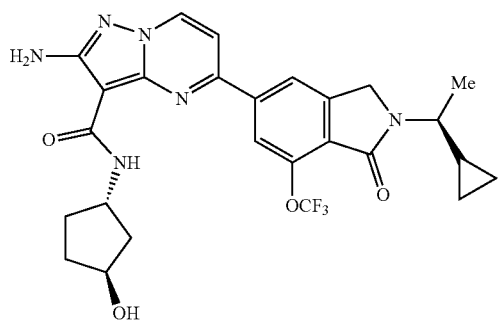 [SMILES: C[C@@H](C1CC1)N1Cc2cc(-c3ccn4nc(N)c(C(=O)N[C@H]5CC[C@H](O)C5)c4n3)cc(OC(F)(F)F)c2C1=O]

The title compound was prepared in a similar manner to example 20. ¹H NMR (400 MHz, DMSO-d$_6$) δ 9.06 (d, J=7.1 Hz, 1H), 8.43 (d, J=1.3 Hz, 1H), 8.18-8.14 (m, 1H), 7.72 (d, J=7.5 Hz, 1H), 7.68 (d, J=7.2 Hz, 1H), 6.63 (s, 2H), 4.69 (s, 2H), 4.48 (h, J=7.4 Hz, 1H), 4.29-4.24 (m, 1H), 3.62-3.55 (m, 1H), 2.24-2.11 (m, 1H), 2.02-1.90 (m, 2H), 1.66 (ddd, J=13.4, 7.6, 5.8 Hz, 1H), 1.60-1.41 (m, 2H), 1.32 (d, J=6.8 Hz, 3H), 1.24-1.09 (m, 1H), 0.63-0.54 (m, 1H), 0.47-0.35 (m, 2H), 0.30-0.23 (m, 1H). ESI MS [M+H]⁺ for C$_{26}$H$_{28}$F$_3$N$_6$O$_4$, calcd 545.2, found 545.2.

Example 37: 2-Amino-5-{2-[(1S)-1-cyclopropyl-ethyl]-1-oxo-7-(trifluoromethoxy)-2,3-dihydro-1H-isoindol-5-yl}-N-[(1R,3R)-3-hydroxycyclopentyl]pyrazolo[1,5-a]pyrimidine-3-carboxamide

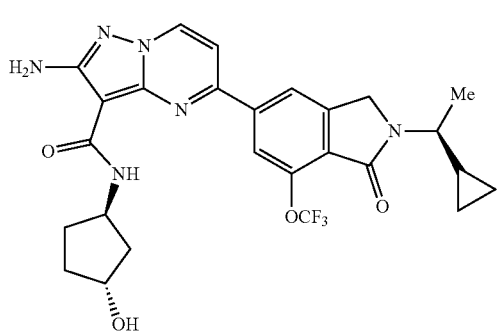 [SMILES: C[C@@H](C1CC1)N1Cc2cc(-c3ccn4nc(N)c(C(=O)N[C@@H]5CC[C@@H](O)C5)c4n3)cc(OC(F)(F)F)c2C1=O]

The title compound was prepared in a similar manner to example 20. ¹H NMR (400 MHz, DMSO-d$_6$) δ 9.06 (d, J=7.1 Hz, 1H), 8.43 (d, J=1.2 Hz, 1H), 8.16 (t, J=1.4 Hz, 1H), 7.72 (d, J=7.5 Hz, 1H), 7.68 (d, J=7.2 Hz, 1H), 6.62 (s, 2H), 4.69 (s, 2H), 4.48 (h, J=7.4 Hz, 1H), 4.28-4.23 (m, 1H), 3.63-3.53 (m, 1H), 2.27-2.13 (m, 1H), 2.04-1.90 (m, 2H), 1.66 (ddd, J=13.3, 7.7, 5.9 Hz, 1H), 1.61-1.41 (m, 2H), 1.32 (d, J=6.8 Hz, 3H), 1.24-1.13 (m, 1H), 0.63-0.55 (m, 1H), 0.48-0.36 (m, 2H), 0.30-0.23 (m, 1H). ESI MS [M+H]⁺ for C$_{26}$H$_{28}$F$_3$N$_6$O$_4$, calcd 545.2, found 545.2.

Example 38: 2-Amino-5-{2-[(1S)-1-cyclopropyl-ethyl]-1-oxo-7-(trifluoromethoxy)-2,3-dihydro-1H-isoindol-5-yl}-N-[(3R,4S)-4-hydroxyoxolan-3-yl]pyrazolo[1,5-a]pyrimidine-3-carboxamide

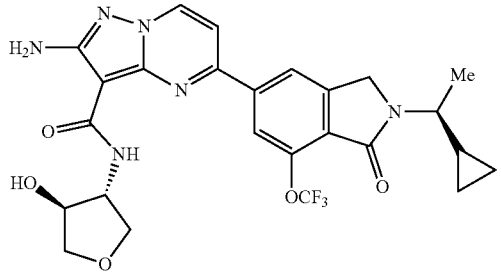 [SMILES: C[C@@H](C1CC1)N1Cc2cc(-c3ccn4nc(N)c(C(=O)N[C@@H]5COC[C@H]5O)c4n3)cc(OC(F)(F)F)c2C1=O]

The title compound was prepared in a similar manner to example 20. ¹H NMR (400 MHz, DMSO-d$_6$) δ 9.08 (d, J=7.1 Hz, 1H), 8.46 (d, J=1.3 Hz, 1H), 8.20-8.16 (m, 1H), 7.94 (d, J=7.6 Hz, 1H), 7.72 (d, J=7.2 Hz, 1H), 6.63 (s, 2H), 4.68 (s, 2H), 4.33-4.27 (m, 1H), 4.23-4.19 (m, 1H), 4.01 (td, J=9.2, 4.6 Hz, 2H), 3.71 (dd, J=9.0, 1.9 Hz, 1H), 3.63-3.56 (m, 2H), 1.32 (d, J=6.8 Hz, 3H), 1.23-1.13 (m, 1H), 0.63-0.55 (m, 1H), 0.47-0.34 (m, 2H), 0.30-0.22 (m, 1H). ESI MS [M+H]⁺ for C$_{25}$H$_{26}$F$_3$N$_6$O$_5$, calcd 547.2, found 547.2.

Example 39: 5-{2-[(S)-1-Cyclopropylethyl]-7-trifluoromethoxy-5-isoindolinoyl}-2-amino-1,4,7a-triaza-3-indenecarboxamide

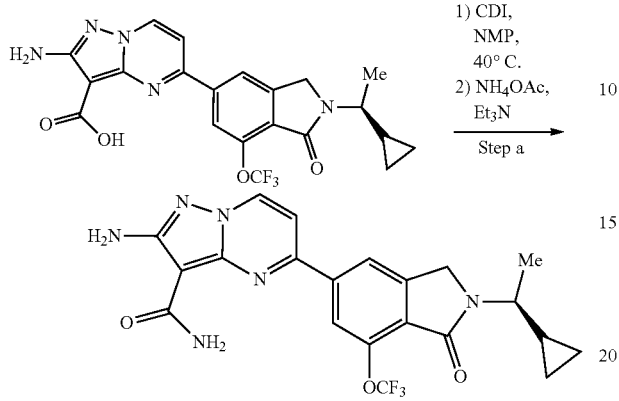

Step a: A solution of the carboxylic acid (55 mg, 0.12 mmol) and CDI (29.2 mg, 1.8 mmol, 1.5 equiv.) in NMP (1.2 mL) was heated to 40° C. for 2 h. Upon complete consumption of starting material, NH$_4$OAc (74 mg, 0.96 mmol, 8 equiv.) and Et$_3$N (88 µL, 0.72 mmol, 6 equiv.) were added and the reaction was heated to 80° C. for overnight. The reaction mixture was cooled to rt, and the yellow product was precipitated from solution with the addition of 30 mL of H$_2$O. The solid was further purified by flash chromatography (SiO$_2$, MeOH/CH$_2$Cl$_2$ gradient 0% to 10%). Yield: 41.3 mg (75%). $^1$H NMR (400 MHz, DMSO-d$_6$) δ 9.02 (d, J=7.1 Hz, 1H), 8.51 (s, 1H), 8.19 (s, 1H), 7.68 (d, J=7.2 Hz, 1H), 7.41 (s, 1H), 7.31 (s, 1H), 6.63 (s, 2H), 4.68 (s, 2H), 3.64-3.48 (m, 1H), 1.28 (d, J=6.8 Hz, 3H), 1.21-1.07 (m, 1H), 0.60-0.54 (m, 1H), 0.45-0.32 (m, 2H), 0.29-0.19 (m, 1H). ESI MS [M+H]$^+$ for C$_{21}$H$_{19}$F$_3$N$_6$O$_3$, calcd 461.1, found 461.1.

Example 40: (S)-2-Amino-5-(2-(1-cyclopropylethyl)-1-oxo-7-(trifluoromethoxy)isoindolin-5-yl)-N-(pyridin-4-yl)pyrazolo[1,5-a]pyrimidine-3-carboxamide

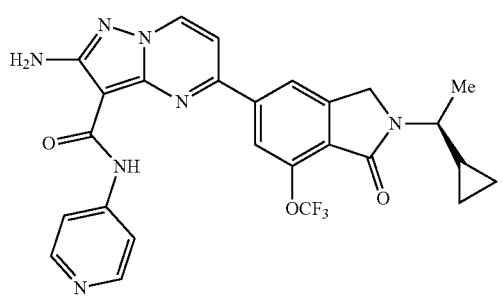 [SMILES: C[C@@H](C1CC1)N1Cc2cc(-c3ccn4nc(N)c(C(=O)Nc5ccncc5)c4n3)cc(OC(F)(F)F)c2C1=O]

The title compound was prepared in a similar manner to examples 20 and 99 (vide infra). $^1$H NMR (400 MHz, CD$_3$OD) δ 8.84 (d, J=7.1 Hz, 1H), 8.61 (d, J=6.6 Hz, 2H), 8.36 (s, 1H), 8.25 (s, 1H), 8.19 (d, J=6.6 Hz, 2H), 7.66 (d, J=7.1 Hz, 1H), 4.81 (d, J=18.5 Hz, 1H), 4.75 (d, J=18.5 Hz, 1H), 3.76-3.60 (m, 1H), 1.44 (d, J=6.9 Hz, 3H), 1.25-1.14 (m, 1H), 0.79-0.61 (m, 1H), 0.59-0.49 (m, 1H), 0.48-0.41 (m, 1H), 0.42-0.33 (m, 1H). $^{19}$F NMR (376 MHz, CD$_3$OD) δ −58.93. ESI MS [M+H]$^+$ for C$_{26}$H$_{23}$F$_3$N$_7$O$_3$, calcd 538.2, found 538.1.

Example 41: (S)-2-Amino-5-(2-(1-cyclopropylethyl)-1-oxo-7-(trifluoromethoxy)isoindolin-5-yl)-N-(pyridin-3-yl)pyrazolo[1,5-a]pyrimidine-3-carboxamide

The title compound was prepared in a similar manner to example 40. $^1$H NMR (400 MHz, DMSO-d$_6$) δ 9.86 (s, 1H), 9.14 (d, J=7.1 Hz, 1H), 8.86 (dd, J=2.7, 0.7 Hz, 1H), 8.53 (s, 1H), 8.37 (s, 1H), 8.30 (dd, J=4.7, 1.5 Hz, 1H), 8.21 (ddd, J=8.4, 2.6, 1.5 Hz, 1H), 7.78 (d, J=7.2 Hz, 1H), 7.40 (ddd, J=8.3, 4.7, 0.7 Hz, 1H), 6.77 (br. s, 2H), 4.72 (s, 2H), 3.65-3.51 (m, 1H), 1.33 (d, J=6.8 Hz, 3H), 1.27-1.10 (m, 1H), 0.66-0.53 (m, 1H), 0.48-0.35 (m, 2H), 0.32-0.22 (m, 1H). $^{19}$F NMR (376 MHz, DMSO-d$_6$) δ −56.75. ESI MS [M+H]$^+$ for C$_{26}$H$_{23}$F$_3$N$_7$O$_3$, calcd 538.2, found 538.2.

Example 42: 2-Amino-5-{2-[(1S)-1-cyclopropylethyl]-1-oxo-7-(trifluoromethoxy)-2,3-dihydro-1H-isoindol-5-yl}-N-(5-fluoropyridin-3-yl)pyrazolo[1,5-a]pyrimidine-3-carboxamide

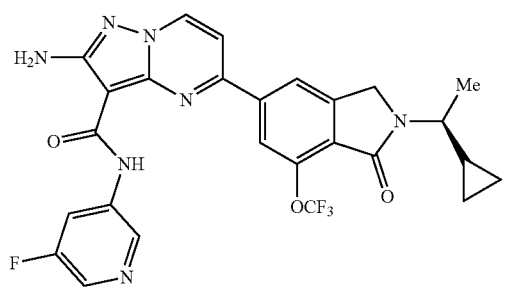 [SMILES: C[C@@H](C1CC1)N1Cc2cc(-c3ccn4nc(N)c(C(=O)Nc5cncc(F)c5)c4n3)cc(OC(F)(F)F)c2C1=O]

The title compound was synthesized in similar fashion to example 40. $^1$H NMR (400 MHz, DMSO-d$_6$) δ 9.99 (s, 1H), 9.12 (d, J=7.1 Hz, 1H), 8.66 (t, J=1.8 Hz, 1H), 8.50 (d, J=1.3 Hz, 1H), 8.37 (s, 1H), 8.28 (dd, J=2.6, 0.5 Hz, 1H), 8.18 (ddd, J=11.4, 2.7, 2.1 Hz, 1H), 7.77 (d, J=7.2 Hz, 1H), 6.75 (s, 2H), 4.69 (s, 2H), 3.71-3.47 (m, 1H), 1.30 (d, J=6.9 Hz, 3H), 1.22-1.09 (m, 1H), 0.62-0.53 (m, 1H), 0.44-0.36 (m, 2H), 0.29-0.22 (m, 1H). ESI MS [M+H]$^+$ for C$_{26}$H$_{21}$F$_4$N$_7$O$_3$, calcd 556.2, found 556.1.

Example 43: 2-Amino-5-{2-[(1S)-1-cyclopropyl-ethyl]-1-oxo-7-(trifluoromethoxy)-2,3-dihydro-1H-isoindol-5-yl}-N-(5-methoxypyridin-3-yl)pyrazolo[1,5-a]pyrimidine-3-carboxamide

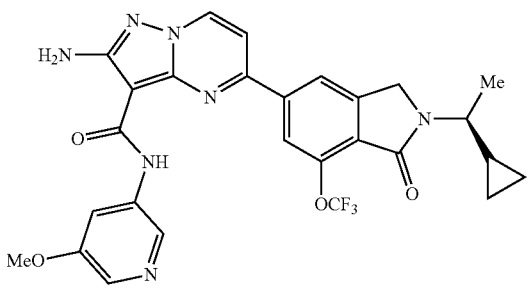 [SMILES: COc1cncc(NC(=O)c2c(N)nn3ccc(-c4cc5c(c(OC(F)(F)F)c4)C(=O)N([C@@H](C)C4CC4)C5)nc23)c1]

The title compound was synthesized in similar fashion to example 40. ¹H NMR (400 MHz, DMSO-d₆) δ 9.85 (s, 1H), 9.11 (d, J=7.1 Hz, 1H), 8.51 (d, J=1.3 Hz, 1H), 8.42 (d, J=2.0 Hz, 1H), 8.33 (t, J=1.4 Hz, 1H), 8.01 (d, J=2.6 Hz, 1H), 7.90 (dd, J=2.6, 2.1 Hz, 1H), 7.76 (d, J=7.2 Hz, 1H), 6.75 (s, 2H), 4.68 (s, 2H), 3.85 (s, 3H), 3.64-3.52 (m, 1H), 1.30 (d, J=6.8 Hz, 3H), 1.22-1.08 (m, 1H), 0.62-0.52 (m, 1H), 0.46-0.34 (m, 2H), 0.30-0.21 (m, 1H). ESI MS [M−H]⁻ for $C_{27}H_{24}F_3N_7O_4$, calcd 568.2, found 568.1.

Example 44: 2-[(S)-1-Cyclopropylethyl]-5-{2-amino-3-[(2-methyl-3-pyridylamino)carbonyl]-1,4,7a-triaza-5-indenyl}-7-trifluoromethoxy-1-isoindolinone

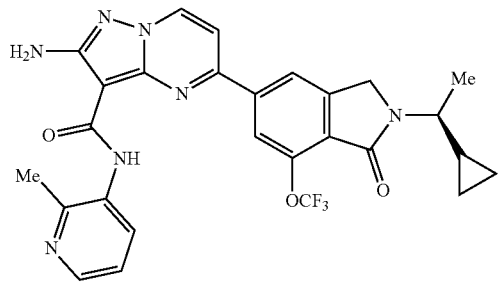 [SMILES: Cc1ncccc1NC(=O)c1c(N)nn2ccc(-c3cc4c(c(OC(F)(F)F)c3)C(=O)N([C@@H](C)C3CC3)C4)nc12]

The title compound was prepared in a similar manner to example 40. ¹H NMR (400 MHz, DMSO-d₆) δ 9.68 (s, 1H), 9.16 (d, J=7.1 Hz, 1H), 8.89 (d, J=8.3 Hz, 1H), 8.49 (d, J=1.3 Hz, 1H), 8.39 (dd, J=1.4, 5.3 Hz, 1H), 8.21 (t, J=1.3 Hz, 1H), 7.72 (d, J=7.1 Hz, 1H), 7.68-7.60 (m, 1H), 6.81 (br., 2H), 4.66 (s, 2H), 3.64-3.51 (m, 1H), 2.69 (s, 3H), 1.30 (d, J=6.8 Hz, 3H), 1.14 (ddt, J=4.5, 8.2, 13.0 Hz, 1H), 0.64-0.52 (m, 1H), 0.47-0.33 (m, 2H), 0.30-0.18 (m, 1H). ESI MS [M+H]⁺ for $C_{27}H_{24}F_3N_7O_3$, calcd 552.2, found 552.2.

Example 45: 2-[(S)-1-Cyclopropylethyl]-5-{2-amino-3-[(6-methyl-3-pyridylamino)carbonyl]-1,4,7a-triaza-5-indenyl}-7-trifluoromethoxy-1-isoindolinone

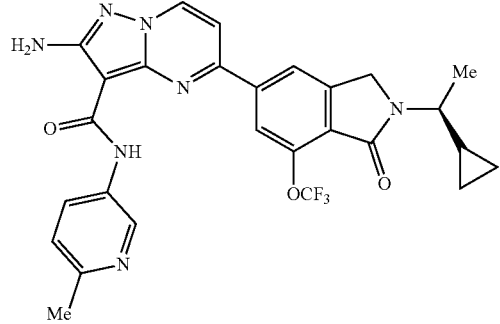 [SMILES: Cc1ccc(NC(=O)c2c(N)nn3ccc(-c4cc5c(c(OC(F)(F)F)c4)C(=O)N([C@@H](C)C4CC4)C5)nc23)cn1]

The title compound was prepared in a similar manner to example 40. ¹H NMR (400 MHz, DMSO-d₆) δ 9.99 (s, 1H), 9.14 (d, J=7.1 Hz, 1H), 9.02 (s, 1H), 8.53 (d, J=1.3 Hz, 1H), 8.39 (s, 1H), 8.30 (d, J=8.8 Hz, 1H), 7.79 (d, J=7.1 Hz, 1H), 7.62 (d, J=8.3 Hz, 1H), 6.77 (br, 2H), 4.70 (s, 2H), 3.32-3.23 (m, 1H), 2.57 (s, 3H), 1.31 (d, J=6.8 Hz, 3H), 1.22-1.10 (m, 1H), 0.57 (dq, J=3.4, 3.8, 8.6 Hz, 1H), 0.40 (ddq, J=5.2, 9.3, 14.3 Hz, 2H), 0.30-0.20 (m, 1H). ESI MS [M+H]⁺ for $C_{27}H_{24}F_3N_7O_3$, calcd 552.2, found 552.2.

Example 46: 2-[(S)-1-Cyclopropylethyl]-5-{2-amino-3-[(6-amino-3-pyridylamino)carbonyl]-1,4,7a-triaza-5-indenyl}-7-trifluoromethoxy-1-isoindolinone

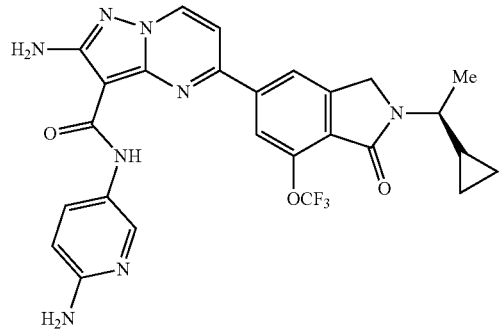 [SMILES: C[C@@H](C1CC1)N1Cc2cc(-c3ccn4nc(N)c(C(=O)Nc5ccc(N)nc5)c4n3)cc(OC(F)(F)F)c2C1=O]

The title compound was prepared in a similar manner to example 40. ¹H NMR (400 MHz, DMSO-d₆) δ 9.68 (s, 1H), 9.13 (d, J=7.1 Hz, 1H), 8.51 (dd, J=1.8, 10.7 Hz, 2H), 8.36 (s, 1H), 7.99 (dd, J=2.5, 9.4 Hz, 1H), 7.77 (d, J=7.2 Hz, 1H), 6.96 (d, J=9.5 Hz, 1H), 6.71 (br., 2H), 4.69 (s, 2H), 3.64-3.51 (m, 1H), 1.30 (d, J=6.8 Hz, 3H), 1.14 (ddt, J=4.4, 8.5, 13.0 Hz, 1H), 0.62-0.52 (m, 1H), 0.47-0.33 (m, 2H), 0.30-0.20 (m, 1H). ESI MS [M+H]⁺ for $C_{26}H_{23}F_3N_8O_3$, calcd 553.2, found 553.2.

Example 47: (S)-2-Amino-5-(2-(1-cyclopropylethyl)-1-oxo-7-(trifluoromethoxy)isoindolin-5-yl)-N-(4-methylpyridin-3-yl)pyrazolo[1,5-a]pyrimidine-3-carboxamide

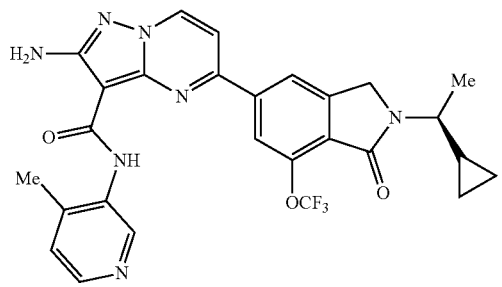 [SMILES: Cc1ccncc1NC(=O)c1c(N)nn2ccc(-c3cc4c(c(OC(F)(F)F)c3)C(=O)N([C@@H](C)C3CC3)C4)nc12]

The title compound was prepared in a similar manner to example 40. $^1$H NMR (400 MHz, CDCl$_3$) δ 9.35 (s, 1H), 9.26 (s, 1H), 8.59 (d, J=7.0 Hz, 1H), 8.30 (d, J=4.9 Hz, 1H), 8.00 (s, 1H), 7.88 (s, 1H), 7.23 (d, J=7.0 Hz, 1H), 7.17 (d, J=4.9 Hz, 1H), 5.86 (br. s, 2H), 4.62 (d, J=17.6 Hz, 1H), 4.51 (d, J=17.7 Hz, 1H), 3.85-3.65 (m, 1H), 2.38 (s, 3H), 1.37 (d, J=6.8 Hz, 3H), 1.08-0.93 (m, 1H), 0.76-0.57 (m, 1H), 0.52-0.30 (m, 3H). $^{19}$F NMR (376 MHz, CDCl$_3$) δ −57.51. ESI MS [M+H]$^+$ for C$_{27}$H$_{28}$F$_3$N$_7$O$_3$, calcd 552.2, found 552.2.

Example 48: (S)-2-Amino-5-(2-(1-cyclopropylethyl)-1-oxo-7-(trifluoromethoxy)isoindolin-5-yl)-N-(4-methoxypyridin-3-yl)pyrazolo[1,5-a]pyrimidine-3-carboxamide

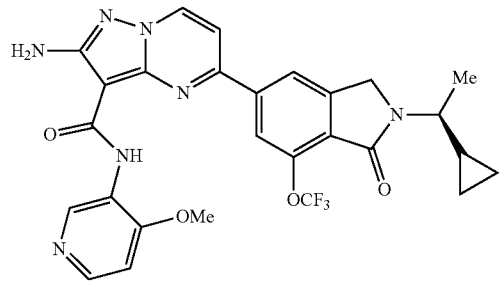 [SMILES: COc1ccncc1NC(=O)c1c(N)nn2ccc(-c3cc4c(c(OC(F)(F)F)c3)C(=O)N([C@@H](C)C3CC3)C4)nc12]

The title compound was prepared in a similar manner to example 40. $^1$H NMR (400 MHz, CDCl$_3$) δ 9.85 (s, 1H), 9.65 (s, 1H), 8.55 (d, J=7.1 Hz, 1H), 8.29 (d, J=5.5 Hz, 1H), 8.15 (s, 1H), 8.06 (s, 1H), 7.26 (d, J=7.1 Hz, 1H), 6.88 (d, J=5.5 Hz, 1H), 5.86 (s, 2H), 4.65 (d, J=17.5 Hz, 1H), 4.54 (d, J=17.5 Hz, 1H), 3.90 (s, 3H), 3.85-3.65 (m, 1H), 1.38 (d, J=6.8 Hz, 3H), 1.09-0.97 (m, 1H), 0.72-0.62 (m, 1H), 0.55-0.36 (m, 3H). $^{19}$F NMR (376 MHz, CDCl$_3$) δ −57.66. ESI MS [M+H]$^+$ for C$_{27}$H$_{28}$F$_3$N$_7$O$_4$, calcd 568.2, found 568.2.

Example 49: 2-Amino-5-{2-[(1S)-1-cyclopropylethyl]-1-oxo-7-(trifluoromethyl)-2,3-dihydro-1H-isoindol-5-yl}-N-[(3S)-2-oxopyrrolidin-3-yl]pyrazolo[1,5-a]pyrimidine-3-carboxamide

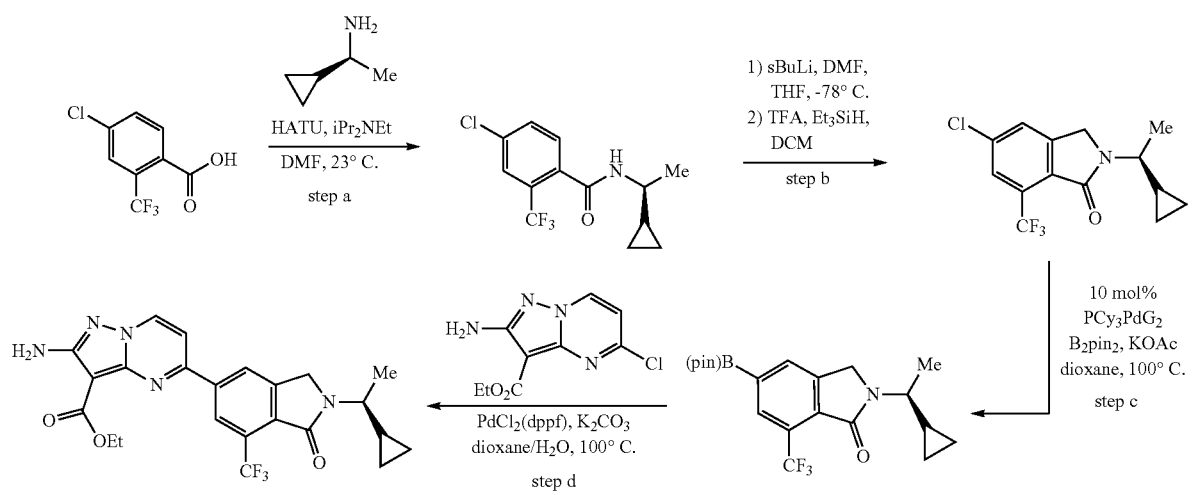

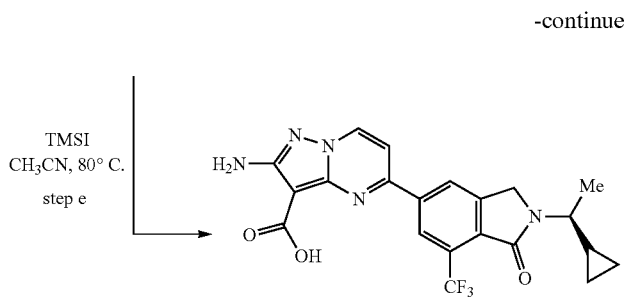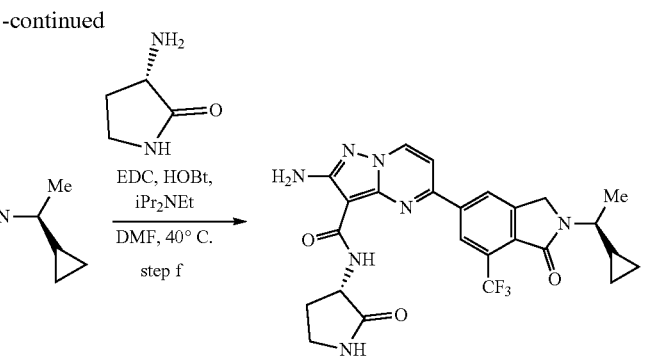

Step a: A mixture of 4-chloro-2-(trifluoromethyl)benzoic acid (20.0 g, 89 mmol), (S)-1-cyclopropylethan-1-amine (9.32 g, 107 mmol, 1.2 equiv.), HATU (40.7 g, 107 mmol, 1.2 equiv.) and DIPEA (48 mL, 267 mmol, 3 equiv.) in anhydrous DMF (297 mL) was stirred at 23° C. for 2 h. The reaction mixture was quenched with saturated NH$_4$Cl, extracted with EtOAc, evaporated and the crude product was purified by column chromatography (0 to 40% gradient of EtOAc in Hexanes) to give the product as a white solid in 98% yield (25.5 g).

Step b: The product from Step a (8.20 g, 28 mmol) was dissolved in THF (140 mL) and cooled to −78° C., then sec-Butyllithium (1.4 M in cyclohexane, 50 mL, 70 mmol, 2.5 equiv.) was added dropwise. After 20 min at −78° C., DMF (10.8 mL, 140 mmol, 5.0 equiv.) was added dropwise. The reaction mixture was stirred at −78° C. for 1 h, then was carefully quenched with saturated NH$_4$Cl and extracted with EtOAc. The crude product was then dissolved in CH$_2$Cl$_2$ (90 ml), Et$_3$SiH (4.5 ml) and TFA (45 ml) at 0° C. and the reaction mixture was stirred at 23° C. for 20 mins. The reaction mixture was evaporated, quenched with saturated NaHCO$_3$ and extracted with CH$_2$Cl$_2$. The crude mixture was purified by column chromatography (0 to 30% gradient of EtOAc in Hexanes) to give the product as a white solid in 84% yield (7.15 g).

Step c: A mixture of the product from Step b (6.64 g, 21.9 mmol), B$_2$pin$_2$ (6.11 g, 24.0 mmol, 1.1 equiv.), KOAc (7.52 g, 76.7 mmol, 3.5 equiv.) and PCy$_3$ Pd G$_2$ (1.29 g, 2.19 mmol, 0.1 equiv.) in anhydrous dioxane (109 mL) was stirred at 100° C. for 1 h. The reaction mixture was filtered, evaporated and the crude product was purified by column chromatography (0 to 30% gradient of EtOAc in Hexanes) to give the product as a brown solid in 94% yield (8.80 g).

Step d: A mixture of the product from Step c (7.10 g, 18 mmol), 2-amino-5-chloropyrazolo[1,5-a]pyrimidine-3-carboxylic acid ethyl ester (4.31 g, 18 mmol, 1 equiv.), 1 M Na$_2$CO$_3$ (72 ml, 72 mmol, 4 equiv.) and PdCl$_2$(dppf) (658 mg, 0.90 mmol, 0.05 equiv.) in anhydrous dioxane (90 mL) was stirred at 100° C. for 1 h. The reaction mixture was quenched with saturated NaCl, extracted with EtOAc, evaporated and the crude product was purified by column chromatography (30 to 100% gradient of EtOAc in Hexanes) to give the product as a brown solid in 68% yield (5.77 g).

Step e: A mixture of the product from Step d (5.77 g, 12.2 mmol) and TMSI (12.2 ml, 85.4 mmol, 7 equiv.) in anhydrous CH$_3$CN (61 mL) was stirred at 80° C. for 15 h. The reaction mixture was quenched with saturated sodium bisulfite, extracted with CH$_2$Cl$_2$:MeOH (9:1) and evaporated. The crude product triturated in MTBE and filtered to give the product as a yellow solid in 59% yield (3.23 g).

Step f: A mixture of the product from Step e (60 mg, 0.13 mmol), the amine (0.20 mmol, 1.5 equiv.), EDCI-HCl (38 mg, 0.20 mmol, 1.5 equiv.), HOBt (31 mg, 0.20 mmol, 1.5 equiv.) and DIPEA (70 μL, 0.39 mmol, 3 equiv.) in anhydrous DMF (1.3 mL) was stirred at 23° C. for 2 h. The reaction mixture was quenched with sat. aq. NaCl, extracted with EtOAc, evaporated and the crude product was purified by reverse phase HPLC (C18 column, 10 to 90% gradient of CH$_3$CN and H$_2$O with 0.1% TFA) to give the product as a yellow solid. $^1$H NMR (400 MHz, DMSO-d$_6$) δ 9.05 (d, J=7.1 Hz, 1H), 8.90 (s, 1H), 8.58 (s, 1H), 8.27 (d, J=5.3 Hz, 1H), 8.06 (s, 1H), 7.81 (d, J=7.2 Hz, 1H), 6.61 (s, 2H), 4.69 (s, 2H), 4.37 (ddd, J=10.8, 8.1, 5.3 Hz, 1H), 3.58 (m, 1H), 3.29-3.23 (m, 2H), 2.71-2.60 (m, 1H), 1.92 (m, 1H), 1.31 (d, J=6.8 Hz, 3H), 1.15 (m, 1H), 0.58 (m, 1H), 0.47-0.34 (m, 2H), 0.26 (m, 1H). ESI MS [M+H]$^+$ for C$_{25}$H$_{25}$F$_3$N$_7$O$_3$, calcd 528.2, found 528.2.

Example 50: 5-(3-{[(R)-2-Hydroxy-1-methylethyl-amino]carbonyl}-2-amino-1,4,7a-triaza-5-indenyl)-2-[(S)-1-cyclopropylethyl]-7-(trifluoromethyl)-1-isoindolinone

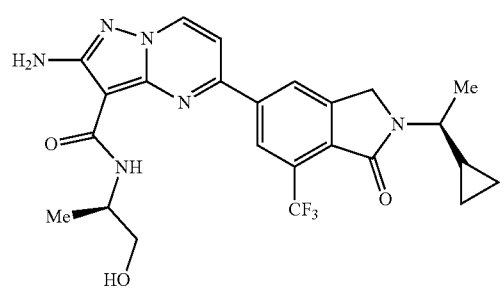 [SMILES: C[C@H](CO)NC(=O)c1c(N)nn2ccc(-c3cc4c(c(C(F)(F)F)c3)C(=O)N([C@@H](C)C3CC3)C4)nc12]

The title compound was prepared in a similar manner to example 49. $^1$H NMR (400 MHz, DMSO-d$_6$) δ 9.05 (d, J=7.1 Hz, 1H), 8.83 (s, 1H), 8.59 (s, 1H), 8.10 (d, J=8.0 Hz, 1H), 7.80 (d, J=7.1 Hz, 1H), 6.61 (s, 2H), 5.02 (t, J=5.2 Hz, 1H), 4.70 (s, 2H), 4.12-4.00 (m, 1H), 3.65-3.45 (m, 3H), 1.31 (d, J=6.8 Hz, 3H), 1.22 (d, J=6.6 Hz, 3H), 1.20-1.13 (m, 1H), 0.63-0.53 (m, 1H), 0.48-0.36 (m, 2H), 0.32-0.18 (m, 1H). ESI MS [M+H]$^+$ for C$_{24}$H$_{28}$F$_3$N$_6$O$_3$, calcd 503.2, found 503.1.

Example 51: 2-[(S)-1-Cyclopropylethyl]-5-{2-amino-3-[(2-hydroxyethylamino)carbonyl]-1,4,7a-triaza-5-indenyl}-7-(trifluoromethyl)-1-isoindolinone

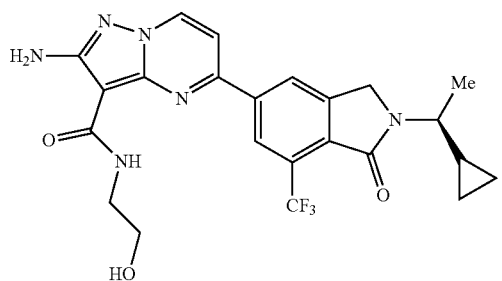 [SMILES: C[C@@H](C1CC1)N1Cc2cc(-c3ccn4nc(N)c(C(=O)NCCO)c4n3)cc(C(F)(F)F)c2C1=O]

The title compound was prepared in a similar manner to example 49. $^1$H NMR (400 MHz, DMSO-d$_6$) δ 9.04 (d, J=7.1 Hz, 1H), 8.86 (s, 1H), 8.57 (s, 1H), 8.22 (t, J=5.3 Hz, 1H), 7.80 (d, J=7.1 Hz, 1H), 6.61 (s, 2H), 5.01 (br s, 1H), 4.69 (s, 2H), 3.66-3.55 (m, 3H), 3.46 (dd, J=5.4, 5.4 Hz, 2H), 1.30 (d, J=6.8 Hz, 3H), 1.20-1.10 (m, 1H), 0.62-0.53 (m, 1H), 0.46-0.34 (m, 2H), 0.28-0.20 (m, 1H). ESI MS [M+H]$^+$ for C$_{23}$H$_{23}$F$_3$N$_6$O$_3$, calcd 489.2, found 489.2.

Example 52: 2-[(S)-1-Cyclopropylethyl]-5-{2-amino-3-[(3-hydroxypropylamino)carbonyl]-1,4,7a-triaza-5-indenyl}-7-(trifluoromethyl)-1-isoindolinone

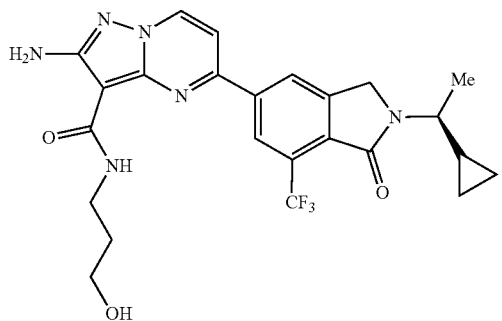 [SMILES: C[C@@H](C1CC1)N1Cc2cc(-c3ccn4nc(N)c(C(=O)NCCCO)c4n3)cc(C(F)(F)F)c2C1=O]

The title compound was prepared in a similar manner to example 49. $^1$H NMR (400 MHz, DMSO-d$_6$) δ 9.04 (d, J=7.1 Hz, 1H), 8.76 (s, 1H), 8.56 (s, 1H), 7.87 (t, J=5.6 Hz, 1H), 7.75 (d, J=7.1 Hz, 1H), 6.62 (s, 2H), 4.70 (s, 2H), 4.60 (t, J=5.1 Hz, 1H), 3.65-3.51 (m, 3H), 3.45 (dt, J=6.4, 6.4 Hz, 2H), 1.73 (tt, J=1.73 Hz, 2H), 1.30 (d, J=6.8 Hz, 3H), 1.24-1.09 (m, 1H), 0.62-0.52 (m, 1H), 0.46-0.33 (m, 2H), 0.30-0.21 (m, 1H). ESI MS [M+H]$^+$ for C$_{24}$H$_{25}$F$_3$N$_6$O$_3$, calcd 503.2, found 503.1.

Example 53: 2-[(S)-1-Cyclopropylethyl]-5-{2-amino-3-[(3-oxetanylamino)carbonyl]-1,4,7a-triaza-5-indenyl}-7-(trifluoromethyl)-1-isoindolinone

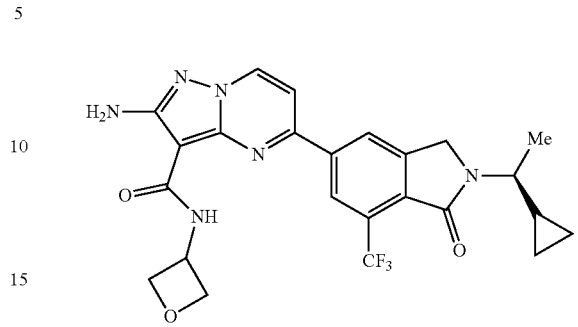

The title compound was prepared in a similar manner to example 49. $^1$H NMR (400 MHz, DMSO-d$_6$) δ 9.09 (d, J=7.2 Hz, 1H), 8.77 (s, 1H), 8.71 (s, 1H), 8.31 (d, J=6.6 Hz, 1H), 7.80 (d, J=7.2 Hz, 1H), 6.60 (s, 2H), 5.08-5.01 (m, 1H), 4.85 (dd, J=6.9, 6.9 Hz, 2H), 4.73 (s, 2H), 4.58 (dd, J=6.4 Hz, 2H), 3.60 (dt, J=9.2, 6.8 Hz, 1H), 1.32 (d, J=6.8 Hz, 3H), 1.23-1.09 (m, 1H), 0.62-0.55 (m, 1H), 0.47-0.34 (m, 2H), 0.29-0.27 (m, 1H). ESI MS [M+H]$^+$ for C$_{24}$H$_{23}$F$_3$N$_6$O$_3$, calcd 501.2, found 501.1.

Example 54: 2-[(S)-1-Cyclopropylethyl]-5-{2-amino-3-[(cis-4-hydroxy-4-methylcyclohexylamino)carbonyl]-1,4,7a-triaza-5-indenyl}-7-(trifluoromethyl)-1-isoindolinone

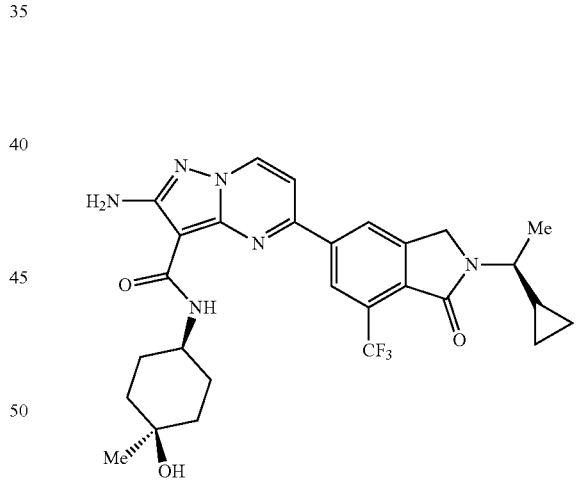

The title compound was prepared in a similar manner to example 49. $^1$H NMR (400 MHz, DMSO-d$_6$) δ 9.06 (d, J=7.1 Hz, 1H), 8.69 (s, 1H), 8.59 (s, 1H), 7.73 (d, J=7.1 Hz, 1H), 7.69 (d, J=7.3 Hz, 1H), 6.61 (s, 2H), 4.70 (s, 2H), 4.09 (s, 2H), 3.77-3.66 (m, 1H), 3.59 (dq, J=9.2, 6.6 Hz, 1H), 1.82-1.52 (m, 6H), 1.46-1.36 (m, 2H), 1.31 (d, J=6.6 Hz, 3H), 1.20-1.12 (m, 4H), 0.60-0.54 (m, 2H), 0.48-0.34 (m, 2H), 0.30-0.23 (m, 1H). ESI MS [M+H]$^+$ for C$_{28}$H$_{23}$F$_3$N$_6$O$_3$, calcd 557.2, found 557.1.

Example 55: 2-[(S)-1-Cyclopropylethyl]-5-(2-amino-3-{[cis-4-hydroxy-4-(trifluoromethyl)cyclohexylamino]carbonyl}-1,4,7a-triaza-5-indenyl)-7-(trifluoromethyl)-1-isoindolinone

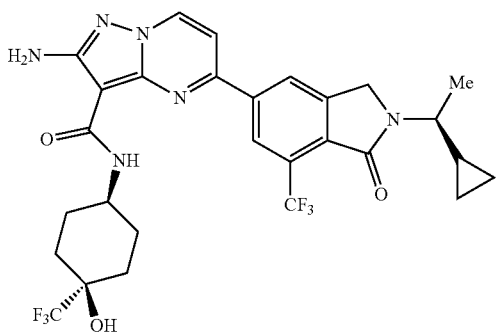 [SMILES: C[C@@H](C1CC1)N1Cc2cc(-c3ccn4nc(N)c(C(=O)N[C@H]5CC[C@](O)(C(F)(F)F)CC5)c4n3)cc(C(F)(F)F)c2C1=O]

The title compound was prepared in a similar manner to example 49. $^1$H NMR (400 MHz, DMSO-d$_6$) δ 9.07 (d, J=7.1 Hz, 1H), 8.69 (s, 1H), 8.61 (s, 1H), 7.74 (d, J=7.1 Hz, 1H), 7.68 (d, J=7.2 Hz, 1H), 6.61 (s, 2H), 4.70 (s, 2H), 3.78 (br s, 1H), 3.64-3.54 (m, 1H), 1.99-1.91 (m, 2H), 1.82-1.74 (m, 2H), 1.69-1.59 (m, 4H), 1.31 (d, J=6.8 Hz, 3H), 1.26-1.08 (m, 1H), 0.61-0.52 (m, 1H), 0.48-0.35 (m, 2H), 0.30-0.21 (m, 1H). ESI MS [M+H]$^+$ for C$_{28}$H$_{28}$F$_6$N$_6$O$_3$, calcd 611.2, found 611.1.

Example 56: 2-[(S)-1-Cyclopropylethyl]-5-{2-amino-3-[(3-methyl-3-oxetanylamino)carbonyl]-1,4,7a-triaza-5-indenyl}-7-(trifluoromethyl)-1-isoindolinone

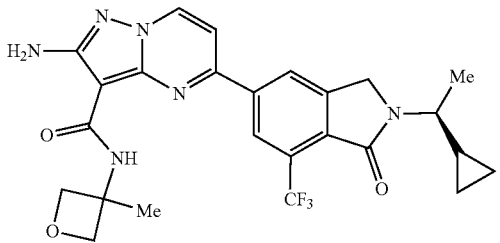 [SMILES: C[C@@H](C1CC1)N1Cc2cc(-c3ccn4nc(N)c(C(=O)NC5(C)COC5)c4n3)cc(C(F)(F)F)c2C1=O]

The title compound was prepared in a similar manner to example 49. $^1$H NMR (400 MHz, DMSO-d$_6$) δ 9.06 (d, J=7.1 Hz, 1H), 8.73 (s, 1H) 8.64 (s, 1H), 8.14 (s, 1H), 7.77 (d, J=7.1 Hz, 1H), 6.61 (s, 2H), 4.81 (d, J=6.1 Hz, 2H), 4.70 (s, 2H), 4.44 (d, J=6.1 Hz, 2H), 3.64-3.54 (m, 1H), 1.69 (s, 3H), 1.30 (d, J=6.8 Hz, 3H), 1.23-1.14 (m, 1H), 061-0.53 (m, 1H), 0.47-0.34 (m, 2H), 0.29-0.20 (m, 1H). ESI MS [M+H]$^+$ for C$_{25}$H$_{25}$F$_3$N$_6$O$_3$, calcd 515.2, found 515.1.

Example 57: 5-(3-{[(R)-3-Hydroxy-1-methylpropylamino]carbonyl}-2-amino-1,4,7a-triaza-5-indenyl)-2-[(S)-1-cyclopropylethyl]-7-(trifluoromethyl)-1-isoindolinone

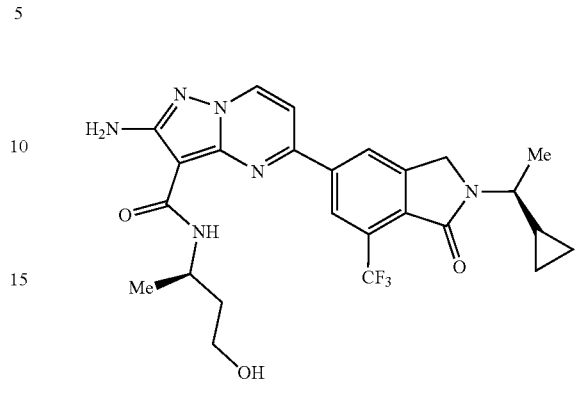

The title compound was prepared in a similar manner to example 49. $^1$H NMR (400 MHz, DMSO-d$_6$) δ 9.06 (d, J=7.1 Hz, 1H), 8.71 (s, 1H), 8.60 (s, 1H), 7.78-7.73 (m, 2H), 6.61 (s, 2H), 4.71 (s, 2H), 4.51 (t, J=5.0 Hz, 1H), 4.19-4.12 (m, 1H), 3.67-3.42 (m, 3H), 1.71 (dd, J=6.5, 6.5 Hz, 2H), 1.30 (d, J=6.8 Hz, 3H), 1.24 (d, J=6.6 Hz, 3H), 1.22-1.12 (m, 1H), 0.62-0.53 (m, 1H), 0.45-0.36 (m, 2H), 0.28-0.22 (m, 1H). ESI MS [M+H]$^+$ for C$_{28}$H$_{27}$F$_3$N$_6$O$_3$, calcd 517.2, found 517.1.

Example 58: 2-[(S)-1-Cyclopropylethyl]-5-{2-amino-3-[(4-hydroxybutylamino)carbonyl]-1,4,7a-triaza-5-indenyl}-7-(trifluoromethyl)-1-isoindolinone

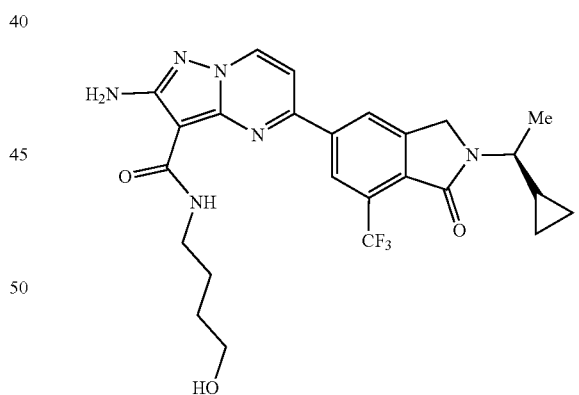

The title compound was prepared in a similar manner to example 49. $^1$H NMR (400 MHz, DMSO-d$_6$) δ 9.05 (d, J=7.1 Hz, 1H), 8.71 (s, 1H), 8.55 (s, 1H), 7.81-7.71 (m, 2H), 6.61 (s, 2H), 4.72 (s, 2H), 4.43 (t, J=5.1 Hz, 1H), 3.66-3.53 (m, 1H), 3.46-3.35 (m, 5H), 1.67-1.50 (m, 4H), 1.30 (d, J=6.8 Hz, 3H), 1.22-1.12 (m, 1H), 0.63-0.52 (m, 1H), 0.48-0.34 (m, 2H), 0.28-0.24 (m, 1H). ESI MS [M+H]$^+$ for C$_{28}$H$_{27}$F$_3$N$_6$O$_3$, calcd 517.2, found 517.1.

Example 59: 2-[(S)-1-Cyclopropylethyl]-5-{2-amino-3-[(3-hydroxy-3-methylbutylamino)carbonyl]-1,4,7a-triaza-5-indenyl}-7-(trifluoromethyl)-1-isoindolinone

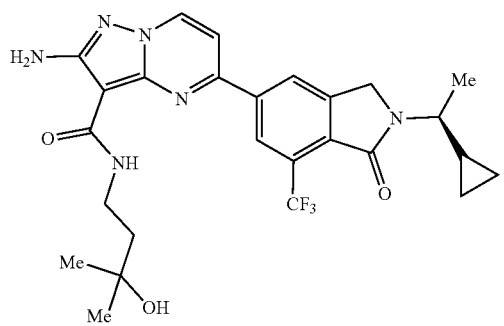 [SMILES: C[C@@H](C1CC1)N1Cc2cc(-c3ccn4nc(N)c(C(=O)NCCC(C)(C)O)c4n3)cc(C(F)(F)F)c2C1=O]

The title compound was prepared in a similar manner to example 49. $^1$H NMR (400 MHz, DMSO-d$_6$) δ 9.03 (d, J=7.1 Hz, 1H), 8.85 (s, 1H), 8.57 (s, 1H), 7.98 (t, J=5.1 Hz, 1H), 7.75 (d, J=7.1 Hz, 1H), 6.62 (s, 2H), 4.71 (s, 2H), 4.45 (s, 1H), 3.69-3.51 (m, 1H), 3.49-3.45 (m, 2H), 1.71 (dd, J=7.1, 7.1 Hz, 2H), 1.29 (d, J=6.8 Hz, 3H), 1.23-1.04 (m, 7H), 0.61-0.51 (m, 1H), 0.50-0.29 (m, 2H), 0.32-0.19 (m, 1H). ESI MS [M+H]$^+$ for C$_{26}$H$_{29}$F$_3$N$_6$O$_3$, calcd 531.2, found 531.1.

Example 60: 2-Amino-5-(2-((S)-1-cyclopropylethyl)-1-oxo-7-(trifluoromethyl)isoindolin-5-yl)-N-(trans-4-(hydroxymethyl)cyclohexyl)pyrazolo[1,5-a]pyrimidine-3-carboxamide

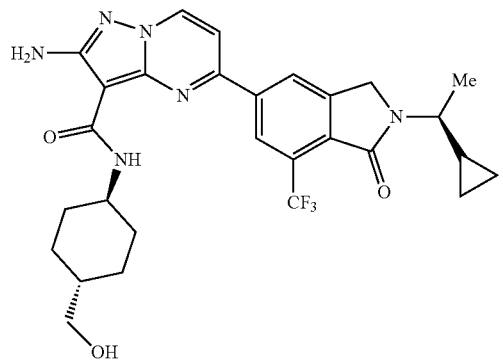 [SMILES: C[C@@H](C1CC1)N1Cc2cc(-c3ccn4nc(N)c(C(=O)N[C@H]5CC[C@H](CO)CC5)c4n3)cc(C(F)(F)F)c2C1=O]

The title compound was prepared in a similar manner to example 49. $^1$H NMR (400 MHz, CDCl$_3$) δ 8.61-8.46 (m, 2H), 8.26-8.15 (m, 1H), 7.77 (d, J=7.8 Hz, 1H), 7.28 (d, J=7.0 Hz, 1H), 5.28 (br. s, 2H), 4.69 (d, J=17.7 Hz, 1H), 4.57 (d, J=17.6 Hz, 1H), 3.99-3.87 (m, 1H), 3.86-3.75 (m, 1H), 3.53 (d, J=6.4 Hz, 2H), 2.30-2.18 (m, 2H), 1.97-1.88 (m, 2H), 1.64-1.50 (m, 1H), 1.39 (d, J=6.9 Hz, 3H), 1.37-1.22 (m, 4H), 1.10-1.01 (m, 1H), 0.71-0.63 (m, 1H), 0.53-0.38 (m, 3H). $^{19}$F NMR (376 MHz, CDCl$_3$) δ −59.95. ESI MS [M+H]$^+$ for C$_{28}$H$_{32}$F$_3$N$_6$O$_3$, calcd 557.3, found 557.2.

Example 61: 2-Amino-5-(2-((S)-1-cyclopropylethyl)-1-oxo-7-(trifluoromethyl)isoindolin-5-yl)-N-(trans-4-(2-hydroxypropan-2-yl)cyclohexyl)pyrazolo[1,5-a]pyrimidine-3-carboxamide

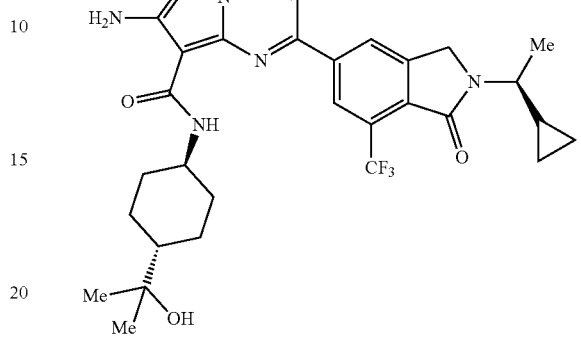

The title compound was prepared in a similar manner to example 49. $^1$H NMR (400 MHz, DMSO-d$_6$) δ 9.05 (d, J=7.1 Hz, 1H), 8.69 (s, 1H), 8.61 (s, 1H), 7.73 (d, J=7.1 Hz, 1H), 7.66 (d, J=7.6 Hz, 1H), 6.60 (s, 2H), 4.71 (s, 2H), 4.10 (s, 1H), 3.79-3.52 (m, 2H), 2.14-2.05 (m, 2H), 1.88-1.79 (m, 2H), 1.31 (d, J=6.8 Hz, 3H), 1.27-1.08 (m, 6H), 1.04 (s, 6H), 0.68-0.51 (m, 1H), 0.51-0.34 (m, 2H), 0.30-0.22 (m, 1H). $^{19}$F NMR (376 MHz, DMSO-d$_6$) δ −58.46. ESI MS [M+H]$^+$ for C$_{30}$H$_{36}$F$_3$N$_6$O$_3$, calcd 585.3, found 585.1.

Example 62: 2-Amino-5-(2-((S)-1-cyclopropylethyl)-1-oxo-7-(trifluoromethyl)isoindolin-5-yl)-N-(trans-4-(1-hydroxycyclopropyl)cyclohexyl)pyrazolo[1,5-a]pyrimidine-3-carboxamide

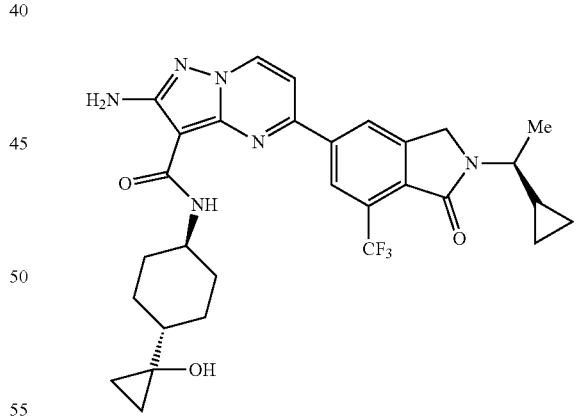

The title compound was prepared in a similar manner to example 49. $^1$H NMR (400 MHz, CDCl$_3$) δ 8.57 (s, 1H), 8.53 (d, J=7.1 Hz, 1H), 8.19 (s, 1H), 7.68 (d, J=7.1 Hz, 1H), 5.77 (br. s, 2H), 4.68 (d, J=17.3 Hz, 1H), 4.56 (d, J=17.3 Hz, 1H), 4.01-3.88 (m, 1H), 3.87-3.76 (m, 1H), 2.34-2.20 (m, 2H), 1.96-1.86 (m, 2H), 1.59-1.44 (m, 2H), 1.42-1.26 (m, 5H), 1.12-0.99 (m, 2H), 0.77-0.71 (m, 2H), 0.70-0.63 (m, 1H), 0.54-0.47 (m, 3H), 0.46-0.37 (m, 2H). $^{19}$F NMR (376 MHz, CDCl$_3$) δ −59.98. ESI MS [M+H]$^+$ for C$_{30}$H$_{34}$F$_3$N$_6$O$_3$, calcd 583.3, found 583.1.

Example 63: 2-Amino-5-{2-[(1S)-1-cyclopropyl-ethyl]-1-oxo-7-(trifluoromethyl)-2,3-dihydro-1H-isoindol-5-yl}-N-[(1S,3R)-3-hydroxycyclohexyl]pyrazolo[1,5-a]pyrimidine-3-carboxamide

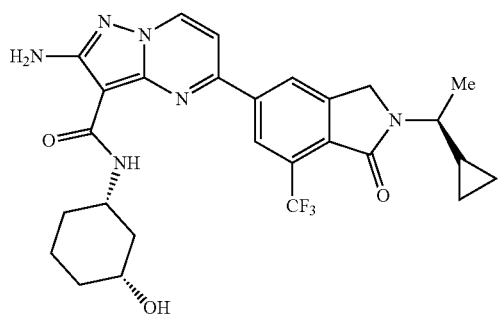 [SMILES: C[C@@H](C1CC1)N1Cc2cc(-c3ccn4nc(N)c(C(=O)N[C@H]5CCC[C@@H](O)C5)c4n3)cc(C(F)(F)F)c2C1=O]

The title compound was prepared in a similar manner to example 49. $^1$H NMR (400 MHz, DMSO-$d_6$) δ 9.05 (d, J=7.1 Hz, 1H), 8.74 (m, 1H), 8.60 (m, 1H), 7.89 (d, J=8.1 Hz, 1H), 7.74 (d, J=7.2 Hz, 1H), 4.68 (s, 2H), 3.88 (m, 1H), 3.65-3.52 (m, 2H), 2.13 (m, 1H), 1.86 (m, 1H), 1.82-1.71 (m, 2H), 1.30 (d, J=6.8 Hz, 3H), 1.27-1.10 (m, 5H), 0.57 (m, 1H), 0.46-0.35 (m, 2H), 0.26 (m, 1H). ESI MS [M+H]$^+$ for $C_{27}H_{30}F_3N_6O_3$, calcd 543.2, found 543.2.

Example 64: 2-Amino-5-{2-[(1S)-1-cyclopropyl-ethyl]-1-oxo-7-(trifluoromethyl)-2,3-dihydro-1H-isoindol-5-yl}-N-[(3R)-5-oxopyrrolidin-3-yl]pyrazolo[1,5-a]pyrimidine-3-carboxamide

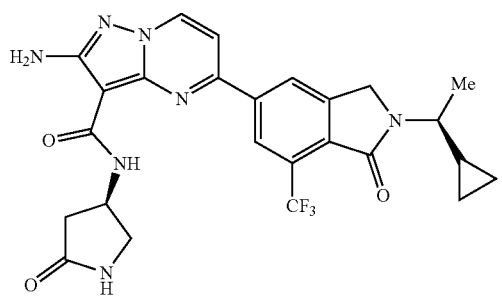

The title compound was prepared in a similar manner to example 49. $^1$H NMR (400 MHz, DMSO-$d_6$) δ 9.05 (d, J=7.1 Hz, 1H), 8.65 (s, 1H), 8.57 (s, 1H), 8.10 (d, J=7.1 Hz, 1H), 7.78 (d, J=7.2 Hz, 1H), 7.75 (s, 1H), 6.59 (s, 2H), 4.74 (d, J=2.5 Hz, 2H), 4.63 (m, 1H), 3.68-3.56 (m, 2H), 3.21 (dd, J=9.9, 4.5 Hz, 1H), 2.64 (dd, J=16.5, 7.9 Hz, 1H), 2.22 (dd, J=16.5, 5.3 Hz, 1H), 1.31 (d, J=6.8 Hz, 3H), 1.15 (m, 1H), 0.58 (m, 1H), 0.47-0.34 (m, 2H), 0.26 (m, 1H). ESI MS [M+H]$^+$ for $C_{25}H_{25}F_3N_7O_3$, calcd 528.2, found 528.2.

Example 65: 2-Amino-5-{2-[(1S)-1-cyclopropyl-ethyl]-1-oxo-7-(trifluoromethyl)-2,3-dihydro-1H-isoindol-5-yl}-N-[trans-3-hydroxycyclobutyl]pyrazolo[1,5-a]pyrimidine-3-carboxamide

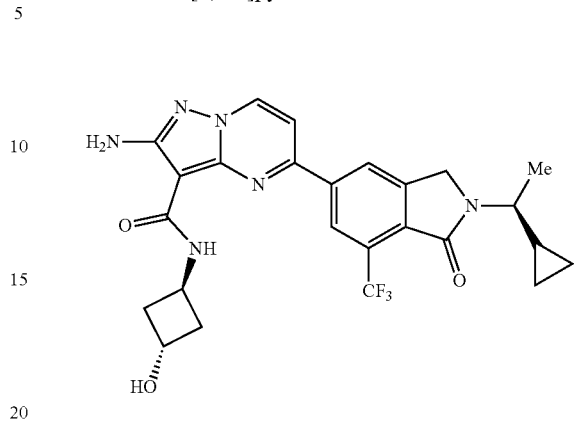

The title compound was prepared in a similar manner to example 49. $^1$H NMR (400 MHz, DMSO-$d_6$) δ 9.09 (d, J=7.1 Hz, 1H), 8.73 (s, 1H), 8.67 (s, 1H), 7.99 (d, J=6.8 Hz, 1H), 7.77 (d, J=7.1 Hz, 1H), 6.62 (s, 2H), 5.13 (d, J=5.4 Hz, 1H), 4.74 (s, 2H), 4.48 (h, J=6.7 Hz, 1H), 4.44-4.32 (m, 1H), 3.62 (dq, J=9.3, 6.8 Hz, 1H), 2.34-2.22 (m, 4H), 1.34 (d, J=6.8 Hz, 3H), 1.25-1.15 (m, 1H), 0.64-0.57 (m, 1H), 0.49-0.37 (m, 2H), 0.33-0.24 (m, 1H). ESI MS [M+H]$^+$ for $C_{25}H_{26}F_3N_6O_3$, calcd 515.2, found 515.1.

Example 66: 5-{2-[(S)-1-Cyclopropylethyl]-7-(trifluoromethyl)-5-isoindolinoyl}-2-amino-1,4,7a-triaza-3-indenecarboxamide

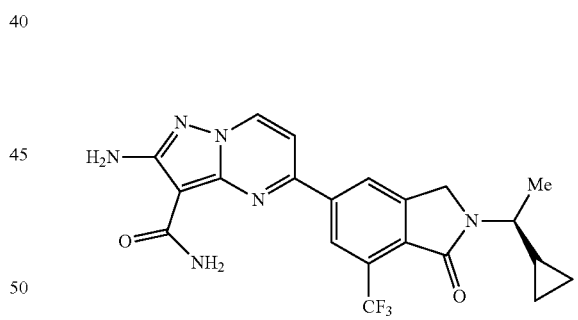

The title compound was prepared in a similar manner to examples 39 and 49. $^1$H NMR (400 MHz, DMSO-$d_6$) δ 9.03 (d, J=7.1 Hz, 1H), 8.77 (s, 1H), 8.50 (s, 1H), 7.75 (d, J=7.1 Hz, 1H), 7.42 (s, 1H), 7.32 (s, 1H), 6.63 (s, 2H), 4.72 (s, 2H), 3.64-3.54 (m, 1H), 1.29 (d, J=6.8 Hz, 3H), 1.20-1.10 (m, 1H), 0.61-0.54 (m, 1H), 0.46-0.35 (m, 2H), 0.29-0.22 (m, 1H). ESI MS [M+H]$^+$ for $C_{21}H_{19}F_3N_6O_2$, calcd 445.2, found 445.0.

Example 67: 2-[(S)-1-Cyclopropylethyl]-5-[2-amino-3-(methylamino)carbonyl-1,4,7a-triaza-5-indenyl]-7-(trifluoromethyl)-1-isoindolinone

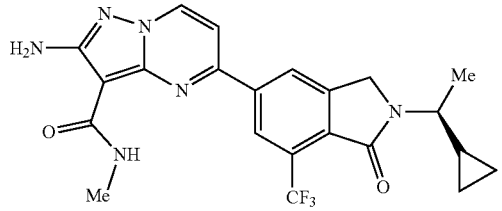 [SMILES: CNC(=O)c1c(N)nn2ccc(-c3cc4c(c(C(F)(F)F)c3)C(=O)N([C@@H](C)C3CC3)C4)nc12]

The title compound was prepared in a similar manner to example 49. $^1$H NMR (400 MHz, DMSO-d$_6$) δ 9.03 (d, J=7.1 Hz, 1H), 8.81 (s, 1H), 8.54 (s, 1H), 7.75 (d, J=7.1 Hz, 1H), 7.68 (q, J=4.7 Hz, 1H), 6.63 (s, 2H), 4.72 (s, 2H), 3.66-3.54 (m, 1H), 2.91 (d, J=4.7 Hz, 3H), 1.30 (d, J=6.8 Hz, 3H), 1.24-1.09 (m, 1H), 0.63-0.53 (m, 1H), 0.48-0.34 (m, 2H), 0.29-0.21 (m, 1H). ESI MS [M+H]$^+$ for C$_{22}$H$_{21}$F$_3$N$_6$O$_2$, calcd 459.2, found 459.1.

Example 68: 2-[(S)-1-Cyclopropylethyl]-5-[2-amino-3-(ethylamino)carbonyl-1,4,7a-triaza-5-indenyl]-7-(trifluoromethyl)-1-isoindolinone

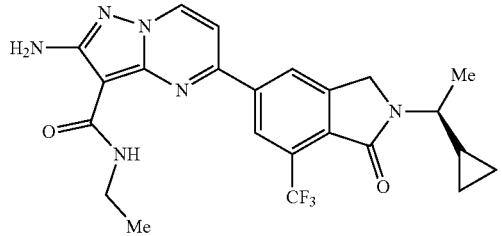 [SMILES: CCNC(=O)c1c(N)nn2ccc(-c3cc4c(c(C(F)(F)F)c3)C(=O)N([C@@H](C)C3CC3)C4)nc12]

The title compound was prepared in a similar manner to example 49. $^1$H NMR (400 MHz, DMSO-d$_6$) δ 9.05 (d, J=7.1 Hz, 1H), 8.73 (s, 1H), 8.60 (s, 1H), 7.77-7.69 (m, 2H), 6.61 (s, 2H), 4.72 (s, 2H), 3.65-3.54 (m, 1H), 3.44-3.34 (m, 2H), 1.30 (d, J=6.8 Hz, 3H), 1.25-1.10 (m, 4H), 0.62-0.55 (m, 1H), 0.45-0.35 (m, 2H), 0.30-0.21 (m, 1H). ESI MS [M+H]$^+$ for C$_{23}$H$_{23}$F$_3$N$_6$O$_2$, calcd 473.2, found 473.1.

Example 69: (S)-2-Amino-5-(2-(1-cyclopropylethyl)-1-oxo-7-(trifluoromethyl)isoindolin-5-yl)-N-(pyridin-4-yl)pyrazolo[1,5-a]pyrimidine-3-carboxamide

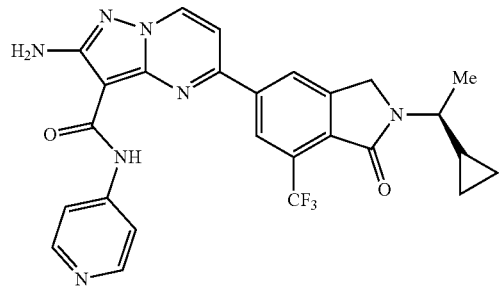 [SMILES: C[C@@H](C1CC1)N1Cc2cc(-c3ccn4nc(N)c(C(=O)Nc5ccncc5)c4n3)cc(C(F)(F)F)c2C1=O]

The title compound was prepared in a similar manner to examples 49 and 99 (vide infra). $^1$H NMR (400 MHz, CDCl$_3$) δ 9.94 (s, 1H), 8.63-8.59 (m, 2H), 8.55 (d, J=6.0 Hz, 2H), 8.28 (s, 1H), 7.64 (d, J=6.0 Hz, 2H), 7.37 (d, J=7.1 Hz, 1H), 5.83 (s, 2H), 4.72 (d, J=17.6 Hz, 1H), 4.60 (d, J=17.6 Hz, 1H), 3.92-3.78 (m, 1H), 1.41 (d, J=6.8 Hz, 3H), 1.12-1.03 (m, 1H), 0.80-0.63 (m, 1H), 0.58-0.38 (m, 3H). $^{19}$F NMR (376 MHz, CDCl$_3$) δ −59.81. ESI MS [M+H]$^+$ for C$_{26}$H$_{23}$F$_3$N$_7$O$_2$, calcd 522.2, found 522.1.

Example 70: (S)-2-Amino-5-(2-(1-cyclopropylethyl)-1-oxo-7-(trifluoromethyl)isoindolin-5-yl)-N-(pyridin-3-yl)pyrazolo[1,5-a]pyrimidine-3-carboxamide

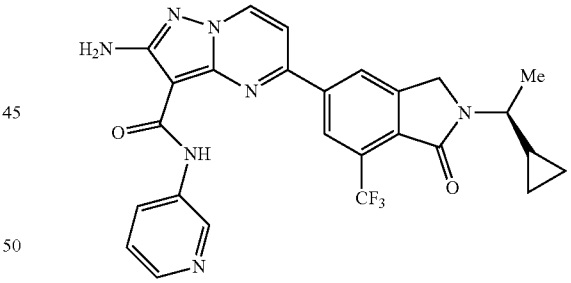

The title compound was prepared in a similar manner to examples 49 and 99 (vide infra). $^1$H NMR (400 MHz, DMSO-d$_6$) δ 9.92 (s, 1H), 9.15 (d, J=7.1 Hz, 1H), 8.87 (dd, J=2.6, 0.7 Hz, 1H), 8.79 (d, J=9.0 Hz, 2H), 8.30 (dd, J=4.7, 1.5 Hz, 1H), 8.23 (ddd, J=8.3, 2.6, 1.5 Hz, 1H), 7.86 (d, J=7.2 Hz, 1H), 7.41 (ddd, J=8.3, 4.7, 0.7 Hz, 1H), 6.76 (br. s, 2H), 4.75 (s, 2H), 3.69-3.56 (m, 1H), 1.34 (d, J=6.8 Hz, 3H), 1.27-1.13 (m, 1H), 0.66-0.55 (m, 1H), 0.50-0.36 (m, 2H), 0.33-0.24 (m, 1H). $^{19}$F NMR (376 MHz, DMSO-d$_6$) δ −58.23. ESI MS [M+H]$^+$ for C$_{26}$H$_{23}$F$_3$N$_7$O$_2$, calcd 522.2, found 522.2.

Example 71: 6-[(S)-1-Cyclopropylethyl]-19-amino-10.13-dioxa-6.16.20.21.24-pentaazapentacyclo[16.5.2.12,9.04,8.021,25]hexacosa-1(24),2,4(8),9(26),18(25),19,22-heptaene-7,17-dione

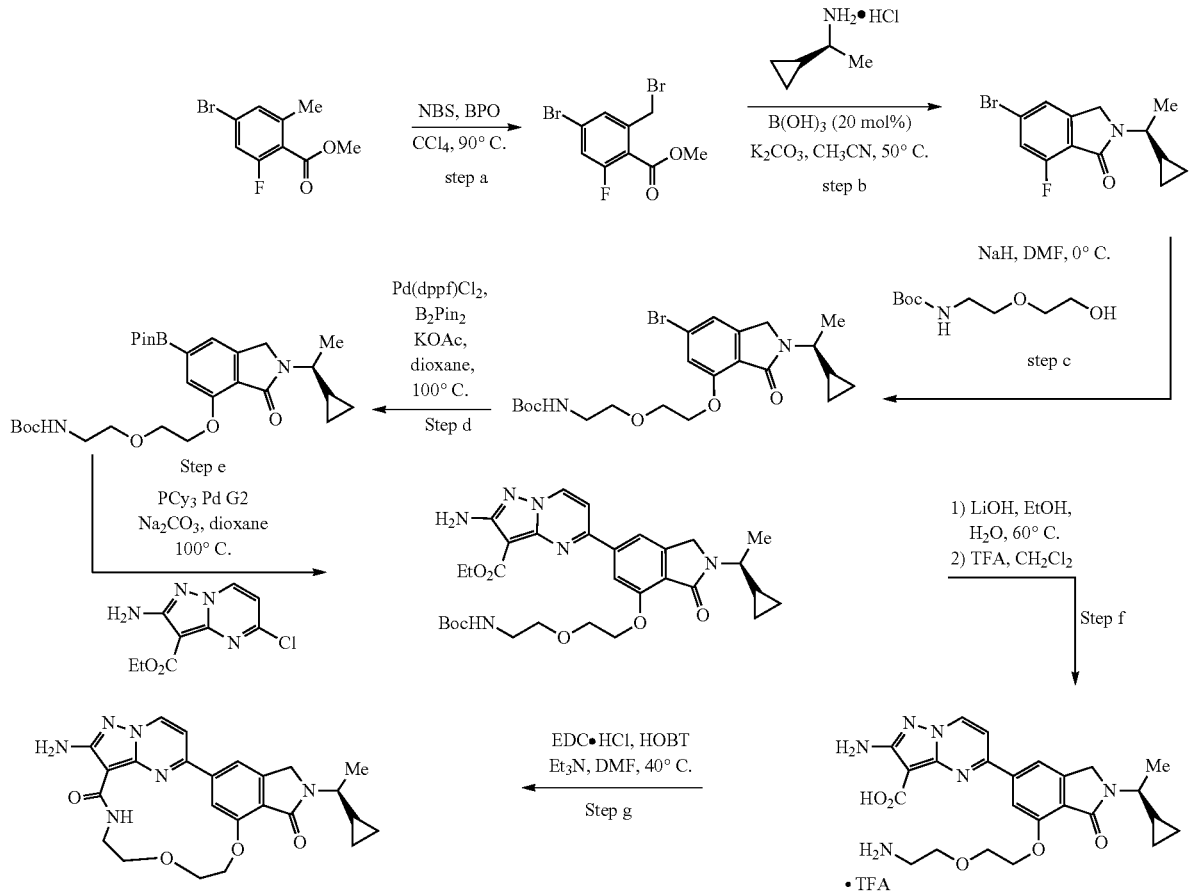

Step a: To a solution of 4-bromo-2-fluoro-6-methylbenzoic acid methyl ester (45.0 g, 182 mmol, 1.0 equiv.) in CCl₄ (1.14 L) were added NBS (35.7 g, 200 mmol, 1.1 equiv.) and BPO (80 wt. %, 5.51 g, 18.2 mmol, 0.1 equiv.). The resulting mixture was stirred at reflux for 3 h. Upon completion, the reaction mixture was cooled to rt and filtered to remove the precipitate. The filtrate was concentrated in vacuo to afford the crude benzyl bromide, which was used directly in Step b.

Step b: In a round-bottom flask equipped with a reflux condenser and a balloon of N₂, the product of Step a (45.0 g, 138 mmol, 1.0 equiv.) was combined with (αS)-α-methyl-cyclopropanemethanamine hydrochloride (33.6 g, 276 mmol, 2.0 equiv.), K₂CO₃ (57.2 g, 414 mmol, 3.0 equiv.), and B(OH)₃ (1.71 g, 27.6 mmol, 0.2 equiv.) in CH₃CN (552 mL). The resulting mixture was stirred at 50° C. for 72 h. Upon completion, the reaction mixture was cooled to rt and ~75% of the solvent was removed in vacuo. The mixture was partitioned between EtOAc (300 mL) and H₂O (200 mL). The organic phase was separated and the aq. phase was extracted again with EtOAc. The combined organic extracts were washed with H₂O and brine, then dried (Na₂SO₄), filtered and concentrated in vacuo. Purification by column chromatography (SiO₂, 0-30% EtOAc/hexanes) afforded the product as an off-white solid (35.0 g, 58% yield over 2 steps).

Step c: Sodium hydride (60% in mineral oil, 600 mg, 15 mmol, 3.0 equiv.) was added portion-wise at 0° C. to a solution of 2-(2-tert-butoxycarbonylaminoethoxy)ethanol (1.03 g, 5.0 mmol, 1.0 equiv.) in DMF (25 mL). After stirring 15 mins., 2-[(S)-1-cyclopropylethyl]-5-bromo-7-fluoro-1-isoindolinone (1.5 g, 5.0 mmol, 1.0 equiv.) was dissolved in DMF (5.0 mL) and added to the solution. The reaction was stirred for 10 mins. at 0° C. before quenching with sat. NH₄Cl and extraction with EtOAc. The collected organics were purified by flash chromatography (SiO₂, EtOAc/hexanes gradient 10% to 50%) to yield the aryl ether product (1.18 g, 49%).

Step d: The product of Step c (1.18 g, 2.44 mmol, 1.0 equiv.) was combined with Pd(dppf)Cl₂ (175 mg, 0.24 mmol, 0.1 equiv.), B₂pin₂ (813 mg, 3.2 mmol, 1.3 equiv.) and KOAc (530 mg, 5.2 mmol, 2.2 equiv.) in dioxane (24.4 mL). The resulting solution was heated to 100° C. for 2 h, cooled to rt, filtered through Celite (washed with EtOAc) and concentrated. The resulting residue was used directly in the next step without purification.

Step e: The product from Step d (2.44 mmol, 1.0 equiv.) was combined with 2-amino-5-chloropyrazolo[1,5-a]pyrimidine-3-carboxylic acid ethyl ester (587 mg, 2.44 mmol, 1.0 equiv.), PCy$_3$ Pd G2 (142 mg, 0.24 mmol, 0.1 equiv.) and Na$_2$CO$_3$ (2 M aq. solution, 7.32 mmol, 3.66 mL) in dioxane (25 mL). The resulting solution was heated to 100° C. for 1 h, concentrated, and purified by flash chromatography (SiO$_2$, 80% EtOAc in hexanes followed by 10% MeOH in CH$_2$Cl$_2$) to yield the cross-coupled ethyl ester (0.92 g, 62%, 2 steps).

Step f: The ethyl ester product (225 mg, 0.41 mmol, 1.0 equiv.) of Step e was dissolved in EtOH (2.0 mL). H$_2$O (1.39 ml) and aq. 2 N LiOH (615 μL, 1.23 mmol, 3 equiv.) were added, followed by dioxane (2.0 mL) for improved solubility. The resulting solution was heated to 60° C. overnight, then acidified to pH 3 with 2 N HCl. The solution was extracted with EtOAc, dried (Na$_2$SO$_4$) and concentrated (238 mg, 100%). Some of the resulting material (90 mg, 0.15 mmol) was dissolved in CH$_2$Cl$_2$ (2.0 mL). TFA (0.2 mL) was added, and the solution was stirred at rt for 20 mins. Upon completion, the reaction mixture was diluted with toluene (2.0 mL) and concentrated to the TFA salt. This material was taken forward without purification.

Step g: The TFA salt from Step f (0.15 mmol) was dissolved in DMF (7.5 mL, 0.02 M). HOBT (25.2 mg, 0.165 mmol, 1.1 equiv.), Et$_3$N (105 μL, 0.75 mmol, 5.0 equiv.) and EDC-HCl (43.1 mg, 0.225 mmol, 1.5 equiv.) were sequentially added, and the solution was heated to 40° C. After 2 h, the reaction solution was diluted with H$_2$O (60 ml) and extracted with EtOAc (×2) followed by 2:1 CH$_2$Cl$_2$:iPrOH (×1). The combined organics were concentrated and purified by flash chromatography (SiO$_2$, MeOH/CH$_2$Cl$_2$ gradient 0% to 5%) to yield the title compound. $^1$H NMR (400 MHz, DMSO-d$_6$) δ 8.99 (d, J=7.1 Hz, 1H), 8.79 (t, J=4.2 Hz, 1H), 8.43 (s, 1H), 7.97 (s, 1H), 7.65 (d, J=7.3 Hz, 1H), 6.47 (s, 2H), 4.53 (s, 2H), 4.49 (t, J=4.4 Hz, 2H), 3.89 (br s, 2H), 3.68 (t, J=5.0 Hz, 2H), 3.55-3.44 (m, 3H), 1.25 (d, J=6.8 Hz, 3H), 1.16-1.05 (m, 1H), 0.60-0.49 (m, 1H), 0.43-0.31 (m, 2H), 0.24-0.15 (m, 1H). ESI MS [M+H]$^+$ for C$_{24}$H$_{26}$N$_6$O$_4$, calcd 463.2, found 463.2.

Example 72: 2-Amino-5-{2-[(1S)-1-cyclopropylethyl]-7-methanesulfonamido-1-oxo-2,3-dihydro-1H-isoindol-5-yl}-N-[(1R,2R)-2-hydroxycyclopentyl]pyrazolo[1,5-a]pyrimidine-3-carboxamide

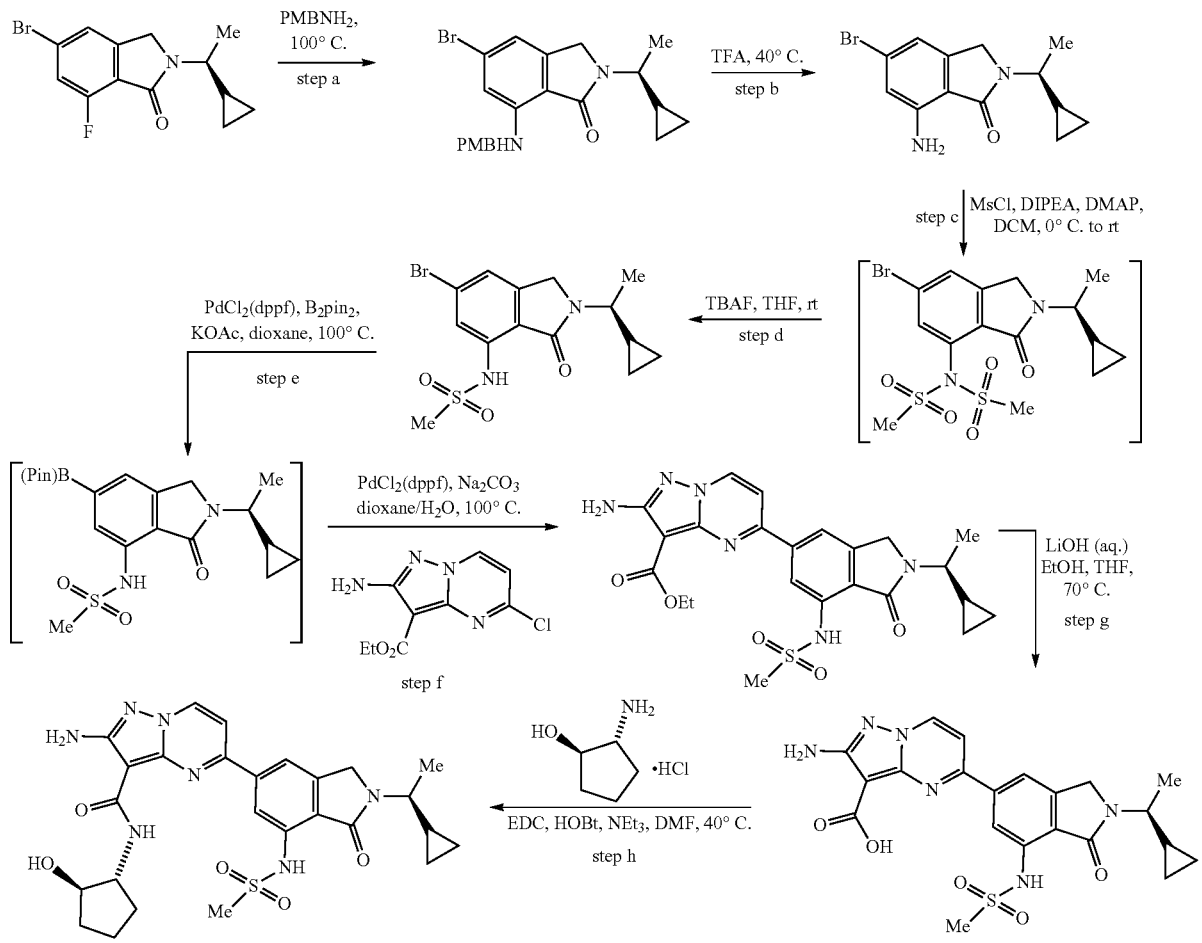

Step a: The C7-F-isoindolinone (3.00 g, 10.0 mmol, 1.0 equiv.) was combined with neat PMBNH$_2$ (4 mL) and heated to 100° C. for 14 h. The reaction mixture was cooled and partitioned between 10% aq. citric acid solution and EtOAc. The aq. layer was separated and back extracted with additional EtOAc. The organic layers were combined and washed with additional 10% aq. citric acid solution, brine, and dried over MgSO$_4$. Concentration under reduced pressure furnished the PMB amine adduct that was used crude in the next step.

Step b: The product of Step a was combined with TFA (15 mL) and stirred at 40° C. for 3 h. The reaction mixture was concentrated under reduced pressure and quenched with sat. aq. NaHCO$_3$ solution and diluted with EtOAc. The organic layers were combined, washed with brine and dried over MgSO$_4$. Concentration under reduced pressure and purification by column chromatography (SiO$_2$, hexanes to 50% EtOAc gradient) furnished the aniline product as a white solid (2.89 g, ~98%, minor impurity co-eluted that was taken forward in the next step).

Step c: The product of Step b (1.00 g, 3.38 mmol, 1.0 equiv.) was dissolved in CH$_2$Cl$_2$ (10 mL) and the mixture was cooled to 0° C. To this solution was added DMAP (40 mg, 0.34 mmol, 10 mol %), DIPEA (1.6 mL, 10.1 mmol, 3.0 equiv.) and MsCl (0.7 mL, 8.5 mmol, 2.5 equiv.). The reaction mixture was warmed to rt and stirred for 1 h. The reaction was quenched with 1 M aq. HCl solution and diluted with EtOAc. The aq. layer was separated and back extracted with additional EtOAc. The organic layers were combined, washed with brine and dried over MgSO$_4$. Concentration under reduced pressure furnished bis-sulfonylated product that was taken crude into the next step.

Step d: The product of Step c was dissolved in THF (5 mL) and TBAF (1 M in THF, 5.4 mL, 5.4 mmol, 1.6 equiv.) was added. An additional portion of TBAF (1 M in THF, 3.0 mL, 0.9 equiv.) was added after 15 min, followed by a final portion of TBAF (1 M in THF, 3.0 mL, 0.9 equiv.) after 2 h. The reaction mixture was stirred for an additional 1 h, then quenched with 1 M aq. HCl solution and diluted with EtOAc. The aq. layer was separated and back extracted with additional EtOAc. The organic layers were combined, washed with brine and dried over MgSO$_4$. Concentration under reduced pressure and purification by flash column chromatography (SiO$_2$, hexanes to 50% EtOAc gradient) furnished the reverse sulfonamide as a yellow solid (0.766 g, 2.1 mmol, 60% over 2 steps).

Step e: The product of Step d (2.00 g, 5.36 mmol, 1.0 equiv.) was combined with Pd(dppf)Cl$_2$ (390 mg, 0.54 mmol, 0.1 equiv.), B$_2$pin$_2$ (1.80 g, 7.10 mmol, 1.3 equiv.) and KOAc (1.15 g, 11.8 mmol, 2.20 equiv.) in dioxane (30 mL). The resulting mixture was heated to 100° C. and stirred for 1 h. After this time, a second portion of Pd(dppf)Cl$_2$ (100 mg, 0.137 mmol, 0.03 equiv.) was added. The reaction mixture was stirred for an additional 1 h, then cooled to rt, filtered through Celite (washed with EtOAc) and concentrated under reduced pressure. The resulting residue was used directly in the next step without purification.

Step f: The crude pinacol boronic ester was combined with Pd(dppf)Cl$_2$ (390 mg, 0.54 mmol, 0.1 equiv.), 1 M aq. Na$_2$CO$_3$ solution (16 mmol, 16 mL, 3.0 equiv.), ethyl 2-amino-5-chloro-1,4,7a-triaza-3-indenecarboxylate (1.29 g, 5.36 mmol, 1.0 equiv.) and dioxane (20 mL). The resulting mixture was heated to 100° C. and stirred for 40 mins. The reaction mixture was cooled to rt and diluted with CH$_2$Cl$_2$ and H$_2$O. The aq. phase was separated and back extracted with additional CH$_2$Cl$_2$, then once with EtOAc. The organic layers were combined and dried over MgSO$_4$. Concentration under reduced pressure and purification by column chromatography (SiO$_2$, CH$_2$Cl$_2$ to 5% MeOH gradient) furnished the cross-coupled ester product as a golden brown solid (2.48 g, 92% over 2 steps).

Step g: The ethyl ester product of Step f (500 mg, 1.00 mmol, 1.0 equiv.) was dissolved in EtOH (2 mL), THF (4 mL) and H$_2$O (2 ml). LiOH·H$_2$O (250 mg, 6.00 mmol, 6.0 equiv.) was added and the reaction mixture was heated to 70° C. for 15 h. The resulting mixture was cooled to rt and the solvent was removed in vacuo. The mixture was diluted with H$_2$O and acidified to pH 3 with 2 N HCl. The resulting precipitate was collected by vacuum filtration and dried under vacuum at 40° C. for 2 h to afford the carboxylic acid product (369 mg, 78%), which was used in the next step without purification.

Step h: The product of Step g (50 mg, 0.106 mmol) was dissolved in DMF (1.0 mL) and HOBt (20 mg, 0.127 mmol, 1.2 equiv., 20% H$_2$O by wt.), Et$_3$N (50 µL, 0.32 mmol, 3.0 equiv.), (1R,2R)-2-aminocyclopentanol hydrochloride, (22 mg, 0.159 mmol, 1.5 equiv.) and EDC·HCl (31 mg, 0.159 mmol, 1.5 equiv.) were sequentially added, and the solution was heated to 40° C. After 0.5 h, the reaction mixture was purified directly by reverse phase HPLC (20 to 80% gradient of CH$_3$CN and H$_2$O with 0.1% TFA) to afford the title compound as a yellow solid. $^1$H NMR (400 MHz, DMSO-d$_6$) δ 9.64 (s, 1H), 9.00 (d, J=7.1 Hz, 1H), 8.21-8.11 (m, 1H), 8.05-7.93 (m, 1H), 7.67 (d, J=7.4 Hz, 1H), 7.53 (d, J=7.2 Hz, 1H), 6.60 (s, 2H), 4.66 (s, 2H), 4.09-3.93 (m, 2H), 3.60-3.48 (m, 1H), 3.26 (s, 3H), 2.12-1.97 (m, 1H), 1.95-1.82 (m, 1H), 1.77-1.62 (m, 2H), 1.60-1.40 (m, 2H), 1.31 (d, J=6.8 Hz, 3H), 1.24-1.10 (m, 1H), 0.63-0.51 (m, 1H), 0.49-0.33 (m, 2H), 0.29-0.20 (m, 1H). ESI MS [M+H]$^+$ for C$_{26}$H$_{32}$N$_7$O$_5$S, calcd 554.2, found 554.2.

Example 73: 2-Amino-5-{2-[(1S)-1-cyclopropyl-ethyl]-7-methanesulfonamido-1-oxo-2,3-dihydro-1H-isoindol-5-yl}-N-methylpyrazolo[1,5-a]pyrimidine-3-carboxamide

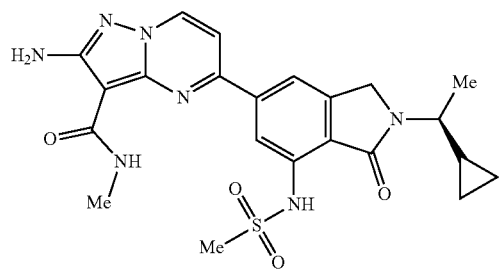 [SMILES: CNC(=O)c1c(N)nn2ccc(-c3cc4c(c(NS(C)(=O)=O)c3)C(=O)N([C@@H](C)C3CC3)C4)nc12]

The title compound was synthesized in similar fashion to example 72. $^1$H NMR (400 MHz, DMSO-d$_6$) δ 9.55 (s, 1H), 8.99 (d, J=7.1 Hz, 1H), 8.34 (d, J=1.2 Hz, 1H), 8.13 (d, J=1.2 Hz, 1H), 7.74 (q, J=4.8 Hz, 1H), 7.58 (d, J=7.2 Hz, 1H), 4.67 (s, 2H), 3.61-3.45 (m, 1H), 3.32 (s, 3H), 2.90 (d, J=4.8 Hz, 3H), 1.31 (d, J=6.8 Hz, 3H), 1.23-1.09 (m, 1H), 0.57 (m, 1H), 0.41 (m, 2H), 0.30-0.21 (m, 1H). ESI MS [M+H]$^+$ for C$_{22}$H$_{25}$N$_7$O$_4$S, calcd 484.2, found 484.1.

Example 74: 2-Amino-5-{2-[(1S)-1-cyclopropylethyl]-7-methanesulfonamido-1-oxo-2,3-dihydro-1H-isoindol-5-yl}-N-ethylpyrazolo[1,5-a]pyrimidine-3-carboxamide

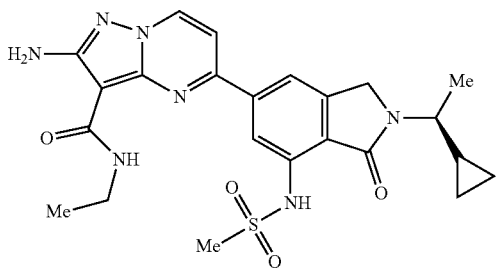 [SMILES: CCNC(=O)c1c(N)nn2ccc(-c3cc4c(c(NS(C)(=O)=O)c3)C(=O)N([C@@H](C)C3CC3)C4)nc12]

The title compound was synthesized in similar fashion to example 72. ¹H NMR (400 MHz, DMSO-d₆) δ 9.59 (s, 1H), 9.00 (d, J=7.1 Hz, 1H), 8.32 (d, J=1.2 Hz, 1H), 8.08 (d, J=1.2 Hz, 1H), 7.80 (t, J=5.9 Hz, 1H), 7.58 (d, J=7.2 Hz, 1H), 4.67 (s, 2H), 3.58-3.48 (m, 1H), 3.46-3.34 (m, 2H), 3.29 (s, 3H), 1.31 (d, J=6.8 Hz, 3H), 1.19 (m, 4H), 0.62-0.53 (m, 1H), 0.46-0.35 (m, 2H), 0.30-0.21 (m, 1H). ESI MS [M+H]⁺ for C₂₃H₂₇N₇O₄S, calcd 498.2, found 498.1.

Example 75: 2-Amino-5-{2-[(1S)-1-cyclopropylethyl]-7-methanesulfonamido-1-oxo-2,3-dihydro-1H-isoindol-5-yl}-N-(propan-2-yl)pyrazolo[1,5-a]pyrimidine-3-carboxamide

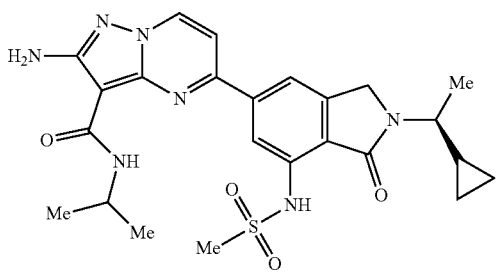 [SMILES: CC(C)NC(=O)c1c(N)nn2ccc(-c3cc4c(c(NS(C)(=O)=O)c3)C(=O)N([C@@H](C)C3CC3)C4)nc12]

The title compound was synthesized in similar fashion to example 72. ¹H NMR (400 MHz, DMSO-d₆) δ 9.65 (s, 1H), 9.00 (d, J=7.1 Hz, 1H), 8.23 (d, J=1.2 Hz, 1H), 8.03 (d, J=1.2 Hz, 1H), 7.55 (dd, J=7.6, 3.6 Hz, 2H), 4.67 (s, 2H), 4.24-4.04 (m, 1H), 3.62-3.45 (m, 1H), 1.31 (d, J=6.8 Hz, 3H), 1.24 (d, J=6.6 Hz, 6H), 1.20-1.09 (m, 1H), 0.63-0.51 (m, 1H), 0.47-0.33 (m, 2H), 0.30-0.19 (m, 1H). ESI MS [M+H]⁺ for C₂₄H₂₉N₇O₄S, calcd 512.2, found 512.1.

Example 76: 5-{2-[(S)-1-Cyclopropylethyl]-7-(methylsulfonylamino)-5-isoindolinoyl}-2-amino-1,4,7a-triaza-3-indenecarboxamide

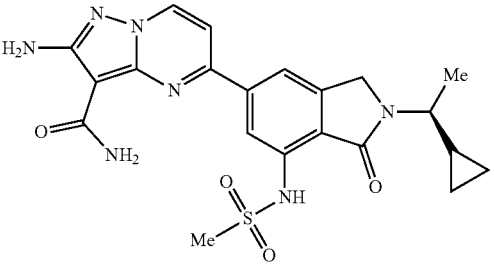 [SMILES: C[C@@H](C1CC1)N1Cc2cc(-c3ccn4nc(N)c(C(N)=O)c4n3)cc(NS(C)(=O)=O)c2C1=O]

The title compound was prepared in a similar manner to examples 39 and 72. ¹H NMR (400 MHz, DMSO-d₆) δ 9.57 (s, 1H), 8.99 (d, J=7.1 Hz, 1H), 8.4 (s, 1H), 8.10 (s, 1H), 7.53 (d, J=7.1 Hz, 1H), 7.44 (s, 1H), 7.31 (s, 1H), 6.59 (s, 2H), 4.67 (s, 2H), 3.58-3.49 (m, 1H), 1.30 (d, J=6.8 Hz, 3H), 1.22-1.10 (m, 1H), 0.61-0.52 (m, 1H), 0.45-0.34 (m, 2H), 0.28-0.21 (m, 1H). ESI MS [M+H]⁺ for C₂₁H₂₃N₇O₄S, calcd 470.2, found 470.0.

Example 77: 2-[(S)-1-Cyclopropylethyl]-5-(2-amino-3-{(1-spiro[2.2]pentylamino)carbonyl}-1,4,7a-triaza-5-indenyl)-7-(methylsulfonylamino)-1-isoindolinone

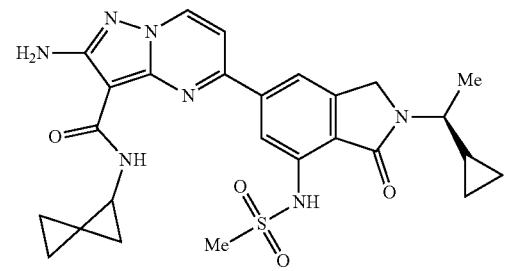 [SMILES: C[C@@H](C1CC1)N1Cc2cc(-c3ccn4nc(N)c(C(=O)NC5CC56CC6)c4n3)cc(NS(C)(=O)=O)c2C1=O]

The title compound was prepared in a similar manner to example 72. ¹H NMR (400 MHz, DMSO-d₆) δ 9.62 (s, 1H), 8.99 (d, J=7.1 Hz, 1H), 8.11 (d, J=1.2 Hz, 1H), 8.02 (dd, J=0.7, 1.3 Hz, 1H), 7.80 (d, J=4.4 Hz, 1H), 7.51 (d, J=7.2 Hz, 1H), 6.59 (br, 2H), 4.67 (s, 2H), 3.60-3.48 (m, 1H), 3.26 (s, 3H), 3.19 (dt, J=3.8, 7.2 Hz, 1H), 1.30 (m, 4H), 1.17 (ddt, J=4.5, 8.1, 13.1 Hz, 1H), 1.07-0.94 (m, 2H), 0.92-0.80 (m, 3H), 0.63-0.52 (m, 1H), 0.41 (m, 2H), 0.30-0.22 (m, 1H). ESI MS [M+H]⁺ for C₂₆H₂₉N₇O₄S, calcd 536.2, found 536.1.

Example 78: 2-Amino-5-{2-[(1S)-1-cyclopropyl-ethyl]-7-methanesulfonamido-1-oxo-2,3-dihydro-1H-isoindol-5-yl}-N-(oxetan-3-yl)pyrazolo[1,5-a]pyrimidine-3-carboxamide

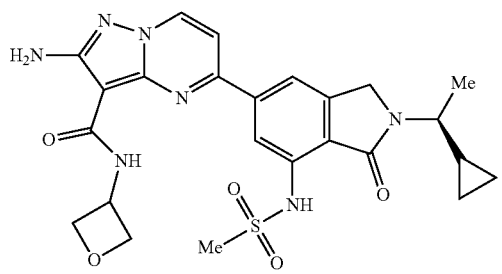 [SMILES: C[C@@H](C1CC1)N1Cc2cc(-c3ccn4nc(N)c(C(=O)NC5COC5)c4n3)cc(NS(C)(=O)=O)c2C1=O]

The title compound was prepared in a similar manner to example 72. $^1$H NMR (400 MHz, DMSO-d$_6$) δ 9.66 (s, 1H), 9.02 (d, J=7.1, 0.6 Hz, 1H), 8.27 (s, 1H), 8.16-8.05 (m, 2H), 7.60 (d, J=7.2 Hz, 1H), 6.60 (s, 2H), 5.10 (q, J=7.2 Hz, 1H), 4.79 (t, J=7.1 Hz, 2H), 4.70-4.62 (m, 4H), 3.62-3.46 (m, 1H), 3.31 (s, 3H), 1.32 (d, J=6.8 Hz, 3H), 1.24-1.14 (m, 1H), 0.66-0.51 (m, 1H), 0.48-0.33 (m, 2H), 0.31-0.19 (m, 1H). ESI MS [M+H]$^+$ for C$_{24}$H$_{28}$N$_7$O$_5$S, calcd 526.2, found 526.2.

Example 79: 2-Amino-5-{2-[(1S)-1-cyclopropyl-ethyl]-7-methanesulfonamido-1-oxo-2,3-dihydro-1H-isoindol-5-yl}-N-(3-methyloxetan-3-yl)pyrazolo[1,5-a]pyrimidine-3-carboxamide

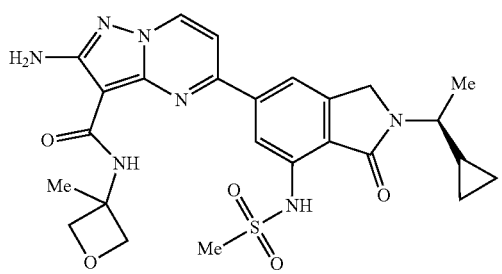 [SMILES: C[C@@H](C1CC1)N1Cc2cc(-c3ccn4nc(N)c(C(=O)NC5(C)COC5)c4n3)cc(NS(C)(=O)=O)c2C1=O]

The title compound was prepared in a similar manner to example 72. $^1$H NMR (400 MHz, DMSO-d$_6$) δ 9.65 (s, 1H), 9.04 (d, J=7.1 Hz, 1H), 8.27 (s, 1H), 8.10 (s, 1H), 8.05 (s, 1H), 7.61 (d, J=7.2 Hz, 1H), 6.62 (s, 2H), 4.80 (d, J=6.3 Hz, 2H), 4.69 (s, 2H), 4.45 (d, J=6.4 Hz, 2H), 3.65-3.46 (m, 1H), 3.31 (s, 3H), 1.69 (s, 3H), 1.34 (d, J=6.8 Hz, 3H), 1.29-1.12 (m, 1H), 0.69-0.52 (m, 1H), 0.51-0.34 (m, 2H), 0.33-0.19 (m, 1H). ESI MS [M+H]$^+$ for C$_{25}$H$_{30}$N$_7$P$_5$S, calcd 540.2, found 540.2.

Example 80: 2-Amino-N-(3-cyanooxetan-3-yl)-5-{2-[(1S)-1-cyclopropylethyl]-7-methanesulfona-mido-1-oxo-2,3-dihydro-1H-isoindol-5-yl}pyrazolo[1,5-a]pyrimidine-3-carboxamide

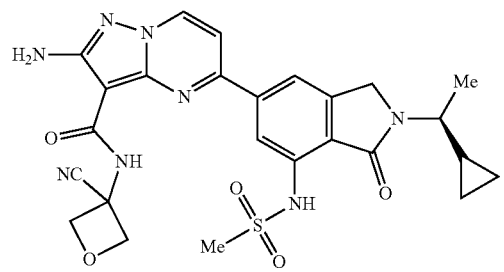 [SMILES: C[C@@H](C1CC1)N1Cc2cc(-c3ccn4nc(N)c(C(=O)NC5(C#N)COC5)c4n3)cc(NS(C)(=O)=O)c2C1=O]

The title compound was prepared in a similar manner to example 72. $^1$H NMR (400 MHz, DMSO-d$_6$) δ 9.66 (s, 1H), 9.04 (d, J=7.1 Hz, 1H), 8.65 (s, 1H), 8.27 (s, 1H), 8.19 (s, 1H), 7.66 (d, J=7.2 Hz, 1H), 6.65 (s, 2H), 4.97 (d, J=7.5 Hz, 2H), 4.84 (d, 2H), 4.67 (s, 2H), 3.59-3.47 (m, 1H), 3.36 (s, 3H), 1.32 (d, J=6.8 Hz, 3H), 1.26-1.09 (m, 1H), 0.66-0.51 (m, 1H), 0.50-0.32 (m, 2H), 0.32-0.14 (m, 1H). ESI MS [M+H]$^+$ for C$_{25}$H$_{27}$N$_8$O$_5$S, calcd 551.2, found 551.2.

Example 81: 2-Amino-N-(1-cyanocyclobutyl)-5-{2-[(1S)-1-cyclopropylethyl]-7-methanesulfonamido-1-oxo-2,3-dihydro-1H-isoindol-5-yl}pyrazolo[1,5-a]pyrimidine-3-carboxamide

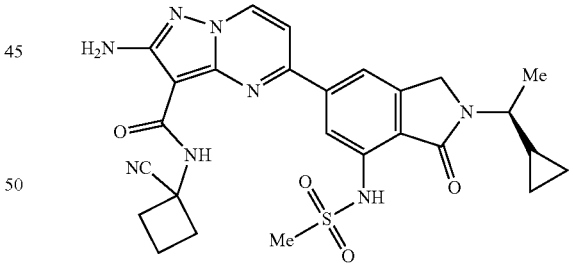

The title compound was prepared in a similar manner to example 72. $^1$H NMR (400 MHz, DMSO-d$_6$) δ 9.68 (s, 1H), 9.07 (d, J=7.1 Hz, 1H), 8.23 (s, 1H), 8.20 (s, 1H), 8.13 (s, 1H), 7.63 (d, J=7.2 Hz, 1H), 6.66 (s, 2H), 4.69 (s, 2H), 3.61-3.48 (m, 1H), 3.32 (s, 3H), 2.82-2.71 (m, 2H), 2.60-2.48 (m, 2H), 2.17-2.03 (m, 2H), 1.34 (d, J=6.8 Hz, 3H), 1.27-1.13 (m, 1H), 0.64-0.54 (m, 1H), 0.51-0.36 (m, 2H), 0.34-0.21 (m, 1H). ESI MS [M+H]$^+$ for C$_{26}$H$_{29}$N$_8$O$_4$S, calcd 549.2, found 549.2.

Example 82: 2-Amino-5-{2-[(1S)-1-cyclopropyl-ethyl]-7-methanesulfonamido-1-oxo-2,3-dihydro-1H-isoindol-5-yl}-N-[trans-3-hydroxy-3-methylcyclobutyl]pyrazolo[1,5-a]pyrimidine-3-carboxamide

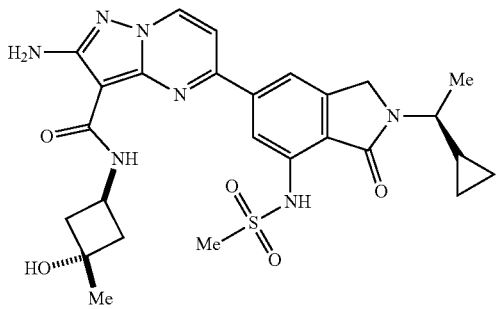

The title compound was prepared in a similar manner to example 72. ¹H NMR (400 MHz, DMSO-d₆) δ 9.69 (s, 1H), 9.03 (d, J=7.1 Hz, 1H), 8.19 (s, 1H), 8.07 (s, 1H), 7.78 (d, J=7.6 Hz, 1H), 7.56 (d, J=7.2 Hz, 1H), 6.63 (s, 2H), 4.95 (s, 1H), 4.70 (s, 2H), 4.09 (q, J=7.9 Hz, 1H), 3.56 (dd, J=9.2, 6.7 Hz, 1H), 3.37 (s, 3H), 2.45-2.36 (m, 2H), 2.14-2.04 (m, 2H), 1.34 (d, J=6.8 Hz, 3H), 1.29 (s, 3H), 1.25-1.12 (m, 1H), 0.64-0.55 (m, 1H), 0.49-0.38 (m, 2H), 0.32-0.23 (m, 1H). ESI MS [M+H]⁺ for C₂₆H₃₂N₇O₅S; calcd 554.2, found 554.1.

Example 83: 2-Amino-5-{2-[(1S)-1-cyclopropyl-ethyl]-7-methanesulfonamido-1-oxo-2,3-dihydro-1H-isoindol-5-yl}-N-[trans-3-hydroxy-1-methylcyclobutyl]pyrazolo[1,5-a]pyrimidine-3-carboxamide

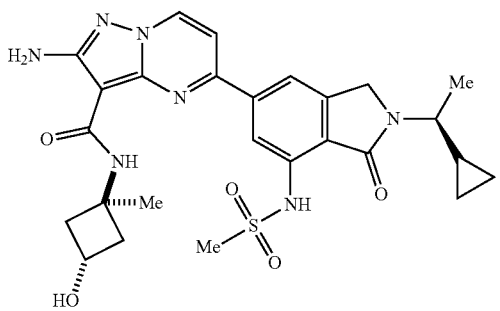

The title compound was prepared in a similar manner to example 72. ¹H NMR (400 MHz, DMSO-d₆) δ 9.67 (s, 1H), 9.02 (d, J=7.1 Hz, 1H), 8.15 (s, 1H), 8.03 (s, 1H), 7.76 (s, 1H), 7.53 (d, J=7.2 Hz, 1H), 6.61 (s, 2H), 5.01 (d, J=5.8 Hz, 1H), 4.69 (s, 2H), 4.21 (q, J=6.6 Hz, 1H), 3.56 (dd, J=9.2, 6.8 Hz, 1H), 3.28 (s, 3H), 2.75-2.65 (m, 2H), 1.99-1.87 (m, 2H), 1.54 (s, 3H), 1.34 (d, J=6.8 Hz, 3H), 1.26-1.13 (m, 1H), 0.64-0.53 (m, 1H), 0.50-0.34 (m, 2H), 0.32-0.22 (m, 1H). ESI MS [M+H]⁺ for C₂₆H₃₂N₇O₅S; calcd 554.2, found 554.1.

Example 84: 2-Amino-5-{2-[(1S)-1-cyclopropyl-ethyl]-7-methanesulfonamido-1-oxo-2,3-dihydro-1H-isoindol-5-yl}-N-[trans-3-methoxycyclobutyl]pyrazolo[1,5-a]pyrimidine-3-carboxamide

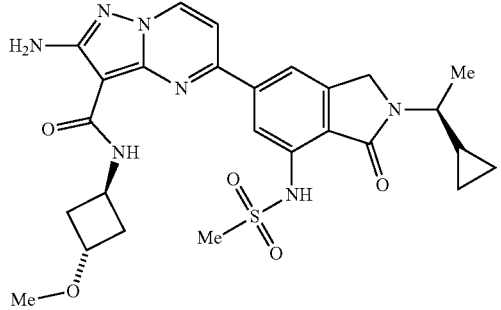 [SMILES: CO[C@H]1C[C@H](NC(=O)c2c(N)nn3ccc(-c4cc5c(c(NS(C)(=O)=O)c4)C(=O)N([C@@H](C)C4CC4)C5)nc23)C1]

The title compound was prepared in a similar manner to example 72. ¹H NMR (400 MHz, DMSO-d₆) δ 9.68 (s, 1H), 9.03 (d, J=7.1 Hz, 1H), 8.30 (s, 1H), 8.09 (s, 1H), 7.89 (s, 1H), 7.59 (d, J=7.2 Hz, 1H), 6.62 (s, 2H), 4.70 (s, 2H), 4.59 (q, J=7.4 Hz, 1H), 4.07-3.99 (m, 1H), 3.64-3.51 (m, 1H), 3.30 (s, 3H), 3.18 (s, 3H), 2.32 (dd, J=7.4, 4.9 Hz, 4H), 1.34 (d, J=6.8 Hz, 3H), 1.28-1.13 (m, 1H), 0.68-0.55 (m, 1H), 0.54-0.34 (m, 2H), 0.31-0.22 (m, 1H). ESI MS [M+H]⁺ for C₂₆H₃₂N₇O₅S, calcd 554.2, found 554.2.

Example 85: 2-Amino-5-{2-[(1S)-1-cyclopropyl-ethyl]-7-methanesulfonamido-1-oxo-2,3-dihydro-1H-isoindol-5-yl}-N-{[trans-3-hydroxycyclobutyl]methyl}pyrazolo[1,5-a]pyrimidine-3-carboxamide

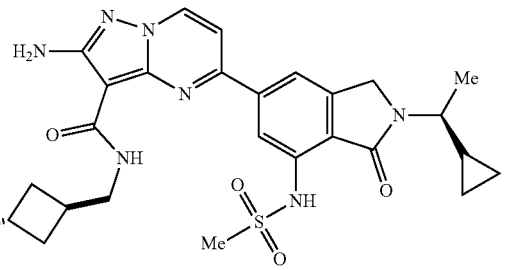

The title compound was prepared in a similar manner to example 72. ¹H NMR (400 MHz, DMSO-d₆) δ 9.63 (s, 1H), 9.03 (d, J=7.1 Hz, 1H), 8.30 (s, 1H), 8.10 (s, 1H), 7.92 (t, J=6.0 Hz, 1H), 7.60 (d, J=7.2 Hz, 1H), 6.61 (s, 2H), 4.99-4.93 (m, 1H), 4.69 (s, 2H), 4.30-4.22 (m, 1H), 3.61-3.50 (m, 1H), 3.46-3.39 (m, 2H), 3.31 (s, 3H), 2.47-2.34 (m, 1H), 2.10-2.00 (m, 2H), 1.97-1.85 (m, 2H), 1.34 (d, J=6.8 Hz, 3H), 1.26-1.12 (m, 1H), 0.64-0.55 (m, 1H), 0.50-0.37 (m, 2H), 0.31-0.23 (m, 1H). ESI MS [M+H]⁺ for C₂₆H₃₂N₇O₅S; calcd 554.2, found 554.1.

Example 86: 2-Amino-5-{2-[(1S)-1-cyclopropyl-ethyl]-7-methanesulfonamido-1-oxo-2,3-dihydro-1H-isoindol-5-yl}-N-[(1R,3R)-3-hydroxycyclopentyl]pyrazolo[1,5-a]pyrimidine-3-carboxamide

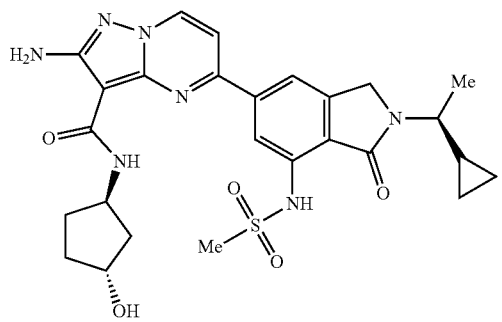 [SMILES: C[C@@H](C1CC1)N1Cc2cc(-c3ccn4nc(N)c(C(=O)N[C@@H]5CC[C@@H](O)C5)c4n3)cc(NS(C)(=O)=O)c2C1=O]

The title compound was prepared in a similar manner to example 72. $^1$H NMR (400 MHz, DMSO-d$_6$) δ 9.67 (s, 1H), 9.02 (d, J=7.1 Hz, 1H), 8.21 (d, J=1.2 Hz, 1H), 8.04 (d, J=1.2 Hz, 1H), 7.66 (d, J=8.0 Hz, 1H), 7.56 (d, J=7.2 Hz, 1H), 6.62 (s, 2H), 4.69 (s, 2H), 4.53 (h, J=7.6 Hz, 1H), 4.28-4.23 (m, 1H), 3.61-3.51 (m, 1H), 3.27 (s, 3H), 2.18-1.89 (m, 3H), 1.72 (ddd, J=13.0, 8.6, 5.9 Hz, 1H), 1.57-1.46 (m, 2H), 1.34 (d, J=6.8 Hz, 3H), 1.24-1.13 (m, 1H), 0.65-0.53 (m, 1H), 0.48-0.35 (m, 2H), 0.31-0.24 (m, 1H). ESI MS [M+H]$^+$ for C$_{26}$H$_{32}$N$_7$O$_5$S, calcd 554.2, found 554.2.

Example 87: 2-Amino-N-cyclopropyl-5-{2-[(1S)-1-cyclopropylethyl]-7-methanesulfonamido-1-oxo-2,3-dihydro-1H-isoindol-5-yl}pyrazolo[1,5-a]pyrimidine-3-carboxamide

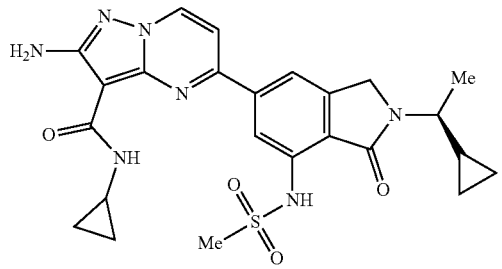 [SMILES: C[C@@H](C1CC1)N1Cc2cc(-c3ccn4nc(N)c(C(=O)NC5CC5)c4n3)cc(NS(C)(=O)=O)c2C1=O]

The title compound was prepared in a similar manner to example 72. $^1$H NMR (400 MHz, DMSO-d$_6$) δ 9.67 (s, 1H), 9.02 (d, J=7.1 Hz, 1H), 8.22-8.18 (m, 1H), 8.07-8.01 (m, 1H), 7.71 (d, J=3.6 Hz, 1H), 7.57 (d, J=7.2 Hz, 1H), 6.64 (s, 2H), 4.70 (s, 2H), 3.56 (dt, J=9.3, 6.8 Hz, 1H), 3.33 (s, 3H), 2.90-2.76 (m, 1H), 1.34 (d, J=6.8 Hz, 3H), 1.28-1.13 (m, 1H), 0.80-0.72 (m, 2H), 0.70-0.64 (m, 2H), 0.63-0.53 (m, 1H), 0.50-0.36 (m, 2H), 0.33-0.21 (m, 1H). ESI MS [M+H]$^+$ for C$_{24}$H$_{28}$N$_7$O$_4$S, calcd 510.2, found 510.2.

Example 88: 2-Amino-5-{2-[(1S)-1-cyclopropyl-ethyl]-7-methanesulfonamido-1-oxo-2,3-dihydro-1H-isoindol-5-yl}-N-[(3R,4S)-4-hydroxyoxolan-3-yl]pyrazolo[1,5-a]pyrimidine-3-carboxamide

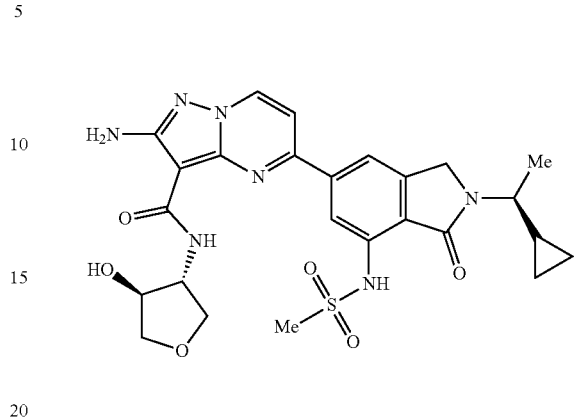

The title compound was prepared in a similar manner to example 72. $^1$H NMR (400 MHz, DMSO-d$_6$) δ 9.68 (s, 1H), 9.03 (d, J=7.1 Hz, 1H), 8.07 (dd, J=19.5, 1.2 Hz, 2H), 7.86 (d, J=7.4 Hz, 1H), 7.54 (d, J=7.2 Hz, 1H), 6.62 (s, 2H), 4.67 (s, 2H), 4.32-4.24 (m, 2H), 3.99 (ddd, J=13.1, 9.3, 4.8 Hz, 2H), 3.73-3.70 (m, 1H), 3.60-3.55 (m, 2H), 3.31 (s, 3H), 1.34 (d, J=6.8 Hz, 3H), 1.24-1.14 (m, 1H), 0.64-0.54 (m, 1H), 0.49-0.37 (m, 2H), 0.31-0.23 (m, 1H). ESI MS [M+H]$^+$ for C$_{25}$H$_{30}$N$_7$O$_6$S, calcd 556.2, found 556.2.

Example 89: 2-Amino-5-{2-[(1S)-1-cyclopropyl-ethyl]-7-methanesulfonamido-1-oxo-2,3-dihydro-1H-isoindol-5-yl}-N-[cis-4-hydroxy-4-methylcyclohexyl]pyrazolo[1,5-a]pyrimidine-3-carboxamide

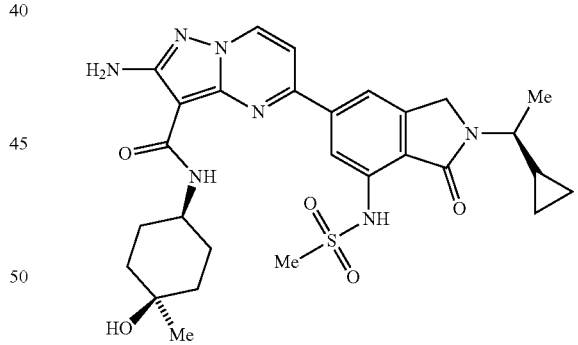

The title compound was prepared in a similar manner to example 72. $^1$H NMR (400 MHz, DMSO-d$_6$) δ 9.64 (s, 1H), 9.02 (d, J=7.1 Hz, 1H), 8.20-8.13 (m, 1H), 8.07-7.99 (m, 1H), 7.72 (d, J=7.8 Hz, 1H), 7.54 (d, J=7.1 Hz, 1H), 6.63 (s, 2H), 4.67 (s, 2H), 3.94 (s, 1H), 3.66-3.52 (m, 1H), 3.27 (s, 3H), 1.95-1.81 (m, 2H), 1.67-1.42 (m, 6H), 1.33 (d, J=6.8 Hz, 3H), 1.28-1.16 (m, 1H), 1.14 (s, 3H), 0.65-0.55 (m, 1H), 0.53-0.37 (m, 2H), 0.34-0.23 (m, 1H). ESI MS [M+H]$^+$ for C$_{28}$H$_{36}$N$_7$O$_5$S, calcd 582.2, found 582.2.

Example 90: 2-Amino-5-{2-[(1S)-1-cyclopropyl-ethyl]-7-methanesulfonamido-1-oxo-2,3-dihydro-1H-isoindol-5-yl}-N-[cis-4-hydroxy-4-(trifluoromethyl)cyclohexyl]pyrazolo[1,5-a]pyrimidine-3-carboxamide

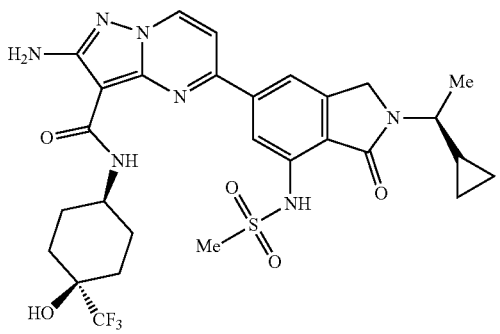 [SMILES: C[C@@H](C1CC1)N1Cc2cc(-c3ccn4nc(N)c(C(=O)N[C@H]5CC[C@](O)(C(F)(F)F)CC5)c4n3)cc(NS(C)(=O)=O)c2C1=O]

The title compound was synthesized in similar fashion to 72. $^1$H NMR (400 MHz, DMSO-d$_6$) δ 9.66 (s, 1H), 9.00 (d, J=7.1 Hz, 1H), 8.15 (d, J=1.2 Hz, 1H), 7.98 (d, J=1.2 Hz, 1H), 7.52 (dd, J=7.5, 3.4 Hz, 2H), 4.66 (s, 2H), 3.92-3.76 (m, 1H), 3.64-3.48 (m, 1H), 3.32 (s, 3H), 1.87 (d, J=10.9 Hz, 2H), 1.79 (d, J=10.5 Hz, 2H), 1.73-1.57 (m, 4H), 1.32 (d, J=6.8 Hz, 3H), 1.21-1.11 (m, 1H), 0.57 (m, 1H), 0.41 (m, 2H), 0.31-0.18 (m, 1H). ESI MS [M–H]$^-$ for C$_{28}$H$_{32}$F$_3$N$_7$O$_5$S, calcd 636.2, found 636.1.

Example 91: 2-Amino-5-{2-[(1S)-1-cyclopropyl-ethyl]-7-methanesulfonamido-1-oxo-2,3-dihydro-1H-isoindol-5-yl}-N-[trans-4-(2-hydroxypropan-2-yl)cyclohexyl]pyrazolo[1,5-a]pyrimidine-3-carboxamide

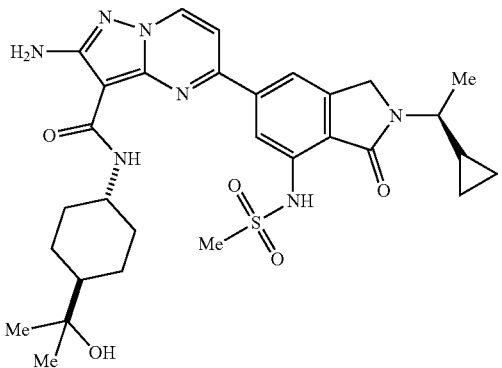

The title compound was prepared in a similar manner to example 72. $^1$H NMR (400 MHz, DMSO-d$_6$) δ 9.69 (s, 1H), 9.02 (d, J=7.1 Hz, 1H), 8.25 (s, 1H), 8.05 (s, 1H), 7.61-7.50 (m, 2H), 6.63 (s, 2H), 4.69 (s, 2H), 4.09 (s, 1H), 3.83-3.69 (m, 1H), 3.61-3.49 (m, 1H), 3.28 (s, 3H), 2.53-2.49 (m, 1H), 2.03-1.94 (m, 2H), 1.90-1.80 (m, 2H), 1.48-0.99 (m, 13H), 0.64-0.55 (m, 1H), 0.50-0.36 (m, 2H), 0.33-0.22 (m, 1H). ESI MS [M+H]$^+$ for C$_{30}$H$_{40}$N$_7$O$_5$S; calcd 610.3, found 610.2.

Example 92: 2-Amino-5-{2-[(1S)-1-cyclopropyl-ethyl]-7-methanesulfonamido-1-oxo-2,3-dihydro-1H-isoindol-5-yl}-N-[trans-4-(1-hydroxycyclopropyl)cyclohexyl]pyrazolo[1,5-a]pyrimidine-3-carboxamide

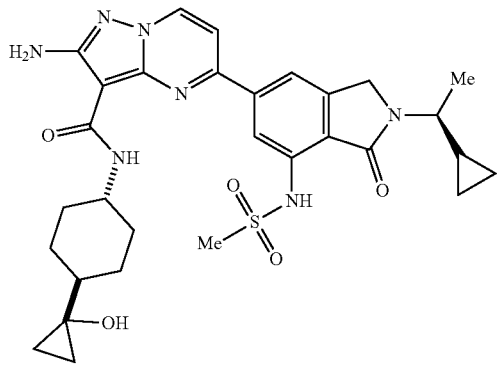

The title compound was prepared in a similar manner to example 72. $^1$H NMR (400 MHz, DMSO-d$_6$) δ 9.67 (s, 1H), 9.02 (d, J=7.1 Hz, 1H), 8.24 (s, 1H), 8.05 (s, 1H), 7.61-7.48 (m, 2H), 6.62 (s, 2H), 4.91 (s, 1H), 4.69 (s, 2H), 3.84-3.69 (m, 1H), 3.61-3.50 (m, 1H), 3.25 (s, 3H), 2.03-1.92 (m, 2H), 1.80-1.69 (m, 2H), 1.49-1.26 (m, 7H), 1.26-1.13 (m, 1H), 1.07-0.93 (m, 1H), 0.63-0.54 (m, 1H), 0.53-0.47 (m, 2H), 0.47-0.37 (m, 1H), 0.37-0.32 (m, 2H), 0.32-0.23 (m, 1H). ESI MS [M+H]$^+$ for C$_{30}$H$_{38}$N$_7$O$_5$S; calcd 608.3, found 608.2.

Example 93: 2-Amino-5-{2-[(1S)-1-cyclopropyl-ethyl]-7-methanesulfonamido-1-oxo-2,3-dihydro-1H-isoindol-5-yl}-N-[(2R)-1-hydroxypropan-2-yl]pyrazolo[1,5-a]pyrimidine-3-carboxamide

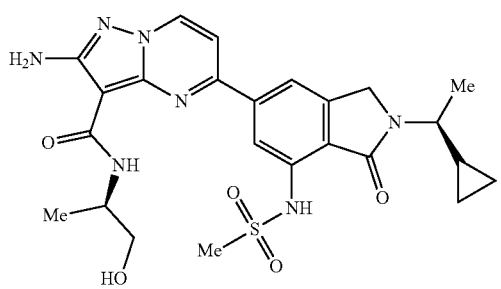 [SMILES: C[C@H](CO)NC(=O)c1c(N)nn2ccc(-c3cc4c(c(NS(C)(=O)=O)c3)C(=O)N([C@@H](C)C3CC3)C4)nc12]

The title compound was prepared in a similar manner to example 72. $^1$H NMR (400 MHz, DMSO-d$_6$) δ 9.66 (s, 1H), 9.01 (d, J=7.1 Hz, 1H), 8.21 (s, 1H), 8.13 (s, 1H), 7.95 (d, J=8.3 Hz, 1H), 7.56 (d, J=7.2 Hz, 1H), 6.62 (s, 2H), 4.68 (s, 2H), 4.16-4.05 (m, 1H), 3.60-3.46 (m, 3H), 3.32 (s, 3H), 1.34 (d, J=6.8 Hz, 3H), 1.23 (d, J=6.7 Hz, 3H), 1.21-1.09 (m, 1H), 0.67-0.54 (m, 1H), 0.50-0.35 (m, 2H), 0.33-0.22 (m, 1H). ESI MS [M+H]$^+$ for C$_{24}$H$_{30}$N$_7$O$_5$S, calcd 528.2, found 528.2.

Example 94: 2-Amino-5-{2-[(1S)-1-cyclopropyl-ethyl]-7-methanesulfonamido-1-oxo-2,3-dihydro-1H-isoindol-5-yl}-N-(1-hydroxy-2-methylpropan-2-yl)pyrazolo[1,5-a]pyrimidine-3-carboxamide

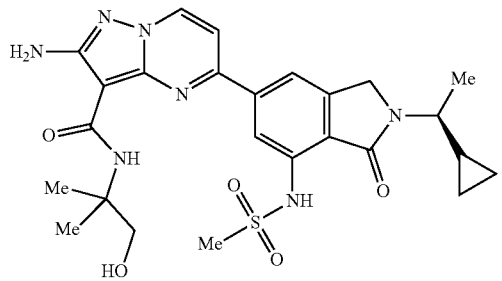 [SMILES: C[C@@H](C1CC1)N1Cc2cc(-c3ccn4nc(N)c(C(=O)NC(C)(C)CO)c4n3)cc(NS(C)(=O)=O)c2C1=O]

The title compound was prepared in a similar manner to example 72. ¹H NMR (400 MHz, DMSO-d₆) δ 9.65 (s, 1H), 9.00 (d, J=7.1 Hz, 1H), 8.25 (s, 1H), 8.03 (s, 1H), 8.01 (s, 1H), 7.50 (d, J=7.2 Hz, 1H), 6.60 (s, 2H), 4.68 (s, 2H), 3.61-3.49 (m, 3H), 3.31 (s, 3H), 1.41 (s, 6H), 1.34 (d, J=6.8 Hz, 3H), 1.25-1.12 (m, 1H), 0.67-0.55 (m, 1H), 0.51-0.36 (m, 2H), 0.34-0.24 (m, 1H). ESI MS [M+H]⁺ for $C_{25}H_{32}N_7O_5S$, calcd 542.2, found 542.2.

Example 95: 2-Amino-5-{2-[(1S)-1-cyclopropyl-ethyl]-7-methanesulfonamido-1-oxo-2,3-dihydro-1H-isoindol-5-yl}-N-(3-hydroxy-3-methylbutyl)pyrazolo[1,5-a]pyrimidine-3-carboxamide

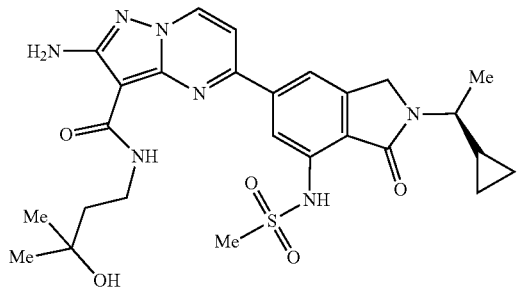 [SMILES: C[C@@H](C1CC1)N1Cc2cc(-c3ccn4nc(N)c(C(=O)NCCC(C)(C)O)c4n3)cc(NS(C)(=O)=O)c2C1=O]

The title compound was prepared in a similar manner to example 72. ¹H NMR (400 MHz, CDCl₃) δ 9.64 (s, 1H), 8.49 (d, J=7.1 Hz, 1H), 8.41 (s, 1H), 8.13-8.04 (m, 1H), 7.80 (s, 1H), 7.20 (d, J=7.1 Hz, 1H), 5.77 (s, 2H), 4.74-4.42 (m, 2H), 3.78-3.58 (m, 3H), 3.13 (s, 3H), 2.42 (s, 1H), 1.90 (t, J=6.8 Hz, 2H), 1.40 (d, J=6.8 Hz, 3H), 1.32 (s, 6H), 1.11-0.98 (m, 1H), 0.74-0.64 (m, 1H), 0.55-0.33 (m, 3H). ESI MS [M+H]⁺ for $C_{26}H_{34}N_7O_5S$; calcd 556.2, found 556.2.

Example 96: 2-Amino-5-{2-[(1S)-1-cyclopropyl-ethyl]-7-methanesulfonamido-1-oxo-2,3-dihydro-1H-isoindol-5-yl}-N-[(2R)-1-hydroxy-3-methylbutan-2-yl]pyrazolo[1,5-a]pyrimidine-3-carboxamide

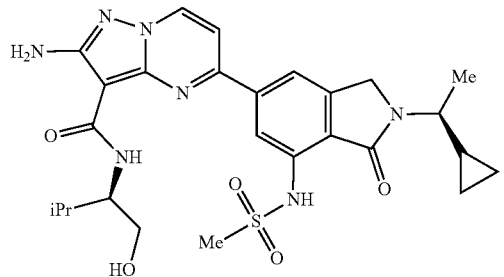 [SMILES: CC(C)[C@H](CO)NC(=O)c1c(N)nn2ccc(-c3cc4c(c(NS(C)(=O)=O)c3)C(=O)N([C@@H](C)C3CC3)C4)nc12]

The title compound was prepared in a similar manner to example 72. ¹H NMR (400 MHz, DMSO-d₆) δ 9.65 (s, 1H), 9.02 (d, J=7.1 Hz, 1H), 8.16 (s, 1H), 8.06 (s, 1H), 7.97 (d, J=9.4 Hz, 1H), 7.53 (d, J=7.2 Hz, 1H), 6.62 (s, 2H), 4.83 (t, J=5.1 Hz, 1H), 4.66 (s, 2H), 3.95-3.83 (m, 1H), 3.72-3.61 (m, 1H), 3.60-3.47 (m, 2H), 3.30 (s, 3H), 2.12-1.94 (m, 1H), 1.34 (d, J=6.8 Hz, 3H), 1.25-1.09 (m, 1H), 0.95 (dd, J=6.8, 2.5 Hz, 6H), 0.70-0.52 (m, 1H), 0.49-0.36 (m, 2H), 0.32-0.22 (m, 1H). ESI MS [M+H]⁺ for $C_{26}H_{34}N_7O_5S$, calcd 556.2, found 556.2.

Example 97: 2-Amino-N—((R)-1-cyclopropyl-2-hydroxyethyl)-5-(2-((S)-1-cyclopropylethyl)-7-(methylsulfonamido)-1-oxoisoindolin-5-yl)pyrazolo[1,5-a]pyrimidine-3-carboxamide

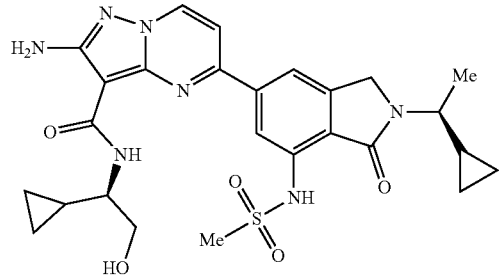 [SMILES: C[C@@H](C1CC1)N1Cc2cc(-c3ccn4nc(N)c(C(=O)N[C@@H](CO)C5CC5)c4n3)cc(NS(C)(=O)=O)c2C1=O]

The title compound was prepared in a similar manner to example 72. ¹H NMR (400 MHz, CDCl₃) δ 9.64 (s, 1H), 8.46 (d, J=7.1 Hz, 1H), 8.27 (d, J=1.2 Hz, 1H), 8.18 (d, J=7.4 Hz, 1H), 7.80 (d, J=1.2 Hz, 1H), 7.21 (d, J=7.1 Hz, 1H), 5.70 (s, 2H), 4.60 (d, J=17.5 Hz, 1H), 4.51 (d, J=17.5 Hz, 1H), 3.94-3.88 (m, 2H), 3.74-3.62 (m, 2H), 3.59-3.48 (m, 1H), 3.09 (s, 3H), 1.39 (d, J=6.8 Hz, 3H), 1.28-1.17 (m, 1H), 1.12-0.98 (m, 1H), 0.71-0.44 (m, 4H), 0.45-0.33 (m, 3H). ESI MS [M+H]⁺ for $C_{26}H_{32}N_7O_5S$, calcd 554.2, found 554.2.

Example 98: 2-Amino-5-{2-[(1S)-1-cyclopropyl-ethyl]-7-methanesulfonamido-1-oxo-2,3-dihydro-1H-isoindol-5-yl}-N-[(1R)-1-(1-methyl-1H-pyrazol-4-yl)ethyl]pyrazolo[1,5-a]pyrimidine-3-carboxamide

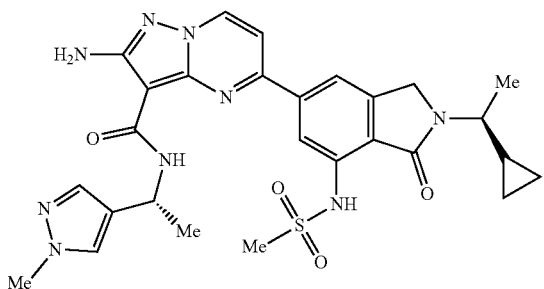 [SMILES: C[C@@H](NC(=O)c1c(N)nn2ccc(-c3cc4c(c(NS(C)(=O)=O)c3)C(=O)N([C@@H](C)C3CC3)C4)nc12)c1cnn(C)c1]

The title compound was prepare in a similar manner to example 72. $^1$H NMR (400 MHz, DMSO-$d_6$) δ 9.65 (s, 1H), 9.02 (d, J=7.1 Hz, 1H), 8.10 (s, 1H), 7.94 (s, 1H), 7.91 (d, J=8.0 Hz, 1H), 7.68 (s, 1H), 7.54 (d, J=7.1 Hz, 1H), 7.49 (s, 1H), 6.63 (s, 2H), 5.23-5.11 (m, 1H), 4.69 (s, 2H), 3.78 (s, 3H), 3.63-3.50 (m, 1H), 3.21 (s, 3H), 1.56 (d, J=6.8 Hz, 3H), 1.34 (d, J=6.8 Hz, 3H), 1.25-1.11 (m, 1H), 0.70-0.54 (m, 1H), 0.53-0.38 (m, 2H), 0.35-0.24 (m, 1H). ESI MS [M+H]$^+$ for $C_{27}H_{32}N_9O_4S$, calcd 578.2, found 578.2.

Example 99: (S)-2-Amino-5-(2-(1-cyclopropyl-ethyl)-7-(methylsulfonamido)-1-oxoisoindolin-5-yl)-N-(pyridin-3-yl)pyrazolo[1,5-a]pyrimidine-3-carboxamide Step a: EDC-HCl (0.32 g, 1.68 mmol, 1.5 equiv.) and HOBt hydrate (0.33 g, 1.68 mmol, 1.5 equiv., 20% H$_2$O by wt.) were added to a solution of the carboxylic acid (0.50 g, 1.12 mmol, 1.0 equiv.) in DMF (5.5 mL). The reaction mixture was stirred at 40° C. for 1 h. Then the resulting solution was cooled to rt. Upon addition of 50 mL of H$_2$O, the product precipitated from the mixture and was collected by filtration. The precipitate was thoroughly washed with H$_2$O and dried under high vacuum until constant weight was observed. The prepared hydroxybenzotriazole ester was used for the next step without further purification. Yield: 0.56 g (85%).

Step b: A mixture of hydroxybenzotriazole ester (80 mg, 0.14 mmol, 1 equiv.), 3-aminopyridine (64 mg, 0.68 mmol, 5 equiv.) and NMP (0.7 mL) was stirred in a sealed vial at 110° C. for 2 h. Upon complete consumption of hydroxybenzotriazole ester, the reaction was cooled to rt and diluted with H$_2$O. The formed precipitate of the product was collected by filtration and washed twice with H$_2$O. Purification by reverse phase HPLC (10 to 90% gradient of CH$_3$CN and H$_2$O with 0.1% TFA) afforded the title compound as a pale yellow solid. Yield: 32 mg (43%). $^1$H NMR (400 MHz, DMSO-$d_6$) δ 9.81 (s, 1H), 9.68 (s, 1H), 9.06 (d, J=7.1 Hz, 1H), 8.99 (s, 1H), 8.39-8.23 (m, 3H), 8.10 (s, 1H), 7.63 (d, J=7.1 Hz, 1H), 7.50 (dd, J=8.4, 4.8 Hz, 1H), 6.73 (br. s, 2H), 4.67 (s, 2H), 3.61-3.47 (m, 1H), 3.32 (s, 3H), 1.32 (d, J=6.8 Hz, 3H), 1.23-1.08 (m, 1H), 0.62-0.54 (m, 1H), 0.49-0.34 (m, 2H), 0.32-0.20 (m, 1H). ESI MS [M+H]$^+$ for $C_{26}H_{27}N_8O_4S$, calcd 547.2, found 547.1.

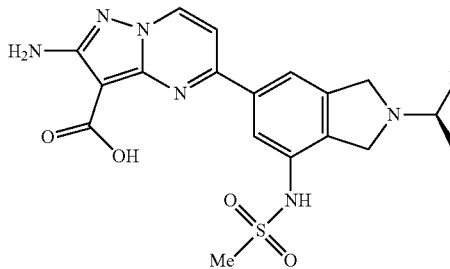

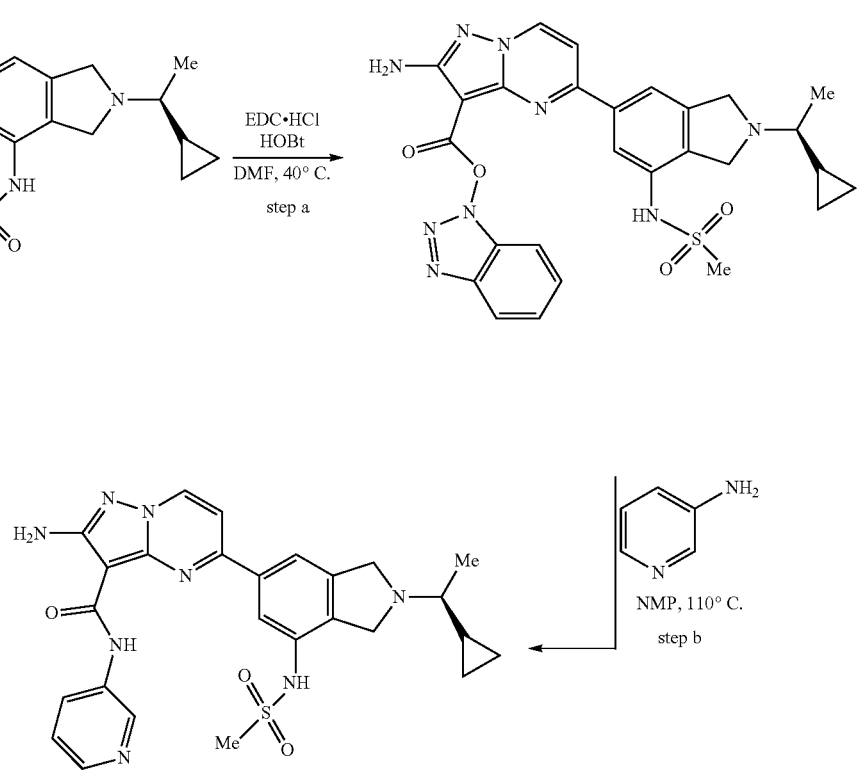

Example 100: (S)-2-Amino-5-(2-(1-cyclopropylethyl)-7-(methylsulfonamido)-1-oxoisoindolin-5-yl)-N-(pyridin-4-yl)pyrazolo[1,5-a]pyrimidine-3-carboxamide

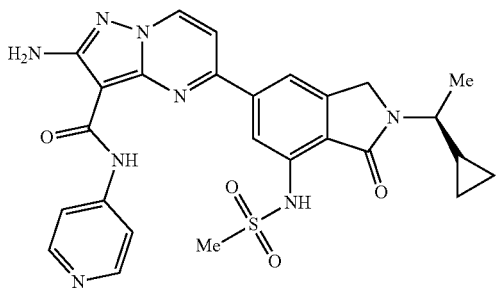 [SMILES: C[C@@H](C1CC1)N1Cc2cc(-c3ccn4nc(N)c(C(=O)Nc5ccncc5)c4n3)cc(NS(C)(=O)=O)c2C1=O]

The title compound was prepared in a similar manner to example 99. ¹H NMR (400 MHz, DMSO-$d_6$) δ 10.58 (s, 1H), 9.73 (s, 1H), 9.13 (d, J=7.1 Hz, 1H), 8.71 (d, J=6.5 Hz, 2H), 8.27 (s, 1H), 8.18 (d, J=6.5 Hz, 2H), 8.14 (s, 1H), 7.74 (d, J=7.1 Hz, 1H), 6.84 (br. s, 2H), 4.70 (s, 2H), 3.65-3.47 (m, 1H), 3.37 (s, 3H), 1.33 (d, J=6.8 Hz, 3H), 1.25-1.08 (m, 1H), 0.64-0.51 (m, 1H), 0.50-0.34 (m, 2H), 0.34-0.21 (m, 1H). ESI MS [M+H]⁺ for $C_{26}H_{27}N_8O_4S$, calcd 547.2, found 547.1.

Example 101: (S)-2-Amino-5-(2-(1-cyclopropylethyl)-7-(methylsulfonamido)-1-oxoisoindolin-5-yl)-N-(2-methylpyridin-4-yl)pyrazolo[1,5-a]pyrimidine-3-carboxamide

The title compound was prepared in a similar manner to example 99. ¹H NMR (400 MHz, DMSO-$d_6$) δ 9.88 (s, 1H), 9.72 (s, 1H), 9.11 (d, J=7.1 Hz, 1H), 8.33 (d, J=5.6 Hz, 1H), 8.26 (d, J=1.2 Hz, 1H), 8.13 (d, J=1.2 Hz, 1H), 7.71-7.61 (m, 2H), 7.53 (d, J=2.2 Hz, 1H), 6.78 (s, 2H), 4.72 (s, 2H), 3.66-3.49 (m, 1H), 3.31 (s, 3H), 2.46 (s, 3H), 1.35 (d, J=6.8 Hz, 3H), 1.28-1.08 (m, 1H), 0.67-0.53 (m, 1H), 0.51-0.35 (m, 2H), 0.37-0.22 (m, 1H). ESI MS [M+H]⁺ for $C_{27}H_{29}N_8O_4S$, calcd 561.2, found 561.2.

Example 102: (S)-2-Amino-5-(2-(1-cyclopropylethyl)-7-(methylsulfonamido)-1-oxoisoindolin-5-yl)-N-(2,6-dimethylpyridin-4-yl)pyrazolo[1,5-a]pyrimidine-3-carboxamide

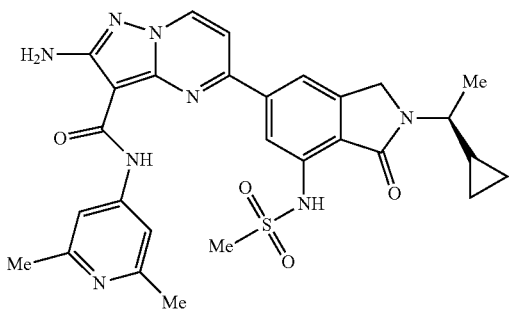 [SMILES: Cc1cc(NC(=O)c2c(N)nn3ccc(-c4cc5c(c(NS(C)(=O)=O)c4)C(=O)N([C@@H](C)C4CC4)C5)nc23)cc(C)n1]

The title compound was prepared in a similar manner to example 99. ¹H NMR (400 MHz, DMSO-$d_6$) δ 10.43 (s, 1H), 9.72 (s, 1H), 9.14 (d, J=7.1 Hz, 1H), 8.31 (d, J=1.2 Hz, 1H), 8.12 (d, J=1.2 Hz, 1H), 7.89 (s, 2H), 7.74 (d, J=7.1 Hz, 1H), 6.84 (br. s, 2H), 4.69 (s, 2H), 3.75-3.42 (m, 1H), 3.28 (s, 3H), 2.61 (s, 6H), 1.32 (d, J=6.8 Hz, 3H), 1.24-1.06 (m, 1H), 0.65-0.53 (m, 1H), 0.50-0.35 (m, 2H), 0.33-0.21 (m, 1H). ESI MS [M+H]⁺ for $C_{28}H_{31}N_8O_4S$, calcd 575.2, found 575.2.

Example 103: 2-Amino-5-{2-[(1S)-1-cyclopropylethyl]-7-methanesulfonamido-1-oxo-2,3-dihydro-1H-isoindol-5-yl}-N-[6-(2-hydroxypropan-2-yl)pyridin-3-yl]pyrazolo[1,5-a]pyrimidine-3-carboxamide

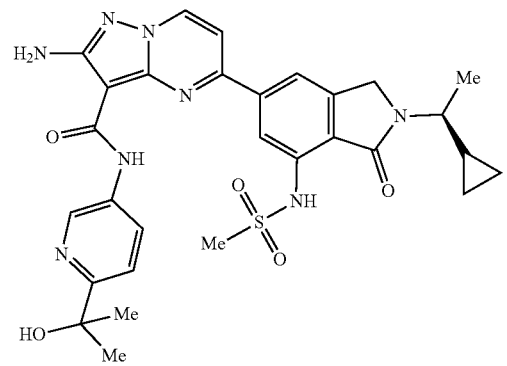 [SMILES: C[C@@H](C1CC1)N1Cc2cc(-c3ccn4nc(N)c(C(=O)Nc5ccc(C(C)(C)O)nc5)c4n3)cc(NS(C)(=O)=O)c2C1=O]

The title compound was prepared in a similar manner to example 99. ¹H NMR (400 MHz, CDCl₃) δ 10.02 (s, 1H), 9.74 (s, 1H), 9.45 (s, 1H), 8.75 (d, J=8.7 Hz, 1H), 8.58 (s, 1H), 8.40 (s, 1H), 7.79 (s, 1H), 7.73 (d, J=8.7 Hz, 1H), 7.42-7.31 (m, 1H), 4.78-4.55 (m, 2H), 3.69 (q, J=7.4, 6.9 Hz, 2H), 3.15 (s, 3H), 1.74 (s, 6H), 1.42 (d, J=6.8 Hz, 3H), 1.16-0.97 (m, 1H), 0.77-0.62 (m, 1H), 0.59-0.28 (m, 3H). ESI MS [M+H]⁺ for $C_{29}H_{33}N_8O_5S$; calcd 605.2, found 605.2.

Example 104: (S)-2-Amino-5-(2-(1-cyclopropylethyl)-7-(methylsulfonamido)-1-oxoisoindolin-5-yl)-N-phenylpyrazolo[1,5-a]pyrimidine-3-carboxamide

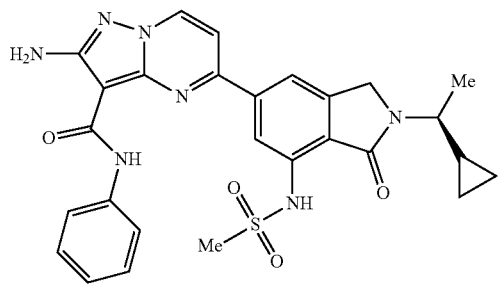 [SMILES: C[C@@H](C1CC1)N1Cc2cc(-c3ccn4nc(N)c(C(=O)Nc5ccccc5)c4n3)cc(NS(C)(=O)=O)c2C1=O]

The title compound was prepared in a similar manner to example 99. $^1$H NMR (400 MHz, CDCl$_3$) δ 9.68 (s, 1H), 9.62 (s, 1H), 8.52 (d, J=7.0 Hz, 1H), 8.25 (s, 1H), 7.80 (s, 1H), 7.72 (d, J=7.9 Hz, 2H), 7.37 (t, J=7.7 Hz, 2H), 7.27-7.22 (m, 1H), 7.12 (t, J=7.4 Hz, 1H), 4.63 (d, J=17.6 Hz, 1H), 4.53 (d, J=17.6 Hz, 1H), 3.77-3.61 (m, 1H), 3.10 (s, 3H), 1.40 (d, J=6.8 Hz, 3H), 1.13-0.98 (m, 1H), 0.73-0.66 (m, 1H), 0.58-0.30 (m, 3H). ESI MS [M+H]$^+$ for C$_{27}$H$_{28}$N$_7$O$_4$S, calcd 546.2, found 546.1.

Example 105: 2-Amino-5-{2-[(1S)-1-cyclopropylethyl]-7-methanesulfonamido-1-oxo-2,3-dihydro-1H-isoindol-5-yl}-N-[4-(hydroxymethyl)phenyl]pyrazolo[1,5-a]pyrimidine-3-carboxamide

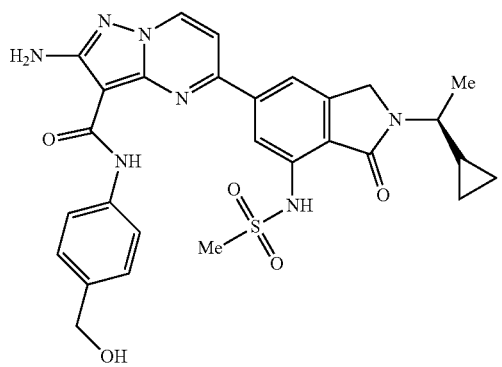 [SMILES: C[C@@H](C1CC1)N1Cc2cc(-c3ccn4nc(N)c(C(=O)Nc5ccc(CO)cc5)c4n3)cc(NS(C)(=O)=O)c2C1=O]

The title compound was prepared in a similar manner to example 99 (Step b of amide coupling was performed at 150° C. for 1 h). $^1$H NMR (400 MHz, CDCl$_3$) δ 9.71 (s, 1H), 9.70 (s, 1H), 8.54 (d, J=7.1 Hz, 1H), 8.31 (s, 1H), 7.85 (s, 1H), 7.75 (d, J=8.4 Hz, 2H), 7.38 (d, J=8.4 Hz, 2H), 7.29-7.26 (m, 1H), 4.72-4.50 (m, 4H), 3.76-3.66 (m, 1H), 3.12 (s, 3H), 1.41 (d, J=6.8 Hz, 3H), 1.15-0.97 (m, 1H), 0.76-0.61 (m, 1H), 0.58-0.33 (m, 3H). ESI MS [M+H]$^+$ for C$_{28}$H$_{30}$N$_7$O$_5$S; calcd 576.2, found 576.3.

Example 106: 2-Amino-5-{2-[(1S)-1-cyclopropylethyl]-7-methanesulfonamido-1-oxo-2,3-dihydro-1H-isoindol-5-yl}-N-[1-(2,2,2-trifluoroethyl)-1H-pyrazol-4-yl]pyrazolo[1,5-a]pyrimidine-3-carboxamide

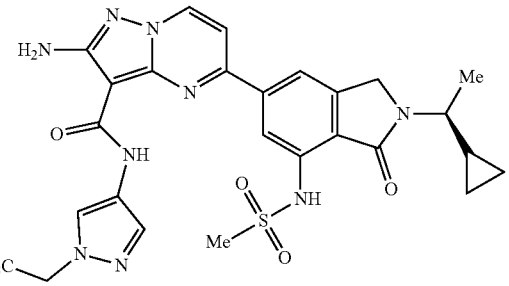

The title compound was prepared in a similar manner to example 99. $^1$H NMR (400 MHz, CDCl$_3$) δ 9.68 (s, 1H), 9.41 (s, 1H), 8.49 (d, J=7.1 Hz, 1H), 8.32 (d, J=1.2 Hz, 1H), 8.25 (s, 1H), 7.94 (s, 1H), 7.76 (s, 1H), 7.24 (d, J=7.1 Hz, 1H), 4.78-4.49 (m, 4H), 3.78-3.62 (m, 1H), 3.11 (s, 3H), 1.42 (d, J=6.9 Hz, 3H), 1.07 (ddt, J=13.2, 9.1, 4.4 Hz, 1H), 0.77-0.64 (m, 1H), 0.61-0.30 (m, 3H). $^{19}$F NMR (376 MHz, CDCl$_3$) δ −71.65 (t). ESI MS [M+H]$^+$ for C$_{26}$H$_{27}$F$_3$N$_9$O$_4$S; calcd 618.2, found 618.1.

Example 107: 2-Amino-5-{2-[(1S)-1-cyclopropylethyl]-7-methanesulfonamido-1-oxo-2,3-dihydro-1H-isoindol-5-yl}-N-(1,3-dimethyl-1H-pyrazol-4-yl)pyrazolo[1,5-a]pyrimidine-3-carboxamide

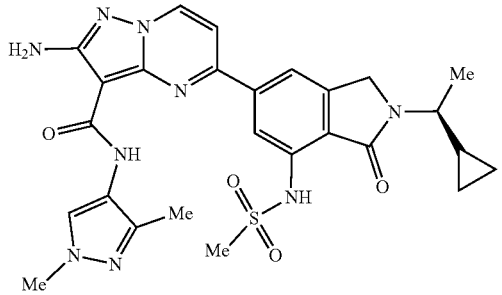 [SMILES: Cc1nn(C)cc1NC(=O)c1c(N)nn2ccc(-c3cc4c(c(NS(C)(=O)=O)c3)C(=O)N([C@@H](C)C3CC3)C4)nc12]

The title compound was prepared in a similar manner to example 99. $^1$H NMR (400 MHz, CDCl$_3$) δ 9.66 (s, 1H), 9.46 (s, 1H), 8.59 (d, J=7.1 Hz, 1H), 8.20 (d, J=1.2 Hz, 1H), 8.09 (s, 1H), 7.93 (d, J=1.1 Hz, 1H), 7.32 (d, J=7.1 Hz, 1H), 4.67-4.45 (m, 2H), 3.96 (s, 3H), 3.75-3.64 (m, 1H), 3.11 (s, 3H), 2.44 (s, 3H), 1.41 (d, J=6.8 Hz, 3H), 1.13-1.01 (m, 1H), 0.76-0.65 (m, 1H), 0.58-0.31 (m, 3H). ESI MS [M+H]$^+$ for C$_{26}$H$_{30}$N$_9$O$_4$S; calcd 564.2, found 564.3.

Example 108: 2-Amino-5-{2-[(1S)-1-cyclopropyl-ethyl]-7-methanesulfonamido-1-oxo-2,3-dihydro-1H-isoindol-5-yl}-N-(1,5-dimethyl-1H-pyrazol-4-yl)pyrazolo[1,5-a]pyrimidine-3-carboxamide

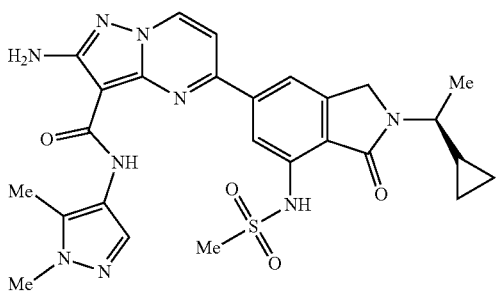 [SMILES: Cc1c(NC(=O)c2c(N)nn3ccc(-c4cc5c(c(NS(C)(=O)=O)c4)C(=O)N([C@@H](C)C4CC4)C5)nc23)cnn1C]

The title compound was prepared in a similar manner to example 99. ¹H NMR (400 MHz, CDCl₃) δ 9.60 (s, 1H), 9.22 (s, 1H), 8.61 (d, J=7.0 Hz, 1H), 8.32 (d, J=1.1 Hz, 1H), 7.95 (s, 1H), 7.77 (d, J=1.2 Hz, 1H), 7.31 (d, J=7.0 Hz, 1H), 4.70-4.48 (m, 2H), 3.94 (s, 3H), 3.75-3.63 (m, 1H), 3.08 (s, 3H), 2.36 (s, 3H), 1.39 (d, J=6.8 Hz, 3H), 1.11-0.98 (m, 1H), 0.76-0.63 (m, 1H), 0.57-0.30 (m, 3H). ESI MS [M+H]⁺ for $C_{26}H_{30}N_9O_4S$; calcd 564.2, found 564.2.

Example 109: 2-Amino-5-{2-[(1S)-1-cyclopropyl-ethyl]-7-methanesulfonamido-1-oxo-2,3-dihydro-1H-isoindol-5-yl}-N-(1-methyl-1H-1,2,4-triazol-3-yl)pyrazolo[1,5-a]pyrimidine-3-carboxamide

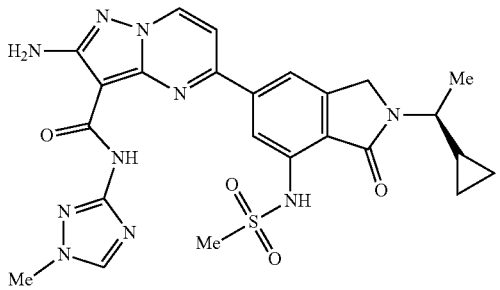 [SMILES: C[C@@H](C1CC1)N1Cc2cc(-c3ccn4nc(N)c(C(=O)Nc5ncn(C)n5)c4n3)cc(NS(C)(=O)=O)c2C1=O]

The title compound was prepared in a similar manner to example 99. ¹H NMR (400 MHz, CDCl₃) δ 10.21 (s, 1H), 9.65 (s, 1H), 8.53 (d, J=7.0 Hz, 1H), 8.33 (s, 1H), 8.13 (s, 1H), 7.91 (s, 1H), 7.31 (d, J=7.1 Hz, 1H), 4.71-4.48 (m, 2H), 3.98 (s, 3H), 3.76-3.62 (m, 1H), 3.16 (s, 3H), 1.39 (d, J=6.8 Hz, 3H), 1.11-0.99 (m, 1H), 0.75-0.61 (m, 1H), 0.57-0.30 (m, 3H). ESI MS [M+H]⁺ for $C_{24}H_{27}N_{10}O_4S$; calcd 551.2, found 551.2.

Example 110: 2-Amino-N-cyclopropyl-5-{2-[(1S)-1-cyclopropylethyl]-7-ethanesulfonamido-1-oxo-2,3-dihydro-1H-isoindol-5-yl}pyrazolo[1,5-a]pyrimidine-3-carboxamide

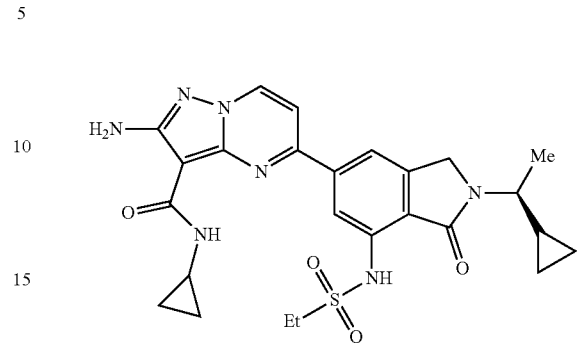

This molecule was prepared in analogous fashion to example 113 (vide infra), with replacement of 2-methoxy-ethanesulfonyl chloride with ethanesulfonyl chloride in Step a, and the final compound obtained through the same chemical steps, using cyclopropylamine for the final amide coupling. ¹H NMR (400 MHz, DMSO-d₆) δ 9.66 (s, 1H), 9.00 (d, J=7.2 Hz, 1H), 8.21 (s, 1H), 8.04 (s, 1H), 7.67 (d, J=3.7 Hz, 1H), 7.54 (d, J=7.2 Hz, 1H), 4.68 (s, 2H), 3.61-3.51 (m, 1H), 3.39 (q, J=7.3 Hz, 2H), 2.92-2.75 (m, 1H), 1.32 (d, J=6.9 Hz, 3H), 1.23 (t, J=7.3 Hz, 3H), 1.20-1.10 (m, 1H), 0.79-0.71 (m, 2H), 0.67-0.62 (m, 2H), 0.62-0.51 (m, 1H), 0.47-0.34 (m, 2H), 0.30-0.21 (m, 1H). ESI MS [M+H]⁺ for $C_{25}H_{30}N_7O_4S$, calcd 524.1, found 524.1.

Example 111: 2-Amino-5-{2-[(1S)-1-cyclopropyl-ethyl]-7-ethanesulfonamido-1-oxo-2,3-dihydro-1H-isoindol-5-yl}-N-[trans-3-hydroxy-3-methylcyclobutyl]pyrazolo[1,5-a]pyrimidine-3-carboxamide

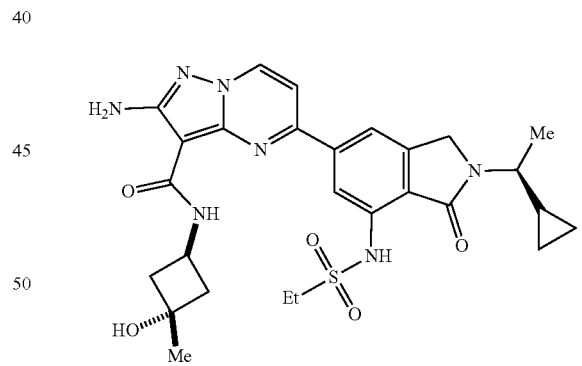

The title compound was prepared in a similar manner to example 72. ¹H NMR (400 MHz, DMSO-d₆) δ 9.67 (s, 1H), 9.02 (d, J=7.1 Hz, 1H), 8.28 (s, 1H), 8.07 (s, 1H), 7.80 (d, J=7.6 Hz, 1H), 7.55 (d, J=7.2 Hz, 1H), 6.63 (s, 2H), 4.88 (s, 1H), 4.69 (s, 2H), 4.58 (q, J=7.8 Hz, 1H), 3.57 (dd, J=9.2, 6.7 Hz, 1H), 3.40-3.32 (m, 2H), 2.39-2.30 (m, 2H), 2.14-2.02 (m, 2H), 1.37-1.28 (m, 6H), 1.27-1.12 (m, 4H), 0.64-0.52 (m, 1H), 0.51-0.34 (m, 2H), 0.32-0.19 (m, 1H). ESI MS [M+H]⁺ for $C_{27}H_{34}N_7O_5S$; calcd 568.2, found 568.2.

Example 112: 2-Amino-5-{2-[(1S)-1-cyclopropyl-ethyl]-7-ethanesulfonamido-1-oxo-2,3-dihydro-1H-isoindol-5-yl}-N-(pyridin-3-yl)pyrazolo[1,5-a]pyrimidine-3-carboxamide

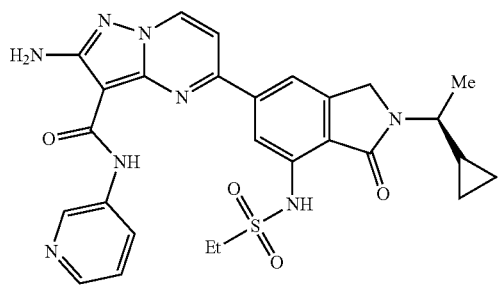 [SMILES: CCS(=O)(=O)Nc1cc(-c2ccn3nc(N)c(C(=O)Nc4cccnc4)c3n2)cc2c1C(=O)N([C@@H](C)C1CC1)C2]

The title compound was prepared in a similar manner to example 99. $^1$H NMR (400 MHz, DMSO-$d_6$) δ 9.77 (s, 1H), 9.72 (s, 1H), 9.11 (d, J=7.1 Hz, 1H), 8.94 (dd, J=2.6, 0.7 Hz, 1H), 8.32-8.29 (m, 2H), 8.21 (ddd, J=8.3, 2.6, 1.5 Hz, 1H), 8.15 (d, J=1.2 Hz, 1H), 7.65 (d, J=7.1 Hz, 1H), 7.40 (ddd, J=8.3, 4.7, 0.7 Hz, 1H), 6.76 (s, 2H), 4.72 (s, 2H), 3.63-3.52 (m, 1H), 3.43 (q, J=7.3 Hz, 2H), 1.35 (d, J=6.8 Hz, 3H), 1.27-1.15 (m, 4H), 0.63-0.54 (m, 1H), 0.49-0.37 (m, 2H), 0.32-0.25 (m, 1H). ESI MS [M+H]$^+$ for $C_{27}H_{29}N_8O_4S$; calcd 561.2, found 561.2.

Example 113: 2-Amino-N-cyclopropyl-5-{2-[(1S)-1-cyclopropylethyl]-7-(2-methoxyethanesulfonamido)-1-oxo-2,3-dihydro-1H-isoindol-5-yl}pyrazolo[1,5-a]pyrimidine-3-carboxamide

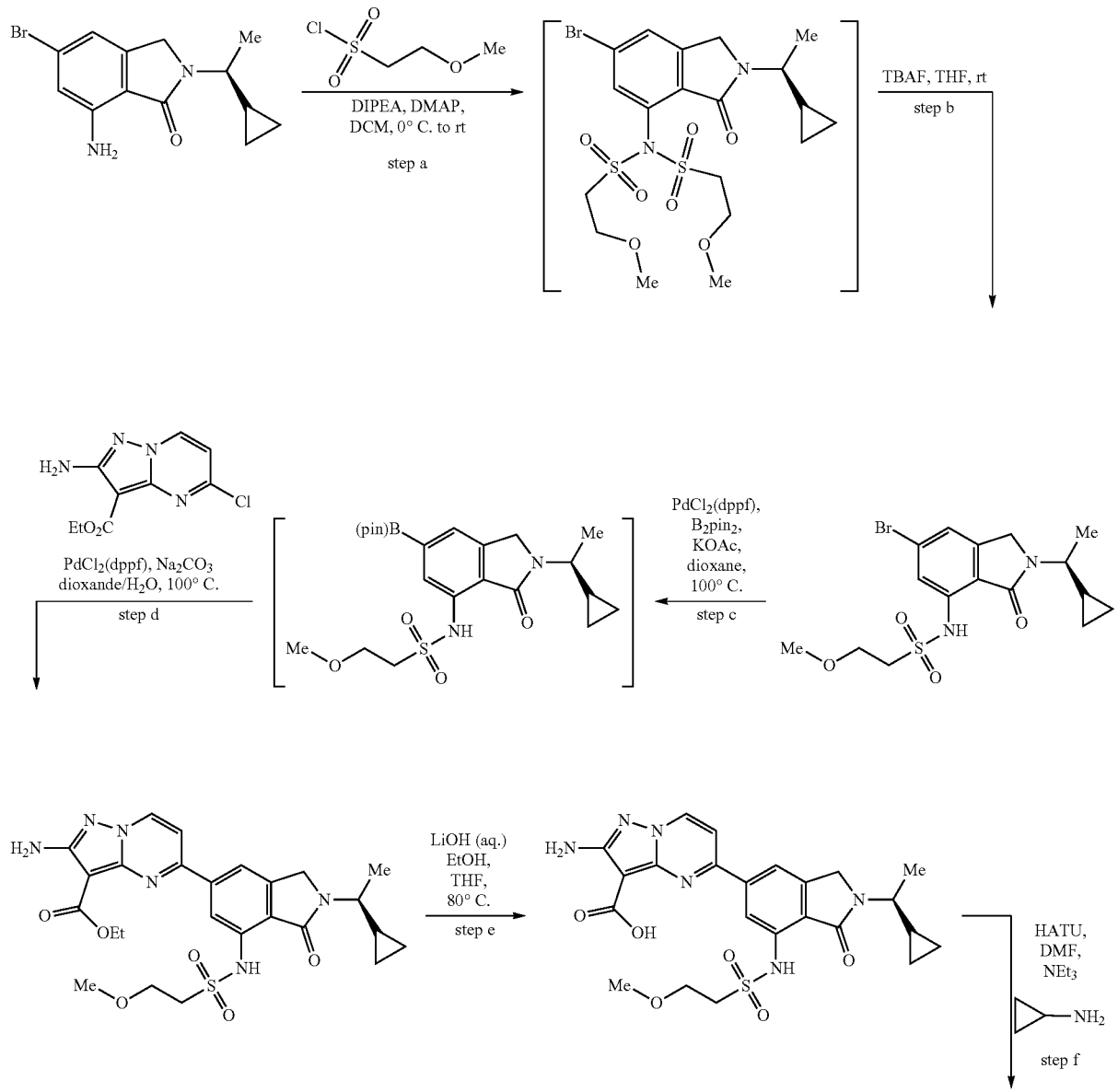

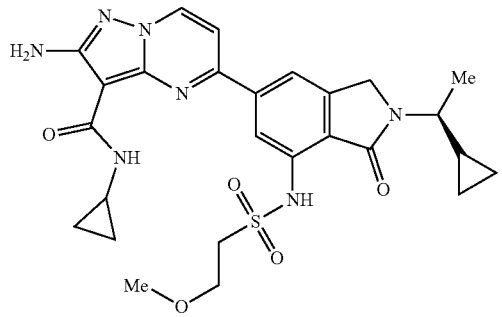

Step a: The aniline product of Step b, example 72 (500 mg, 1.69 mmol, 1.0 equiv.) was dissolved in $CH_2Cl_2$ (6 mL) and the mixture was cooled to 0° C. To this solution was added DMAP (21 mg, 0.169 mmol, 10 mol %), DIPEA (0.90 mL, 5.07 mmol, 3.0 equiv.) and 2-methoxy-ethanesulfonyl chloride, (670 mg, 4.23 mmol, 2.5 equiv.). The reaction mixture was warmed to rt and stirred for 2 h. The reaction was quenched with 1 M aq. HCl solution and diluted with EtOAc. The aq. layer was separated and back extracted with additional EtOAc. The organic layers were combined, washed with brine and dried over $MgSO_4$. Concentration under reduced pressure furnished bis-sulfonylated product that was taken crude onto the next step.

Step b: The product of Step a was dissolved in THF (5 mL) and TBAF (1.0 M in THF, 2.70 mL, 2.70 mmol, 1.6 equiv.) was added. The reaction mixture was stirred for 1 h, then quenched with 1 M aq. HCl solution and diluted with EtOAc. The aq. layer was separated and back extracted with additional EtOAc. The organic layers were combined, washed with brine and dried over $MgSO_4$. Concentration under reduced pressure and purification by flash column chromatography ($SiO_2$, hexanes to 50% EtOAc gradient) furnished the reverse sulfonamide as a white solid (318 mg, 0.763 mmol, 45% over 2 steps).

Step c: The product of Step b (215 mg, 0.515 mmol, 1.0 equiv.) was combined with $Pd(dppf)Cl_2$ (38 mg, 0.052 mmol, 0.1 equiv.), $B_2pin_2$ (170 mg, 0.670 mmol, 1.3 equiv.) and KOAc (111 mg, 1.13 mmol, 2.2 equiv.) in dioxane (3 mL). The resulting mixture was heated to 100° C. and stirred for 1 h. The mixture was cooled to rt, filtered through Celite (washed with EtOAc) and concentrated under reduced pressure. The resulting residue was used directly in the next step without purification.

Step d: The crude pinacol boronic ester obtained from Step c was combined with $Pd(dppf)Cl_2$ (38 mg, 0.052 mmol, 0.1 equiv.), 1 M aq. $Na_2CO_3$ solution (1.5 mmol, 1.5 mL, 3.0 equiv.), 2-amino-5-chloropyrazolo[1,5-a]pyrimidine-3-carboxylic acid ethyl ester (124 mg, 0.515 mmol, 1.0 equiv.) and dioxane (2 mL). The resulting mixture was heated to 100° C. and stirred for 1 h. The reaction mixture was cooled to rt and diluted with $CH_2Cl_2$ and $H_2O$. The aq. phase was separated and back extracted with additional $CH_2Cl_2$, then once with EtOAc. The organic layers were combined and dried over $MgSO_4$. Concentration under reduced pressure and purification by column chromatography ($SiO_2$, 100% $CH_2Cl_2$ to 100% EtOAc gradient) furnished the cross-coupled ester product (95 mg, 34% over 2 steps).

Step e: The ethyl ester product of Step d (95 mg, 0.175 mmol, 1.0 equiv.) was dissolved in EtOH (0.2 mL), THF (1 mL) and $H_2O$ (0.2 ml). $LiOH \cdot H_2O$ (88 mg, 2.1 mmol, 12.0 equiv.) was added and the reaction mixture was heated to 80° C. for 4 h. The resulting mixture was cooled to rt and the solvent was removed in vacuo. The mixture was diluted with $H_2O$ and acidified to pH 3 with 2 N HCl. The resulting precipitate was collected by vacuum filtration and dried under vacuum at 40° C. for 2 h to afford the carboxylic acid product (65 mg, 72%), which was used in the next step without purification.

Step f: The product of Step e (65 mg, 0.126 mmol) was dissolved in DMF (1.0 mL) and cyclopropylamine (20 µL, 0.35 mmol, 2.0 equiv.), $Et_3N$ (50 µL, 0.38 mmol, 3.0 equiv.), and HATU (96 mg, 0.252 mmol, 2.0 equiv.) were sequentially added, and the solution was stirred at rt. After 0.5 h, the reaction mixture was quenched with 2 M aq. HCl solution and diluted with EtOAc. The aq. layer was separated and back extracted with additional EtOAc. The organic layers were combined, washed with brine and dried over $MgSO_4$. Concentration under reduced pressure and purification by flash column chromatography ($SiO_2$, 100% DCM to 100% EtOAc to 100% $CH_2Cl_2$ to 10% MeOH series of gradients) furnished the title compound as a yellow solid (26.8 mg, 38%). $^1H$ NMR (400 MHz, $CDCl_3$) δ 9.74 (s, 1H), 8.48 (d, J=7.1 Hz, 1H), 8.33 (s, 1H), 7.82 (s, 1H), 7.73 (s, 1H), 7.20 (d, J=7.1 Hz, 1H), 5.80 (s, 2H), 4.67-4.49 (m, 2H), 3.82 (t, J=5.9 Hz, 2H), 3.77-3.63 (m, 1H), 3.45 (t, J=5.9 Hz, 2H), 3.27 (s, 3H), 3.05-2.86 (m, 1H), 1.40 (d, J=6.8 Hz, 3H), 1.15-1.00 (m, 1H), 0.93-0.83 (m, 2H), 0.79-0.61 (m, 3H), 0.55-0.32 (m, 3H). ESI MS $[M+H]^+$ for $C_{26}H_{32}N_7O_5S$, calcd 554.2, found 554.2.

Example 114: 2-Amino-N-cyclopropyl-5-{2-[(1S)-1-cyclopropylethyl]-7-(N-methylmethanesulfonamido)-1-oxo-2,3-dihydro-1H-isoindol-5-yl}pyrazolo[1,5-a]pyrimidine-3-carboxamide

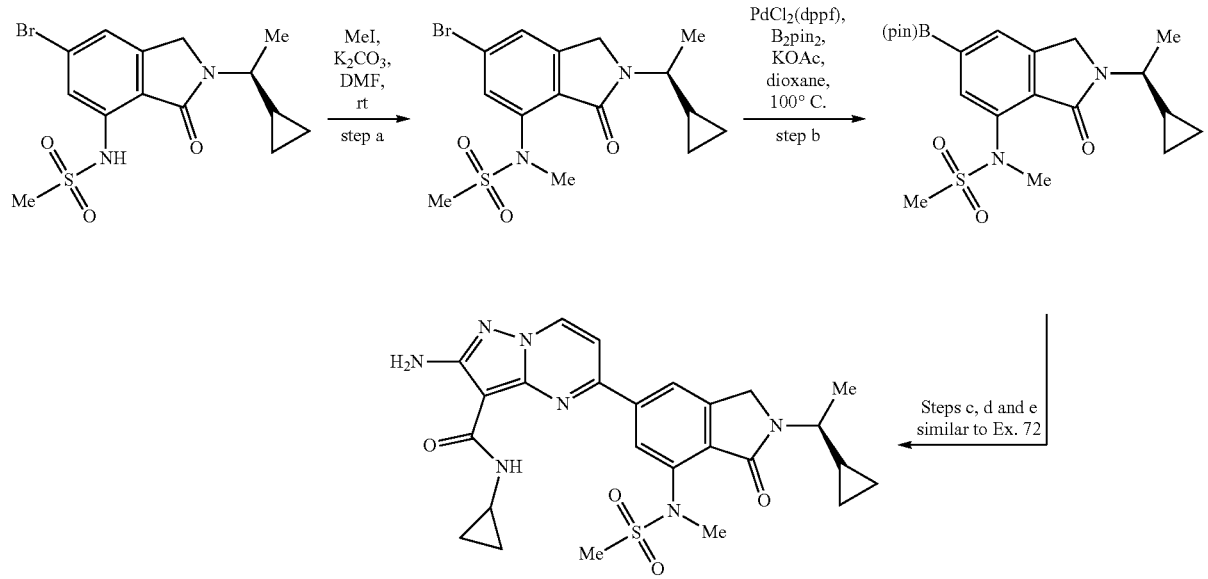

Step a: To a solution of the aryl bromide (800 mg, 2.14 mmol, 1.0 equiv.) in DMF (7 mL) was added K₂CO₃ (590 mg, 4.28 mmol, 2.0 equiv.) and MeI (0.45 mL, 4.28 mmol, 2.0 equiv.). The resulting mixture was stirred at rt for 3 h. The reaction was quenched with 2 M aq. HCl solution and diluted with EtOAc. The aq. layer was separated and back extracted with additional EtOAc. The organic layers were combined, washed with H₂O, brine, and dried over MgSO₄. Concentration under reduced pressure furnished crude methylated reverse sulfonamide that was used directly in the next step.

Step b: The product of Step a (~2.14 mmol, 1.0 equiv.) was combined with Pd(dppf)Cl₂ (150 mg, 0.21 mmol, 0.1 equiv.), B₂pin₂ (700 mg, 2.78 mmol, 1.3 equiv.) and KOAc (460 mg, 4.70 mmol, 2.2 equiv.) in dioxane (10 mL). The resulting mixture was heated to 100° C. and stirred for 2 h. The mixture was cooled to rt, filtered through Celite (washed with EtOAc) and concentrated under reduced pressure. The resulting residue was used directly in the next step without purification.

Step c: The crude pinacol boronic ester obtained from Step b was combined with Pd(dppf)Cl₂ (150 mg, 0.21 mmol, 0.1 equiv.), 1 M aq. Na₂CO₃ solution (6.5 mmol, 6.5 mL, 3.0 equiv.), 2-amino-5-chloropyrazolo[1,5-a]pyrimidine-3-carboxylic acid ethyl ester (513 mg, 0.515 mmol, 1.0 equiv.) and dioxane (6.5 mL). The resulting mixture was heated to 100° C. and stirred for 1.5 h. The reaction mixture was cooled to rt and diluted with CH₂Cl₂ and H₂O. The aq. phase was separated and back extracted with additional CH₂Cl₂, then once with EtOAc. The organic layers were combined and dried over MgSO₄. Concentration under reduced pressure and purification by column chromatography (SiO₂, 100% DCM to 100% EtOAc gradient) furnished the cross-coupled ester product (550 mg, 50% over 3 steps).

Step d: The ethyl ester product of Step c (300 mg, 0.586 mmol, 1.0 equiv.) was dissolved in EtOH (1 mL), THF (2 mL) and H₂O (1 mL). LiOH·H₂O (147 mg, 3.52 mmol, 6.0 equiv.) was added and the reaction mixture was heated to 70° C. for 15 h. The resulting mixture was cooled to rt and the solvent was removed in vacuo. The mixture was diluted with H₂O and acidified to pH 3 with 2 N HCl. The resulting precipitate was collected by vacuum filtration and dried under vacuum at 40° C. for 2 h to afford the carboxylic acid product (130 mg, 46%), which was used in the next step without purification.

Step e: The product of Step d (50 mg, 0.103 mmol) was dissolved in DMF (1.0 mL) and HOBt (24 mg, 0.134 mmol, 1.3 equiv., 20% H₂O by wt.), Et₃N (50 µL, 0.31 mmol, 3.0 equiv.), cyclopropylamine (10 mg, 0.165 mmol, 1.6 equiv.) and EDC·HCl (31 mg, 0.162 mmol, 1.6 equiv.) were sequentially added, and the solution was heated to 40° C. After 2 days, the reaction mixture was purified directly by reverse phase HPLC (20 to 80% gradient of CH₃CN and H₂O with 0.1% TFA) to afford the title compound as a yellow solid. $^1$H NMR (400 MHz, DMSO-d₆) δ 9.04 (d, J=7.1 Hz, 1H), 8.35 (s, 1H), 8.14 (s, 1H), 7.82 (d, J=4.0 Hz, 1H), 7.65 (d, J=7.2 Hz, 1H), 6.62 (s, 2H), 4.67 (s, 2H), 3.69-3.57 (m, 1H), 3.38 (s, 3H), 3.12 (s, 3H), 2.92-2.83 (m, 1H), 1.32 (d, J=6.8 Hz, 3H), 1.23-1.11 (m, 1H), 0.84-0.73 (m, 2H), 0.68-0.53 (m, 3H), 0.50-0.34 (m, 2H), 0.34-0.23 (m, 1H). ESI MS [M+H]⁺ for C₂₅H₃₀N₇O₄S, calcd 524.2, found 524.2.

Example 115: 2-Amino-N-cyclopropyl-5-{7-methanesulfonamido-1-oxo-2-[(2S)-1,1,1-trifluoropropan-2-yl]-2,3-dihydro-1H-isoindol-5-yl}pyrazolo[1,5-a]pyrimidine-3-carboxamide

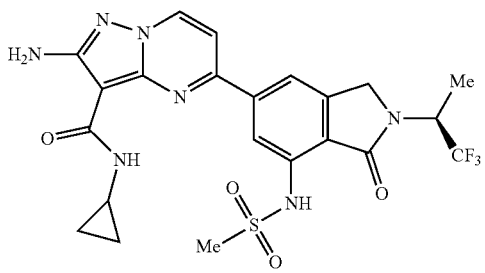 [SMILES: C[C@H](N1Cc2cc(-c3ccn4nc(N)c(C(=O)NC5CC5)c4n3)cc(NS(C)(=O)=O)c2C1=O)C(F)(F)F]

Example 117: (S)-2-Amino-N-(3-cyanooxetan-3-yl)-5-(7-(methylsulfonamido)-1-oxo-2-(1,1,1-trifluoropropan-2-yl)isoindolin-5-yl)pyrazolo[1,5-a]pyrimidine-3-carboxamide

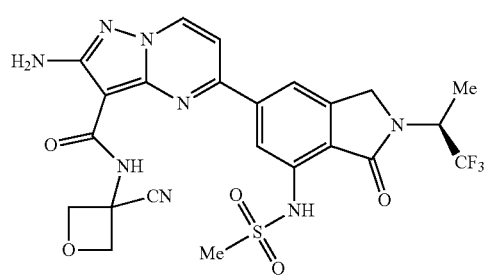 [SMILES: C[C@H](N1Cc2cc(-c3ccn4nc(N)c(C(=O)NC5(C#N)COC5)c4n3)cc(NS(C)(=O)=O)c2C1=O)C(F)(F)F]

The title compound was prepared in a similar manner to examples 27 and 72. $^1$H NMR (400 MHz, DMSO-d$_6$) δ 9.43 (s, 1H), 9.01 (d, J=7.1 Hz, 1H), 8.21 (s, 1H), 8.04 (s, 1H), 7.67 (d, J=3.6 Hz, 1H), 7.54 (d, J=7.1 Hz, 1H), 6.63 (s, 2H), 5.03 (p, J=7.6 Hz, 1H), 4.77 (d, J=17.7 Hz, 1H), 4.54 (d, J=17.7 Hz, 1H), 3.31 (s, 3H), 2.81 (tq, J=7.4, 3.8 Hz, 1H), 1.51 (d, J=7.1 Hz, 3H), 0.85-0.70 (m, 2H), 0.70-0.55 (m, 2H). ESI MS [M+H]$^+$ for C$_{22}$H$_{22}$F$_3$N$_7$O$_4$S; calcd 538.1, found 538.0.

The title compound was prepared in a similar manner to example 123 (vide infra). $^1$H NMR (400 MHz, DMSO-d$_6$) δ 9.44 (s, 1H), 9.06 (d, J=7.1 Hz, 1H), 8.65 (s, 1H), 8.30 (d, J=1.2 Hz, 1H), 8.20 (d, J=1.2 Hz, 1H), 7.65 (d, J=7.1 Hz, 1H), 6.67 (br. s, 2H), 5.10-4.99 (m, 1H), 4.97 (d, J=7.4 Hz, 2H), 4.84 (dd, J=7.6, 1.9 Hz, 2H), 4.77 (d, J=17.7 Hz, 1H), 4.54 (d, J=17.7 Hz, 1H), 3.39 (s, 3H), 1.51 (d, J=7.1 Hz, 3H). $^{19}$F NMR (376 MHz, DMSO-d$_6$) δ −73.53 (d, J=8.2 Hz). ESI MS [M+H]$^+$ for C$_{23}$H$_{22}$F$_3$N$_8$O$_5$S, calcd 579.1, found 579.1.

Example 116: 2-Amino-5-{7-methanesulfonamido-1-oxo-2-[(2S)-1,1,1-trifluoropropan-2-yl]-2,3-dihydro-1H-isoindol-5-yl}-N-(oxetan-3-yl)pyrazolo[1,5-a]pyrimidine-3-carboxamide

Example 118: 2-Amino-N-[(2R)-1-hydroxypropan-2-yl]-5-{7-methanesulfonamido-1-oxo-2-[(2S)-1,1,1-trifluoropropan-2-yl]-2,3-dihydro-1H-isoindol-5-yl}pyrazolo[1,5-a]pyrimidine-3-carboxamide

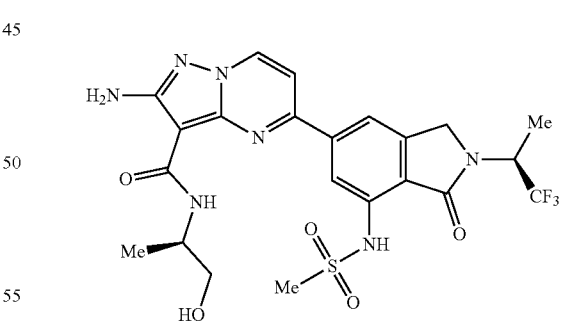

The title compound was prepared in a similar manner to example 123 (vide infra). $^1$H NMR (400 MHz, DMSO-d$_6$) δ 9.44 (s, 1H), 9.04 (d, J=7.1 Hz, 1H), 8.30 (s, 1H), 8.14-8.02 (m, 2H), 7.58 (d, J=7.2 Hz, 1H), 6.61 (s, 2H), 5.18-4.94 (m, 2H), 4.84-4.73 (m, 3H), 4.66 (t, J=6.6 Hz, 2H), 4.55 (d, J=17.6 Hz, 1H), 3.31 (s, 3H), 1.51 (d, J=7.1 Hz, 3H). ESI MS [M+H]$^+$ for C$_{22}$H$_{22}$F$_3$N$_7$O$_5$S; calcd 554.1, found 554.1.

The title compound was prepared in a similar manner to example 123 (vide infra). $^1$H NMR (400 MHz, DMSO-d$_6$) δ 9.47 (s, 1H), 9.00 (d, J=7.1 Hz, 1H), 8.19 (s, 1H), 8.12 (s, 1H), 7.96 (d, J=8.2 Hz, 1H), 7.52 (d, J=7.1 Hz, 1H), 6.60 (s, 2H), 5.18-4.88 (m, 2H), 4.74 (d, J=17.7 Hz, 1H), 4.53 (d, J=17.6 Hz, 1H), 4.15-4.00 (m, 1H), 3.62-3.41 (m, 2H), 3.31 (s, 3H), 1.51 (d, J=7.1 Hz, 3H), 1.20 (d, J=6.7 Hz, 3H). ESI MS [M+H]$^+$ for C$_{22}$H$_{24}$F$_3$N$_7$O$_5$S; calcd 556.2, found 556.0.

Example 119: 2-Amino-N-[(2R)-1-hydroxybutan-2-yl]-5-{7-methanesulfonamido-1-oxo-2-[(2S)-1,1,1-trifluoropropan-2-yl]-2,3-dihydro-1H-isoindol-5-yl}pyrazolo[1,5-a]pyrimidine-3-carboxamide

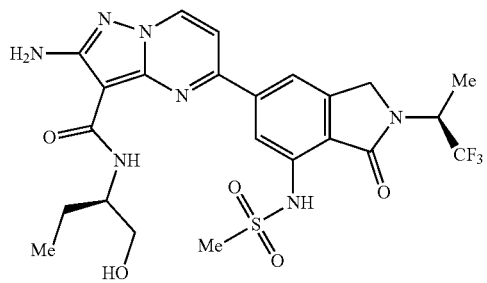 [SMILES: CC[C@H](CO)NC(=O)c1c(N)nn2ccc(-c3cc4c(c(NS(C)(=O)=O)c3)C(=O)N([C@@H](C)C(F)(F)F)C4)nc12]

The title compound was prepared in a similar manner to example 123 (vide infra). $^1$H NMR (400 MHz, DMSO-$d_6$) δ 9.43 (s, 1H), 9.00 (d, J=7.1 Hz, 1H), 8.19 (s, 1H), 8.10 (s, 1H), 7.94 (d, J=8.7 Hz, 1H), 7.52 (d, J=7.1 Hz, 1H), 6.61 (s, 2H), 5.03 (p, J=7.6 Hz, 1H), 4.91 (t, J=5.0 Hz, 1H), 4.73 (d, J=17.7 Hz, 1H), 4.52 (d, J=17.6 Hz, 1H), 3.96-3.83 (m, 1H), 3.67-3.55 (m, 1H), 3.54-3.42 (m, 1H), 3.30 (s, 3H), 1.67 (dt, J=13.7, 6.7 Hz, 1H), 1.61-1.44 (m, 4H), 0.89 (t, J=7.4 Hz, 3H). ESI MS [M+H]$^+$ for $C_{23}H_{26}F_3N_7O_5S$; calcd 570.2, found 570.0.

Example 120: 2-Amino-N—((R)-1-cyclopropyl-2-hydroxyethyl)-5-(7-(methylsulfonamido)-1-oxo-2-((S)-1,1,1-trifluoropropan-2-yl)isoindolin-5-yl)pyrazolo[1,5-a]pyrimidine-3-carboxamide

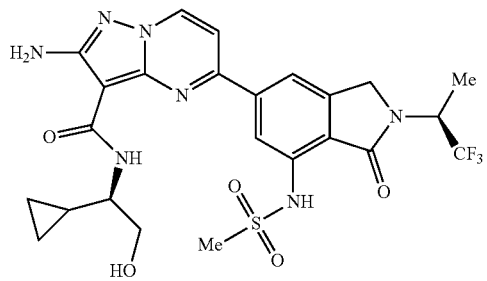 [SMILES: C[C@H](N1Cc2cc(-c3ccn4nc(N)c(C(=O)N[C@@H](CO)C5CC5)c4n3)cc(NS(C)(=O)=O)c2C1=O)C(F)(F)F]

The title compound was prepared in a similar manner to example 123 (vide infra). $^1$H NMR (400 MHz, DMSO-$d_6$) δ 9.42 (s, 1H), 9.01 (d, J=7.1 Hz, 1H), 8.27 (s, 1H), 8.16 (d, J=8.8 Hz, 1H), 8.12 (s, 1H), 7.54 (d, J=7.1 Hz, 1H), 6.59 (br. s, 2H), 5.12-4.94 (m, 1H), 4.74 (d, J=17.8 Hz, 1H), 4.53 (d, J=17.8 Hz, 1H), 3.69 (dd, J=10.6, 4.2 Hz, 1H), 3.60 (dd, J=10.6, 4.2 Hz, 1H), 3.50-3.42 (m, 1H), 3.31 (s, 3H), 1.51 (d, J=7.1 Hz, 3H), 1.23-1.06 (m, 1H), 0.55-0.33 (m, 3H), 0.31-0.21 (m, 1H). ESI MS [M+H]$^+$ for $C_{24}H_{27}F_3N_7O_5S$, calcd 582.2, found 582.2.

Example 121: 2-Amino-5-{7-methanesulfonamido-1-oxo-2-[(2S)-1,1,1-trifluoropropan-2-yl]-2,3-dihydro-1H-isoindol-5-yl}-N-[trans-3-hydroxycyclobutyl]pyrazolo[1,5-a]pyrimidine-3-carboxamide

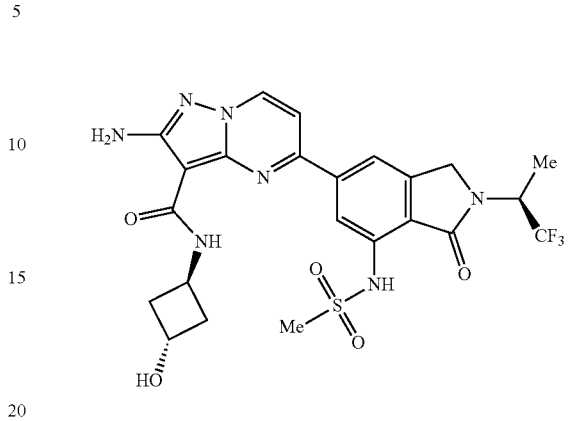

The title compound was prepared in a similar manner to example 123 (vide infra). $^1$H NMR (400 MHz, DMSO-$d_6$) δ 9.45 (s, 1H), 9.02 (d, J=7.1 Hz, 1H), 8.25 (s, 1H), 8.06 (s, 1H), 7.80 (d, J=7.4 Hz, 1H), 7.54 (d, J=7.1 Hz, 1H), 6.61 (s, 2H), 5.14-4.92 (m, 1H), 4.83-4.69 (m, 1H), 4.62-4.48 (m, 2H), 4.32-4.25 (m, 1H), 3.30 (s, 3H), 2.37-2.27 (m, 2H), 2.24-2.13 (m, 2H), 1.51 (d, J=7.0 Hz, 4H). ESI MS [M+H]$^+$ for $C_{23}H_{24}F_3N_7O_5S$; calcd 568.2, found 568.1.

Example 122: 2-Amino-5-{7-methanesulfonamido-1-oxo-2-[(2S)-1,1,1-trifluoropropan-2-yl]-2,3-dihydro-1H-isoindol-5-yl}-N-[cis-4-hydroxy-4-methylcyclohexyl]pyrazolo[1,5-a]pyrimidine-3-carboxamide

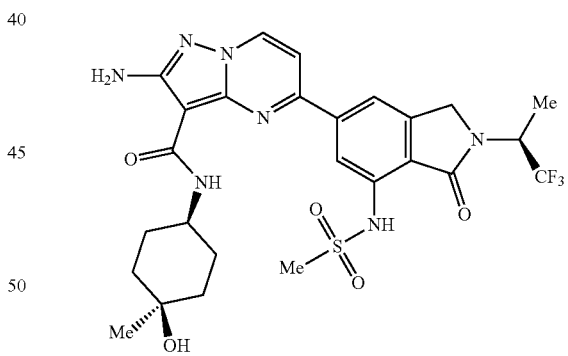

The title compound was prepared in a similar manner to example 123 (vide infra). $^1$H NMR (400 MHz, DMSO-$d_6$) δ 9.44 (s, 1H), 9.01 (d, J=7.1 Hz, 1H), 8.15 (s, 1H), 8.00 (s, 1H), 7.57-7.46 (m, 2H), 6.70-6.56 (m, 2H), 5.03 (p, J=7.6 Hz, 1H), 4.75 (d, J=17.8 Hz, 1H), 4.53 (d, J=17.7 Hz, 1H), 3.81 (q, J=7.3 Hz, 1H), 3.36 (s, 3H), 1.74-1.62 (m, 4H), 1.64-1.54 (m, 2H), 1.51 (d, J=7.1 Hz, 3H), 1.46-1.33 (m, 2H), 1.12 (s, 3H). ESI MS [M+H]$^+$ for $C_{26}H_{30}F_3N_7O_5S$; calcd 610.2, found 610.1.

Example 123: 2-Amino-5-{7-methanesulfonamido-1-oxo-2-[(2S)-1,1,1-trifluorobutan-2-yl]-2,3-dihydro-1H-isoindol-5-yl}-N-(oxetan-3-yl)pyrazolo[1,5-a]pyrimidine-3-carboxamide
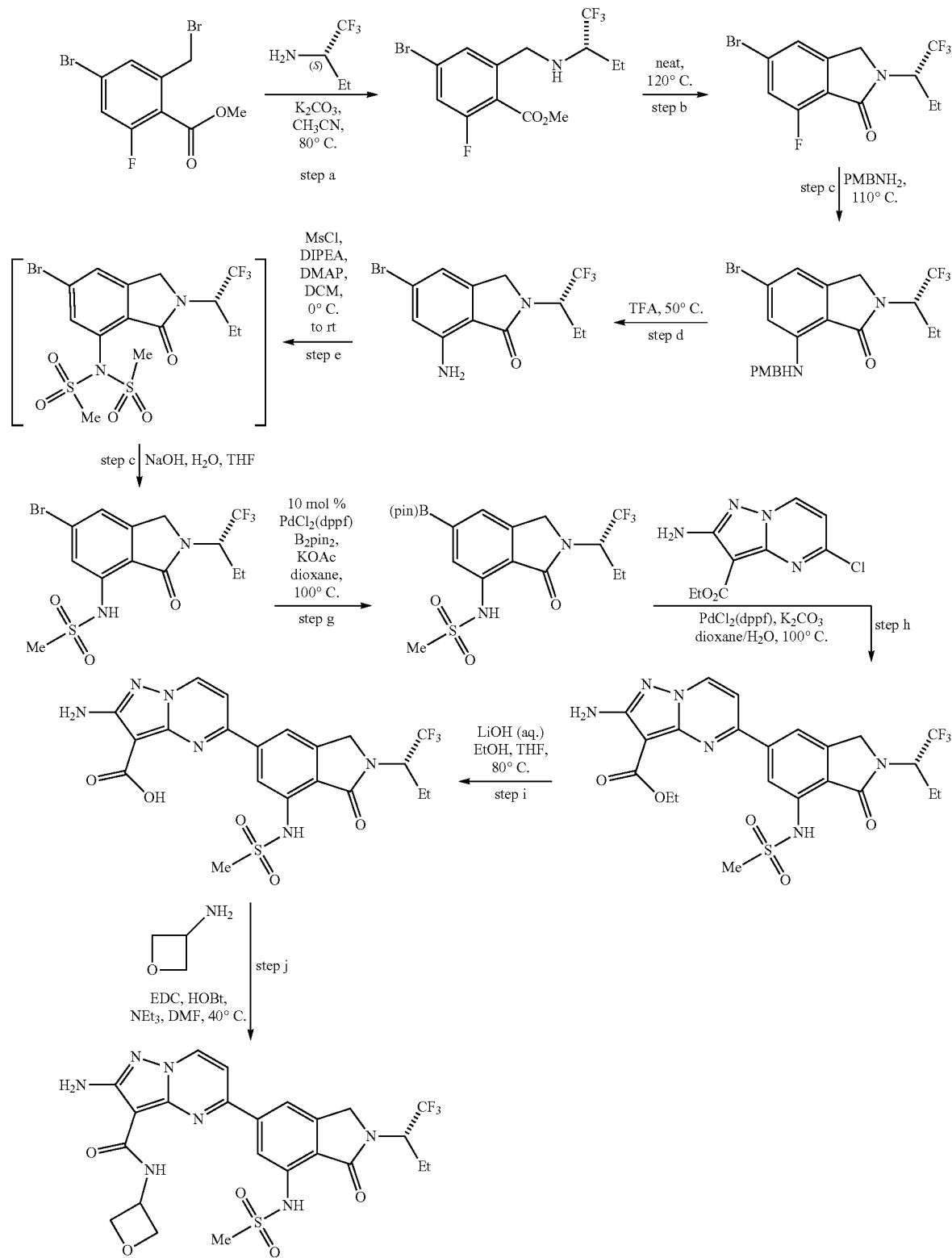

Step a: The crude benzyl bromide starting material (6.40 g, 19.6 mmol, 1.0 equiv.) was combined with $CH_3CN$ (150 mL), (2S)-1,1,1-trifluoro-2-butanamine (2.5 mL, 19.6 mmol, 1.0 equiv.) and $K_2CO_3$ (8.11 g, 58.8 mmol, 3.0 equiv.). The resulting mixture was stirred at 80° C. for 14 h, then cooled to rt. The mixture was filtered and concentrated onto Celite. Purification by column chromatography ($SiO_2$, hexane to 20% EtOAc gradient) furnished the substitution product as a pale yellow oil (4.62 g, 63%) that was taken directly onto the next step.

Step b: The amine product of Step a (4.62 g) was heated neat at 120° C. for 4 h. Purification by column chromatography ($SiO_2$, hexane to 20% EtOAc gradient) furnished the isoindolinone product as a white solid (1.4 g, 33%).

Step c: The product of Step b (1.1 g, 3.24 mmol, 1.0 equiv.) was combined with neat $PMBNH_2$ (3.5 mL) and heated to 100° C. for 14 h. The reaction mixture was cooled and partitioned between 10% aq. citric acid solution and EtOAc. The aq. layer was separated and back extracted with additional EtOAc. The organic layers were combined and washed with additional 10% aq. citric acid solution, brine, and dried over $MgSO_4$. Concentration under reduced pressure furnished the PMB amine adduct that was used crude in the next step.

Step d: The product of Step c was combined with TFA (6 mL) and stirred at 50° C. for 4 h. The reaction mixture was concentrated under reduced pressure and quenched with sat. aq. $NaHCO_3$ solution and diluted with EtOAc. The organic layers were combined, washed with brine and dried over $MgSO_4$. Concentration under reduced pressure and purification by column chromatography ($SiO_2$, hexanes to 20% EtOAc gradient) furnished the aniline product as a white solid (630 mg, 58% over 2 steps).

Step e: The product of Step d (630 mg, 1.87 mmol, 1.0 equiv.) was dissolved in $CH_2Cl_2$ (10 mL) and the mixture was cooled to 0° C. To this solution was added DMAP (22 mg, 0.19 mmol, 10 mol %), DIPEA (1.0 mL, 5.60 mmol, 3.0 equiv.) and MsCl (0.40 mL, 4.70 mmol, 2.5 equiv.). The reaction mixture was warmed to rt and stirred for 1 h. The reaction was quenched with 1 M aq. HCl solution and diluted with EtOAc. The aq. layer was separated and back extracted with additional EtOAc. The organic layers were combined, washed with brine and dried over $MgSO_4$. Concentration under reduced pressure furnished bis-sulfonylated product that was taken crude onto the next step.

Step f: The product of Step e was combined with THF (4 mL), $H_2O$ (2 mL) and NaOH (150 mg, 3.75 mmol, 2.0 equiv.). The mixture was stirred at rt for 3 h. The reaction was quenched with 1 M aq. HCl solution and diluted with EtOAc. The aq. layer was separated and back extracted with additional EtOAc. The organic layers were combined, washed with brine and dried over $MgSO_4$. Concentration under reduced pressure furnished crude reverse sulfonamide material (810 mg) that was taken directly onto the next step.

Step g: The product of Step f (810 mg, 1.95 mmol, 1.0 equiv.) was combined with $Pd(dppf)Cl_2$ (142 mg, 0.19 mmol, 0.1 equiv.), $B_2pin_2$ (642 mg, 2.54 mmol, 1.3 equiv.) and KOAc (420 mg, 4.30 mmol, 2.2 equiv.) in dioxane (13 mL). The resulting mixture was heated to 100° C. and stirred for 3 h. The reaction was cooled to rt, filtered through Celite (washed with EtOAc) and concentrated under reduced pressure. The resulting residue was used directly in the next step without purification.

Step h: The crude pinacol boronic ester obtained from Step g was combined with $Pd(dppf)Cl_2$ (142 mg, 0.19 mmol, 0.1 equiv.), 1 M aq. $Na_2CO_3$ solution (6.0 mmol, 6.0 mL, 3.0 equiv.), 2-amino-5-chloropyrazolo[1,5-a]pyrimidine-3-carboxylic acid ethyl ester (470 mg, 1.95 mmol, 1.0 equiv.) and dioxane (6 mL). The resulting mixture was heated to 100° C. and stirred for 1 h. The reaction mixture was cooled to rt and diluted with $CH_2Cl_2$ and $H_2O$. The aqueous phase was separated and back extracted with additional $CH_2Cl_2$, then once with EtOAc. The organic layers were combined and dried over $MgSO_4$. Concentration under reduced pressure and purification by column chromatography ($SiO_2$, $CH_2Cl_2$ to 5% MeOH gradient) furnished the cross-coupled ester product (970 mg, 92% over 2 steps).

Step i: The ethyl ester product of Step h (970 mg, 1.80 mmol, 1.0 equiv.) was dissolved in EtOH (5 mL), THF (10 mL) and $H_2O$ (5 ml). $LiOH·H_2O$ (460 mg, 10.8 mmol, 6.0 equiv.) was added and the reaction mixture was heated to 80° C. for 15 h. The resulting mixture was cooled to rt and the solvent was removed in vacuo. The mixture was diluted with $H_2O$ and acidified to pH 3 with 2 N HCl. The resulting precipitate was collected by vacuum filtration and dried under vacuum at 40° C. for 2 h to afford the carboxylic acid product (479 mg, 52%), which was used in the next step without purification.

Step j: The product of Step i (55 mg, 0.107 mmol) was dissolved in DMF (1.0 mL) and HOBt (21 mg, 0.139 mmol, 1.3 equiv., 20% $H_2O$ by wt.), $Et_3N$ (50 µL, 0.32 mmol, 3.0 equiv.), 3-oxetanamine (13 mg, 0.171 mmol, 1.6 equiv.) and EDC-HCl (33 mg, 0.171 mmol, 1.6 equiv.) were sequentially added, and the solution was heated to 40° C. After 2 h, the reaction mixture was diluted with $H_2O$ and EtOAc. The aq. layer was separated and back extracted with additional EtOAc. The organic layers were combined, washed with $H_2O$, and dried over $MgSO_4$. Concentration under reduced pressure and purification by column chromatography ($SiO_2$, DCM to 5% MeOH gradient) furnished the title compound as a yellow solid (23 mg, 38%). $^1H$ NMR (400 MHz, DMSO-$d_6$) δ 9.46 (s, 1H), 9.07 (d, J=7.1 Hz, 1H), 8.32 (s, 1H), 8.18-8.06 (m, 2H), 7.61 (d, J=7.2 Hz, 1H), 6.64 (s, 2H), 5.23-5.05 (m, 1H), 4.95-4.72 (m, 4H), 4.68 (t, J=6.7 Hz, 2H), 4.57 (d, J=17.9 Hz, 1H), 3.38 (s, 3H), 2.05-1.91 (m, 2H), 0.89 (t, J=7.3 Hz, 3H). ESI MS $[M+H]^+$ for $C_{23}H_{25}F_3N_7O_5S$, calcd 568.2, found 568.2.

Example 124: 2-Amino-N-cyclopropyl-5-{7-methanesulfonamido-1-oxo-2-[(2S)-1,1,1-trifluorobutan-2-yl]-2,3-dihydro-1H-isoindol-5-yl}pyrazolo[1,5-a]pyrimidine-3-carboxamide

The title compound was prepared in a similar manner to example 123. $^1H$ NMR (400 MHz, DMSO-$d_6$) δ 9.45 (s, 1H), 9.04 (d, J=7.1 Hz, 1H), 8.23 (s, 1H), 8.05 (s, 1H), 7.70 (d, J=3.6 Hz, 1H), 7.56 (d, J=7.2 Hz, 1H), 6.66 (s, 2H), 4.94-4.80 (m, 1H), 4.75 (d, J=17.9 Hz, 1H), 4.56 (d, J=17.8 Hz, 1H), 3.35 (s, 3H), 2.84 (td, J=7.1, 3.6 Hz, 1H), 1.97 (dq, J=14.9, 7.2 Hz, 2H), 0.89 (t, J=7.3 Hz, 3H), 0.81-0.73 (m, 2H), 0.69-0.62 (m, 2H). ESI MS [M+H]+ for C23H25F3N7O4S, calcd 552.2, found 552.2.

Example 125: 2-Amino-5-{7-methanesulfonamido-1-oxo-2-[(2S)-1,1,1-trifluorobutan-2-yl]-2,3-dihydro-1H-isoindol-5-yl}-N-(3-methyloxetan-3-yl)pyrazolo[1,5-a]pyrimidine-3-carboxamide

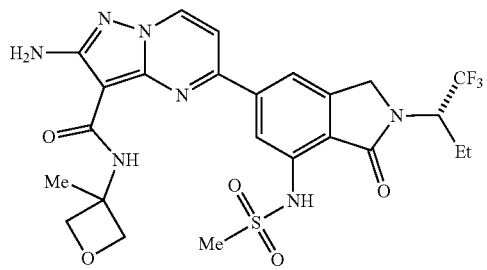 [SMILES: CC[C@H](N1Cc2cc(-c3ccn4nc(N)c(C(=O)NC5(C)COC5)c4n3)cc(NS(C)(=O)=O)c2C1=O)C(F)(F)F]

The title compound was prepared in a similar manner to example 123. 1H NMR (400 MHz, DMSO-d6) δ 9.40 (s, 1H), 9.03 (d, J=7.1 Hz, 1H), 8.36-8.21 (m, 1H), 8.11-8.05 (m, 1H), 8.02 (s, 1H), 7.57 (d, J=7.2 Hz, 1H), 6.61 (s, 2H), 4.90-4.79 (m, 1H), 4.77 (d, J=6.4 Hz, 2H), 4.72 (d, J=18.0 Hz, 1H), 4.53 (d, J=17.8 Hz, 1H), 4.42 (d, J=6.4 Hz, 2H), 3.32 (s, 3H), 2.01-1.84 (m, 2H), 1.66 (s, 3H), 0.86 (t, J=7.3 Hz, 3H). ESI MS [M+H]+ for C24H27F3N7O5S, calcd 582.2, found 582.2.

Example 126: 2-Amino-5-{7-methanesulfonamido-1-oxo-2-[(2S)-1,1,1-trifluorobutan-2-yl]-2,3-dihydro-1H-isoindol-5-yl}-N-[trans-3-(2-hydroxypropan-2-yl)cyclobutyl]pyrazolo[1,5-a]pyrimidine-3-carboxamide

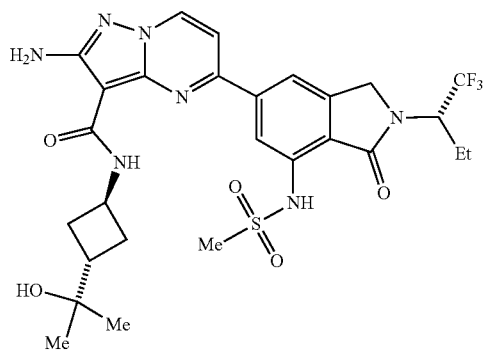

The title compound was prepared in a similar manner to example 123. 1H NMR (400 MHz, DMSO-d6) δ 9.46 (s, 1H), 9.05 (d, J=7.1 Hz, 1H), 8.31 (d, J=1.3 Hz, 1H), 8.09 (d, J=1.2 Hz, 1H), 7.88 (d, J=7.9 Hz, 1H), 7.56 (d, J=7.2 Hz, 1H), 6.64 (s, 2H), 4.86 (p, J=7.9 Hz, 1H), 4.75 (d, J=17.9 Hz, 1H), 4.55 (d, J=17.8 Hz, 1H), 4.49-4.39 (m, 1H), 4.25 (s, 1H), 3.33 (s, 3H), 2.40-2.24 (m, 3H), 2.11-1.91 (m, 4H), 1.07 (s, 6H), 0.89 (t, J=7.3 Hz, 3H). ESI MS [M+H]+ for C27H33F3N7O5S, calcd 624.2, found 624.2.

Example 127: 2-Amino-5-{7-methanesulfonamido-1-oxo-2-[(2S)-1,1,1-trifluorobutan-2-yl]-2,3-dihydro-1H-isoindol-5-yl}-N-[trans-4-hydroxy-4-methylcyclohexyl]pyrazolo[1,5-a]pyrimidine-3-carboxamide

The title compound was prepared in a similar manner to example 123. 1H NMR (400 MHz, DMSO-d6) δ 9.43 (s, 1H), 9.04 (d, J=7.1 Hz, 1H), 8.18 (s, 1H), 8.03 (d, J=1.2 Hz, 1H), 7.72 (d, J=7.9 Hz, 1H), 7.52 (d, J=7.1 Hz, 1H), 6.64 (br. s, 2H), 4.87 (q, J=8.0 Hz, 1H), 4.72 (d, J=18.0 Hz, 1H), 4.53 (d, J=17.7 Hz, 1H), 3.95-3.90 (m, 1H), 3.31 (s, 3H), 1.96 (p, J=7.4 Hz, 2H), 1.92-1.83 (m, 2H), 1.60-1.45 (m, 6H), 1.12 (s, 3H), 0.88 (t, J=7.3 Hz, 3H). ESI MS [M+H]+ for C27H33F3N7O5S, calcd 624.2, found 624.2.

Example 128: 2-Amino-N-cyclopropyl-5-{2-[(1S)-1-cyclopropyl-2,2,2-trifluoroethyl]-7-methanesulfonamido-1-oxo-2,3-dihydro-1H-isoindol-5-yl}pyrazolo[1,5-a]pyrimidine-3-carboxamide

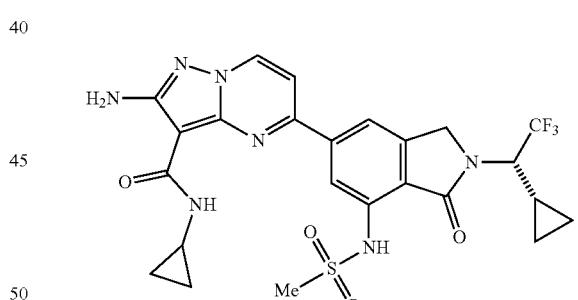

This molecule was prepared in analogous fashion to example 123, with replacement of (2S)-1,1,1-trifluoro-2-butanamine with (αS)-α-(trifluoromethyl)cyclopropanemethanamine in Step a, and cyclopropylamine was used in the final amide coupling. 1H NMR (400 MHz, DMSO-d) δ 9.43 (s, 1H), 9.04 (d, J=7.1 Hz, 1H), 8.24 (s, 1H), 8.08 (s, 1H), 7.70 (d, J=3.6 Hz, 1H), 7.57 (d, J=7.2 Hz, 1H), 6.65 (s, 2H), 4.92 (d, J=17.9 Hz, 1H), 4.70 (d, J=17.9 Hz, 1H), 4.26-4.11 (m, 1H), 3.35 (s, 3H), 2.88-2.79 (m, 1H), 1.57-1.43 (m, 1H), 0.91-0.57 (m, 7H), 0.33-0.18 (m, 1H). ESI MS [M+H]+ for C24H25F3N7O4S, calcd 564.2, found 564.2.

Example 129: 2-Amino-N-cyclopropyl-5-{2-[(1R)-1-cyclopropyl-2,2,2-trifluoroethyl]-7-methanesulfonamido-1-oxo-2,3-dihydro-1H-isoindol-5-yl}pyrazolo[1,5-a]pyrimidine-3-carboxamide

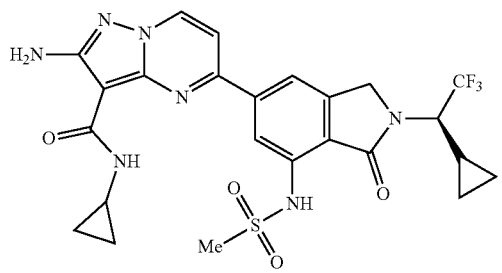 [SMILES: CS(=O)(=O)Nc1cc(-c2ccn3nc(N)c(C(=O)NC4CC4)c3n2)cc2c1C(=O)N([C@H](C1CC1)C(F)(F)F)C2]

This molecule was prepared in analogous fashion to example 123, with replacement of (2S)-1,1,1-trifluoro-2-butanamine with (αR)-α-(trifluoromethyl)cyclopropanemethanamine in Step a, and cyclopropylamine was used in the final amide coupling. $^1$H NMR (400 MHz, DMSO-d) δ 9.43 (s, 1H), 9.04 (d, J=7.1 Hz, 1H), 8.24 (s, 1H), 8.08 (s, 1H), 7.70 (d, J=3.6 Hz, 1H), 7.57 (d, J=7.2 Hz, 1H), 6.65 (s, 2H), 4.92 (d, J=17.9 Hz, 1H), 4.70 (d, J=17.9 Hz, 1H), 4.26-4.11 (m, 1H), 3.35 (s, 3H), 2.88-2.79 (m, 1H), 1.57-1.43 (m, 1H), 0.91-0.57 (m, 7H), 0.33-0.18 (m, 1H). ESI MS [M+H]$^+$ for $C_{24}H_{25}F_3N_7O_4S$, calcd 564.2, found 564.2.

Example 130: 2-Amino-5-{2-[(1S)-1-cyclopropylethyl]-7-methanesulfonyl-1-oxo-2,3-dihydro-1H-isoindol-5-yl}-N-(1-methyl-1H-pyrazol-4-yl)pyrazolo[1,5-a]pyrimidine-3-carboxamide

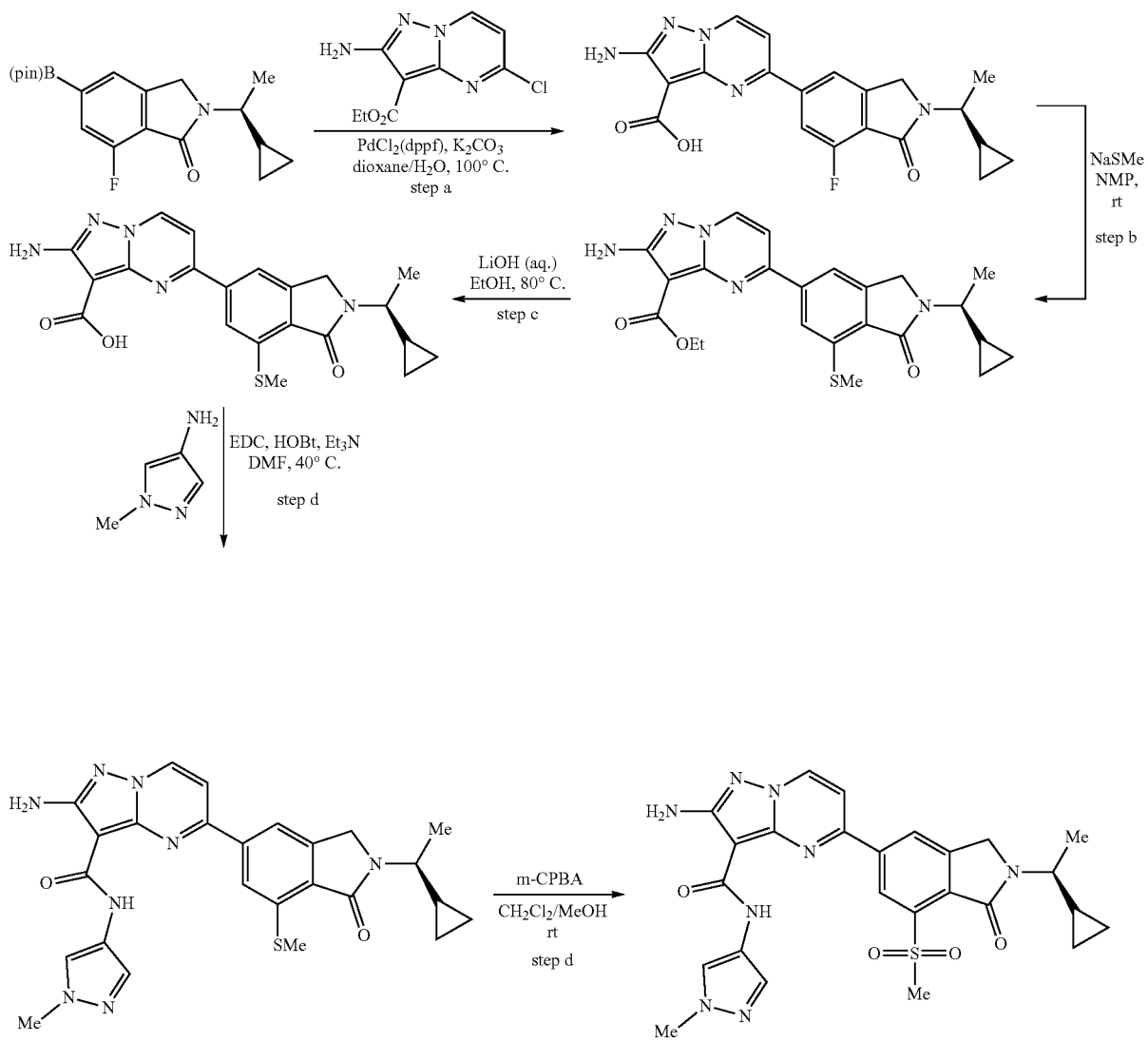

Step a: Performed in a similar manner to example 1, Step h.

Step b: To a mixture of the product from Step a (1.00 g, 2.35 mmol) and NMP (7.8 mL) at rt was added sodium methanethiolate (165 mg, 2.35 mmol) in one portion. The reaction mixture was stirred at rt for 3 h. EtOAc (100 mL) was added and the organic phase washed with 1:1 H$_2$O:brine (4×100 mL). The organic phase was dried over Na$_2$SO$_4$ and concentrated. The crude material was purified by column chromatography (SiO$_2$, 0 to 10% MeOH in CH$_2$Cl$_2$) to afford the desired product as an orange solid (968 mg; 910%).

Step c: The reaction was performed in a similar manner to example 1, Step i to afford the desired product as a yellow solid (906 mg, 85%).

Step d: The reaction was performed in a similar manner to example 1, Step j to afford the desired product as a yellow solid (91 mg, 60%).

Step e: To a mixture of the product from Step c (91 mg, 0.182 mmol) in 9:1 CH$_2$Cl$_2$:MeOH (3.6 mL) was added m-CPBA (125 mg, 0.543 mmol, 75% by wt. in H$_2$O) in one portion. The reaction mixture was stirred at rt for 3 h and concentrated under reduced pressure. The crude material was purified by column chromatography (SiO$_2$, 0 to 15% MeOH in CH$_2$Cl$_2$) and subsequently by reverse phase HPLC (5 to 95% CH$_3$CN in H$_2$O with 0.1% TFA) to afford the desired product as a yellow solid (10 mg; 10%). $^1$H NMR (400 MHz, DMSO-d$_6$) δ 9.63 (s, 1H), 9.14 (d, J=7.1 Hz, 1H), 9.05 (d, J=1.5 Hz, 1H), 8.85 (d, J=1.5 Hz, 1H), 8.12 (s, 1H), 7.81 (d, J=7.2 Hz, 1H), 7.79 (s, 1H), 6.72 (s, 2H), 4.80 (s, 2H), 3.85 (s, 3H), 3.72 (s, 3H), 3.70-3.62 (m, 1H), 1.36 (d, J=6.8 Hz, 3H), 1.28-1.17 (m, 1H), 0.67-0.57 (m, 1H), 0.51-0.39 (m, 2H), 0.36-0.27 (m, 1H). ESI MS [M+H]$^+$ for C$_{25}$H$_{27}$N$_8$O$_4$S, calcd 535.2, found 535.1.

Example 131: 2-Amino-5-{2-[(1S)-1-cyclopropyl-ethyl]-7-methanesulfonyl-1-oxo-2,3-dihydro-1H-isoindol-5-yl}-N-[cis-4-hydroxy-4-methylcyclo-hexyl]pyrazolo[1,5-a]pyrimidine-3-carboxamide

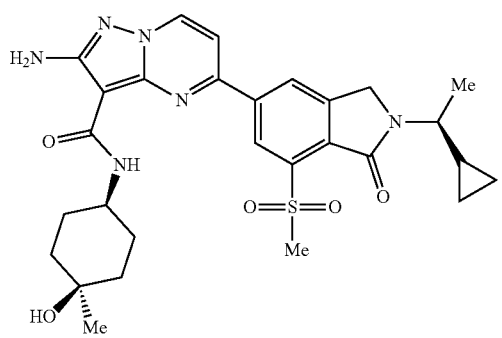 [SMILES: C[C@@H](C1CC1)N1Cc2cc(-c3ccn4nc(N)c(C(=O)N[C@H]5CC[C@@](C)(O)CC5)c4n3)cc(S(C)(=O)=O)c2C1=O]

The title compound was prepared in a similar manner to example 130. $^1$H NMR (400 MHz, DMSO-d$_6$) δ 9.08 (d, J=7.1 Hz, 1H), 8.79 (d, J=1.5 Hz, 1H), 8.71 (d, J=1.5 Hz, 1H), 7.71 (d, J=7.3 Hz, 1H), 7.68 (d, J=7.2 Hz, 1H), 6.65 (s, 2H), 4.77 (s, 2H), 4.06 (s, 1H), 3.83-3.70 (m, 1H), 3.70-3.60 (m, 4H), 1.85-1.67 (m, 4H), 1.65-1.56 (m, 2H), 1.49-1.38 (m, 2H), 1.35 (d, J=6.8 Hz, 3H), 1.27-1.17 (m, 1H), 1.14 (s, 3H), 0.66-0.57 (m, 1H), 0.51-0.39 (m, 2H), 0.34-0.27 (m, 1H). ESI MS [M+H]$^+$ for C$_{28}$H$_{35}$N$_6$O$_5$S, calcd 567.2, found 567.1.

Example 132: 2-Amino-N-cyclopropyl-5-{2-[(1S)-1-cyclopropylethyl]-7-methanesulfonyl-1-oxo-2,3-dihydro-1H-isoindol-5-yl}pyrazolo[1,5-a]pyrimidine-3-carboxamide

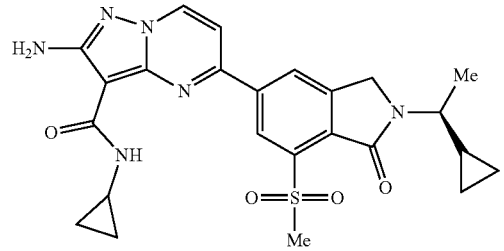 [SMILES: C[C@@H](C1CC1)N1Cc2cc(-c3ccn4nc(N)c(C(=O)NC5CC5)c4n3)cc(S(C)(=O)=O)c2C1=O]

The title compound was prepared in a similar manner to example 130. $^1$H NMR (400 MHz, DMSO-d$_6$) δ 9.08 (d, J=7.1 Hz, 1H), 8.87 (d, J=1.5 Hz, 1H), 8.76 (d, J=1.5 Hz, 1H), 7.75 (d, J=4.2 Hz, 1H), 7.73 (d, J=7.2 Hz, 1H), 6.66 (s, 2H), 4.77 (s, 2H), 3.69 (s, 4H), 3.68-3.60 (m, 1H), 2.96-2.87 (m, 1H), 1.35 (d, J=6.8 Hz, 3H), 1.27-1.15 (m, 1H), 0.83-0.75 (m, 2H), 0.76-0.69 (m, 2H), 0.65-0.57 (m, 1H), 0.50-0.40 (m, 2H), 0.34-0.27 (m, 1H). ESI MS [M+H]$^+$ for C$_{24}$H$_{27}$N$_6$O$_4$S, calcd 495.2, found 495.0.

Example 133: 2-Amino-N-cyclopropyl-5-{2-[(1S)-1-cyclopropylethyl]-7-(ethanesulfonyl)-1-oxo-2,3-dihydro-1H-isoindol-5-yl}pyrazolo[1,5-a]pyrimidine-3-carboxamide

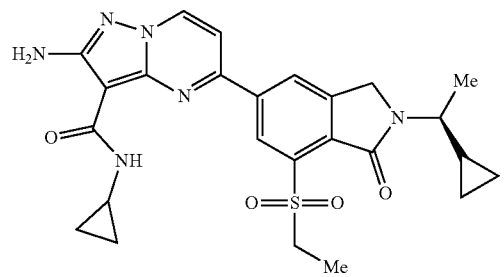 [SMILES: CCS(=O)(=O)c1cc(-c2ccn3nc(N)c(C(=O)NC4CC4)c3n2)cc2c1C(=O)N([C@@H](C)C1CC1)C2]

The title compound was prepared in a similar manner to example 130. $^1$H NMR (400 MHz, DMSO-d$_6$) δ 9.09 (d, J=7.1 Hz, 1H), 8.85 (d, J=1.6 Hz, 1H), 8.76 (d, J=1.6 Hz, 1H), 7.78 (d, J=4.2 Hz, 1H), 7.72 (d, J=7.2 Hz, 1H), 6.66 (s, 2H), 4.77 (s, 2H), 3.98-3.87 (m, 2H), 3.64 (dq, J=8.9, 6.8 Hz, 1H), 2.96-2.88 (m, 1H), 1.34 (d, J=6.8 Hz, 3H), 1.26-1.13 (m, 4H), 0.83-0.75 (m, 2H), 0.73-0.67 (m, 2H), 0.66-0.58 (m, 1H), 0.50-0.38 (m, 2H), 0.33-0.25 (m, 1H). ESI MS [M+H]$^+$ for C$_{25}$H$_{29}$N$_6$O$_4$S, calcd 509.2, found 509.1.

Example 134: 2-Amino-N-cyclopropyl-5-{2-[(1S)-1-cyclopropylethyl]-1-oxo-7-(propane-2-sulfonyl)-2,3-dihydro-1H-isoindol-5-yl}pyrazolo[1,5-a]pyrimidine-3-carboxamide

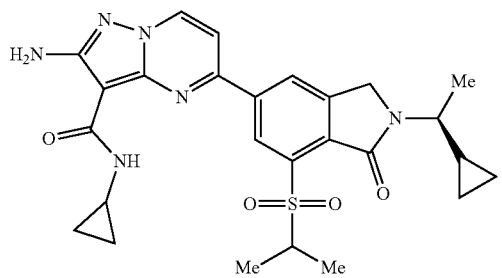 [SMILES: CC(C)S(=O)(=O)c1cc(-c2ccn3nc(N)c(C(=O)NC4CC4)c3n2)cc2c1C(=O)N([C@@H](C)C1CC1)C2]

The title compound was prepared in a similar manner to example 130. ¹H NMR (400 MHz, DMSO-$d_6$) δ 9.09 (d, J=7.1 Hz, 1H), 8.82 (d, J=1.6 Hz, 1H), 8.74 (d, J=1.5 Hz, 1H), 7.79 (d, J=4.3 Hz, 1H), 7.71 (d, J=7.2 Hz, 1H), 6.66 (s, 2H), 4.77 (s, 2H), 4.58 (h, J=6.8 Hz, 1H), 3.63 (dq, J=9.0, 6.8 Hz, 1H), 2.97-2.87 (m, 1H), 1.34 (d, J=6.8 Hz, 3H), 1.28-1.16 (m, 7H), 0.83-0.75 (m, 2H), 0.72-0.66 (m, 2H), 0.65-0.58 (m, 1H), 0.50-0.37 (m, 2H), 0.33-0.26 (m, 1H). ESI MS [M+H]⁺ for $C_{26}H_{31}N_6O_4S$, calcd 523.2, found 523.1.

Example 135: 2-Amino-N-cyclopropyl-5-{2-[(1S)-1-cyclopropylethyl]-7-cyclopropylmethanesulfonyl-1-oxo-2,3-dihydro-1H-isoindol-5-yl}pyrazolo[1,5-a]pyrimidine-3-carboxamide

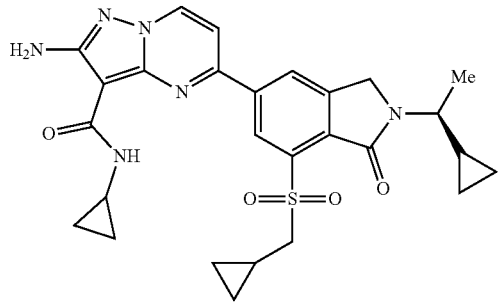 [SMILES: C[C@@H](C1CC1)N1Cc2cc(-c3ccn4nc(N)c(C(=O)NC5CC5)c4n3)cc(S(=O)(=O)CC3CC3)c2C1=O]

The title compound was prepared in a similar manner to example 130. ¹H NMR (400 MHz, DMSO-$d_6$) δ 9.05 (d, J=7.1 Hz, 1H), 8.86 (d, J=1.6 Hz, 1H), 8.72 (d, J=1.5 Hz, 1H), 7.75 (d, J=4.3 Hz, 1H), 7.69 (d, J=7.3 Hz, 1H), 4.76 (s, 2H), 3.88 (d, J=7.2 Hz, 2H), 3.66-3.56 (m, 1H), 2.94-2.87 (m, 1H), 1.31 (d, J=6.8 Hz, 3H), 1.17 (m, 1H), 0.88 (m, 1H), 0.79-0.73 (m, 2H), 0.73-0.66 (m, 2H), 0.61-0.55 (m, 1H), 0.47-0.36 (m, 4H), 0.28-0.16 (m, 3H). ESI MS [M+H]⁺ for $C_{27}H_{31}N_6O_4S$, calcd 535.2, found 535.2.

Example 136: 2-Amino-5-[7-(cyclobutanesulfonyl)-2-[(1S)-1-cyclopropylethyl]-1-oxo-2,3-dihydro-1H-isoindol-5-yl]-N-cyclopropylpyrazolo[1,5-a]pyrimidine-3-carboxamide

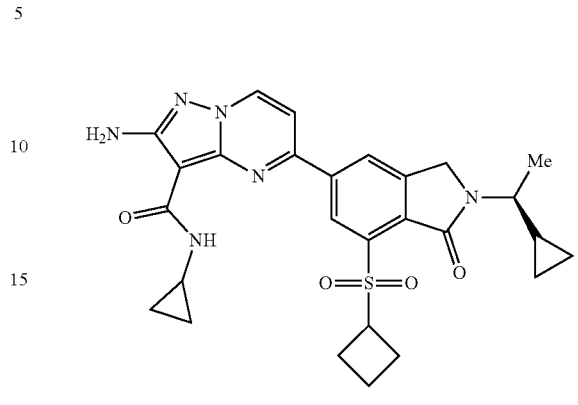

The title compound was prepared in a similar manner to example 130. ¹H NMR (400 MHz, DMSO-$d_6$) δ 9.06 (d, J=7.1 Hz, 1H), 8.83 (d, J=1.6 Hz, 1H), 8.70 (d, J=1.6 Hz, 1H), 7.79 (d, J=4.2 Hz, 1H), 7.68 (d, J=7.3 Hz, 1H), 5.15 (p, J=8.1 Hz, 1H), 4.75 (s, 2H), 3.61 (m, 1H), 2.91 (td, J=7.2, 3.8 Hz, 1H), 2.39-2.26 (m, 2H), 2.22-2.10 (m, 2H), 2.03-1.93 (m, 2H), 1.31 (d, J=6.8 Hz, 3H), 1.17 (m, 1H), 0.81-0.76 (m, 2H), 0.71-0.66 (m, 2H), 0.57 (m, 1H), 0.47-0.35 (m, 2H), 0.27 (m, 1H). ESI MS [M+H]⁺ for $C_{27}H_{31}N_6O_4S$, calcd 535.2, found 535.2.

Example 137: 2-Amino-5-[7-(cyclopentanesulfonyl)-2-[(1S)-1-cyclopropylethyl]-1-oxo-2,3-dihydro-1H-isoindol-5-yl]-N-cyclopropylpyrazolo[1,5-a]pyrimidine-3-carboxamide

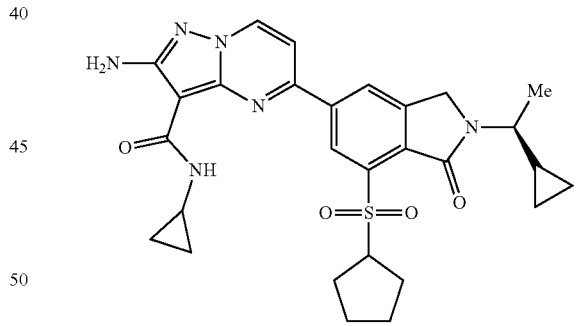

The title compound was prepared in a similar manner to example 130. ¹H NMR (400 MHz, DMSO-$d_6$) δ 9.09 (d, J=7.1 Hz, 1H), 8.84 (d, J=1.5 Hz, 1H), 8.73 (d, J=1.5 Hz, 1H), 7.79 (d, J=4.3 Hz, 1H), 7.71 (d, J=7.2 Hz, 1H), 6.66 (s, 2H), 4.93 (tt, J=9.1, 6.0 Hz, 1H), 4.77 (s, 2H), 3.64 (dq, J=8.9, 6.8 Hz, 1H), 2.98-2.88 (m, 1H), 1.99-1.80 (m, 4H), 1.79-1.67 (m, 2H), 1.67-1.54 (m, 2H), 1.34 (d, J=6.8 Hz, 3H), 1.26-1.15 (m, 1H), 0.82-0.74 (m, 2H), 0.71-0.64 (m, 2H), 0.64-0.57 (m, 1H), 0.50-0.37 (m, 2H), 0.34-0.25 (m, 1H). ESI MS [M+H]⁺ for $C_{28}H_{33}N_6O_4S$, calcd 549.2, found 549.1.

Example 138: 2-Amino-5-[7-(cyclohexanesulfonyl)-2-[(1S)-1-cyclopropylethyl]-1-oxo-2,3-dihydro-1H-isoindol-5-yl]-N-cyclopropylpyrazolo[1,5-a]pyrimidine-3-carboxamide

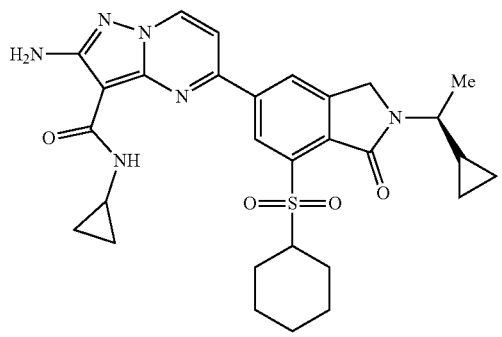 [SMILES: C[C@@H](C1CC1)N1Cc2cc(-c3ccn4nc(N)c(C(=O)NC5CC5)c4n3)cc(S(=O)(=O)C3CCCCC3)c2C1=O]

The title compound was prepared in a similar manner to example 130. $^1$H NMR (400 MHz, DMSO-$d_6$) δ 9.09 (d, J=7.1 Hz, 1H), 8.80 (d, J=1.6 Hz, 1H), 8.74 (d, J=1.5 Hz, 1H), 7.79 (d, J=4.2 Hz, 1H), 7.71 (d, J=7.2 Hz, 1H), 6.66 (s, 2H), 4.77 (s, 2H), 4.37 (tt, J=12.0, 3.4 Hz, 1H), 3.66 (dq, J=9.0, 6.9 Hz, 1H), 2.96-2.88 (m, 1H), 1.93-1.76 (m, 5H), 1.70-1.58 (m, 1H), 1.55-1.40 (m, 2H), 1.34 (d, J=6.8 Hz, 3H), 1.26-1.14 (m, 5H), 0.83-0.76 (m, 2H), 0.72-0.66 (m, 2H), 0.65-0.57 (m, 1H), 0.49-0.39 (m, 2H), 0.34-0.27 (m, 1H). ESI MS [M+H]$^+$ for $C_{29}H_{35}N_6O_4S$, calcd 563.2, found 563.1.

Example 139: 2-Amino-N-cyclopropyl-5-[7-(methylsulfamoyl)-1-oxo-2-[(2S)-1,1,1-trifluoropropan-2-yl]-2,3-dihydro-1H-isoindol-5-yl]pyrazolo[1,5-a]pyrimidine-3-carboxamide

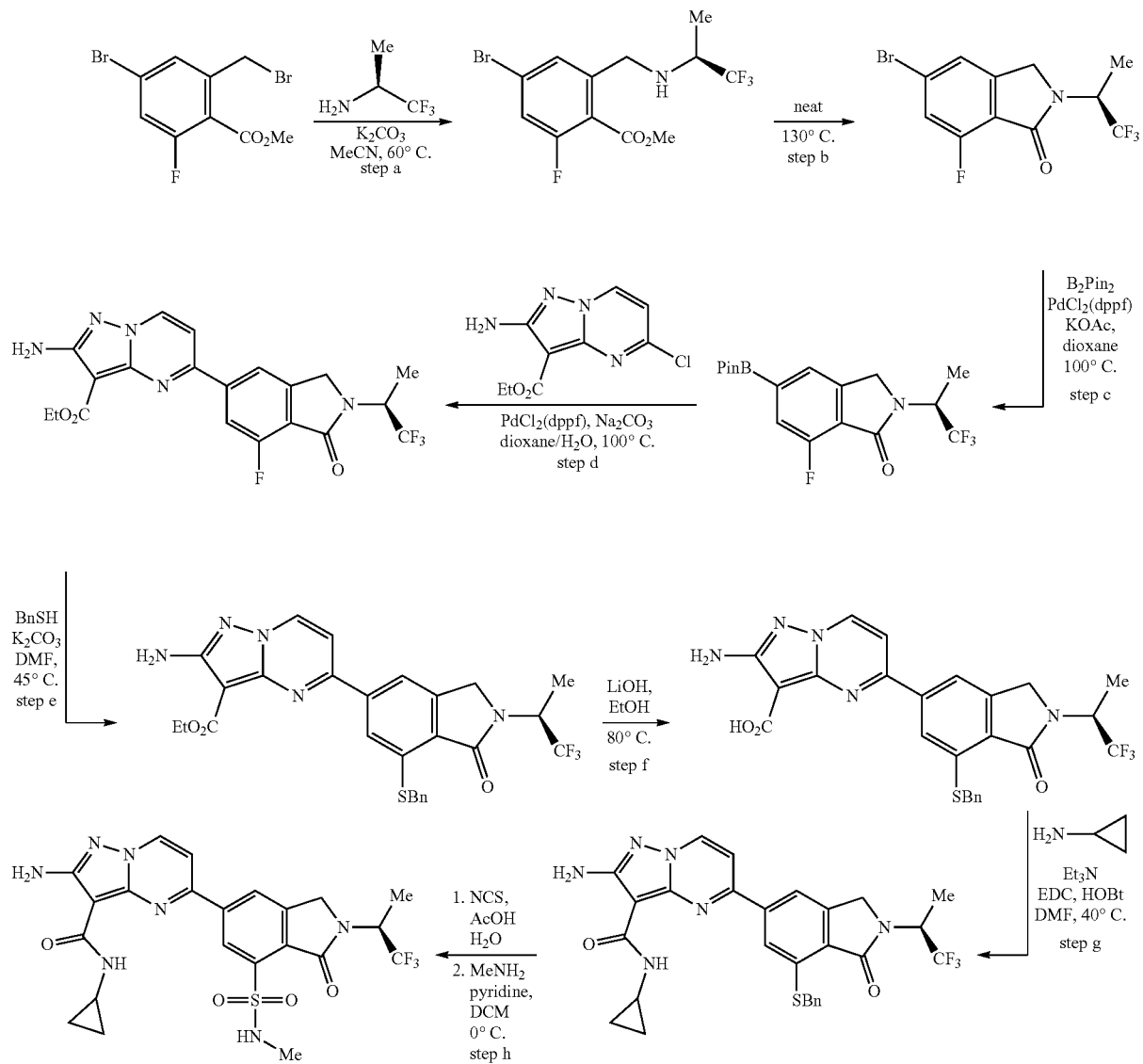

Step a: To a solution of methyl 4-bromo-2-(bromomethyl)-6-fluorobenzoate (23.4 g, 71.8 mmol, 1.0 equiv.) and (2S)-1,1,1-trifluoro-2-propanamine (7.41 mL, 75.4 mmol, 1.05 equiv.) in CH$_3$CN (360 mL, 0.2 M) was added K$_2$CO$_3$ (29.8 g, 215.4 mmol, 3.0 equiv.). The mixture was heated to 60° C. overnight. The mixture was filtered, concentrated to dryness, and purified by flash chromatography (SiO$_2$, 0->20% EtOAc/hexane) to yield the desired product as a colorless oil (15.9 g, 62%). ESI MS [M+H]$^+$ for C$_{12}$H$_{12}$BrF$_4$NO$_2$; calcd 358.0, found 358.0.

Step b: A flask charged with the product from Step a (5.0 g, 15.3 mmol) was heated to 130° C. overnight under N$_2$. The desired product was used without further purification. ESI MS [M+H]$^+$ for C$_{11}$H$_8$BrF$_4$NO$_3$; calcd 326.0, found 326.0.

Step c: The product of Step b (661 mg, 0.2.03 mmol, 1.0 equiv.) was combined with Pd(dppf)Cl$_2$ (146 mg, 0.20 mmol, 0.1 equiv.), B$_2$pin$_2$ (618 mg, 2.43 mmol, 1.2 equiv.) and KOAc (497 mg, 5.08 mmol, 2.5 equiv.) in dioxane (6.8 mL). The resulting solution was heated to 100° C. for 2 h, cooled to rt, filtered through Celite (washed with EtOAc) and concentrated. The resulting residue was used directly in the next step without purification.

Step d: The product residue from Step c (511 mg, 1.37 mmol, 1.0 equiv.) was combined with 2-amino-5-chloropyrazolo[1,5-a]pyrimidine-3-carboxylic acid ethyl ester (330 mg, 1.37 mmol, 1.0 equiv.), Pd(dppf)Cl$_2$ (102 mg, 0.14 mmol, 0.1 equiv.) and Na$_2$CO$_3$ (1 M aq. solution, 5.5 mL) in dioxane (13.7 mL). The resulting solution was heated to 100° C. for 1 h, concentrated, and purified by flash chromatography (SiO$_2$, 0→10% MeOH/CH$_2$Cl$_2$) to yield the cross-coupled ethyl ester (340 mg, 37%, 2 steps). ESI MS [M+H]$^+$ for C$_{20}$H$_{17}$F$_4$N$_5$O$_3$; calcd 452.1, found 452.1.

Step e: To a solution of the product from Step d (500 mg, 1.11 mmol, 1.0 equiv.) and benzyl mercaptan (143 μL, 1.22 mmol, 1.1 equiv.) in DMF (3.7 mL, 0.3 M) was added K$_2$CO$_3$ (460 mg, 3.33 mmol, 3.0 equiv.). The mixture was heated to 55° C. for 4 h. After cooling to rt, the mixture was partitioned between EtOAc and H$_2$O. The organic layer was washed with H$_2$O (2×) and brine, dried over MgSO$_4$ and concentrated to dryness. Flash chromatography (SiO$_2$, 0-10% MeOH/CH$_2$Cl$_2$) to yield the desired product (494 mg, 84%). ESI MS [M+H]$^+$ for C$_{27}$H$_{24}$F$_3$N$_5$O$_3$S; calcd 556.2, found 556.1.

Step f: To a suspension of the product from Step e (494 mg, 0.936 mmol, 1.0 equiv.) in EtOH (4.7 mL, 0.2 M) was added LiOH (3 M aq. solution, 0.94 mL, 2.81 mmol). The mixture was heated to 80° C. for 1 h. After cooling to rt, the EtOH was removed under reduced pressure. The product was precipitated by addition of 2 M HCl and filtered. The desired product was used without further purification. ESI MS [M+H]$^+$ for C$_{25}$H$_{20}$F$_3$N$_5$O$_3$S; calcd 528.1, found 528.1.

Step g: To a solution of the product from Step f, cyclopropylamine (70 μL, 1.03 mmol, 1.1 equiv), HOBt (158 mg, 1.03 mmol, 1.1 equiv.), and Et$_3$N (652 μL, 4.68 mmol, 5 equiv.) in DMF (9.4 mL, 0.1 M) at rt was added EDC (269 mg, 1.40 mmol 1.5 equiv.). The reaction mixture was heated to 40° C. for 4 h. The mixture was diluted with EtOAc and washed sequentially with 10% citric acid, H$_2$O and brine. The organics were dried over MgSO$_4$, filtered, and concentrated under reduced pressure. Flash chromatography (SiO$_2$, 0-10% MeOH/CH$_2$Cl$_2$) to yield the desired product (230 mg, 44%, 2 steps). ESI MS [M+H]$^+$ for C$_{28}$H$_{25}$F$_3$N$_6$O$_2$S; calcd 567.2, found 567.1.

Step h: To a solution of the product from Step g (230 mg, 0.41 mmol, 1.0 equiv.) in AcOH (2.41 mL) and H$_2$O (266 μL) was added NCS (163 mg, 1.22 mol). The reaction was stirred at rt for 3 h, then partitioned between EtOAc and H$_2$O. The organic layer was washed with H$_2$O and brine, dried over MgSO$_4$ and concentrated to dryness. The crude sulfonyl chloride was reconstituted in CH$_2$Cl$_2$ (3.3 mL, 0.13 M) and cooled to 0° C. in an ice-bath. Pyridine (547 μL, 0.75 M) and methylamine (40 wt % aq. solution, 177 μL, 2.05 mmol, 5 equiv.) were added simultaneously. After 1 h, the reaction mixture was partitioned between EtOAc and 1 M HCl. The organic layer was washed with H$_2$O and brine, dried over MgSO$_4$ and concentrated. The crude product was reconstituted in DMSO and purified by reverse phase HPLC (C18, CH$_3$CN/H$_2$O w/0.1% TFA) to afford the desired product as a white solid following lyophilization (32 mg, 15% yield). $^1$H NMR (400 MHz, DMSO-d$_6$) δ 9.07 (d, J=7.1 Hz, 1H), 8.71 (d, J=11.4 Hz, 2H), 7.77 (d, J=4.2 Hz, 1H), 7.68 (d, J=7.1 Hz, 1H), 7.11 (q, J=5.1 Hz, 1H), 5.12 (p, J=7.6 Hz, 1H), 4.87 (d, J=18.1 Hz, 1H), 4.66 (d, J=18.0 Hz, 1H), 2.89 (tq, J=7.7, 4.0 Hz, 1H), 2.53 (d, J=5.2 Hz, 3H), 1.54 (d, J=7.1 Hz, 3H), 0.89-0.72 (m, 2H), 0.71-0.60 (m, 2H). ESI MS [M+H]$^+$ for C$_{22}$H$_{22}$F$_3$N$_7$O$_4$S; calcd 538.1, found 538.0.

Example 140: 2-Amino-5-{2-[(1S)-1-cyclopropylethyl]-7-(methylsulfamoyl)-1-oxo-2,3-dihydro-1H-isoindol-5-yl}-N-(1-methyl-1H-pyrazol-4-yl)pyrazolo[1,5-a]pyrimidine-3-carboxamide

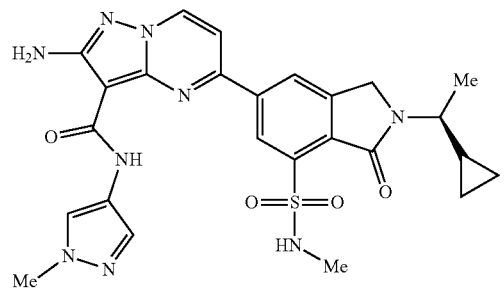 [SMILES: CNS(=O)(=O)c1cc(-c2ccn3nc(N)c(C(=O)Nc4cnn(C)c4)c3n2)cc2c1C(=O)N([C@@H](C)C1CC1)C2]

The title compound was prepared in a similar manner to examples 99 and 139. $^1$H NMR (400 MHz, DMSO-d$_6$) δ 9.69 (s, 1H), 9.14 (d, J=7.1 Hz, 1H), 8.90 (d, J=1.5 Hz, 1H), 8.81 (d, J=1.5 Hz, 1H), 8.11 (s, 1H), 7.82 (d, J=7.2 Hz, 1H), 7.74 (s, 1H), 7.57 (q, J=5.1 Hz, 1H), 4.85 (s, 2H), 3.85 (s, 3H), 3.68 (dq, J=9.6, 6.9 Hz, 1H), 2.56 (d, J=5.1 Hz, 3H), 1.37 (d, J=6.8 Hz, 3H), 1.29-1.18 (m, 1H), 0.69-0.57 (m, 1H), 0.53-0.40 (m, 2H), 0.37-0.28 (m, 1H). ESI MS [M+H]$^+$ for C$_{25}$H$_{28}$N$_9$O$_4$S, calcd 550.2, found 550.1.

Example 141: 2-Amino-5-{2-[(1S)-1-cyclopropylethyl]-7-(methylsulfamoyl)-1-oxo-2,3-dihydro-1H-isoindol-5-yl}-N-[trans-3-hydroxycyclobutyl]pyrazolo[1,5-a]pyrimidine-3-carboxamide

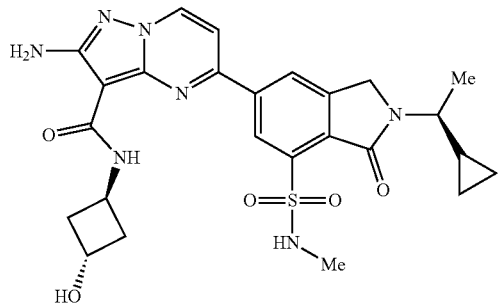 [SMILES: CNS(=O)(=O)c1cc(-c2ccn3nc(N)c(C(=O)N[C@H]4C[C@H](O)C4)c3n2)cc2c1C(=O)N([C@@H](C)C1CC1)C2]

The title compound was prepared in a similar manner to example 139. $^1$H NMR (400 MHz, DMSO-d$_6$) δ 9.09 (d, J=7.1 Hz, 1H), 8.80 (d, J=1.5 Hz, 1H), 8.72 (d, J=1.5 Hz, 1H), 7.99 (d, J=7.1 Hz, 1H), 7.74 (d, J=7.3 Hz, 1H), 7.50 (q, J=5.1 Hz, 1H), 6.63 (s, 2H), 5.07 (d, J=5.2 Hz, 1H), 4.82 (s, 2H), 4.60-4.49 (m, 1H), 4.41-4.31 (m, 1H), 3.73-3.62 (m, 1H), 2.53 (d, J=5.2 Hz, 3H), 2.39-2.23 (m, 4H), 1.36 (d, J=6.8 Hz, 3H), 1.28-1.18 (m, 1H), 0.67-0.58 (m, 1H), 0.52-0.40 (m, 2H), 0.35-0.28 (m, 1H). ESI MS [M+H]$^+$ for C$_{25}$H$_{30}$N$_7$O$_5$S, calcd 503.3, found 503.2.

Example 142: 2-Amino-N-cyclopropyl-5-{2-[(1S)-1-cyclopropylethyl]-7-(methylsulfamoyl)-1-oxo-2,3-dihydro-1H-isoindol-5-yl}pyrazolo[1,5-a]pyrimidine-3-carboxamide

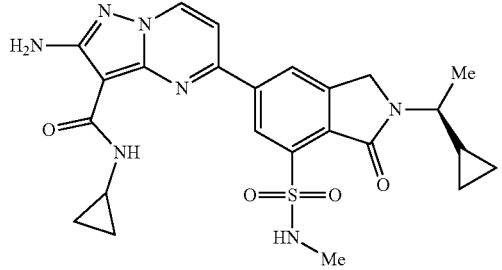 [SMILES: CNS(=O)(=O)c1cc(-c2ccn3nc(N)c(C(=O)NC4CC4)c3n2)cc2c1C(=O)N([C@@H](C)C1CC1)C2]

The title compound was prepared in a similar manner to example 139. $^1$H NMR (400 MHz, DMSO-d$_6$) δ 9.08 (d, J=7.1 Hz, 1H), 8.72 (s, 1H), 8.71 (s, 1H), 7.81 (d, J=4.2 Hz, 1H), 7.73 (d, J=7.1 Hz, 1H), 7.53 (q, J=5.1 Hz, 1H), 6.66 (s, 2H), 4.82 (s, 2H), 3.67 (dq, J=8.5, 6.8 Hz, 1H), 2.91 (tt, J=7.7, 3.8 Hz, 1H), 2.54 (d, J=5.2 Hz, 3H), 1.36 (d, J=6.8 Hz, 3H), 1.28-1.17 (m, 1H), 0.83-0.77 (m, 2H), 0.71-0.65 (m, 2H), 0.65-0.58 (m, 1H), 0.51-0.39 (m, 2H), 0.35-0.27 (m, 1H). ESI MS [M+H]$^+$ for C$_{24}$H$_{28}$N$_7$O$_4$S, calcd 510.2, found 510.1.

Example 143: 2-Amino-N-cyclopropyl-5-{2-[(1S)-1-cyclopropylethyl]-7-(ethylsulfamoyl)-1-oxo-2,3-dihydro-1H-isoindol-5-yl}pyrazolo[1,5-a]pyrimidine-3-carboxamide

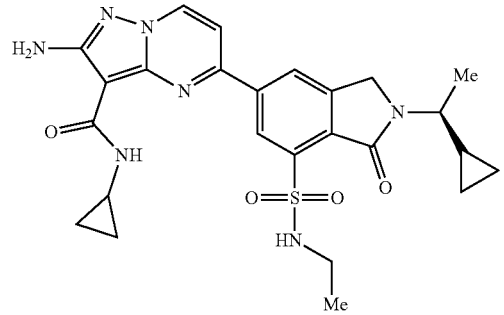 [SMILES: CCNS(=O)(=O)c1cc(-c2ccn3nc(N)c(C(=O)NC4CC4)c3n2)cc2c1C(=O)N([C@@H](C)C1CC1)C2]

The title compound was prepared in a similar manner to example 139. $^1$H NMR (400 MHz, DMSO-d$_6$) δ 9.08 (d, J=7.1 Hz, 1H), 8.74-8.69 (m, 2H), 7.80 (d, J=4.2 Hz, 1H), 7.73 (d, J=7.2 Hz, 1H), 7.70 (t, J=5.8 Hz, 1H), 6.66 (s, 2H), 4.82 (s, 2H), 3.67 (dq, J=8.9, 6.8 Hz, 1H), 2.97-2.87 (m, 3H), 1.37 (d, J=6.8 Hz, 3H), 1.29-1.18 (m, 1H), 0.97 (t, J=7.2 Hz, 3H), 0.84-0.76 (m, 2H), 0.71-0.65 (m, 2H), 0.65-0.59 (m, 1H), 0.50-0.40 (m, 2H), 0.35-0.27 (m, 1H). ESI MS [M+H]$^+$ for C$_{25}$H$_{30}$N$_7$O$_4$S, calcd 524.2, found 524.1.

Example 144: 2-Amino-N-cyclopropyl-5-{2-[(1S)-1-cyclopropylethyl]-7-(dimethylsulfamoyl)-1-oxo-2,3-dihydro-1H-isoindol-5-yl}pyrazolo[1,5-a]pyrimidine-3-carboxamide

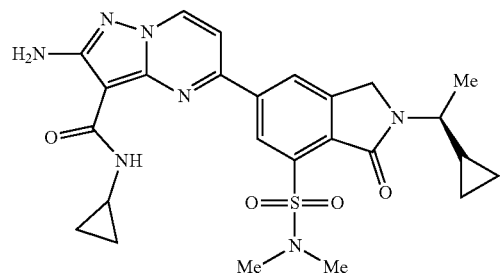 [SMILES: C[C@@H](C1CC1)N1Cc2cc(-c3ccn4nc(N)c(C(=O)NC5CC5)c4n3)cc(S(=O)(=O)N(C)C)c2C1=O]

The title compound was prepared in a similar manner to example 139. $^1$H NMR (400 MHz, DMSO-d$_6$) δ 9.08 (d, J=7.1 Hz, 1H), 8.75 (d, J=1.6 Hz, 1H), 8.68 (d, J=1.6 Hz, 1H), 7.78 (d, J=4.0 Hz, 1H), 7.71 (d, J=7.2 Hz, 1H), 6.66 (s, 2H), 4.70 (s, 2H), 3.63 (dq, J=9.6, 6.8 Hz, 1H), 2.94-2.87 (m, 1H), 2.85 (s, 6H), 1.32 (d, J=6.8 Hz, 3H), 1.23-1.13 (m, 1H), 0.83-0.75 (m, 2H), 0.70-0.64 (m, 2H), 0.64-0.56 (m, 1H), 0.48-0.37 (m, 2H), 0.31-0.24 (m, 1H). ESI MS [M+H]$^+$ for C$_{25}$H$_{30}$N$_7$O$_4$S, calcd 524.2, found 524.1.

Example 145: 2-Amino-5-{2-[(1S)-1-cyclopropyl-ethyl]-1-oxo-7-[(3R)-oxolan-3-yloxy]-2,3-dihydro-1H-isoindol-5-yl}-N-[(3R)-5-oxopyrrolidin-3-yl]pyrazolo[1,5-a]pyrimidine-3-carboxamide

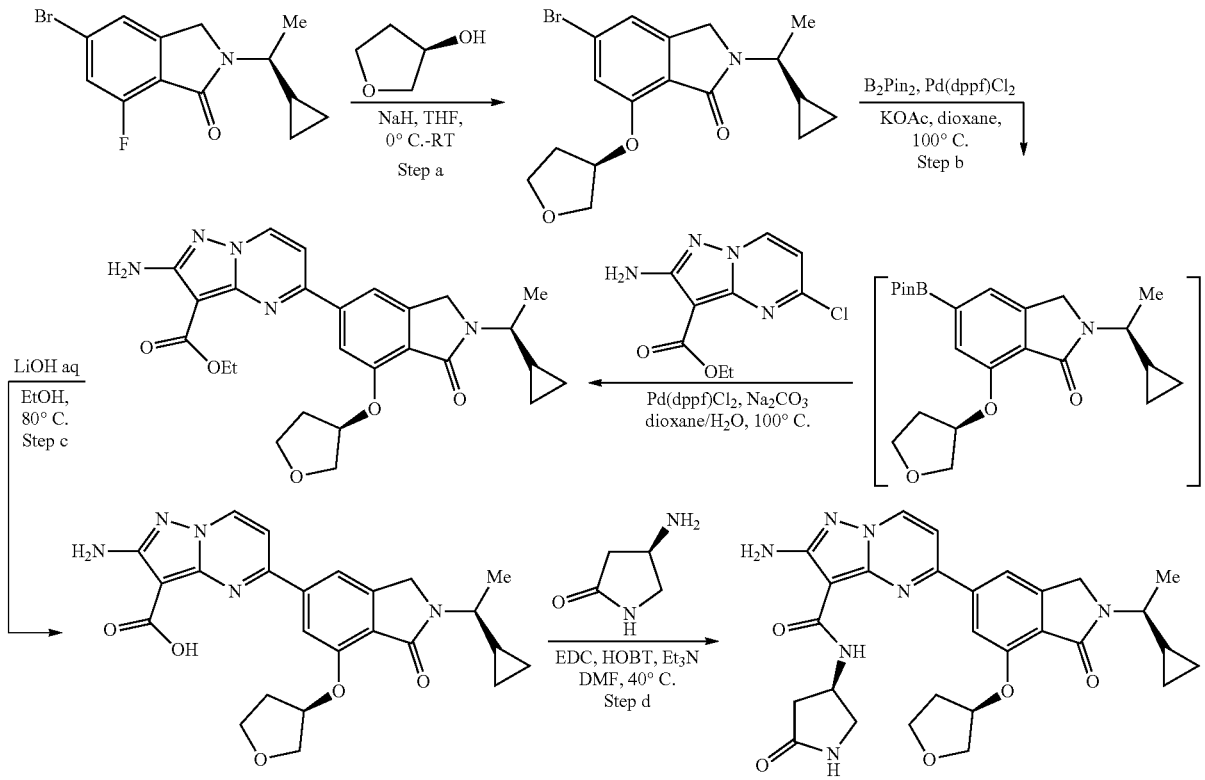

Step a: Sodium hydride 60% in oil (120 mg, 3.0 mmol) was suspended in 3 mL dry THF and cooled to 0° C. To this cold solution was added (R)-3-hydroxy-tetrahydrofuran (176.2 mg, 2.0 mmol) dropwise and stirred at the same temperature for 0.5 h. A 2 mL THF solution of 5-bromo-7-fluoro-isoindolinone (594 mg, 2.0 mmol) was then added dropwise to the alkoxide formed above at 0° C. After addition, ice bath was removed and stirred at rt for 1 h. The reaction was quenched with 2 mL saturated NH$_4$Cl. The aq. layer was extracted with EtOAc (2×10 mL), dried over Na$_2$SO$_4$ and taken to the next step without further purification. ESI MS [M+H]$^+$ for C$_{17}$H$_{20}$BrNO$_3$, calcd 366.1, found 366.1.

Step b: The crude from Step a was dissolved in 10 mL dry-degassed dioxane. To this solution was added B$_2$pin$_2$ (507.9 mg, 2.0 mmol), KOAc (392.6 mg, 2.0 mmol) and Pd(dppf)Cl$_2$ (73.2 mg, 0.1 mmol). The mixture was then heated at 100° C. in a sealed vial for 1 h. After cooling the reaction mixture to rt, 10 mL EtOAc was added the solid was filtered off. The filtrate was concentrated and taken to Suzuki coupling without further purification. The crude boronate ester thus obtained was re-dissolved in 10 mL degassed dioxane/H$_2$O (5:1). To this was added 2-amino-5-chloropyrazolo[1,5-a]pyrimidine-3-carboxylic acid ethyl ester (480 mg, 2.0 mmol), Na$_2$CO$_3$ (212 mg, 4 mmol) and Pd(dppf)Cl$_2$ (73.2 mg, 0.1 mmol). The mixture was then heated at 100° C. in a sealed vial for 1 h. After cooling the reaction mixture to rt, 5 mL saturated NH$_4$Cl was added and the aq. phase was extracted with EtOAc (2×20 mL). The pooled organic layer was dried over Na$_2$SO$_4$, concentrated and purified by CH$_2$Cl$_2$/acetone to yield the desired product (698 mg, 71% over 2 steps). ESI MS [M+H]$^+$ for C$_{27}$H$_{32}$N$_4$O$_5$, calcd 492.2, found 492.2.

Step c: The product from Step c (698 mg, 1.42 mmol) was suspended in 7 mL EtOH. To this suspension was added 3.0 M aq. solution of LiOH (1.42 mL, 4.26 mmol). The mixture was then heated at 80° C. for 3 h. After cooling to rt, 1.0 M HCl solution was added (4.26 mL, 4.26 mmol). The precipitate thus obtained was filtered, washed with H$_2$O and dried to obtain the desired acid, which was used without further purification. ESI MS [M+H]$^+$ for C$_{24}$H$_{27}$N$_5$O$_5$, calcd 464.2, found 464.1.

Step d: A 4-dram glass-vial was charged with the acid obtained from Step c (50 mg, 0.11 mmol), EDC-HCl (32.6 mg, 0.17 mmol), HOBT hydrate (18.53 mg, 0.12 mmol) and Et$_3$N (77 µL, 0.55 mmol). To this vial was added 1 mL DMF and (R)-4-Aminopyrrolidin-2-one (16.5 mg, 0.12 mmol). The reaction mixture was then stirred at 40° C. for 8 h. After cooling to rt, the material was purified by reversed phase HPLC (C18 column, 10 to 90% gradient of CH$_3$CN and H$_2$O with 0.1% TFA) to give the product as a white solid (31 mg, 52% yield): $^1$H NMR (400 MHz, DMSO-d$_6$) δ 9.01 (d, J=7.1 Hz, 1H), 8.14 (d, J=7.4 Hz, 1H), 7.91 (d, J=1.2 Hz, 1H), 7.76 (s, 1H), 7.73-7.64 (m, 2H), 5.37 (td, J=4.5, 2.1 Hz, 1H), 4.71-4.61 (m, 1H), 4.57 (d, J=2.0 Hz, 2H), 3.98-3.85 (m, 3H), 3.77 (td, J=8.2, 4.5 Hz, 1H), 3.64 (ddd, J=10.0, 6.4, 0.7 Hz, 1H), 3.51 (dq, J=9.3, 6.8 Hz, 1H), 3.26-3.16 (m, 1H), 2.66 (dd, J=16.6, 7.8 Hz, 1H), 2.28-2.14 (m, 2H), 2.04 (dddd, J=12.9, 6.6, 3.4, 1.3 Hz, 1H), 1.26 (d, J=6.8 Hz, 3H), 1.16-1.02 (m, 1H), 0.62-0.49 (m, 1H), 0.45-0.30 (m, 2H), 0.28-0.15 (m, 1H). ESI MS [M+H]$^+$ for C$_{28}$H$_{31}$N$_7$O$_5$, calcd 546.2, found 546.2.

Example 146: 2-Amino-N-cyclopropyl-5-{2-[(1S)-1-cyclopropylethyl]-1-oxo-7-[(3S)-oxolan-3-yloxy]-2,3-dihydro-1H-isoindol-5-yl}pyrazolo[1,5-a]pyrimidine-3-carboxamide

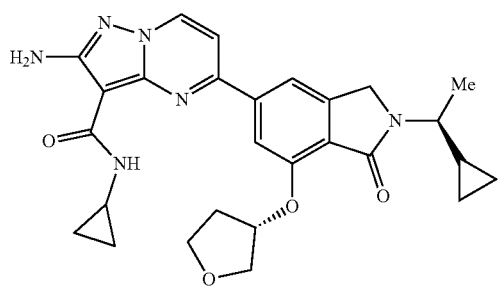 [SMILES: C[C@@H](C1CC1)N1Cc2cc(-c3ccn4nc(N)c(C(=O)NC5CC5)c4n3)cc(O[C@H]3CCOC3)c2C1=O]

The title compound was synthesized in similar fashion to example 145. $^1$H NMR (400 MHz, DMSO-d$_6$) δ 8.99 (d, J=7.1 Hz, 1H), 7.90 (d, J=1.2 Hz, 1H), 7.82 (d, J=3.4 Hz, 1H), 7.70 (d, J=1.2 Hz, 1H), 7.62 (d, J=7.2 Hz, 1H), 6.58 (s, 2H), 5.36 (tt, J=4.7, 2.2 Hz, 1H), 4.55 (s, 2H), 3.96 (dd, J=10.2, 4.6 Hz, 1H), 3.93-3.86 (m, 3H), 3.78 (td, J=8.2, 4.6 Hz, 1H), 3.56-3.45 (m, 1H), 2.81 (tq, J=7.3, 3.8 Hz, 1H), 2.27 (dtd, J=13.4, 8.2, 6.3 Hz, 1H), 2.06 (dt, J=12.6, 5.9 Hz, 1H), 1.26 (d, J=6.8 Hz, 4H), 1.12 (dtd, J=13.2, 8.9, 8.3, 4.9 Hz, 1H), 0.79-0.72 (m, 2H), 0.60-0.56 (m, 2H), 0.43-0.30 (m, 2H), 0.25-0.17 (m, 1H). ESI MS [M+H]$^+$ for C$_{27}$H$_{30}$N$_6$O$_4$, calcd 503.2, found 503.1.

Example 147: 2-Amino-N-[(1R)-1-cyclopropyl-2-hydroxyethyl]-5-{2-[(1S)-1-cyclopropylethyl]-1-oxo-7-[(3R)-oxolan-3-yloxy]-2,3-dihydro-1H-isoindol-5-yl}pyrazolo[1,5-a]pyrimidine-3-carboxamide

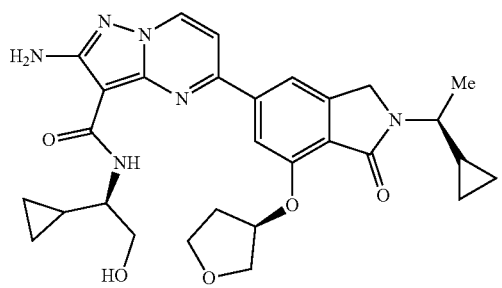 [SMILES: C[C@@H](C1CC1)N1Cc2cc(-c3ccn4nc(N)c(C(=O)N[C@@H](CO)C5CC5)c4n3)cc(O[C@@H]3CCOC3)c2C1=O]

The title compound was synthesized in similar fashion to example 145. $^1$H NMR (400 MHz, DMSO-d$_6$) δ 9.00 (d, J=7.1 Hz, 1H), 8.29 (d, J=8.8 Hz, 1H), 8.15 (d, J=1.2 Hz, 1H), 7.72 (d, J=1.3 Hz, 1H), 7.69 (d, J=7.2 Hz, 1H), 5.40 (ddt, J=6.4, 4.4, 1.8 Hz, 1H), 4.52 (s, 2H), 3.96-3.90 (m, 1H), 3.90-3.82 (m, 2H), 3.76 (td, J=8.2, 4.4 Hz, 1H), 3.69 (dd, J=10.4, 3.1 Hz, 1H), 3.58 (dd, J=10.5, 3.7 Hz, 1H), 3.53-3.45 (m, 2H), 2.22 (dtd, J=13.3, 8.2, 6.1 Hz, 1H), 2.08-1.96 (m, 1H), 1.26 (d, J=6.8 Hz, 3H), 1.18-1.04 (m, 2H), 0.62-0.51 (m, 1H), 0.46-0.30 (m, 5H), 0.30-0.17 (m, 2H). ESI MS [M+H]$^+$ for C$_{29}$H$_{34}$N$_6$O$_5$, calcd 547.2, found 547.2.

Example 148: 2-Amino-N-cyclopropyl-5-{2-[(1S)-1-cyclopropylethyl]-1-oxo-7-[(3R)-oxolan-3-yloxy]-2,3-dihydro-1H-isoindol-5-yl}pyrazolo[1,5-a]pyrimidine-3-carboxamide

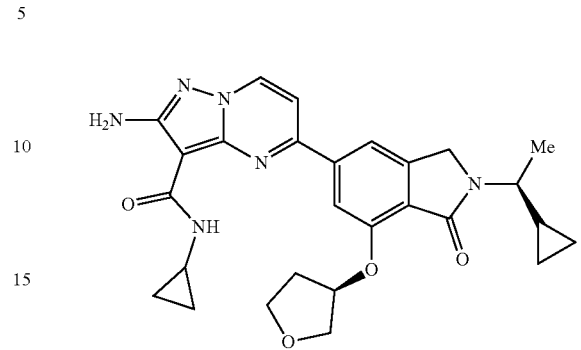

The title compound was synthesized in similar fashion to example 145. $^1$H NMR (400 MHz, DMSO-d$_6$) δ 8.99 (d, J=7.1 Hz, 1H), 7.90 (d, J=1.2 Hz, 1H), 7.82 (d, J=3.4 Hz, 1H), 7.70 (d, J=1.3 Hz, 1H), 7.62 (d, J=7.2 Hz, 1H), 5.36 (ddt, J=6.5, 4.4, 1.9 Hz, 1H), 4.55 (s, 2H), 3.99-3.88 (m, 3H), 3.79 (td, J=8.2, 4.6 Hz, 1H), 3.56-3.47 (m, 1H), 2.81 (tq, J=7.3, 3.8 Hz, 1H), 2.31-2.21 (m, 1H), 2.12-2.03 (m, 1H), 1.26 (d, J=6.8 Hz, 3H), 1.18-1.07 (m, 1H), 0.81-0.72 (m, 2H), 0.61-0.55 (m, 2H), 0.43-0.31 (m, 2H), 0.26-0.19 (m, 1H). ESI MS [M+H]$^+$ for C$_{27}$H$_{30}$N$_6$O$_4$, calcd 503.2, found 503.1.

Example 149: 2-Amino-N-cyclopropyl-5-{2-[(1S)-1-cyclopropylethyl]-1-oxo-7-{[(1R,4R)-4-hydroxycyclohexyl]oxy}-2,3-dihydro-1H-isoindol-5-yl}pyrazolo[1,5-a]pyrimidine-3-carboxamide

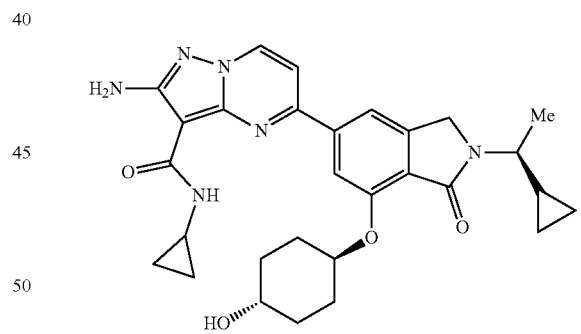

The title compound was synthesized in similar fashion to example 145. $^1$H NMR (400 MHz, DMSO-d$_6$) δ 8.98 (d, J=7.1 Hz, 1H), 7.85 (d, J=1.2 Hz, 1H), 7.82 (d, J=3.6 Hz, 1H), 7.74 (d, J=1.3 Hz, 1H), 7.60 (d, J=7.2 Hz, 1H), 4.69 (dq, J=8.6, 4.7, 4.1 Hz, 1H), 4.53 (s, 2H), 3.59 (tt, J=8.1, 3.7 Hz, 1H), 3.52 (dq, J=9.2, 6.8 Hz, 1H), 2.83 (tq, J=7.3, 3.8 Hz, 1H), 2.02 (d, J=11.9 Hz, 2H), 1.94-1.80 (m, 2H), 1.53 (q, J=10.8 Hz, 2H), 1.41-1.29 (m, 2H), 1.26 (d, J=6.8 Hz, 3H), 1.17-1.03 (m, 1H), 0.84-0.73 (m, 2H), 0.56 (dddd, J=9.5, 8.4, 5.2, 4.2 Hz, 3H), 0.46-0.30 (m, 2H), 0.26-0.15 (m, 1H). ESI MS [M+H]$^+$ for C$_{29}$H$_{34}$N$_6$O$_4$, calcd 531.3, found 531.2.

Example 150: 2-Amino-N-cyclopropyl-5-{2-[(1S)-1-cyclopropylethyl]-7-[(3R)-3-hydroxypyrrolidin-1-yl]-1-oxo-2,3-dihydro-1H-isoindol-5-yl}pyrazolo[1,5-a]pyrimidine-3-carboxamide

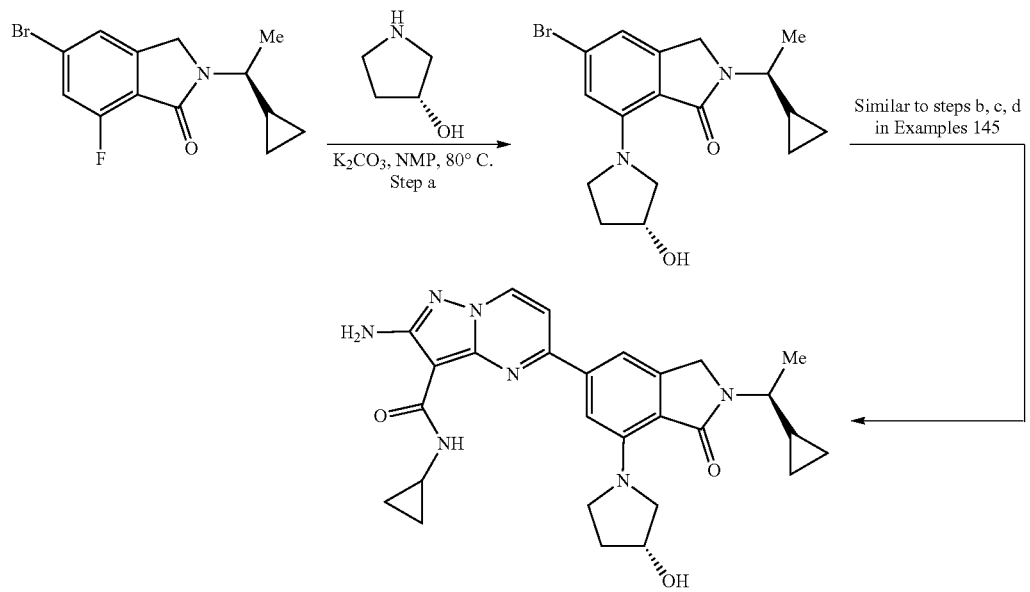 [SMILES: C[C@@H](C1CC1)N1Cc2cc(Br)cc(F)c2C1=O ; O[C@@H]1CCNC1 ; C[C@@H](C1CC1)N1Cc2cc(Br)cc(N3CC[C@@H](O)C3)c2C1=O ; C[C@@H](C1CC1)N1Cc2cc(-c3ccn4nc(N)c(C(=O)NC5CC5)c4n3)cc(N3CC[C@@H](O)C3)c2C1=O]

Step a: A glass vial with pressure-release cap was charged with 5-bromo-7-fluoro-isoindolinone (594 mg, 2.0 mmol), (S)-3-hydroxy pyrrolidine (216 mg, 3.0 mmol), $K_2CO_3$ (555 mg, 4.0 mmol) and 4 mL NMP. The mixture was heated at 80° C. for 2 h. After cooling to rt, 5 mL $H_2O$ was added. The aq. layer was extracted with EtOAc (2×10 mL), dried over $Na_2SO_4$ and concentrated. The crude material thus obtained was taken through subsequent steps similar to Steps b, c, d in example 145 to obtain the title compound. $^1$H NMR (400 MHz, DMSO-$d_6$) δ 8.94 (d, J=7.1 Hz, 1H), 7.88 (d, J=3.5 Hz, 1H), 7.60-7.53 (m, 2H), 7.49-7.45 (m, 1H), 6.54 (s, 2H), 4.86 (s, 1H), 4.50 (s, 2H), 4.34 (s, 1H), 4.00 (dd, J=11.4, 4.7 Hz, 1H), 3.74 (td, J=9.5, 6.7 Hz, 1H), 3.61-3.44 (m, 2H), 3.23 (d, J=11.5 Hz, 1H), 2.83 (tq, J=7.3, 3.8 Hz, 1H), 2.00 (m, 1H), 1.92-1.81 (m, 1H), 1.26 (d, J=6.9 Hz, 3H), 1.15-1.04 (m, 1H), 0.81-0.74 (m, 2H), 0.59-0.49 (m, 3H), 0.40-0.30 (m, 2H), 0.25-0.17 (m, 1H). ESI MS [M+H]$^+$ for $C_{27}H_{31}N_7O_3$, calcd 502.2, found 502.2.

Example 151: 2-Amino-5-{2-[(1S)-1-cyclopropylethyl]-7-[(3R)-3-hydroxypyrrolidin-1-yl]-1-oxo-2,3-dihydro-1H-isoindol-5-yl}-N-[cis-4-hydroxy-4-methylcyclohexyl]pyrazolo[1,5-a]pyrimidine-3-carboxamide

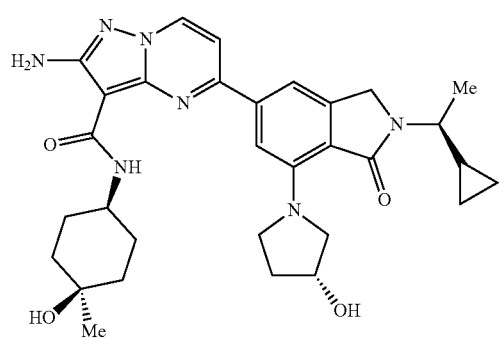 [SMILES: C[C@@H](C1CC1)N1Cc2cc(-c3ccn4nc(N)c(C(=O)N[C@H]5CC[C@@](C)(O)CC5)c4n3)cc(N3CC[C@@H](O)C3)c2C1=O]

The title compound was synthesized in similar fashion to example 150. $^1$H NMR (400 MHz, DMSO-$d_6$) δ 8.94 (d, J=7.1 Hz, 1H), 7.72 (d, J=7.9 Hz, 1H), 7.58-7.52 (m, 2H), 7.46-7.41 (m, 1H), 4.48 (s, 2H), 4.34 (s, 1H), 3.96 (dd, J=11.3, 4.8 Hz, 1H), 3.83-3.66 (m, 2H), 3.60-3.44 (m, 2H), 3.31-3.20 (m, 1H), 2.05-1.93 (m, 1H), 1.88 (dd, J=10.3, 6.0 Hz, 1H), 1.78-1.68 (m, 1H), 1.65-1.53 (m, 2H), 1.41 (td, J=12.9, 4.3 Hz, 2H), 1.26 (d, J=6.9 Hz, 3H), 1.12 (s, 3H), 0.59-0.49 (m, 1H), 0.41-0.29 (m, 2H), 0.25-0.18 (m, 1H). ESI MS [M−H]⁻ for $C_{31}H_{39}N_7O_4$, calcd 574.3, found 574.2.

Example 152: 2-Amino-N-cyclopropyl-5-{2-[(1S)-1-cyclopropylethyl]-7-[(3S)-3-hydroxypyrrolidin-1-yl]-1-oxo-2,3-dihydro-1H-isoindol-5-yl}pyrazolo[1,5-a]pyrimidine-3-carboxamide

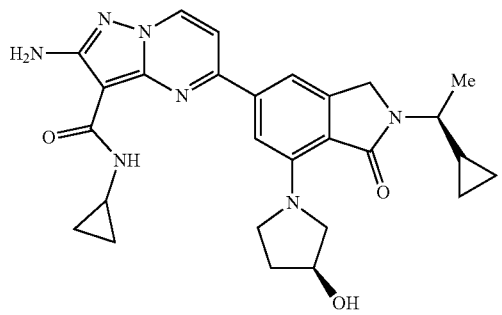 [SMILES: C[C@@H](C1CC1)N1Cc2cc(-c3ccn4nc(N)c(C(=O)NC5CC5)c4n3)cc(N3CC[C@H](O)C3)c2C1=O]

The title compound was synthesized in similar fashion to example 150. ¹H NMR (400 MHz, DMSO-d₆) δ 8.94 (d, J=7.1 Hz, 1H), 7.88 (d, J=3.5 Hz, 1H), 7.59-7.54 (m, 2H), 7.47 (s, 1H), 4.50 (d, J=3.4 Hz, 2H), 4.34 (s, 1H), 3.97 (dd, J=11.4, 4.8 Hz, 1H), 3.75-3.65 (m, 1H), 3.60-3.42 (m, 2H), 3.27 (d, J=11.3 Hz, 1H), 2.82 (tt, J=7.3, 3.7 Hz, 1H), 2.06-1.95 (m, 1H), 1.86 (s, 1H), 1.23 (d, J=6.8 Hz, 3H), 1.10 (ddt, J=12.9, 8.5, 4.3 Hz, 1H), 0.78 (td, J=6.9, 4.7 Hz, 2H), 0.57-0.54 (m, 2H), 0.37 (ddt, J=21.2, 9.5, 4.2 Hz, 2H), 0.28-0.16 (m, 1H). ESI MS [M+H]⁺ for $C_{27}H_{31}N_7O_3$, calcd 502.2, found 502.1.

Example 153: 2-Amino-5-{2-[(1S)-1-cyclopropylethyl]-7-[(3R)-3-hydroxypyrrolidin-1-yl]-1-oxo-2,3-dihydro-1H-isoindol-5-yl}-N-[cis-4-hydroxy-4-(trifluoromethyl)cyclohexyl]pyrazolo[1,5-a]pyrimidine-3-carboxamide

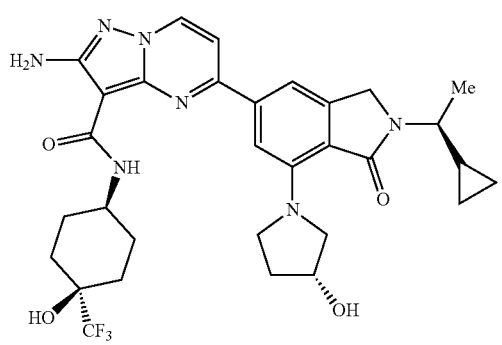 [SMILES: C[C@@H](C1CC1)N1Cc2cc(-c3ccn4nc(N)c(C(=O)N[C@H]5CC[C@](O)(C(F)(F)F)CC5)c4n3)cc(N3CC[C@@H](O)C3)c2C1=O]

The title compound was synthesized in similar fashion to example 150. ¹H NMR (400 MHz, DMSO-d₆) δ 8.95 (d, J=7.1 Hz, 1H), 7.72 (d, J=7.8 Hz, 1H), 7.55 (d, J=7.3 Hz, 2H), 7.46-7.40 (m, 1H), 4.49 (s, 2H), 4.34 (s, 1H), 3.97 (dd, J=11.3, 4.8 Hz, 1H), 3.89-3.76 (m, 1H), 3.71 (q, J=8.9 Hz, 1H), 3.60-3.44 (m, 2H), 3.30-3.21 (m, 1H), 2.06-1.95 (m, 1H), 1.91 (d, J=10.0 Hz, 3H), 1.79 (d, J=10.0 Hz, 2H), 1.70-1.53 (m, 5H), 1.26 (d, J=6.9 Hz, 3H), 1.13-1.03 (m, 1H), 0.58-0.48 (m, 1H), 0.42-0.29 (m, 2H), 0.22 (m, 1H). ESI MS [M−H]⁻ for $C_{31}H_{36}F_3N_7O_4$, calcd 628.3, found 628.2

Example 154: 2-Amino-5-{2-[(1S)-1-cyclopropylethyl]-7-(morpholin-4-yl)-1-oxo-2,3-dihydro-1H-isoindol-5-yl}-N-[cis-4-hydroxy-4-methylcyclohexyl]pyrazolo[1,5-a]pyrimidine-3-carboxamide

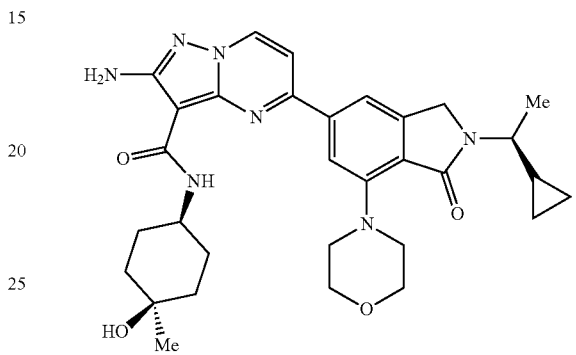

The title compound was synthesized in similar fashion to example 150. ¹H NMR (400 MHz, DMSO-d₆) δ 8.97 (d, J=7.1 Hz, 1H), 7.85 (d, J=1.3 Hz, 1H), 7.69-7.63 (m, 2H), 7.58 (d, J=7.2 Hz, 1H), 4.52 (s, 2H), 3.84-3.26 (m, 10H), 1.73-1.55 (m, 6H), 1.45-1.37 (m, 2H), 1.26 (d, J=6.8 Hz, 3H), 1.12 (s, 3H), 0.61-0.49 (m, 1H), 0.44-0.29 (m, 2H), 0.21 (m, 1H). ESI MS [M−H]⁻ for $C_{31}H_{39}N_7O_4$, calcd 574.3, found 574.2.

Example 155: 2-Amino-N-cyclopropyl-5-{2-[(1S)-1-cyclopropylethyl]-1-oxo-7-(2,2,2-trifluoroethoxy)-2,3-dihydro-1H-isoindol-5-yl}pyrazolo[1,5-a]pyrimidine-3-carboxamide

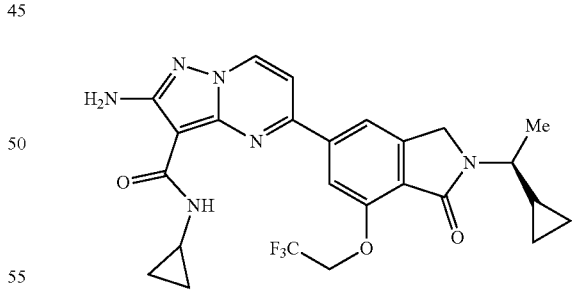

The title compound was prepared in a similar manner to example 145. ¹H NMR (400 MHz, DMSO-d₆) δ 9.02 (d, J=7.1 Hz, 1H), 8.04 (d, J=1.2 Hz, 1H), 7.90 (d, J=1.2 Hz, 1H), 7.82 (d, J=3.7 Hz, 1H), 7.66 (d, J=7.2 Hz, 1H), 6.59 (s, 2H), 5.06 (q, J=8.9 Hz, 2H), 4.59 (s, 2H), 3.58-3.48 (m, 1H), 2.83 (tt, J=7.5, 3.7 Hz, 1H), 1.28 (d, J=6.8 Hz, 3H), 1.18-1.08 (m, 1H), 0.80-0.70 (m, 2H), 0.64-0.57 (m, 2H), 0.57-0.51 (m, 1H), 0.44-0.30 (m, 2H), 0.26-0.18 (m, 1H). ESI MS [M+H]⁺ for $C_{25}H_{26}F_3N_6O_3$, calcd 515.2, found 515.2.

Example 156: 2-Amino-5-{2-[(1S)-1-cyclopropyl-ethyl]-1-oxo-7-(2,2,2-trifluoroethoxy)-2,3-dihydro-1H-isoindol-5-yl}-N-[(2R)-1-hydroxypropan-2-yl]pyrazolo[1,5-a]pyrimidine-3-carboxamide

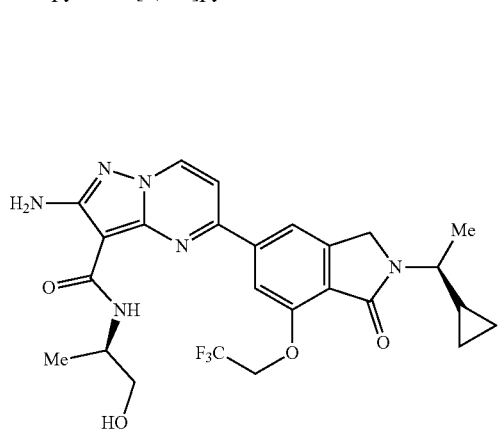

The title compound was prepared in a similar manner to example 145. $^1$H NMR (400 MHz, DMSO-$d_6$) δ 9.05 (d, J=7.1 Hz, 1H), 8.25 (d, J=1.2 Hz, 1H), 8.21 (d, J=7.9 Hz, 1H), 7.91 (d, J=1.2 Hz, 1H), 7.74 (d, J=7.2 Hz, 1H), 6.60 (s, 2H), 5.10-5.01 (m, 2H), 4.59 (s, 2H), 4.14-4.04 (m, 1H), 3.60-3.50 (m, 3H), 1.30 (d, J=6.8 Hz, 3H), 1.23 (d, J=6.6 Hz, 3H), 1.19-1.09 (m, 1H), 0.63-0.55 (m, 1H), 0.46-0.36 (m, 2H), 0.29-0.21 (m, 1H). ESI MS [M+H]$^+$ for $C_{25}H_{28}F_3N_6O_4$, calcd 533.2, found 533.2.

Example 157: 2-Amino-N-cyclopropyl-5-{2-[(1S)-1-cyclopropylethyl]-7-(3,3-difluorocyclobutoxy)-1-oxo-2,3-dihydro-1H-isoindol-5-yl}pyrazolo[1,5-a]pyrimidine-3-carboxamide

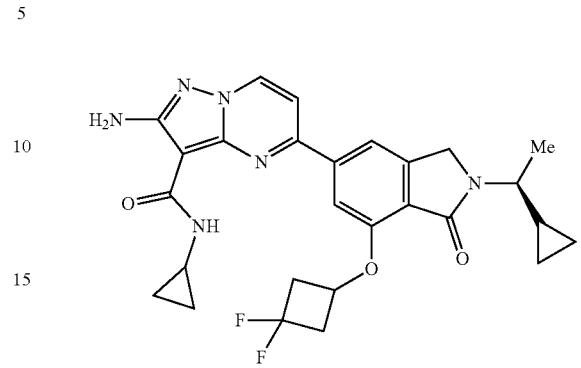

The title compound was prepared in a similar manner to example 145. $^1$H NMR (400 MHz, DMSO-$d_6$) δ 9.02 (d, J=7.1 Hz, 1H), 7.95 (d, J=1.2 Hz, 1H), 7.83 (d, J=3.3 Hz, 1H), 7.66 (d, J=7.2 Hz, 1H), 7.60 (d, J=1.2 Hz, 1H), 6.58 (s, 2H), 5.17-5.05 (m, 1H), 4.59 (s, 2H), 3.58-3.49 (m, 1H), 3.37-3.25 (m, 2H), 2.89-2.75 (m, 3H), 1.29 (d, J=6.8 Hz, 3H), 1.18-1.10 (m, 1H), 0.81-0.75 (m, 2H), 0.64-0.60 (m, 2H), 0.60-0.53 (m, 1H), 0.46-0.34 (m, 2H), 0.28-0.18 (m, 1H). ESI MS [M+H]$^+$ for $C_{27}H_{29}F_2N_6O_3$, calcd 523.2, found 523.2.

Example 158: 2-Amino-N-cyclopropyl-5-{2-[(1S)-1-cyclopropylethyl]-7-(difluoromethoxy)-1-oxo-2,3-dihydro-1H-isoindol-5-yl}pyrazolo[1,5-a]pyrimidine-3-carboxamide

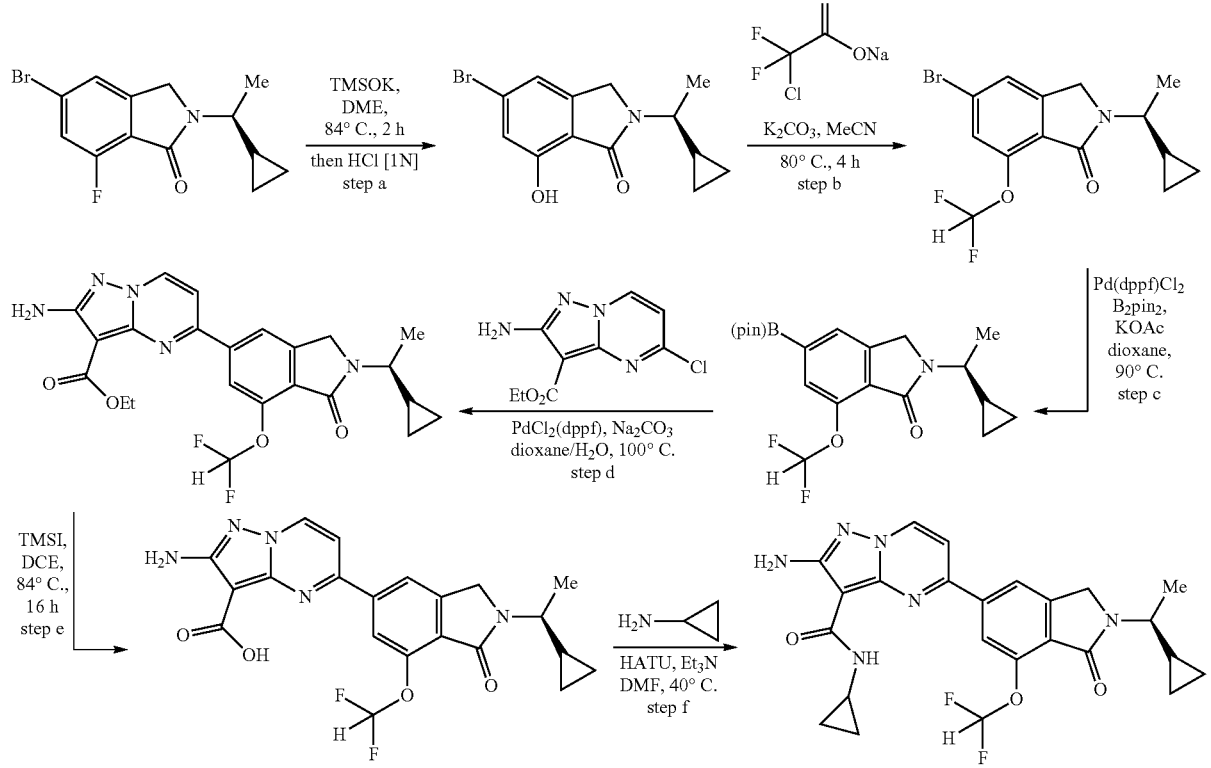

Step a: To a solution of isoindolinone (1.50 g, 5.03 mmol) in DME (0.3 M, 15 mL) at rt was added potassium trimethylsilanolate (2.26 g, 17.61 mmol, 3.5 equiv.). The reaction mixture was stirred at 84° C. for 1.5 h. The reaction mixture was acidified with HCl [1 N] and extracted with EtOAc. The combined organic layers were washed with $H_2O$, dried with $MgSO_4$, filtered and evaporated in vacuo. The resulting residue was purified by chromatography ($SiO_2$, 0 to 15% gradient EtOAc in Hexane) to obtain the product as an orange solid (1.13 g, 76%). $^1$H NMR (400 MHz, DMSO-$d_6$) δ 10.10 (s, 1H), 7.22-7.16 (m, 1H), 6.98-6.96 (m, 1H), 4.41 (s, 2H), 3.45 (dq, J=9.3, 6.8 Hz, 1H), 1.20 (d, J=6.8 Hz, 3H), 1.08-0.98 (m, 1H), 0.57-0.46 (m, 1H), 0.41-0.26 (m, 2H), 0.21-0.12 (m, 1H).

Step b: The product from Step a (1.13 g, 3.82 mmol) was dissolved in $CH_3CN$ (75 mL) at rt and sodium chlorodifluoroacetate (0.93 g, 6.11 mmol, 1.6 equiv.) was added followed by $K_2CO_3$ (1.16 g, 8.40 mmol, 2.2 equiv.). The reaction was stirred at 80° C. for 4 h. The reaction was then cooled and diluted with $CH_2Cl_2$, washed with $NaHCO_3$, dried with $MgSO_4$, filtered and evaporated in vacuo. The resulting residue was purified by chromatography ($SiO_2$, 0 to 15% gradient EtOAc in Hexane) to obtain the product as a white solid (0.96 g, 72%). $^1$H NMR (400 MHz, $CDCl_3$) δ 7.48-7.46 (m, 1H), 7.38-7.36 (m, 1H), 7.08 (t, $J_{H-F}$=75.2 Hz, 1H) 4.54-4.35 (m, 2H), 3.68 (dq, J=9.5, 6.8 Hz, 1H), 1.32 (d, J=6.8 Hz, 3H), 1.04-0.90 (m, 1H), 0.69-0.58 (m, 1H), 0.48-0.29 (m, 3H). $^{19}$F NMR (376 MHz, DMSO-$d_6$) δ −83.6 (dd, J=74.9, 2.7 Hz, 2F).

Step c: The product of Step b (500 mg, 1.44 mmol, 1.0 equiv.) was combined with Pd(dppf)$Cl_2$ (114 mg, 0.14 mmol, 0.1 equiv.), $B_2pin_2$ (366 mg, 1.44 mmol, 1.1 equiv.) and KOAc (423 mg, 4.32 mmol, 3.0 equiv.) in dioxane (7.0 mL, 0.2 M). The resulting solution was heated to 90° C. for 2 h, cooled to rt, filtered through Celite, washed with EtOAc and concentrated. The resulting residue was used directly in the next step without purification.

Step d: The product residue from Step c was combined with ethyl 2-amino-5-chloropyrazolo[1,5-a]pyrimidine-3-carboxylic acid ethyl ester (346 mg, 1.44 mmol, 1.0 equiv.), Pd(dppf)$Cl_2$ (118 mg, 0.144 mmol, 0.1 equiv.) and $Na_2CO_3$ (382 mg, 3.60 mmol, 2.5 equiv.) in dioxane (4.8 mL) and $H_2O$ (2.4 mL). The resulting solution was heated to 100° C. for 1 h, filtered through Celite, concentrated, and purified by flash chromatography ($SiO_2$, EtOAc/hexanes gradient) to yield the cross-coupled ethyl ester (420 mg, 62%, over 2 steps). $^1$H NMR (400 MHz, DMSO-$d_6$) δ 8.98 (d, J=7.1 Hz, 1H), 8.33 (d, J=1.2 Hz, 1H), 8.14 (d, J=1.2 Hz, 1H), 7.74 (d, J=7.2 Hz, 1H), 7.43 (t, $J_{H-F}$=74.5 Hz, 1H), 6.51 (s, 2H), 4.64 (s, 2H), 4.27 (q, J=7.1 Hz, 2H), 3.60-3.48 (m, 1H), 1.36 (t, J=7.1 Hz, 3H), 1.28 (d, J=6.8 Hz, 3H), 1.18-1.09 (m, 1H), 0.59-0.51 (m, 1H), 0.43-0.33 (m, 2H), 0.27-0.18 (m, 1H). $^{19}$F NMR (376 MHz, DMSO-$d_6$) δ −82.6 (dd, J=74.5, 3.1 Hz, 2F).

Step e: The product of Step d (370 mg, 0.786 mmol) was dissolved in DCE (4.0 mL, 0.2 M) and TMSI (0.7 mL, 4.71 mmol, 6.0 equiv.) was added dropwise. The reaction was stirred at 80° C. for 16 h. The reaction mixture was cooled to rt and $NaHSO_3$ (aq. sat. sol.) was added. The pH was adjusted to pH=3 and the product was extracted with $CH_2Cl_2$ (3×), dried with $MgSO_4$, filtered and evaporated in vacuo and the residue was used in the next step without further purification (346 mg, 99%).

Step f: The product of Step e (50 mg, 0.11 mmol) was dissolved in DMF (1.0 mL, 0.1 M). HATU (64 mg, 0.17 mmol, 1.5 equiv.), $Et_3N$ (80 µL, 0.56 mmol, 5.0 equiv.) and cyclopropylamine (12 µL, 0.17 mmol, 1.5 equiv.), were sequentially added, and the solution was heated to 40° C. After 2 h, the reaction solution was diluted with DMSO (2 ml) and the product was purified by reverse phase HPLC (20 to 80% gradient of $CH_3CN$ and $H_2O$ with 0.1% TFA) to afford the title compound as a pale yellow solid. $^1$H NMR (400 MHz, DMSO-$d_6$) δ 9.05 (d, J=7.1 Hz, 1H), 8.26 (d, J=1.2 Hz, 1H), 8.02-7.99 (m, 1H), 7.79 (d, J=3.8 Hz, 1H), 7.67 (d, J=7.1 Hz, 1H), 7.51 (t, J=74.3 Hz, 1H), 6.62 (s, 2H), 4.67 (s, 2H), 3.62-3.53 (m, 1H), 2.91-2.84 (m, 1H), 1.31 (d, J=6.8 Hz, 3H), 1.22-1.12 (m, 1H), 0.82-0.76 (m, 2H), 0.63-0.55 (m, 3H), 0.47-0.36 (m, 2H), 0.30-0.24 (m, 1H). $^{19}$F NMR (376 MHz, DMSO-$d_6$) δ −82.8 (dd, J=74.3, 1.9 Hz, 2F). ESI MS [M+H]$^+$ for $C_{24}H_{25}F_2N_6O_3$, calcd 483.2, found 483.2.

Example 159: 2-Amino-N-[(1R)-1-cyclopropyl-2-hydroxyethyl]-5-{2-[(1S)-1-cyclopropylethyl]-7-(difluoromethoxy)-1-oxo-2,3-dihydro-1H-isoindol-5-yl}pyrazolo[1,5-a]pyrimidine-3-carboxamide

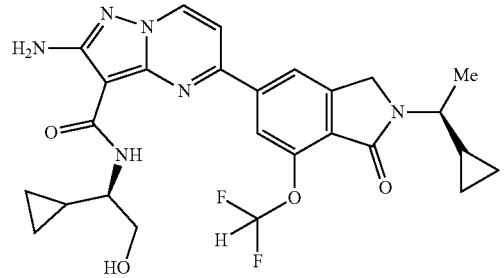 [SMILES: C[C@@H](C1CC1)N1Cc2cc(-c3ccn4nc(N)c(C(=O)N[C@@H](CO)C5CC5)c4n3)cc(OC(F)F)c2C1=O]

The title compound was prepared in a similar manner to example 158. $^1$H NMR (400 MHz, DMSO-$d_6$) δ 9.05 (d, J=7.1 Hz, 1H), 8.52-8.48 (m, 1H), 8.30 (d, J=8.7 Hz, 1H), 8.06 (d, J=1.1 Hz, 1H), 7.72 (d, J=7.2 Hz, 1H), 7.49 (t, J=74.7 Hz, 1H), 6.60 (s, 2H), 4.65 (s, 2H), 3.72 (dd, J=10.6, 3.4 Hz, 1H), 3.65-3.54 (m, 3H), 1.32 (d, J=6.8 Hz, 3H), 1.22-1.11 (m, 2H), 0.64-0.53 (m, 1H), 0.49-0.35 (m, 5H), 0.33-0.22 (m, 2H). $^{19}$F NMR (376 MHz, DMSO-$d_6$) δ −83.0 (dd, J=74.4, 37.6 Hz, 2F). ESI MS [M+H]$^+$ for $C_{26}H_{29}F_2N_6O_4$, calcd 527.2, found 527.2.

Example 160: 2-Amino-5-{2-[(1S)-1-cyclopropyl-ethyl]-7-(difluoromethoxy)-1-oxo-2,3-dihydro-1H-isoindol-5-yl}-N-[cis-4-hydroxy-4-methylcyclohexyl]pyrazolo[1,5-a]pyrimidine-3-carboxamide

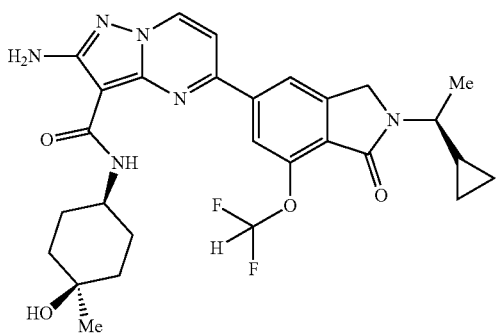 [SMILES: C[C@@H](C1CC1)N1Cc2cc(-c3ccn4nc(N)c(C(=O)N[C@H]5CC[C@@](C)(O)CC5)c4n3)cc(OC(F)F)c2C1=O]

The title compound was prepared in a similar manner to example 158. $^1$H NMR (400 MHz, DMSO-d$_6$) δ 9.05 (d, J=7.1 Hz, 1H), 8.26 (d, J=1.2 Hz, 1H), 7.99-7.95 (m, 1H), 7.71 (d, J=7.4 Hz, 1H), 7.66 (d, J=7.2 Hz, 1H), 7.45 (t, J=74.4 Hz, 1H), 6.62 (s, 2H), 4.66 (s, 2H), 3.82-3.71 (m, 1H), 3.61-3.53 (m, 1H), 1.84-1.53 (m, 6H), 1.49-1.37 (m, 2H), 1.31 (d, J=6.8 Hz, 3H), 1.21-1.14 (m, 1H), 1.14 (s, 3H), 0.63-0.53 (m, 1H), 0.48-0.32 (m, 2H), 0.29-0.22 (m, 1H). $^{19}$F NMR (376 MHz, DMSO-d$_6$) δ 82.7 (dd, J=74.4, 4.5 Hz, 2F). ESI MS [M+H]$^+$ for C$_{28}$H$_{33}$F$_2$N$_6$O$_4$, calcd 555.2, found 555.2.

Example 161: 2-Amino-5-{2-[(1S)-1-cyclopropyl-ethyl]-7-(difluoromethoxy)-1-oxo-2,3-dihydro-1H-isoindol-5-yl}-N-(pyridin-3-yl)pyrazolo[1,5-a]pyrimidine-3-carboxamide

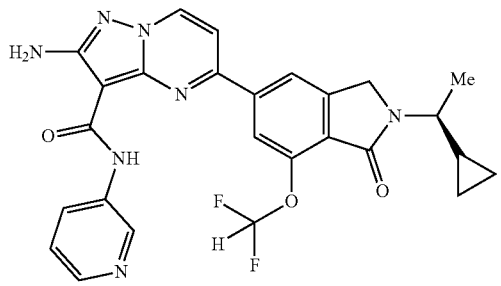 [SMILES: C[C@@H](C1CC1)N1Cc2cc(-c3ccn4nc(N)c(C(=O)Nc5cccnc5)c4n3)cc(OC(F)F)c2C1=O]

The title compound was prepared in a similar manner to examples 158 and 99. $^1$H NMR (400 MHz, DMSO-d$_6$) δ 10.06 (s, 1H), 9.15 (d, J=7.1 Hz, 1H), 9.10 (d, J=2.5 Hz, 1H), 8.44 (dd, J=5.1, 1.4 Hz, 1H), 8.41-8.34 (m, 2H), 8.21-8.17 (m, 1H), 7.79 (d, J=7.2 Hz, 1H), 7.66 (dd, J=8.5, 5.0 Hz, 1H), 7.53 (t, J=74.5 Hz, 1H), 6.78 (s, 2H), 4.70 (s, 2H), 3.63-3.54 (m, 2H), 1.32 (d, J=6.8 Hz, 3H), 1.23-1.12 (m, 1H), 0.65-0.55 (m, 1H), 0.48-0.37 (m, 2H), 0.31-0.23 (m, 1H). ESI MS [M+H]$^+$ for C$_{26}$H$_{24}$F$_2$N$_7$O$_3$, calcd 520.2, found 520.2.

Example 162: 2-Amino-5-{7-chloro-2-[(1S)-1-cyclopropylethyl]-1-oxo-2,3-dihydro-1H-isoindol-5-yl}-N-cyclopropylpyrazolo[1,5-a]pyrimidine-3-carboxamide

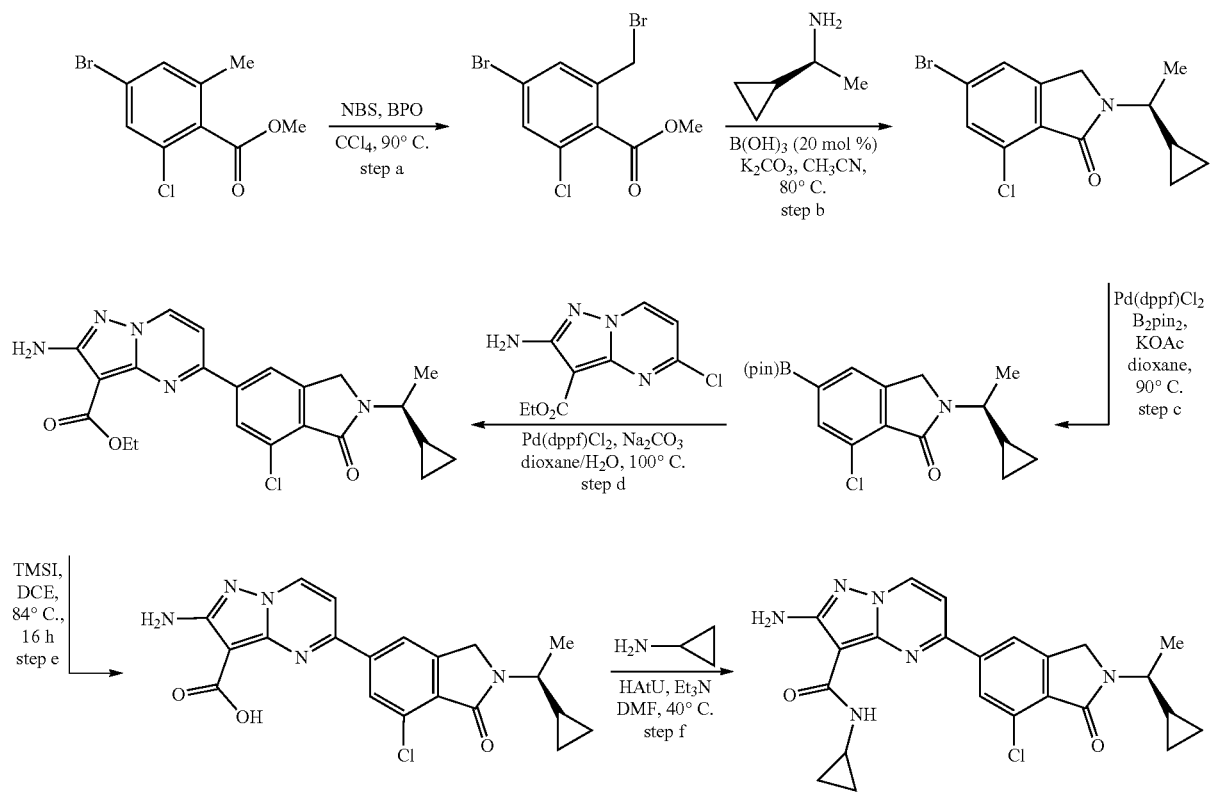

Steps a-d: Performed in a similar manner to example 1, Step e through Step h.

Steps e and f: Performed in a similar manner to example 27 to afford the title compound. $^1$H NMR (400 MHz, DMSO-$d_6$) δ 9.01 (d, J=7.1 Hz, 1H), 8.31 (d, J=1.4 Hz, 1H), 8.23 (d, J=1.3 Hz, 1H), 7.80 (d, J=3.9 Hz, 1H), 7.66 (d, J=7.2 Hz, 1H), 6.59 (s, 2H), 4.63 (s, 2H), 3.60-3.52 (m, 1H), 2.89-2.82 (m, 1H), 1.29 (d, J=6.8 Hz, 3H), 1.20-1.09 (m, 1H), 0.83-0.76 (m, 2H), 0.62-0.52 (m, 3H), 0.45-0.34 (m, 2H), 0.27-0.20 (m, 1H). ESI MS [M+H]$^+$ for $C_{23}H_{24}ClN_6O_2$, calcd 451.2, found 451.2.

Example 163: 2-Amino-5-{7-chloro-2-[(1S)-1-cyclopropylethyl]-1-oxo-2,3-dihydro-1H-isoindol-5-yl}-N-[(2R)-1-hydroxypropan-2-yl]pyrazolo[1,5-a]pyrimidine-3-carboxamide

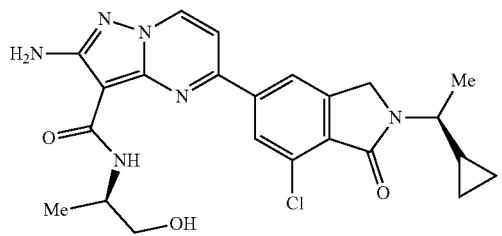 [SMILES: C[C@H](CO)NC(=O)c1c(N)nn2ccc(-c3cc(Cl)c4c(c3)CN([C@@H](C)C3CC3)C4=O)nc12]

The title compound was prepared in a similar manner to example 162. $^1$H NMR (400 MHz, DMSO-$d_6$) δ 9.01 (d, J=7.1 Hz, 1H), 8.54-8.51 (m, 1H), 8.36 (d, J=1.4 Hz, 1H), 8.24 (d, J=7.9 Hz, 1H), 7.72 (d, J=7.2 Hz, 1H), 6.58 (s, 2H), 4.60 (s, 2H), 4.11-3.99 (m, 1H), 3.60-3.51 (m, 3H), 1.30 (d, J=6.8 Hz, 3H), 1.22 (d, J=6.7 Hz, 3H), 1.18-1.09 (m, 1H), 0.60-0.52 (m, 1H), 0.44-0.34 (m, 2H), 0.27-0.19 (m, 1H). ESI MS [M+H]$^+$ for $C_{23}H_{26}ClN_6O_3$, calcd 469.2, found 469.2.

Example 164: 2-Amino-5-{7-chloro-1-oxo-2-[(2S)-1,1,1-trifluorobutan-2-yl]-2,3-dihydro-1H-isoindol-5-yl}-N-[(2R)-1-hydroxypropan-2-yl]pyrazolo[1,5-a]pyrimidine-3-carboxamide

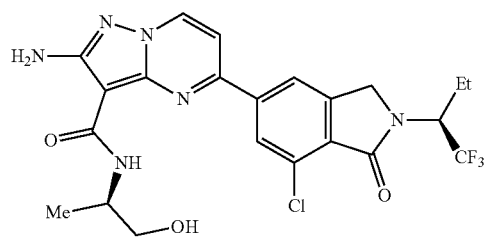 [SMILES: CC[C@H](N1Cc2cc(-c3ccn4nc(N)c(C(=O)N[C@H](C)CO)c4n3)cc(Cl)c2C1=O)C(F)(F)F]

The title compound was prepared in a similar manner to example 162. $^1$H NMR (400 MHz, DMSO-$d_6$) δ 9.03 (d, J=7.1 Hz, 1H), 8.57 (d, J=1.3 Hz, 1H), 8.42 (d, J=1.4 Hz, 1H), 8.26 (d, J=8.0 Hz, 1H), 7.73 (d, J=7.2 Hz, 1H), 6.59 (s, 2H), 4.86 (h, J=8.1 Hz, 1H), 4.64 (d, J=17.8 Hz, 1H), 4.49 (d, J=17.7 Hz, 1H), 4.09-3.99 (m, 1H), 3.56 (d, J=3.7 Hz, 2H), 1.93 (h, J=7.1 Hz, 2H), 1.22 (d, J=6.7 Hz, 3H), 0.85 (t, J=7.3 Hz, 3H). ESI MS [M+H]$^+$ for $C_{22}H_{23}ClF_3N_6O_3$, calcd 511.1, found 511.2.

Example 165: 2-Amino-N-cyclopropyl-5-{7-cyclopropyl-2-[(1S)-1-cyclopropylethyl]-1-oxo-2,3-dihydro-1H-isoindol-5-yl}pyrazolo[1,5-a]pyrimidine-3-carboxamide

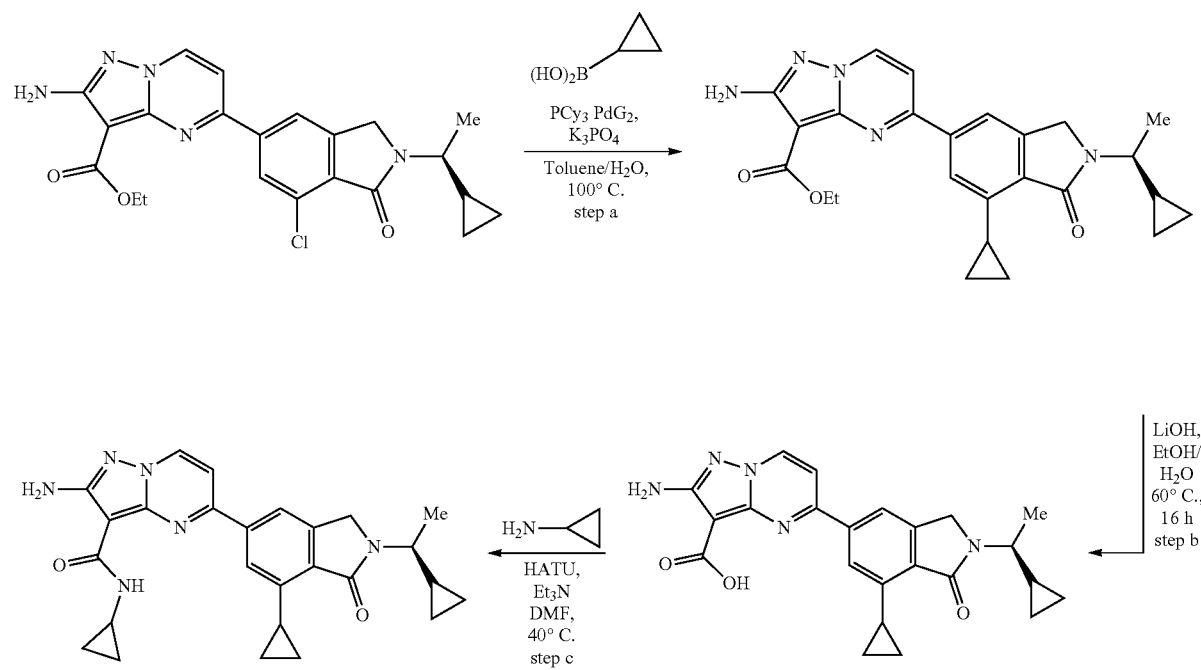

Step a: To a solution of aryl chloride (500 mg, 1.14 mmol), cyclopropyl boronic acid (147 mg, 1.70 mmol, 1.5 equiv.) and potassium phosphate (723 mg, 3.41 mmol, 3.0 equiv.) in toluene (5.0 mL, 0.2 M) and H₂O (0.5 mL) under N₂ was added PCy₃PdG2 (67 mg, 0.114 mmol, 0.1 equiv.). The mixture was heated to 100° C. for 2 h and then cooled to rt. The reaction solution was filtered over a pad of Celite and Na₂SO₄ and concentrated in vacuo. Purification by column chromatography (gradient 100% EtOAc in hexanes) afforded the desired compound as a yellow solid (436 mg, 86%).

Step b: The ethyl ester product of Step a (436 mg, 0.978 mmol, 1.0 equiv.) was dissolved in dioxane (3.0 mL) and EtOH (3.0 mL), H₂O (3.0 mL) and LiOH·H₂O (123 mg, 2.93 mmol, 3.0 equiv.) was added. The resulting solution was heated to 70° C. for 3 h. The resulting mixture was cooled to rt and the solvent was removed in vacuo. The mixture was diluted with H₂O and acidified to pH=3 with HCl [1 N]. The product was extracted using CH₂Cl₂ (3×), the combined organic layers were dried over Na₂SO₄, filtered and concentrated in vacuo to afford the carboxylic acid, which was used in the next step without purification (390 mg, 96%).

Step c: Performed in a similar manner to example 1 to afford the title compound. ¹H NMR (400 MHz, DMSO-d₆) δ 8.96 (d, J=7.1 Hz, 1H), 8.06 (d, J=1.4 Hz, 1H), 7.82 (d, J=3.8 Hz, 1H), 7.61 (d, J=7.2 Hz, 1H), 7.58 (d, J=1.4 Hz, 1H), 6.54 (s, 2H), 4.56 (s, 2H), 3.60-3.55 (m, 1H), 3.51-3.44 (m, 1H), 2.85 (tt, J=7.5, 3.8 Hz, 1H), 1.29 (d, J=6.8 Hz, 3H), 1.19-1.08 (m, 3H), 0.95-0.88 (m, 2H), 0.82-0.75 (m, 2H), 0.60-0.52 (m, 3H), 0.44-0.33 (m, 2H), 0.27-0.20 (m, 1H). ESI MS [M+H]⁺ for C₂₆H₂₉N₆O₂, calcd 457.2, found 457.2.

Example 166: 2-Amino-5-{7-cyclopropyl-2-[(1S)-1-cyclopropylethyl]-1-oxo-2,3-dihydro-1H-isoindol-5-yl}-N-[(2R)-1-hydroxypropan-2-yl]pyrazolo[1,5-a]pyrimidine-3-carboxamide

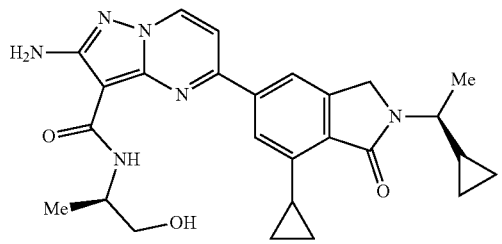 [SMILES: C[C@H](CO)NC(=O)c1c(N)nn2ccc(-c3cc4c(c(C5CC5)c3)C(=O)N([C@@H](C)C3CC3)C4)nc12]

The title compound was prepared in a similar manner to example 165. ¹H NMR (400 MHz, DMSO-d₆) δ 8.95 (d, J=7.1 Hz, 1H), 8.24 (d, J=1.4 Hz, 1H), 8.07 (d, J=8.1 Hz, 1H), 7.66 (d, J=7.2 Hz, 1H), 7.57 (d, J=1.5 Hz, 1H), 6.54 (s, 2H), 4.54 (s, 2H), 4.13-4.03 (m, 1H), 3.62-3.56 (m, 1H), 3.55-3.49 (m, 2H), 3.49-3.43 (m, 1H), 1.29 (d, J=6.8 Hz, 3H), 1.22 (d, J=6.7 Hz, 3H), 1.18-1.10 (m, 1H), 1.10-1.05 (m, 2H), 1.0-0.92 (m, 2H), 0.61-0.53 (m, 1H), 0.45-0.34 (m, 2H), 0.26-0.21 (m, 1H). ESI MS [M+H]⁺ for C₂₆H₃₁N₆O₃, calcd 475.2, found 475.2.

Example 167: 2-Amino-5-{7-cyclopropyl-2-[(1S)-1-cyclopropylethyl]-1-oxo-2,3-dihydro-1H-isoindol-5-yl}-N-[(1R)-1-cyclopropyl-2-hydroxyethyl]pyrazolo[1,5-a]pyrimidine-3-carboxamide

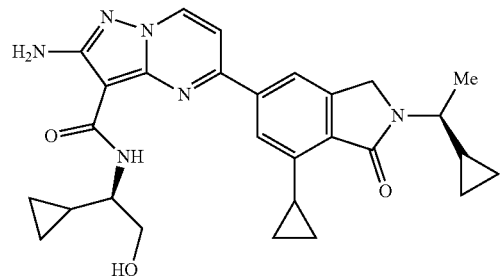 [SMILES: C[C@@H](C1CC1)N1Cc2cc(-c3ccn4nc(N)c(C(=O)N[C@@H](CO)C5CC5)c4n3)cc(C3CC3)c2C1=O]

The title compound was prepared in a similar manner to example 165. ¹H NMR (400 MHz, DMSO-d₆) δ 8.98 (d, J=7.1 Hz, 1H), 8.30 (d, J=1.4 Hz, 1H), 8.24 (d, J=8.8 Hz, 1H), 7.70 (d, J=7.2 Hz, 1H), 7.60 (d, J=1.4 Hz, 1H), 6.52 (s, 2H), 4.56 (s, 2H), 3.70 (dd, J=10.5, 3.6 Hz, 1H), 3.66-3.57 (m, 2H), 3.58-3.44 (m, 2H), 1.32 (d, J=6.8 Hz, 3H), 1.24-1.12 (m, 2H), 1.12-1.05 (m, 2H), 1.02-0.93 (m, 2H), 0.64-0.54 (m, 1H), 0.50-0.36 (m, 5H), 0.32-0.22 (m, 2H). ESI MS [M+H]⁺ for C₂₈H₃₃N₆O₃, calcd 501.2, found 501.2.

Example 168: 2-Amino-N-[(1R)-1-cyclopropyl-2-hydroxyethyl]-5-{2-[(1S)-1-cyclopropylethyl]-7-ethyl-1-oxo-2,3-dihydro-1H-isoindol-5-yl}pyrazolo[1,5-a]pyrimidine-3-carboxamide

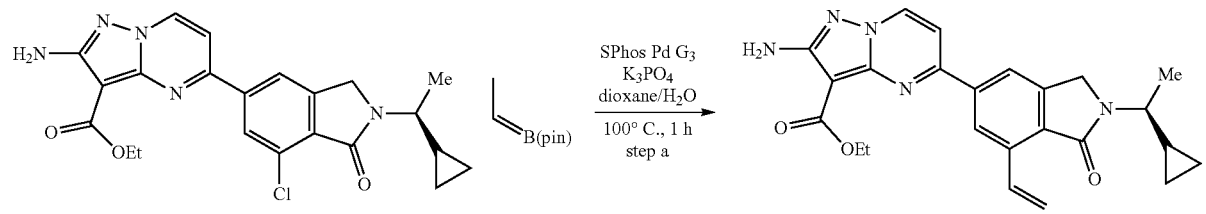

-continued

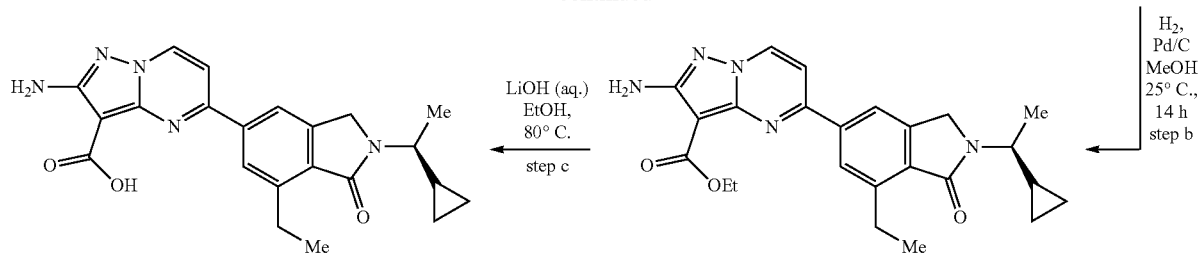

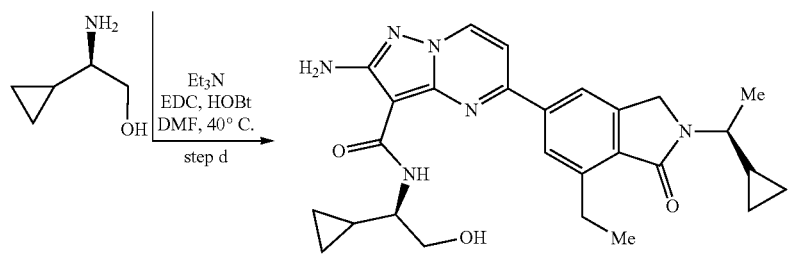

Step a: The aryl chloride (162 mg, 0.368 mmol, 1.0 equiv.) was combined with SPhos Pd G3 (29 mg, 0.037 mmol, 0.1 equiv.) and $K_3PO_4$ (156 mg, 0.735 mmol, 2.0 equiv.) in dioxane (1.84 mL) and $H_2O$ (1.84 mL). The resulting mixture was degassed by bubbling $N_2$ through the solution for ~3 mins. and then heated to 100° C. for 1 h. The mixture was cooled to rt, filtered through Celite (washed with EtOAc) and concentrated. The resulting residue was used directly in the next step without purification.

Step b: The product of Step a was combined with 10% Pd/C (160 mg) in MeOH (5 mL). A balloon of $H_2$ was bubbled through the solution for ~2 mins. and the resulting mixture was stirred under a balloon of $H_2$ for 14 h. The mixture was diluted with EtOAc, filtered through Celite (washed with EtOAc) and concentrated. The resulting residue was used directly in the next step without purification.

Steps c-d: The product of Step b was converted to the title compound in a similar manner to example 1. $^1$H NMR (400 MHz, Chloroform-d) δ 8.57-8.46 (m, 1H), 8.40-8.28 (m, 1H), 7.98 (s, 1H), 7.95 (s, 1H), 7.28 (d, J=6.7 Hz, 1H), 5.56 (brs, 2H), 4.66-4.36 (m, 2H), 4.05-3.97 (m, 1H), 3.93-3.84 (m, 1H), 3.84-3.71 (m, 1H), 3.54-3.38 (m, 1H), 3.26 (q, J=7.4 Hz, 2H), 1.37 (d, J=6.8 Hz, 3H), 1.33 (t, J=7.5 Hz, 3H), 1.18-0.97 (m, 2H), 0.74-0.57 (m, 3H), 0.57-0.34 (m, 5H). ESI MS [M+H]$^+$ for $C_{27}H_{33}N_6O_3$; calcd 489.2, found 489.2.

Example 169: 2-Amino-N-cyclopropyl-5-{2-[(1S)-1-cyclopropylethyl]-1-oxo-7-(propan-2-yl)-2,3-dihydro-1H-isoindol-5-yl}pyrazolo[1,5-a]pyrimidine-3-carboxamide

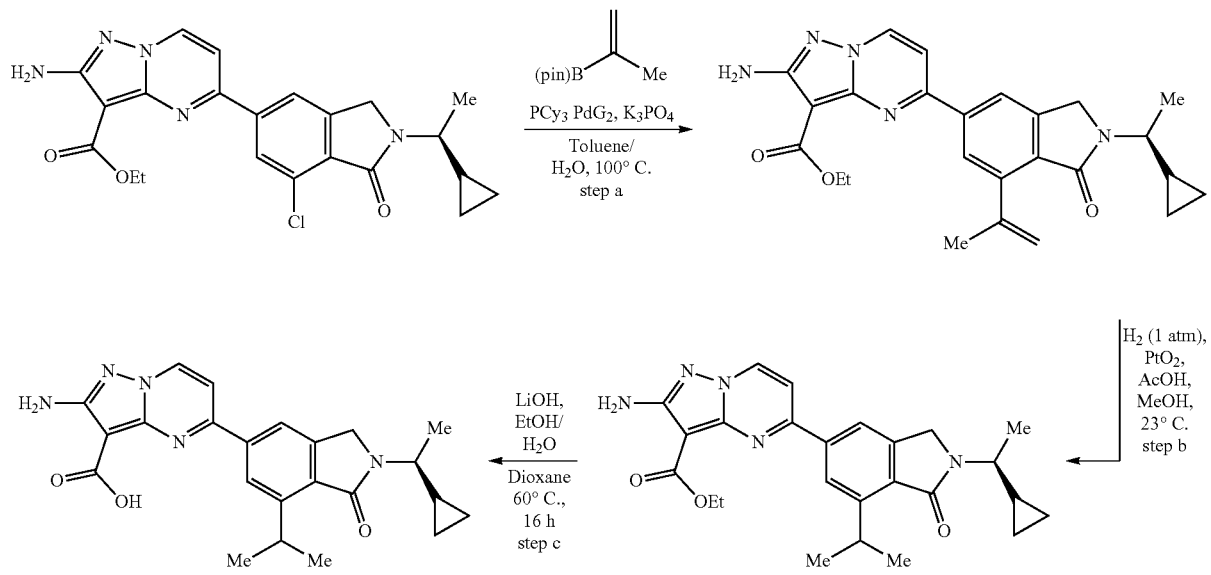

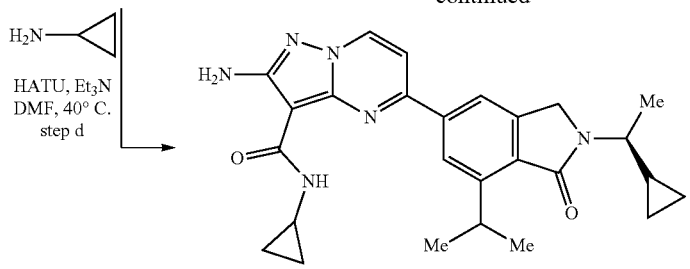

Step a: To a solution of aryl chloride (1.0 g, 2.27 mmol), isopropenylboronic acid pinacol ester (1.28 mL, 6.82 mmol, 3.0 equiv.) and $K_3PO_4$ (1.45 g, 6.82 mmol, 3.0 equiv.) in toluene (10.0 mL, 0.2 M) and $H_2O$ (1.0 mL) under $N_2$ was added $PCy_3PdG2$ (0.13 g, 0.23 mmol, 0.1 equiv.). The mixture was heated to 100° C. for 2 h and then cooled to rt. The reaction solution was filtered over a pad of Celite and $Na_2SO_4$ and concentrated in vacuo. Purification by column chromatography (gradient 100% EtOAc in hexanes) afforded the desired compound as a yellow solid (800 mg, 80%).

Step b: Product of Step a (290 mg, 0.650 mmol) was dissolved in MeOH (4.0 mL, 0.15 M) and $PtO_2$ was added (32 mg) with a catalytic amount of AcOH. The mixture was stirred at rt under $H_2$ atmosphere for 24 h. The reaction mixture was then filtered over a pad of Celite and $Na_2SO_4$ and the filtrate was concentrated. Purification by column chromatography (gradient 100% EtOAc in hexanes) afforded the desired compound as a yellow solid (52 mg, 18%).

Step c: The ethyl ester product of Step b (35 mg, 0.078 mmol, 1.0 equiv.) was dissolved in dioxane (0.5 mL) and EtOH (0.5 mL), $H_2O$ (0.5 mL) and $LiOH \cdot H_2O$ (12 mg, 0.23 mmol, 3.0 equiv.) was added. The resulting solution was heated to 70° C. for 3 h. The resulting mixture was cooled to rt and the solvent was removed in vacuo. The mixture was diluted with $H_2O$ and acidified to pH=3 with HCl [1 N]. The product was extracted using $CH_2Cl_2$ (3×), the combined organic layers were dried over $Na_2SO_4$, filtered and concentrated in vacuo to afford the carboxylic acid, which was used in the next step without purification (28 mg, 85%).

Step d: Performed in a similar manner to example 1. $^1H$ NMR (400 MHz, DMSO-$d_6$) δ 9.00 (d, J=7.1 Hz, 1H), 8.21-8.14 (m, 2H), 7.89 (d, J=3.8 Hz, 1H), 7.64 (d, J=7.2 Hz, 1H), 6.56 (s, 2H), 4.58 (s, 2H), 4.44-4.33 (m, 1H), 3.65-3.57 (m, 1H), 2.93-2.85 (m, 1H), 1.33-1.27 (m, 10H), 1.22-1.12 (m, 1H), 0.84-0.76 (m, 2H), 0.62-0.53 (m, 3H), 0.46-0.34 (m, 2H), 0.29-0.22 (m, 1H). ESI MS $[M+H]^+$ for $C_{26}H_{31}N_6O_2$, calcd 459.2, found 459.2.

Example 170: 2-Amino-N-cyclopropyl-5-{2-[(1S)-1-cyclopropylethyl]-7-(2-hydroxypropan-2-yl)-1-oxo-2,3-dihydro-1H-isoindol-5-yl}pyrazolo[1,5-a]pyrimidine-3-carboxamide

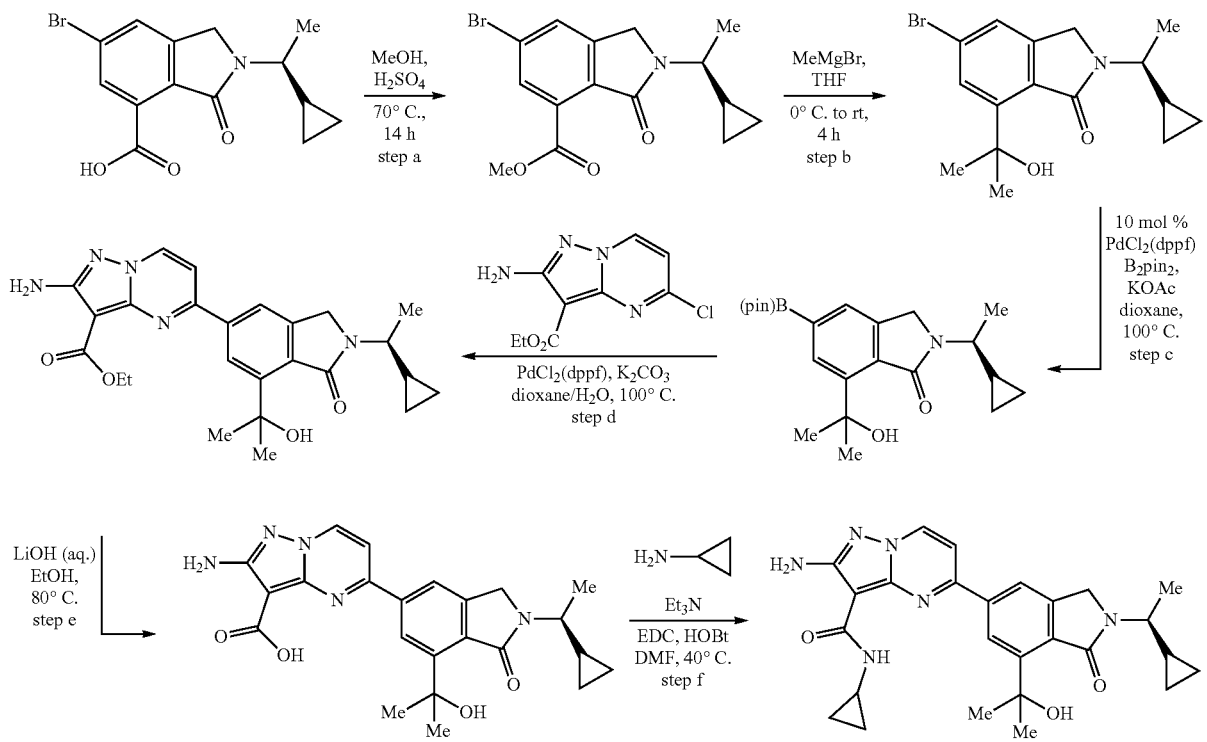

Step a: A mixture of the carboxylic acid starting material (1.03 g, 3.18 mmol, 1.0 equiv, prepared according to PCT Int. Appl., 2017153527, 14 Sep. 2017) and concentrated $H_2SO_4$ (1.6 mL) in MeOH (60 mL) was heated at reflux for 6 h. The reaction mixture was then cooled to rt and the MeOH was removed in vacuo. The mixture was then diluted with EtOAc (60 mL) and washed with sat. aq. $NaHCO_3$ (2×40 mL) and brine (40 mL). The organic phase was dried ($Na_2SO_4$), filtered and concentrated in vacuo to yield the methyl ester product (800 mg), which was used in the next step without purification.

Step b: A solution of the product of Step a (800 mg, 2.36 mmol, 1.0 equiv.) in THF (12 mL) was added dropwise over 15 min. to a solution of MeMgBr in $Et_2O$ (6.31 mL, 3 M) at 0° C. The resulting solution was allowed to warm to rt and stirred an additional 3 h. The reaction mixture was then cooled to 0° C. and quenched by dropwise addition of sat. aq. $NH_4Cl$ (10 mL). The resulting mixture was extracted with EtOAc (20 mL). The organic phase was washed successively with $H_2O$ (2×20 mL) and brine (20 mL), dried ($Na_2SO_4$), filtered and concentrated in vacuo. Purification by column chromatography ($SiO_2$, hexanes/EtOAc gradient) afforded the alcohol product (263 mg, 24% yield over 2 steps).

Step c: The product of Step b (263 mg, 0.777 mmol, 1.0 equiv.) was combined with Pd(dppf)$Cl_2$ (58.5 mg, 0.080 mmol, 0.1 equiv.), $B_2pin_2$ (217 mg, 0.855 mmol, 1.1 equiv.) and KOAc (152 mg, 1.55 mmol, 2.0 equiv.) in dioxane (3.90 mL). The resulting solution was heated to 100° C. for 2 h, cooled to rt, filtered through celite (washed with EtOAc) and concentrated. The resulting residue was used directly in the next step without purification.

Step d: The product residue from Step c was combined with 2-amino-5-chloropyrazolo[1,5-a]pyrimidine-3-carboxylic acid ethyl ester (185 mg, 0.777 mmol, 1.0 equiv.), Pd(dppf)$Cl_2$ (56 mg, 0.077 mmol, 0.1 equiv.) and $K_2CO_3$ (2 M aq. solution, 1.54 mmol, 0.77 mL) in dioxane (7.7 mL). The resulting solution was heated to 100° C. for 1 h, concentrated, and purified by flash chromatography ($SiO_2$, 0→8% MeOH/$CH_2Cl_2$) to yield the cross-coupled ethyl ester (214 mg, 60%, 2 steps).

Step e: The ethyl ester product of Step d (214 mg, 0.462 mmol, 1.0 equiv.) was dissolved in EtOH (4.6 mL) and 3 M aq. LiOH (0.46 mL) was added. The resulting solution was heated to 80° C. for 4 h. The resulting mixture was cooled to rt and the solvent was removed in vacuo. The mixture was diluted with $H_2O$ and acidified to pH 3 with 2 N HCl. The resulting precipitate was collected by vacuum filtration and dried in vacuo for 24 h to afford the carboxylic acid product, which was used in the next step without purification.

Step f: The product of Step e (0.10 mmol) was dissolved in NMP (0.5 mL, 0.2 M). HOBt (84 mg, 0.44 mmol, 4.4 equiv., 20% $H_2O$ by wt.), $Et_3N$ (70 μL, 0.5 mmol, 5.0 equiv.) and EDC-HCl (29 mg, 0.11 mmol, 1.1 equiv.) were sequentially added, and the solution was heated to 40° C. After 2 h, the reaction solution was diluted with $H_2O$ (8 ml) and the resulting precipitate was collected by vacuum filtration. Purification by reverse phase HPLC (10 to 90% gradient of $CH_3CN$ and $H_2O$ with 0.1% TFA) afforded the title compound as a pale yellow solid. $^1$H NMR (400 MHz, CDCl$_3$) δ 8.53 (d, J=7.1 Hz, 1H), 8.10 (s, 1H), 8.03-7.98 (m, 1H), 7.95-7.91 (m, 1H), 7.24 (d, J=7.1 Hz, 1H), 4.77-4.51 (m, 2H), 3.82 (dq, J=9.5, 6.8 Hz, 1H), 2.98-2.89 (m, 1H), 1.79-1.73 (m, 6H), 1.41 (d, J=6.8 Hz, 3H), 1.14-1.00 (m, 1H), 0.97-0.87 (m, 2H), 0.75-0.62 (m, 3H), 0.56-0.34 (m, 3H). ESI MS [M+H]$^+$ for $C_{26}H_{30}N_6O_3$; calcd 475.2, found 475.2.

Example 171: 2-Amino-5-{2-[(1S)-1-cyclopropylethyl]-7-(2-hydroxypropan-2-yl)-1-oxo-2,3-dihydro-1H-isoindol-5-yl}-N-[cis-4-hydroxy-4-methylcyclohexyl]pyrazolo[1,5-a]pyrimidine-3-carboxamide

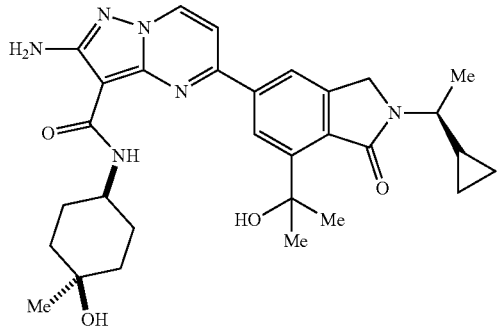 [SMILES: C[C@@H](C1CC1)N1Cc2cc(-c3ccn4nc(N)c(C(=O)N[C@H]5CC[C@@](C)(O)CC5)c4n3)cc(C(C)(C)O)c2C1=O]

The title compound was prepared in a similar manner to example 170. $^1$H NMR (400 MHz, CDCl$_3$) δ 8.49 (d, J=7.1 Hz, 1H), 8.08 (d, J=1.5 Hz, 1H), 7.94 (d, J=1.5 Hz, 1H), 7.78 (d, J=8.0 Hz, 1H), 7.64 (s, 1H), 7.20 (d, J=7.1 Hz, 1H), 5.75 (s, 2H), 4.73-4.50 (m, 2H), 4.06-3.91 (m, 1H), 3.80 (dq, J=9.5, 6.8 Hz, 1H), 2.00-1.88 (m, 2H), 1.80-1.67 (m, 9H), 1.65-1.52 (m, 3H), 1.40 (d, J=6.8 Hz, 3H), 1.28 (s, 3H), 1.16-0.99 (m, 2H), 0.73-0.64 (m, 1H), 0.54-0.30 (m, 3H). ESI MS [M+H]$^+$ for $C_{30}H_{39}N_6O_4$; calcd 547.3, found 547.3.

Analytical Methods:

LC: Agilent 1100 series; Mass spectrometer: Agilent G6120BA, single quad

LC-MS method: Agilent Zorbax Eclipse Plus C18, 4.6× 100 mm, 3.5 μM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile Flash column: ISCO Rf+

Reverse phase HPLC: ISCO-EZ or Agilent 1260; Column: Kinetex 5 μm EVO C18 100 A; 250×21.2 mm (Phenomenex)

Biological Example

Inhibition of PI3K Kinase Activity

Compounds were evaluated to determine the potency with which they inhibited the kinase activity of the Class I PI3K subunits p110α/p85α (Promega, Cat #V1721), p110β/p85α (Promega, Cat #V1751), p120γ (Promega, Cat #V1761) and p110δ/p85α (Promega, Cat #V1771). Activity was determined as a function of ADP (adenosine diphosphate) generated from ATP consumed during the phosphorylation of Phosphatidylinositol 4,5-bisphosphate (PIP2) (Promega, Cat #V1701) to yield Phosphatidylinositol (3,4,5)-trisphosphate (PIP3). ADP levels in the assay mixture at the end of the reaction were quantitated using ADP Glo (Promega, Cat #V9103) according to the manufacturer's recommended protocol.

On the day of the assay, compounds were solubilized in DMSO and dispensed into a 384-well white Opti-plate (Perkin Elmer, Cat #6007290) to generate a 14 point 1:2 titration. Enzyme was prepared for each of the PI3K subunits in 100 mM HEPES, pH 7.4, 100 mM NaCl, 6 mM MgCl$_2$ and 0.05% BSA. p110α/p85α was prepared at 2 nM (2×), p110β/p85α was prepared at 7 nM (2×), p120γ was prepared at 8 nM (2×) and p110δ/p85α was prepared at 2 nM (2×). Five microliters of 2× enzyme dilution of each PI3K subunit were added to a 384-well white Opti-plates pre-dispensed with compound and allowed to incubate for 1 h at rt. A substrate mix containing 0.1 mg/ml (2×) of PIP2 and 50 μM (2×) ATP (Promega, Cat #V915) was prepared in 25 mM HEPES and 0.5 mM EGTA. Reactions were initiated by addition of 5 μl of 2× substrate mix to each well of the plates containing various PI3K isoforms and allowed to proceed for 60 min at rt. Ten microliters of ADP Glo reagent 1 were added to the wells of each plate and allowed to incubate at rt for 45 min according to the manufacturer's directions. Following incubation, 20 μl of ADP Glo reagent 2 was added to each plate and allowed to incubate for an additional 45 min. Luminescent signal, generated by ADP Glo, was quantified by reading on a Perkin Elmer Envision multimode reader. Compound potencies ($IC_{50}$'s) were determined using a standard 4-parameter fit non-linear regression fit.

PI3Kγ Cellular Assay in THP-1 Cells

The day prior to assay, THP-1 cells (ATCC, Cat #TIB-202), were seeded at a density of $1 \times 10^6$ cells per ml in serum free DMEM in a T175 flask (Thermo Fisher, Cat #11965092, Cat #12-562-000) and incubated overnight at 5% $CO_2$ and 37° C.

On the day of experiment, a 14 point, 1:2 titration of test compound was pre-dispensed into 384-well Opti-plates (Perkin Elmer, Cat #6007290). Twenty microliters of serum starved THP-1 cells were added to the compound plate in serum free DMEM at a density of $9 \times 10^6$ cells per ml. Final assay conditions comprised $1.8 \times 10^5$ THP-1 cells per well with test compounds in 2% DMSO across a concentration range from 4 nM to 30 μM. Following 60 min incubation with test compound at 37° C. and 5% $CO_2$, THP-1 cells were stimulated with 25 nM rhMCP-1 (R&D Systems, cat #279-MC-010) for 2 min at 37° C. PI3Kγ stimulated phosphorylation of endogenous AKT Serine residue 473 in THP-1 cells was measured using AlphaLISA SureFire Ultra AKT 1/2/3 (pS473) Assay Kit (Perkin Elmer, Cat #ALSU-PAKT-B50K) according to the manufacturer's recommended protocol. Briefly, 10 μL of 4× lysis buffer was added to cells after stimulation. Following 60 min incubation at rt, 10 μL of cell lysate was transferred to a fresh 384-well Opti-plate to which 5 μL of AlphaLisa acceptor beads and 5 μL of AlphaLisa donor beads had been added. After a further 120 min incubation at rt in the dark, AlphaLisa signal was assessed using an Envision 2102 Multilabel Reader. PI3Kγ activity was evaluated as a correlate of endogenous AKT phosphorylation levels. Percentage maximum activity in each test well was calculated based on DMSO (100% activity) and positive control treated cell wells (0% activity). The potencies ($IC_{50}$'s) of test compounds were determined using a standard 4-parameter fit non-linear regression fit.

TABLE 1

Biochemical and cellular potency of specific examples (PI3Kγ $IC_{50}$: + means > 1 μM, ++ means 100 nM to 1 μM, +++ means < 100 nM)

| Ex. | biochemical potency | cellular potency |
|---|---|---|
| 1 | +++ | +++ |
| 2 | +++ | +++ |
| 3 | +++ | +++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | +++ |
| 38 | +++ | +++ |
| 39 | +++ | +++ |
| 40 | +++ | +++ |
| 41 | +++ | +++ |
| 42 | +++ | +++ |
| 43 | +++ | +++ |
| 44 | +++ | +++ |
| 45 | +++ | +++ |
| 46 | +++ | +++ |
| 47 | +++ | +++ |
| 48 | +++ | +++ |
| 65 | +++ | +++ |
| 50 | +++ | +++ |
| 51 | +++ | +++ |
| 52 | +++ | +++ |
| 53 | +++ | +++ |
| 54 | +++ | +++ |
| 55 | +++ | +++ |
| 56 | +++ | +++ |
| 57 | +++ | +++ |
| 58 | +++ | +++ |
| 59 | +++ | +++ |
| 60 | +++ | +++ |
| 61 | +++ | +++ |
| 62 | +++ | +++ |
| 63 | +++ | +++ |
| 64 | +++ | +++ |
| 49 | +++ | +++ |
| 66 | +++ | ++ |
| 67 | +++ | +++ |
| 68 | +++ | +++ |
| 69 | +++ | +++ |
| 70 | +++ | +++ |
| 71 | +++ | +++ |
| 72 | +++ | +++ |
| 73 | +++ | +++ |
| 74 | +++ | +++ |
| 75 | +++ | +++ |
| 76 | +++ | ++ |
| 77 | +++ | +++ |
| 78 | +++ | +++ |
| 79 | +++ | +++ |
| 80 | +++ | +++ |
| 81 | +++ | +++ |
| 82 | +++ | +++ |
| 83 | +++ | +++ |

TABLE 1-continued

Biochemical and cellular potency of specific examples (PI3Kγ IC$_{50}$: + means > 1 μM, ++ means 100 nM to 1 μM, +++ means < 100 nM)

| Ex. | biochemical potency | cellular potency |
|---|---|---|
| 84 | +++ | +++ |
| 85 | +++ | +++ |
| 86 | +++ | +++ |
| 87 | +++ | +++ |
| 88 | +++ | +++ |
| 89 | +++ | +++ |
| 90 | +++ | +++ |
| 91 | +++ | +++ |
| 92 | +++ | +++ |
| 93 | +++ | +++ |
| 94 | +++ | +++ |
| 95 | +++ | +++ |
| 96 | +++ | +++ |
| 97 | +++ | +++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | +++ |
| 105 | +++ | +++ |
| 106 | +++ | +++ |
| 107 | +++ | +++ |
| 108 | +++ | +++ |
| 109 | +++ | ++ |
| 110 | +++ | +++ |
| 111 | +++ | +++ |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | +++ | +++ |
| 119 | +++ | +++ |
| 120 | +++ | +++ |
| 121 | +++ | +++ |
| 122 | +++ | +++ |
| 123 | +++ | +++ |
| 124 | +++ | +++ |
| 125 | +++ | +++ |
| 126 | +++ | +++ |
| 127 | +++ | +++ |
| 128 | +++ | +++ |
| 129 | +++ | +++ |
| 130 | +++ | +++ |
| 131 | +++ | +++ |
| 132 | +++ | +++ |
| 133 | +++ | +++ |
| 134 | +++ | +++ |
| 135 | +++ | +++ |
| 136 | +++ | +++ |
| 137 | +++ | +++ |
| 138 | +++ | +++ |
| 139 | +++ | +++ |
| 140 | +++ | +++ |
| 141 | +++ | +++ |
| 142 | +++ | +++ |
| 143 | +++ | +++ |
| 144 | +++ | +++ |
| 145 | +++ | +++ |
| 146 | +++ | +++ |
| 147 | +++ | +++ |
| 148 | +++ | +++ |
| 149 | +++ | +++ |
| 150 | +++ | +++ |
| 151 | +++ | +++ |
| 152 | +++ | +++ |
| 153 | +++ | +++ |
| 154 | +++ | +++ |
| 155 | +++ | +++ |
| 156 | +++ | +++ |
| 157 | +++ | +++ |
| 158 | +++ | +++ |
| 159 | +++ | +++ |
| 160 | +++ | +++ |
| 161 | +++ | +++ |
| 162 | +++ | +++ |
| 163 | +++ | +++ |
| 164 | +++ | +++ |
| 165 | +++ | +++ |
| 166 | +++ | +++ |
| 167 | +++ | +++ |
| 168 | +++ | +++ |
| 169 | +++ | +++ |
| 170 | +++ | +++ |
| 171 | +++ | +++ |

TABLE 2

Biochemical and cellular potency of additional specific examples

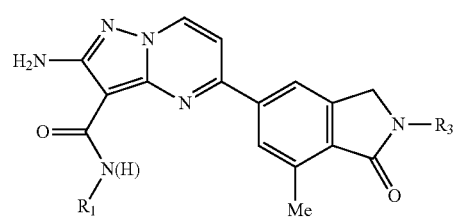

| Ex. | R$_1$ | R$_3$ | cellular potency | biochemical potency |
|---|---|---|---|---|
| 172 | trans-4-hydroxycyclohexyl | (S)-1-cyclopropylethyl | ++ | +++ |

TABLE 2-continued

Biochemical and cellular potency of additional specific examples

| Ex. | R₁ | R₃ | cellular potency | biochemical potency |
|---|---|---|---|---|
| 173 | 1-(pyridin-4-yl)ethyl | 1-cyclopropylethyl (Me) | ++ | +++ |
| 174 | 2-(hydroxymethyl)butyl | 1-cyclopropylethyl (Me) | ++ | +++ |
| 175 | 1-(1-methyl-1H-pyrazol-4-yl)ethyl | 1-cyclopropylethyl (Me) | ++ | +++ |
| 176 | tetrahydrofuran-3-yl | 1-cyclopropylethyl (Me) | ++ | +++ |
| 177 | tetrahydrofuran-3-yl | 1-cyclopropylethyl (Me) | ++ | +++ |
| 178 | 1-(thiazol-2-yl)ethyl | 1-cyclopropylethyl (Me) | ++ | +++ |
| 179 | piperidin-4-yl | 1-cyclopropylethyl (Me) | ++ | +++ |
| 180 | oxetan-3-yl | 1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 181 | 4-tetrahydropyranyl | (S)-1-cyclopropylethyl (Me) | ++ | +++ |
| 182 | cis-3-methoxycyclobutyl | (S)-1-cyclopropylethyl (Me) | ++ | +++ |
| 183 | 2-(hydroxymethyl)butyl | (S)-1-cyclopropylethyl (Me) | ++ | +++ |
| 184 | trans-4-aminocyclohexyl | (S)-1-cyclopropylethyl (Me) | ++ | +++ |
| 185 | cis-3-aminocyclobutyl | (S)-1-cyclopropylethyl (Me) | ++ | +++ |
| 186 | 2-hydroxyethyl (-CH₂CH₂OH) | (S)-1-cyclopropylethyl (Me) | ++ | +++ |
| 187 | trans-4-carboxycyclohexyl | (S)-1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 188 | 1-hydroxycyclopropylmethyl | (S)-1-cyclopropylethyl (Me) | ++ | +++ |
| 189 | cyclobutylmethyl | (S)-1-cyclopropylethyl (Me) | ++ | +++ |
| 190 | (S)-1-methyl-2-amino-2-oxoethyl (propanamide) | (S)-1-cyclopropylethyl (Me) | ++ | +++ |
| 191 | (S)-2-isopropyl-3-hydroxypropyl | (S)-1-cyclopropylethyl (Me) | ++ | +++ |
| 192 | (S)-2-phenyl-2-hydroxymethyl-ethyl | (S)-1-cyclopropylethyl (Me) | ++ | +++ |
| 193 | trans-4-carboxycyclohexyl | (S)-1-cyclopropylethyl (Me) | ++ | +++ |
| 194 | 1-acetylazetidin-3-yl | (S)-1-cyclopropylethyl (Me) | ++ | +++ |
| 195 | (S)-2-cyclopropyl-2-hydroxyethyl | (S)-1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 196 | 3-hydroxy-3-methylcyclobutyl | 1-cyclopropylethyl (Me) | ++ | +++ |
| 197 | 3-hydroxycyclopentyl | 1-cyclopropylethyl (Me) | ++ | +++ |
| 198 | 2-hydroxy-2,3-dihydro-1H-inden-1-yl | 1-cyclopropylethyl (Me) | ++ | +++ |
| 199 | 4-hydroxytetrahydrofuran-3-yl | 1-cyclopropylethyl (Me) | ++ | +++ |
| 200 | 1-(tetrahydro-2H-pyran-4-yl)ethyl | 1-cyclopropylethyl (Me) | ++ | +++ |
| 201 | 2-(pyridin-4-yl)ethyl | 1-cyclopropylethyl (Me) | ++ | +++ |
| 202 | 5-oxopyrrolidin-3-yl | 1-cyclopropylethyl (Me) | ++ | +++ |
| 203 | 2-hydroxy-2-methylpropyl | 1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 204 | trans-4-hydroxycyclobutyl | 1-cyclopropylethyl (Me) | ++ | +++ |
| 205 | trans-4-hydroxycyclohexyl | 1-cyclopropylethyl (Me) | ++ | +++ |
| 206 | (S)-2-hydroxy-1-methylethyl | 1-cyclopropylethyl (Me) | ++ | +++ |
| 207 | (1-methyl-1H-pyrazol-3-yl)methyl | 1-cyclopropylethyl (Me) | ++ | +++ |
| 208 | cyclopropyl | 1-cyclopropylethyl (Me) | ++ | +++ |
| 209 | 1-methylpiperidin-4-yl | 1-cyclopropylethyl (Me) | ++ | +++ |
| 210 | (1R,2S)-2-hydroxycyclopentyl | 1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 211 | (1R,2S)-2-hydroxycyclobutyl | 1-cyclopropylethyl (Me) | ++ | +++ |
| 212 | 1-(pyridin-3-yl)ethyl | 1-cyclopropylethyl (Me) | ++ | +++ |
| 213 | cyclopropylmethyl | 1-cyclopropylethyl (Me) | ++ | +++ |
| 214 | (1-methyl-1H-pyrazol-4-yl)methyl | 1-cyclopropylethyl (Me) | ++ | +++ |
| 215 | (3-hydroxycyclobutyl)methyl | 1-cyclopropylethyl (Me) | ++ | +++ |
| 216 | Me | 1-cyclopropylethyl (Me) | ++ | +++ |
| 217 | 1-(pyridin-2-yl)ethyl | 1-cyclopropylethyl (Me) | ++ | +++ |
| 218 | pyrrolidin-3-yl | 1-cyclopropylethyl (Me) | ++ | +++ |

TABLE 2-continued
Biochemical and cellular potency of additional specific examples
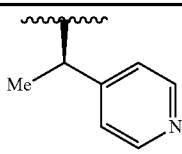
| Ex. | R₁ | R₃ | cellular potency | biochemical potency |
|---|---|---|---|---|
| 219 | 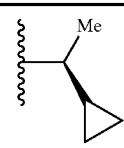 | 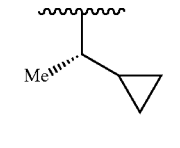 | ++ | +++ |
| 220 | 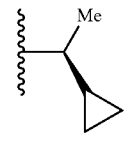 [SMILES: *[C@@H](C)C1CC1] | 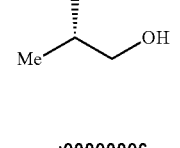 | ++ | +++ |
| 221 | 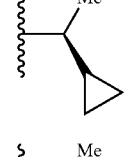 | 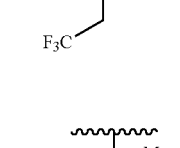 | ++ | +++ |
| 222 | 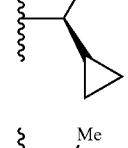 | 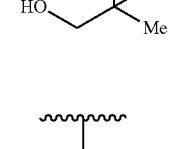 | ++ | +++ |
| 223 | 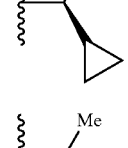 | 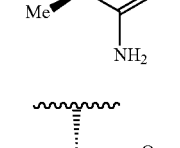 | ++ | +++ |
| 224 | 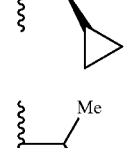 | 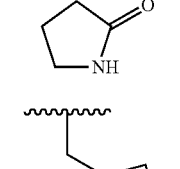 | ++ | +++ |
| 225 | 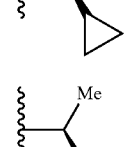 | 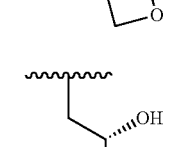 | ++ | +++ |
| 226 | 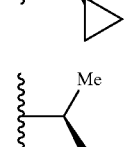 |  | ++ | +++ |
| 227 |  | | ++ | +++ |

TABLE 2-continued

Biochemical and cellular potency of additional specific examples

| Ex. | R₁ | R₃ | cellular potency | biochemical potency |
|---|---|---|---|---|
| 228 | 1-(2-hydroxyethyl)cyclopropyl | 1-cyclopropylethyl (Me) | ++ | +++ |
| 229 | trans-2-hydroxycyclohexyl | 1-cyclopropylethyl (Me) | ++ | +++ |
| 230 | 2-methyl-3-aminopropyl | 1-cyclopropylethyl (Me) | ++ | +++ |
| 231 | piperidin-3-yl | 1-cyclopropylethyl (Me) | ++ | +++ |
| 232 | pyrrolidin-3-yl | 1-cyclopropylethyl (Me) | ++ | +++ |
| 233 | Et | 1-cyclopropylethyl (Me) | ++ | +++ |
| 234 | (2-hydroxypropyl) Me, OH | 1-cyclopropylethyl (Me) | ++ | +++ |
| 235 | 1-(1-methyl-1H-pyrazol-4-yl)ethyl | 1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 236 | -CH₂C(O)NH₂ | Me, cyclopropyl | ++ | +++ |
| 237 | -CH(CH₂OH)C(Me)₃ | Me, cyclopropyl | ++ | +++ |
| 238 | tetrahydrofuran-3-ylmethyl | Me, cyclopropyl | ++ | +++ |
| 239 | 3-hydroxycyclopentyl | Me, cyclopropyl | ++ | +++ |
| 240 | 2-hydroxy-indan-1-yl | Me, cyclopropyl | ++ | +++ |
| 241 | 1,1-dioxo-thietan-3-yl | Me, cyclopropyl | ++ | +++ |
| 242 | 1-methylcyclopropyl | Me, cyclopropyl | ++ | +++ |
| 243 | piperidin-3-yl | Me, cyclopropyl | ++ | +++ |

TABLE 2-continued

Biochemical and cellular potency of additional specific examples

| Ex. | R₁ | R₃ | cellular potency | biochemical potency |
|---|---|---|---|---|
| 244 | cyclohexyl-OH (trans) | CH(Me)(cyclopropyl) | ++ | +++ |
| 245 | H₂N-C(O)-CH(Ph)- | CH(Me)(cyclopropyl) | ++ | +++ |
| 246 | 1-(hydroxymethyl)cyclopropyl | CH(Me)(cyclopropyl) | ++ | +++ |
| 247 | 1-carbamoylcyclopropyl | CH(Me)(cyclopropyl) | ++ | +++ |
| 248 | 2-(pyridin-4-yl)propan-2-yl | CH(Me)(cyclopropyl) | ++ | +++ |
| 249 | 2,2-dimethylcyclopropyl | CH(Me)(cyclopropyl) | ++ | +++ |
| 250 | (1-(hydroxymethyl)cyclopropyl)methyl | CH(Me)(cyclopropyl) | ++ | +++ |
| 251 | 3-hydroxycyclobutyl (or similar diyl-OH) | CH(Me)(cyclopropyl) | ++ | +++ |

TABLE 2-continued

Biochemical and cellular potency of additional specific examples

| Ex. | R₁ | R₃ | cellular potency | biochemical potency |
|---|---|---|---|---|
| 252 | isopropyl (CH(Me)Me) | CH(Me)(cyclopropyl) | ++ | +++ |
| 253 | 1-(1-hydroxyethyl)cyclopropyl | CH(Me)(cyclopropyl) | ++ | +++ |
| 254 | trans-2-hydroxycyclohexyl | CH(Me)(cyclopropyl) | ++ | +++ |
| 255 | 1-cyanocyclobutyl | CH(Me)(cyclopropyl) | ++ | +++ |
| 256 | (1-cyanocyclopropyl)methyl | CH(Me)(cyclopropyl) | ++ | +++ |
| 257 | (tetrahydrofuran-3-yl)methyl | CH(Me)(cyclopropyl) | ++ | +++ |
| 258 | 3,3-difluorocyclobutyl | CH(Me)(cyclopropyl) | ++ | +++ |
| 259 | isochroman-4-yl | CH(Me)(cyclopropyl) | ++ | +++ |

TABLE 2-continued

Biochemical and cellular potency of additional specific examples

| Ex. | R$_1$ | R$_3$ | cellular potency | biochemical potency |
|---|---|---|---|---|
| 260 | CH$_2$CH$_2$CH$_2$-NC | 1-cyclopropylethyl (Me) | ++ | +++ |
| 261 | chroman-4-yl | 1-cyclopropylethyl (Me) | ++ | +++ |
| 262 | 1-(trifluoromethyl)cyclopropyl | 1-cyclopropylethyl (Me) | ++ | +++ |
| 263 | (2-fluorocyclopropyl) | 1-cyclopropylethyl (Me) | ++ | +++ |
| 264 | (2-hydroxycyclopentyl) | 1-cyclopropylethyl (Me) | ++ | +++ |
| 265 | (1-hydroxy-2,3-dihydro-1H-inden-2-yl) | 1-cyclopropylethyl (Me) | + | +++ |
| 266 | azetidin-3-yl | 1-cyclopropylethyl (Me) | + | +++ |
| 267 | 2-(hydroxymethyl)-4-methylpentyl | 1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 268 | 1-cyanocyclopropyl | (S)-1-cyclopropylethyl (Me) | ++ | +++ |
| 269 | (tetrahydrofuran-2-yl)methyl | (S)-1-cyclopropylethyl (Me) | ++ | +++ |
| 270 | 3-hydroxy-3-methylbutan-2,2-diyl (bis-CH₂, HO, Me, Me) | (S)-1-cyclopropylethyl (Me) | ++ | +++ |
| 271 | (5-oxopyrrolidin-2-yl)methyl-CH₂ | (S)-1-cyclopropylethyl (Me) | ++ | +++ |
| 272 | (1S,2R)-2-hydroxy-2,3-dihydro-1H-inden-1-yl | (S)-1-cyclopropylethyl (Me) | + | +++ |
| 273 | trans-4-aminocyclohexyl | (S)-1-cyclopropylethyl (Me) | ++ | +++ |
| 274 | 2-(hydroxymethyl)pentane-1,5-diyl | (S)-1-cyclopropylethyl (Me) | ++ | +++ |
| 275 | (1S,2S)-2-hydroxycyclohexyl | (S)-1-cyclopropylethyl (Me) | ++ | +++ |

TABLE 2-continued

Biochemical and cellular potency of additional specific examples

| Ex. | R₁ | R₃ | cellular potency | biochemical potency |
| --- | --- | --- | --- | --- |
| 276 | (4-substituted pyrrolidin-2-one-CH₂-) | 1-cyclopropylethyl (Me) | ++ | +++ |
| 277 | spiro[2.2]pentyl | 1-cyclopropylethyl (Me) | ++ | +++ |
| 278 | 1-cyclopropylethyl (Me) | 1-cyclopropylethyl (Me) | + | +++ |
| 279 | -CH₂CH₂C(O)NHPh | 1-cyclopropylethyl (Me) | + | +++ |
| 280 | -CH₂CH₂OCH₂CH₂- | 1-cyclopropylethyl (Me) | + | +++ |
| 281 | 1-phenylcyclopropyl | 1-cyclopropylethyl (Me) | + | +++ |
| 282 | -CH₂CH₂N(Me)CH₂CH₂- | 1-cyclopropylethyl (Me) | ++ | +++ |
| 283 | (3-substituted pyrrolidin-2-one) | 1-cyclopropylethyl (Me) | ++ | +++ |

TABLE 2-continued

Biochemical and cellular potency of additional specific examples

| Ex. | R₁ | R₃ | cellular potency | biochemical potency |
|---|---|---|---|---|
| 284 | (1S,2S)-2-hydroxy-2,3-dihydro-1H-inden-1-yl | 1-cyclopropylethyl (Me) | + | +++ |
| 285 | (S)-chroman-4-yl | 1-cyclopropylethyl (Me) | + | +++ |
| 286 | 2-amino-2-oxo-1-phenylethyl | 1-cyclopropylethyl (Me) | + | ++ |
| 287 | 1-(oxetan-3-yl)ethyl | 1-cyclopropylethyl (Me) | ++ | ++ |
| 288 | (S)-1-hydroxyhexan-2-yl (linker) | 1-cyclopropylethyl (Me) | + | ++ |
| 289 | (R)-1-hydroxyhexan-2-yl (linker) | 1-cyclopropylethyl (Me) | + | ++ |
| 290 | (S)-1-(piperidin-4-yl)ethyl | 1-cyclopropylethyl (Me) | + | ++ |
| 291 | 3-(methyl(propyl)amino)propyl linker | 1-cyclopropylethyl (Me) | + | + |

TABLE 2-continued

Biochemical and cellular potency of additional specific examples

| Ex. | R₁ | R₃ | cellular potency | biochemical potency |
|---|---|---|---|---|
| 292 | 1,3-dimethylpyrazol-4-yl | 1-cyclopropylethyl (Me) | ++ | +++ |
| 293 | 4-carboxy-3-methylphenyl | 1-cyclopropylethyl (Me) | ++ | +++ |
| 294 | 1-cyclopropylpyrazol-4-yl | 1-cyclopropylethyl (Me) | ++ | +++ |
| 295 | 1-ethylpyrazol-4-yl | 1-cyclopropylethyl (Me) | ++ | +++ |
| 296 | 5-fluoro-1-methylpyrazol-4-yl | 1-cyclopropylethyl (Me) | ++ | +++ |
| 297 | 2-methylpyridin-4-yl | 1-cyclopropylethyl (Me) | ++ | +++ |
| 298 | phenyl | 1-cyclopropylethyl (Me) | + | +++ |

TABLE 2-continued

Biochemical and cellular potency of additional specific examples

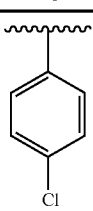

| Ex. | R₁ | R₃ | cellular potency | biochemical potency |
|---|---|---|---|---|
| 299 | 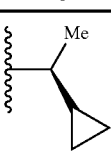 4-Cl-phenyl | 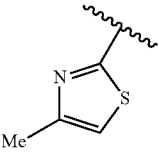 [SMILES: *c1nc(C)cs1] Me, cyclopropyl | + | +++ |
| 300 | 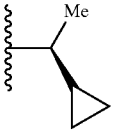 [SMILES: *[C@@H](C)C1CC1] 4-Me-thiazol-2-yl | 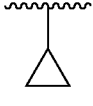 [SMILES: *C1CC1] Me, cyclopropyl | + | +++ |
| 301 | 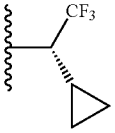 [SMILES: *[C@@H](C1CC1)C(F)(F)F] cyclopropyl | 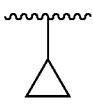 [SMILES: *C1CC1] CF₃, cyclopropyl | ++ | +++ |
| 302 | 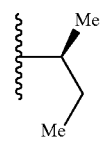 cyclopropyl |  Me, Et | ++ | +++ |
| 303 | 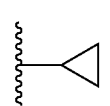 [SMILES: *C1CC1] cyclopropyl |  cyclopropyl | ++ | +++ |
| 304 | 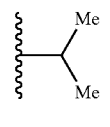 cyclopropyl | 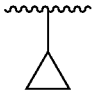 [SMILES: *C1CC1] iPr | ++ | +++ |
| 305 | 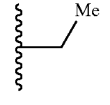 cyclopropyl | 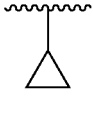 [SMILES: *C1CC1] Et | ++ | +++ |
| 306 | 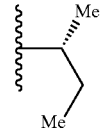 cyclopropyl |  Me, Et | ++ | +++ |
| 307 | 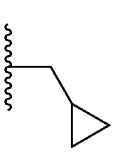 [SMILES: *CC1CC1] cyclopropyl | CH₂-cyclopropyl | ++ | +++ |

TABLE 2-continued

Biochemical and cellular potency of additional specific examples

| Ex. | R₁ | R₃ | cellular potency | biochemical potency |
|---|---|---|---|---|
| 308 | cyclopropyl | CH₂(CH(Me)CH₂-)–CH₂OH (2-methylbutanol) | ++ | +++ |
| 309 | cyclopropyl | CH₂(CH(Me)CH₂-)–CH₂OH | ++ | +++ |
| 310 | cyclopropyl | CH(cyclopropyl)CH₂OH | ++ | +++ |
| 311 | cyclopropyl | CH(cyclopropyl)CH₂OH | ++ | +++ |
| 312 | CH(cyclopropyl)CH₂OH | C(Me)₂CH₂OH | ++ | +++ |
| 313 | CH(Me)(2-F-phenyl) | C(Me)₂CH₂OH | ++ | +++ |
| 314 | 3-Me-oxetan-3-yl | C(Me)₂CH₂OH | ++ | +++ |
| 315 | oxetan-3-yl | C(Me)₂CH₂OH | ++ | +++ |
| 316 | cyclopropyl | C(Me)₂CH₂OH | ++ | +++ |

TABLE 2-continued

Biochemical and cellular potency of additional specific examples

| Ex. | R₁ | R₃ | cellular potency | biochemical potency |
|---|---|---|---|---|
| 317 | 1-(2-fluorophenyl)ethyl | 2-hydroxy-1,1-dimethylethyl (neopentyl alcohol) | + | +++ |
| 318 | 3-methyloxetan-3-yl | 2-hydroxy-2-methylpropyl | ++ | +++ |
| 319 | cyclopropyl | 2-hydroxy-2-methylpropyl | ++ | +++ |
| 320 | oxetan-3-yl | 2-hydroxy-2-methylpropyl | ++ | +++ |
| 321 | 2-cyclopropyl-2-hydroxyethyl | 2-hydroxy-2-methylpropyl | ++ | +++ |
| 322 | cyclopropyl | (1S,3R)-3-hydroxycyclopentyl | ++ | +++ |
| 323 | cyclopropyl | (1R,3S)-3-hydroxycyclopentyl | ++ | +++ |
| 324 | cyclopropyl | trans-3-hydroxycyclohexyl | ++ | +++ |
| 325 | (S)-2-hydroxy-1-methylethyl | trans-3-hydroxycyclohexyl | + | +++ |

TABLE 2-continued

Biochemical and cellular potency of additional specific examples

| Ex. | R₁ | R₃ | cellular potency | biochemical potency |
|---|---|---|---|---|
| 326 | CH(Me)CH₂OH | (1S,3R)-3-hydroxycyclohexyl | + | +++ |
| 327 | cyclopropyl | (1S,3R)-3-hydroxycyclohexyl | ++ | +++ |
| 328 | cyclopropyl | (1R,3S)-3-hydroxycyclohexyl | ++ | +++ |
| 329 | CH(Me)CH₂OH | (1R,3S)-3-hydroxycyclohexyl | + | +++ |
| 330 | CH(Me)CH₂OH | (S)-1-(pyridin-4-yl)ethyl | + | +++ |
| 331 | cyclopropyl | (S)-1-(pyridin-4-yl)ethyl | + | +++ |
| 332 | CH(Me)CH₂OH | (S)-1-(pyridin-3-yl)ethyl | + | +++ |
| 333 | cyclopropyl | (S)-1-(pyridin-3-yl)ethyl | + | +++ |

(PI3Kγ IC₅₀: + means >1 μM, ++ means 100 nM to 1 μM, +++ means <100 nM)

TABLE 3

Biochemical and cellular potency of additional specific examples

| Ex. | R₁ | R₃ | cellular potency | biochemical potency |
|---|---|---|---|---|
| 334 | N-acetyl azetidin-3-yl | 1-cyclopropylethyl (Me) | ++ | +++ |
| 335 | HOCH₂C(Me)₂- | 1-cyclopropylethyl (Me) | ++ | +++ |
| 336 | -(CH₂)₃SO₂Me | 1-cyclopropylethyl (Me) | ++ | +++ |
| 337 | -(CH₂)₂SO₂Me | 1-cyclopropylethyl (Me) | ++ | +++ |
| 338 | 3-(hydroxymethyl)oxetan-3-yl | 1-cyclopropylethyl (Me) | ++ | +++ |
| 339 | (2-methyl-3-methoxy)propyl | 1-cyclopropylethyl (Me) | ++ | +++ |
| 340 | cyclopropyl | 2-cyclopropyl-2-hydroxyethyl (OH) | ++ | +++ |
| 341 | (3R)-3-hydroxybutyl | 1-cyclopropylethyl (Me) | ++ | +++ |

TABLE 3-continued

Biochemical and cellular potency of additional specific examples

| Ex. | R₁ | R₃ | cellular potency | biochemical potency |
|---|---|---|---|---|
| 342 | 1-(hydroxymethyl)cyclopropyl | 1-cyclopropylethyl (Me) | ++ | +++ |
| 343 | sec-butyl (Me, Me) | 1-cyclopropylethyl (Me) | ++ | +++ |
| 344 | (S)-2,3-dihydroxypropyl | 1-cyclopropylethyl (Me) | ++ | +++ |
| 345 | trans-4-hydroxy-4-(trifluoromethyl)cyclohexyl | 1-cyclopropylethyl (Me) | ++ | +++ |
| 346 | (R)-3-hydroxybutyl | 1-cyclopropylethyl (Me) | ++ | +++ |
| 347 | tetrahydro-2H-thiopyran-4-yl 1,1-dioxide | 1-cyclopropylethyl (Me) | ++ | +++ |
| 348 | (R)-2,3-dihydroxypropyl | 1-cyclopropylethyl (Me) | ++ | +++ |
| 349 | cyclopropyl | 1-cyclopropylethyl (Me) | ++ | +++ |

TABLE 3-continued

Biochemical and cellular potency of additional specific examples

| Ex. | R₁ | R₃ | cellular potency | biochemical potency |
|---|---|---|---|---|
| 350 | 2-cyano-pyridin-4-yl | 1-cyclopropylethyl (Me) | ++ | +++ |
| 351 | 5-fluoro-pyridin-3-yl | 1-cyclopropylethyl (Me) | ++ | +++ |
| 352 | -CH₂CH₂CH₂-NH-SO₂Me | 1-cyclopropylethyl (Me) | ++ | +++ |
| 353 | 2-cyclopropyl-2-hydroxymethyl | 1-cyclopropylethyl (Me) | ++ | +++ |
| 354 | 6-(trifluoromethyl)methyl-pyridin-3-yl | 1-cyclopropylethyl (Me) | ++ | +++ |
| 355 | 5-methoxy-pyridin-3-yl | 1-cyclopropylethyl (Me) | ++ | +++ |
| 356 | piperidin-3-yl | 1-cyclopropylethyl (Me) | ++ | +++ |
| 357 | 4-hydroxy-pyrrolidin-3-yl | 1-cyclopropylethyl (Me) | + | +++ |

TABLE 3-continued

Biochemical and cellular potency of additional specific examples

| Ex. | R₁ | R₃ | cellular potency | biochemical potency |
|---|---|---|---|---|
| 358 | 3-aminocyclohexyl | 1-cyclopropylethyl (Me) | ++ | +++ |
| 359 | trans-3-hydroxypyrrolidin-4-yl | 1-cyclopropylethyl (Me) | + | +++ |
| 360 | cis-3-hydroxypyrrolidin-4-yl | 1-cyclopropylethyl (Me) | + | +++ |
| 361 | (CF₃)CH-CH₂OH | 1-cyclopropylethyl (Me) | ++ | +++ |
| 362 | 3-(dimethylamino)cyclohexyl | 1-cyclopropylethyl (Me) | ++ | +++ |
| 363 | phenyl | 1-cyclopropylethyl (Me) | + | +++ |
| 364 | CH(iPr)CH₂OMe (Me,Me,OMe) | 1-cyclopropylethyl (Me) | ++ | +++ |
| 365 | 2-phenylcyclopropyl | 1-cyclopropylethyl (Me) | ++ | +++ |

TABLE 3-continued

Biochemical and cellular potency of additional specific examples

| Ex. | R₁ | R₃ | cellular potency | biochemical potency |
|---|---|---|---|---|
| 366 | (1,3-cis) cyclohexyl-NH₂ | CH(Me)(cyclopropyl) | + | +++ |
| 367 | (1,3-trans) cyclohexyl-NH₂ | CH(Me)(cyclopropyl) | + | +++ |
| 368 | (1,4-trans) cyclohexyl-NH₂ | CH(Me)(cyclopropyl) | ++ | +++ |

(PI3Kγ IC₅₀: + means >1 μM, ++ means 100 nM to 1 μM, +++ means <100 nM)

TABLE 4

Biochemical and cellular potency of additional examples

| Ex. | R₁ | R₂ | R₃ | cellular potency | biochemical potency |
|---|---|---|---|---|---|
| 369 | CH(Me)CH₂OH | F | CH(Me)(cyclopropyl) | ++ | +++ |
| 370 | cyclopropyl | F | CH(Me)(cyclopropyl) | ++ | +++ |

TABLE 4-continued

Biochemical and cellular potency of additional examples

| Ex. | R₁ | R₂ | R₃ | cellular potency | biochemical potency |
|---|---|---|---|---|---|
| 371 | 5-(2-oxo-1,2-dihydropyridin-3-yl) | NHS(O)₂Me | 1-cyclopropylethyl (Me) | ++ | +++ |
| 372 | (S)-2-oxopyrrolidin-3-yl | NHS(O)₂Me | 1-cyclopropylethyl (Me) | ++ | +++ |
| 373 | 1-carbamoyl-1-methylethyl (2-methyl-1-amino-1-oxopropan-2-yl) | NHS(O)₂Me | 1-cyclopropylethyl (Me) | ++ | +++ |
| 374 | 5-oxopyrrolidin-3-yl | NHS(O)₂Me | 1-cyclopropylethyl (Me) | ++ | +++ |
| 375 | 2-(methoxycarbonyl)pyridin-4-yl | NHS(O)₂Me | 1-cyclopropylethyl (Me) | ++ | +++ |
| 376 | (S)-1,1,1-trifluoro-3-hydroxypropan-2-yl | NHS(O)₂Me | 1-cyclopropylethyl (Me) | ++ | +++ |
| 377 | 5-hydroxyadamantan-2-yl | NHS(O)₂Me | 1-cyclopropylethyl (Me) | +++ | +++ |

TABLE 4-continued

Biochemical and cellular potency of additional examples

| Ex. | R₁ | R₂ | R₃ | cellular potency | biochemical potency |
|---|---|---|---|---|---|
| 378 | 3-fluorophenyl | NHSO₂Me | (S)-1-cyclopropylethyl (Me) | ++ | +++ |
| 379 | (2-hydroxymethyl)pyridin-4-yl | NHSO₂Me | (S)-1-cyclopropylethyl (Me) | + | +++ |
| 380 | 4-methoxyphenyl | NHSO₂Me | (S)-1-cyclopropylethyl (Me) | ++ | +++ |
| 381 | (1-hydroxycyclopropyl)methyl | NHSO₂Me | (S)-1-cyclopropylethyl (Me) | ++ | +++ |
| 382 | (S)-1-carbamoyl-ethyl | NHSO₂Me | (S)-1-cyclopropylethyl (Me) | ++ | +++ |
| 383 | 3-hydroxypropyl | NHSO₂Me | (S)-1-cyclopropylethyl (Me) | ++ | +++ |
| 384 | trans-2-hydroxycyclohexyl | NHSO₂Me | (S)-1-cyclopropylethyl (Me) | ++ | +++ |
| 385 | (S)-1-methoxy-2-methylpropyl | NHSO₂Me | (S)-1-cyclopropylethyl (Me) | ++ | +++ |

TABLE 4-continued

Biochemical and cellular potency of additional examples

| Ex. | R₁ | R₂ | R₃ | cellular potency | biochemical potency |
|---|---|---|---|---|---|
| 386 | 3-CN-phenyl | NHS(O)₂Me | (R)-1-cyclopropylethyl-Me | ++ | +++ |
| 387 | 5-MeO-pyridin-3-yl | NHS(O)₂Me | (R)-1-cyclopropylethyl-Me | ++ | +++ |
| 388 | 4-F-phenyl | NHS(O)₂Me | (R)-1-cyclopropylethyl-Me | ++ | +++ |
| 389 | 6-CH₂CF₃-pyridin-3-yl | NHS(O)₂Me | (R)-1-cyclopropylethyl-Me | ++ | +++ |
| 390 | CMe₂CH₂OMe | NHS(O)₂Me | (R)-1-cyclopropylethyl-Me | ++ | +++ |
| 391 | 2-Me-phenyl | NHS(O)₂Me | (R)-1-cyclopropylethyl-Me | ++ | +++ |
| 392 | 4-Cl-phenyl | NHS(O)₂Me | (R)-1-cyclopropylethyl-Me | + | +++ |

TABLE 4-continued

Biochemical and cellular potency of additional examples

| Ex. | R₁ | R₂ | R₃ | cellular potency | biochemical potency |
|---|---|---|---|---|---|
| 393 | 4-CN-phenyl | NHS(O)₂Me | (S)-1-cyclopropylethyl, Me | ++ | +++ |
| 394 | 2,2-dimethylcyclopropyl | NHS(O)₂Me | (S)-1-cyclopropylethyl, Me | ++ | +++ |
| 395 | 6-(methoxycarbonyl)pyridin-3-yl | NHS(O)₂Me | (S)-1-cyclopropylethyl, Me | ++ | +++ |
| 396 | pyridin-2-yl | NHS(O)₂Me | (S)-1-cyclopropylethyl, Me | ++ | +++ |
| 397 | 2-F-phenyl | NHS(O)₂Me | (S)-1-cyclopropylethyl, Me | ++ | +++ |
| 398 | 2-MeO-phenyl | NHS(O)₂Me | (S)-1-cyclopropylethyl, Me | + | +++ |
| 399 | 2-(hydroxymethyl)-3-methylbutyl | NHS(O)₂Me | CHMeCF₃ | ++ | +++ |
| 400 | 2-(hydroxymethyl)-3-methylbutyl | NHS(O)₂Me | (S)-1-cyclopropyl-(CF₃) | ++ | +++ |

TABLE 4-continued

Biochemical and cellular potency of additional examples

| Ex. | R₁ | R₂ | R₃ | cellular potency | biochemical potency |
|---|---|---|---|---|---|
| 401 | 3-pyridyl | MeS(O)₂NH- | (S)-CH(Me)(CF₃) | ++ | +++ |
| 402 | cyclopropyl | MeS(O)₂NH- | (R)-CH(CF₃)CH(Me)₂ | ++ | +++ |
| 403 | phenyl | MeS(O)₂NH- | (S)-CH(Me)(CF₃) | ++ | +++ |

(PI3Kγ IC$_{50}$: + means >1 μM, ++ means 100 nM to 1 μM, +++ means <100 nM)

TABLE 5

Biochemical and cellular potency of additional examples

| Ex. | R₁ | cellular potency | biochemical potency |
|---|---|---|---|
| 404 | trans-3-hydroxy-3-methylcyclobutyl (Me up, OH down) | ++ | +++ |
| 405 | trans-3-hydroxy-3-methylcyclobutyl (OH, Me) | ++ | +++ |
| 406 | trans-4-hydroxy-4-methylcyclohexyl | ++ | +++ |
| 407 | (S)-2-cyclopropyl-2-hydroxyethyl | ++ | +++ |

(PI3Kγ IC$_{50}$: + means >1 μM, ++ means 100 nM to 1 μM, +++ means <100 nM)

TABLE 6

Biochemical and cellular potency of additional specific examples

| Ex. | R₁ | R₂ | R₃ | cellular potency | biochemical potency |
|---|---|---|---|---|---|
| 408 | (S)-CH(Me)CH₂OH | N(Me)SO₂Me (via N) | (S)-CH(Me)cyclopropyl | ++ | +++ |
| 409 | cyclopropyl | morpholine-N-SO₂-NH- | (S)-CH(Me)cyclopropyl | ++ | +++ |
| 410 | cyclopropyl | Me₂N-SO₂-NH- | (S)-CH(Me)cyclopropyl | +++ | +++ |
| 411 | trans-4-CO₂H-cyclohexyl | OCF₃ | (S)-CH(Me)cyclopropyl | ++ | +++ |
| 412 | (S)-6-oxopiperidin-3-yl | OCF₃ | (S)-CH(Me)cyclopropyl | ++ | +++ |
| 413 | (R)-6-oxopiperidin-3-yl | OCF₃ | (S)-CH(Me)cyclopropyl | ++ | +++ |
| 414 | CH₂-(pyridin-3-yl) | OCF₃ | (S)-CH(Me)cyclopropyl | ++ | +++ |

TABLE 6-continued

Biochemical and cellular potency of additional specific examples

| Ex. | R₁ | R₂ | R₃ | cellular potency | biochemical potency |
|---|---|---|---|---|---|
| 415 | cyclopropyl | OCF₃ | CH(CF₃)(Me) | ++ | +++ |
| 416 | cyclopropyl | OCF₃ | CH(cyclopropyl)(CH₂OH) | ++ | +++ |
| 417 | trans-3-hydroxypyrrolidin-4-yl | OCF₃ | CH(Me)(cyclopropyl) | + | +++ |
| 418 | trans-3-hydroxypyrrolidin-4-yl | OCF₃ | CH(Me)(cyclopropyl) | + | +++ |
| 419 | 4-(2-hydroxypropan-2-yl)phenyl | OCF₃ | CH(Me)(cyclopropyl) | ++ | +++ |
| 420 | 3-(2-hydroxypropan-2-yl)phenyl | OCF₃ | CH(Me)(cyclopropyl) | ++ | +++ |
| 421 | piperidin-3-yl | OCF₃ | CH(Me)(cyclopropyl) | ++ | +++ |
| 422 | 4-aminopyridin-3-yl | OCF₃ | CH(Me)(cyclopropyl) | ++ | +++ |

TABLE 6-continued

Biochemical and cellular potency of additional specific examples

| Ex. | R₁ | R₂ | R₃ | cellular potency | biochemical potency |
|---|---|---|---|---|---|
| 423 | 5-(6-methoxypyridyl) | OCF₃ | (S)-1-cyclopropylethyl (Me) | ++ | +++ |
| 424 | trans-3-hydroxypyrrolidin-4-yl | OCF₃ | (S)-1-cyclopropylethyl (Me) | + | +++ |
| 425 | 2-(2-hydroxypropan-2-yl)phenyl | OCF₃ | (S)-1-cyclopropylethyl (Me) | + | +++ |
| 426 | trans-3-aminocyclohexyl | OCF₃ | (S)-1-cyclopropylethyl (Me) | ++ | +++ |
| 427 | phenyl | OCF₃ | (S)-1-cyclopropylethyl (Me) | + | +++ |
| 428 | 2-(trifluoromethyl)pyridin-4-yl | OCF₃ | (S)-1-cyclopropylethyl (Me) | + | +++ |
| 429 | 1,3-dimethylpyrazol-4-yl | OCHF₂ | (S)-1-cyclopropylethyl (Me) | +++ | +++ |
| 430 | cis-3-hydroxy-3-methylcyclobutyl | OCHF₂ | (S)-1-cyclopropylethyl (Me) | +++ | +++ |

TABLE 6-continued

Biochemical and cellular potency of additional specific examples

| Ex. | R₁ | R₂ | R₃ | cellular potency | biochemical potency |
|-----|----|----|----|------------------|---------------------|
| 431 | cyclopropyl | 3-hydroxypyrrolidin-1-yl | -CH(CF₃)Me | ++ | +++ |
| 432 | 3-hydroxy-3-methylcyclobutyl | 3-hydroxypyrrolidin-1-yl | -CH(Me)cyclopropyl | ++ | +++ |
| 433 | cyclopropyl | 3-hydroxyazetidin-1-yl | -CH(Me)cyclopropyl | ++ | +++ |
| 434 | 2-cyclopropyl-2-(hydroxymethyl) | 3-hydroxypyrrolidin-1-yl | -CH(CF₃)Me | ++ | +++ |
| 435 | 2-methyl-2-(hydroxymethyl) | 3,3-difluoroazetidin-1-yl | -CH(Me)cyclopropyl | ++ | +++ |
| 436 | cyclopropyl | 3,3-difluoroazetidin-1-yl | -CH(Me)cyclopropyl | ++ | +++ |
| 437 | 4-hydroxy-4-methylcyclohexyl | 4-methylpiperazin-1-yl | -CH(Me)cyclopropyl | ++ | +++ |

TABLE 6-continued

Biochemical and cellular potency of additional specific examples

| Ex. | R₁ | R₂ | R₃ | cellular potency | biochemical potency |
|---|---|---|---|---|---|
| 438 | 3-pyridyl | (3S)-3-hydroxypyrrolidin-1-yl | (1S)-1-cyclopropylethyl (Me) | ++ | +++ |
| 439 | (2S)-1-hydroxy-2-methylpropyl (Me, OH) | 3,3-difluorocyclobutoxy | (1S)-1-cyclopropylethyl (Me) | ++ | +++ |
| 440 | (2S)-1-hydroxy-2-methylpropyl (Me, OH) | (1S)-2,2,2-trifluoro-1-methylethoxy (F₃C, Me) | (1S)-1-cyclopropylethyl (Me) | ++ | +++ |
| 441 | (3S)-2-oxopyrrolidin-3-yl | (3S)-tetrahydrofuran-3-yloxy | (1S)-1-cyclopropylethyl (Me) | + | +++ |
| 442 | cyclopropyl | (1S)-2,2,2-trifluoro-1-methylethoxy (F₃C, Me) | (1S)-1-cyclopropylethyl (Me) | ++ | +++ |
| 443 | (4R)-5-oxopyrrolidin-3-yl | (3S)-tetrahydrofuran-3-yloxy | (1S)-1-cyclopropylethyl (Me) | + | +++ |
| 444 | 3-hydroxy-3-methylcyclobutyl (HO, Me) | methanesulfonyl (O=S=O, Me) | (1S)-1-cyclopropylethyl (Me) | ++ | +++ |
| 445 | cis-3-hydroxycyclobutyl (OH) | methanesulfonyl (O=S=O, Me) | (1S)-1-cyclopropylethyl (Me) | ++ | +++ |

TABLE 6-continued

Biochemical and cellular potency of additional specific examples

| Ex. | R₁ | R₂ | R₃ | cellular potency | biochemical potency |
|---|---|---|---|---|---|
| 446 | cyclopropyl | -S(=O)₂-NH-CH(Me)₂ | -CH(Me)(cyclopropyl) | ++ | +++ |
| 447 | cyclopropyl | -S(=O)(=NH)-Me | -CH(Me)(cyclopropyl) | ++ | +++ |
| 448 | 4-methyl-4-hydroxycyclohexyl | -S(=O)(=NH)-Me | -CH(Me)(cyclopropyl) | ++ | +++ |
| 449 | cyclopropyl | Cl | -CH(CF₃)(Et) | ++ | +++ |
| 450 | cyclopropyl | Et | -CH(Me)(cyclopropyl) | ++ | +++ |
| 451 | cyclopropyl | CN | -CH(Me)(cyclopropyl) | ++ | +++ |
| 452 | pyridin-3-yl | cyclopropyl | -CH(Me)(cyclopropyl) | ++ | +++ |
| 453 | -CH(cyclopropyl)-CH₂OH | -C(Me)₂-OH | -CH(Me)(cyclopropyl) | ++ | +++ |

(PI3Kγ IC₅₀: + means >1 μM, ++ means 100 nM to 1 μM, +++ means <100 nM)

TABLE 7

Biochemical and cellular potency of additional specific examples

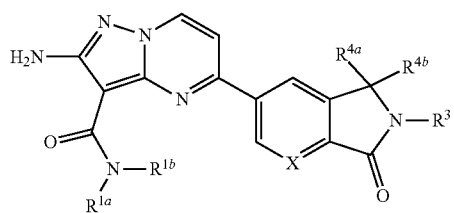

| Ex. | $R_1$ | cellular potency | biochemical potency |
|---|---|---|---|
| 454 | (cyclopropyl-CH(CH2OH)-) | + | +++ |
| 455 | (cyclopropyl-CH<) | ++ | +++ |

(PI3Kγ IC$_{50}$: + means >1 μM, ++ means 100 nM to 1 μM, +++ means <100 nM)

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound represented by Formula (I)

(I)

or a pharmaceutically acceptable salt, hydrate, or solvate thereof, wherein,

X is $C(R^2)$ or N;

$R^{1a}$ and $R^{1b}$ are each a member independently selected from the group consisting of H, $C_{1-6}$ alkyl, $C_{3-6}$ alkenyl, $C_{3-6}$ alkynyl, $C_{1-6}$ haloalkyl, $C_{1-6}$ hydroxyalkyl, —$Y^1$, —$X^1$—C(O)$_2R^a$, —$X^1$—OR$^a$, —$X^1$—NR$^a$R$^b$, —$X^1$—CONR$^a$R$^b$, —$X^1$—N(R$^a$)SO$_2$R$^a$, —$X^1$—SO$_2$R$^a$, —$X^1$—SO$_2$NR$^a$R$^b$, —$X^1$—SO$_3$R$^a$, —$X^1$—CN, —$X^1$—$Y^1$ and —$X^1$—$Y^1$—$Y^{1a}$ wherein each $X^1$ is a bond or $C_{1-6}$ alkylene and is optionally further substituted with from 1 to 3 substituents independently selected from the group consisting of OH, SO$_2$NH$_2$, CONH$_2$, C(O)NHOH, PO$_3$H$_2$, COO—$C_{1-8}$alkyl and CO$_2$H, and each $Y^1$ and $Y^{1a}$ is independently selected from the group consisting of $C_{3-10}$ cycloalkyl, 4- to 8-membered heterocycloalkyl, 5- to 6-membered heteroaryl, and aryl, wherein each heterocycloalkyl and heteroaryl have 1 to 3 heteroatom ring vertices selected from O, N and S; and each $Y^1$ and $Y^{1a}$ is optionally further substituted with one to four substituents independently selected from the group consisting of halogen, oxo, CN, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, NH$_2$, NH($C_{1-4}$ alkyl), N($C_{1-4}$ alkyl)$_2$, SO$_2$NH$_2$, CONH$_2$, C(O)NHOH, PO$_3$H$_2$, CO—$C_{1-8}$alkyl, COO—$C_{1-8}$alkyl, and CO$_2$H;

$R^2$ is a member selected from the group consisting of halogen, CN, $C_{1-6}$ alkyl, $C_{2-6}$ alkenyl, $C_{2-6}$ alkynyl, $C_{1-6}$ haloalkyl, $C_{1-6}$ hydroxyalkyl, —$Y^2$, —$X^2$—C(O)$_2R^a$, —$X^2$—OR$^a$, —$X^2$—NR$^a$R$^b$, —$X^2$—CONR$^a$R$^b$, —$X^2$—SO$_2$R$^a$, —$X^2$—N(R$^a$)SO$_2$R$^a$, —$X^2$—SO$_2$NR$^a$R$^b$, —$X^2$—SO$_3$R$^a$, —O—$X^2$—$Y^2$ and —$X^2$—$Y^2$ wherein each $X^2$ is a bond or $C_{1-6}$ alkylene and is optionally further substituted with from 1 to 3 substituents independently selected from the group consisting of OH, SO$_2$NH$_2$, CONH$_2$, C(O)NHOH, PO$_3$H$_2$, COO—$C_{1-8}$ alkyl and CO$_2$H, and each $Y^2$ is selected from the group consisting of $C_{3-6}$ cycloalkyl, 4- to 8-membered heterocycloalkyl, and 5- to 6-membered heteroaryl, wherein each heterocycloalkyl and heteroaryl have 1 to 3 heteroatom ring vertices selected from O, N and S; and each $Y^2$ is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO$—$C_{1-8}$alkyl, and $CO_2H$;

$R^3$ is a member selected from the group consisting of $C_{1-6}$ alkyl, $C_{3-6}$ cycloalkyl, $C_{3-6}$ cycloalkyl$C_{1-3}$ alkyl, $C_{1-6}$ hydroxyalkyl, $C_{1-6}$ haloalkyl and —$X^3$—$Y^3$ wherein each $X^3$ is a bond, $C_{1-6}$ alkylene or $C_{1-6}$ haloalkylene and is optionally further substituted with OH, $SO_2NH_2$, $CONH_2$, $C(O)NHOH$, $PO_3H_2$, $COO$—$C_{1-8}$ alkyl or $CO_2H$, and each $Y^3$ is selected from the group consisting of $C_{3-6}$ cycloalkyl, 4- to 8-membered heterocycloalkyl, and 5- to 6-membered heteroaryl, wherein each heterocycloalkyl and heteroaryl have 1 to 3 heteroatom ring vertices selected from O, N and S; and each $Y^3$ is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO$—$C_{1-8}$alkyl, and $CO_2H$;

$R^{4a}$ and $R^{4b}$ are each a member independently selected from the group consisting of H, halogen, $C_{1-6}$ alkyl, $C_{2-6}$ alkenyl, $C_{2-6}$ alkynyl, $C_{1-6}$ haloalkyl, and $C_{1-6}$ hydroxyalkyl;

each $R^a$ is independently selected from the group consisting of H, $C_{1-6}$ alkyl, $C_{1-6}$ haloalkyl, $C_{1-6}$ hydroxyalkyl, $C_{1-6}$ alkylene-$CO_2H$, $C_{1-6}$ alkylene-$SO_3H$, $C_{3-6}$ cycloalkyl, $C_{3-6}$ cycloalkyl$C_{1-3}$ alkyl, $C_{1-3}$ alkyl$C_{3-6}$ cycloalkyl, phenyl and 3- to 7-membered heterocycloalkyl having from one to three heteroatom ring vertices selected from O, N and S; and each $R^a$ is optionally further substituted with one or two members independently selected from halogen, OH, $C_{1-4}$ alkoxy, $SO_2NH_2$, $CONH_2$, $C(O)NHOH$, $PO_3H_2$, $COO$—$C_{1-8}$ alkyl and $CO_2H$; and each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$, each of which is optionally further substituted with one or two members independently selected from OH, $SO_2NH_2$, $CONH_2$, $C(O)NHOH$, $PO_3H_2$, $COO$—$C_{1-8}$alkyl and $CO_2H$.

2. The compound of claim 1, or a pharmaceutically acceptable salt, hydrate, or solvate thereof, wherein:

X is $C(R^2)$ or N;

$R^{1a}$ and $R^{1b}$ are each a member independently selected from the group consisting of H, $C_{1-6}$ alkyl, $C_{3-6}$ alkenyl, $C_{3-6}$ alkynyl, $C_{1-6}$ haloalkyl, $C_{1-6}$ hydroxyalkyl, —$Y^1$, —$X^1$—$C(O)_2R^a$, —$X^1$—$OR^a$, —$X^1$—$NR^aR^b$, —$X^1$—$CONR^aR^b$, —$X^1$—$N(R^a)SO_2R^a$, —$X^1$—$SO_2R^a$, —$X^1$—$SO_2NR^aR^b$, —$X^1$—$SO_3R^a$, —$X^1$—$CN$, —$X^1$—$Y^1$ and —$X^1$—$Y^1$—$Y^{1a}$ wherein each $X^1$ is a bond or $C_{1-6}$ alkylene and is optionally further substituted with OH, $SO_2NH_2$, $CONH_2$, $C(O)NHOH$, $PO_3H_2$, $COO$—$C_{1-8}$alkyl or $CO_2H$, and each $Y^1$ and $Y^{1a}$ is independently selected from the group consisting of $C_{3-10}$ cycloalkyl, 4- to 8-membered heterocycloalkyl, 5- to 6-membered heteroaryl, and aryl, each of which is optionally further substituted with one to four substituents independently selected from the group consisting of halogen, oxo, CN, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $NH_2$, $NH(C_{1-4}$ alkyl), $N(C_{1-4}$ alkyl)$_2$, $SO_2NH_2$, $CONH_2$, $C(O)NHOH$, $PO_3H_2$, $CO$—$C_{1-8}$alkyl, $COO$—$C_{1-8}$alkyl, and $CO_2H$;

$R^2$ is a member selected from the group consisting of halogen, CN, $C_{1-6}$ alkyl, $C_{2-6}$ alkenyl, $C_{2-6}$ alkynyl, $C_{1-6}$ haloalkyl, $C_{1-6}$ hydroxyalkyl, —$Y^2$, —$X^2$—$C(O)_2R^a$, —$X^2$—$OR^a$, —$X^2$—$NR^aR^b$, —$X^2$—$CONR^aR^b$, —$X^2$—$SO_2R^a$, —$X^2$—$N(R^a)SO_2R^a$, —$X^2$—$SO_2NR^aR^b$, —$X^2$—$SO_3R^a$, —$O$—$X^2$—$Y^2$ and —$X^2$—$Y^2$ wherein each $X^2$ is a bond or $C_{1-6}$ alkylene and is optionally further substituted with OH, $SO_2NH_2$, $CONH_2$, $C(O)NHOH$, $PO_3H_2$, $COO$—$C_{1-8}$ alkyl or $CO_2H$, and each $Y^2$ is selected from the group consisting of $C_{3-6}$ cycloalkyl, 4- to 8-membered heterocycloalkyl, and 5- to 6-membered heteroaryl, each of which is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO$—$C_{1-8}$alkyl, and $CO_2H$;

$R^3$ is a member selected from the group consisting of $C_{1-6}$ alkyl, $C_{3-6}$ cycloalkyl, $C_{3-6}$ cycloalkyl$C_{1-3}$ alkyl, $C_{1-6}$ hydroxyalkyl, $C_{1-6}$ haloalkyl and —$X^3$—$Y^3$ wherein each $X^3$ is a bond, $C_{1-6}$ alkylene or $C_{1-6}$ haloalkylene and is optionally further substituted with OH, $SO_2NH_2$, $CONH_2$, $C(O)NHOH$, $PO_3H_2$, $COO$—$C_{1-8}$ alkyl or $CO_2H$, and each $Y^3$ is selected from the group consisting of $C_{3-6}$ cycloalkyl, 4- to 8-membered heterocycloalkyl, and 5- to 6-membered heteroaryl, each of which is optionally further substituted with one to four substituents independently selected from the group consisting of halogen, oxo, OH, $C_{1-4}$ alkyl, $C_{1-4}$ haloalkyl, $C_{1-4}$ hydroxyalkyl, $C_{1-4}$ alkoxy, $C_{1-4}$ haloalkoxy, $C_{1-4}$ hydroxyalkoxy, $SO_2NH_2$, $CONH_2$, $C(O)NHOH$, $PO_3H_2$, $COO$—$C_{1-8}$alkyl, and $CO_2H$;

$R^{4a}$ and $R^{4b}$ are each a member independently selected from the group consisting of H, halogen, $C_{1-6}$ alkyl, $C_{2-6}$ alkenyl, $C_{2-6}$ alkynyl, $C_{1-6}$ haloalkyl, and $C_{1-6}$ hydroxyalkyl;

each $R^a$ is independently selected from the group consisting of H, $C_{1-6}$ alkyl, $C_{1-6}$ haloalkyl, $C_{1-6}$ hydroxyalkyl, $C_{1-6}$ alkylene-$CO_2H$, $C_{1-6}$ alkylene-$SO_3H$, $C_{3-6}$ cycloalkyl, $C_{3-6}$ cycloalkyl$C_{1-3}$ alkyl, phenyl and 3- to 7-membered heterocycloalkyl, each of which is optionally further substituted with one or two members independently selected from OH, $SO_2NH_2$, $CONH_2$, $C(O)NHOH$, $PO_3H_2$, $COO$—$C_{1-8}$alkyl and $CO_2H$; and each $R^b$ is independently selected from the group consisting of H, $C_{1-6}$ alkyl, $C_{3-6}$ cycloalkyl, $C_{1-6}$ haloalkyl, $C_{1-6}$ hydroxyalkyl, $C_{1-6}$ alkylene-$CO_2H$, and $C_{1-6}$ alkylene-$SO_3H$, each of which is optionally further substituted with one or two members independently selected from OH, $SO_2NH_2$, $CONH_2$, $C(O)NHOH$, $PO_3H_2$, $COO$—$C_{1-8}$alkyl and $CO_2H$.

3. The compound of claim 1, wherein X is $C(R^2)$.

4. The compound of claim 1, wherein X is N.

5. The compound of claim 1, having Formula (Ia):

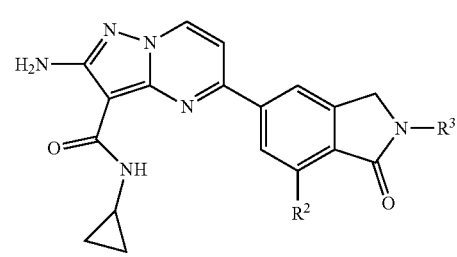

(Ia)

or a pharmaceutically acceptable salt thereof.

6. The compound of claim 1, having a formula selected from the group consisting of Formula (Ib), Formula (Ic), Formula (Id), Formula (Ie), Formula (If), Formula (Ig), Formula (Ih), and Formula (Ii):
(Ib)
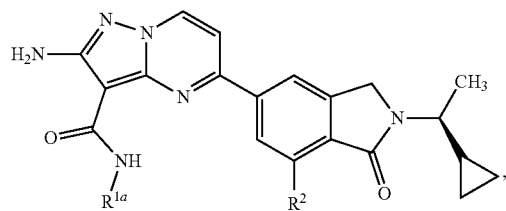
(Ic)
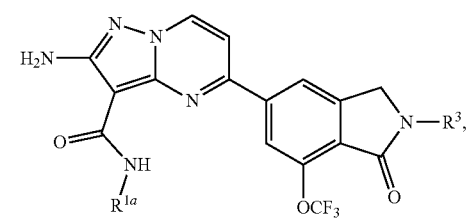
(Id)
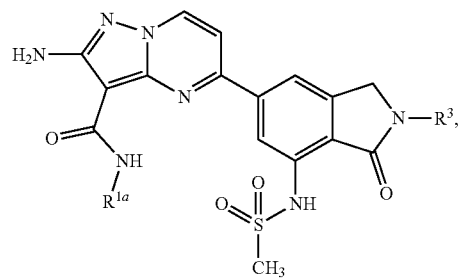
(Ie)
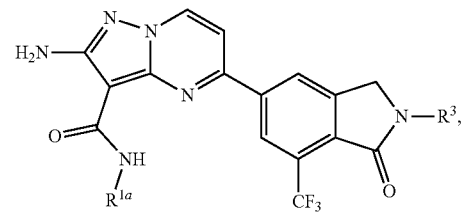
(If)
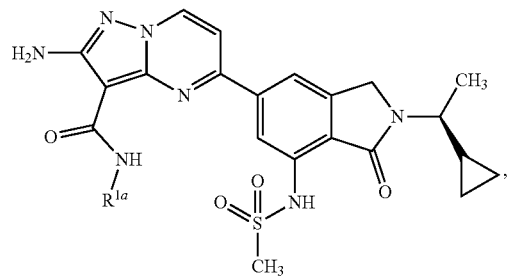
(Ig)
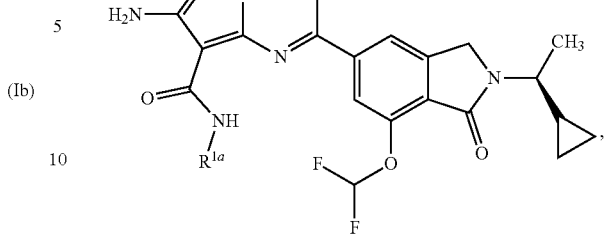
(Ih)
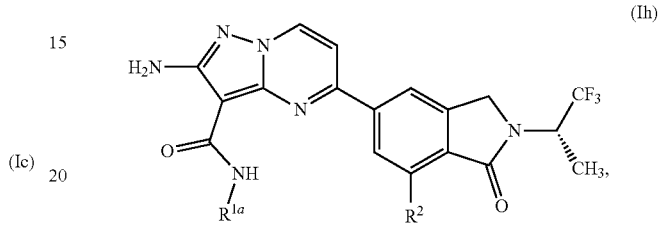
(Ii)
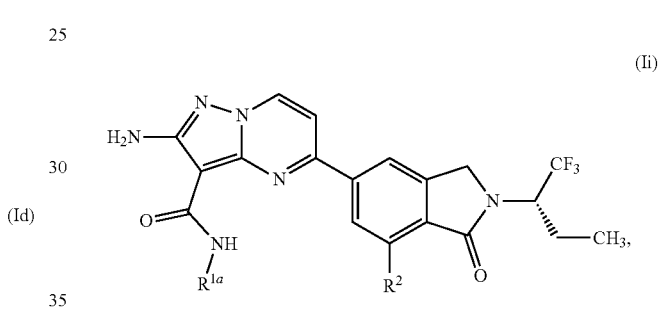
or a pharmaceutically acceptable salt thereof.
7. The compound of claim 1, or a pharmaceutically acceptable salt thereof, wherein $R^{1b}$ is H
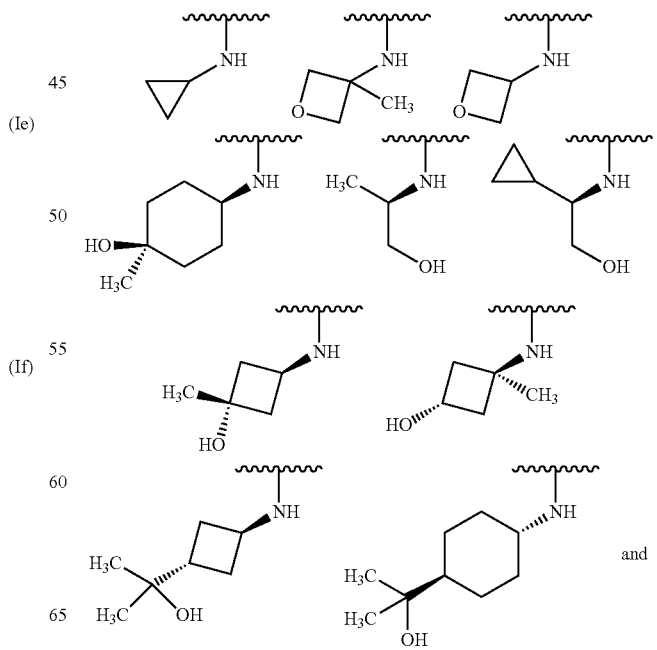
and 257
-continued
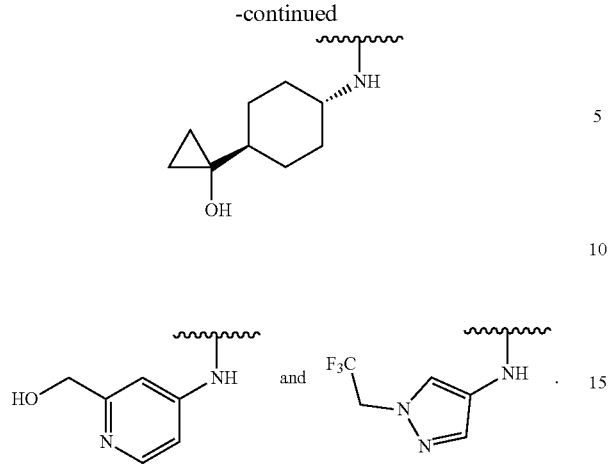
8. The compound of claim 7, or a pharmaceutically acceptable salt thereof, wherein $R^{1a}$ forms a substituent with N and $R^{1b}$ and selected from the group consisting of:
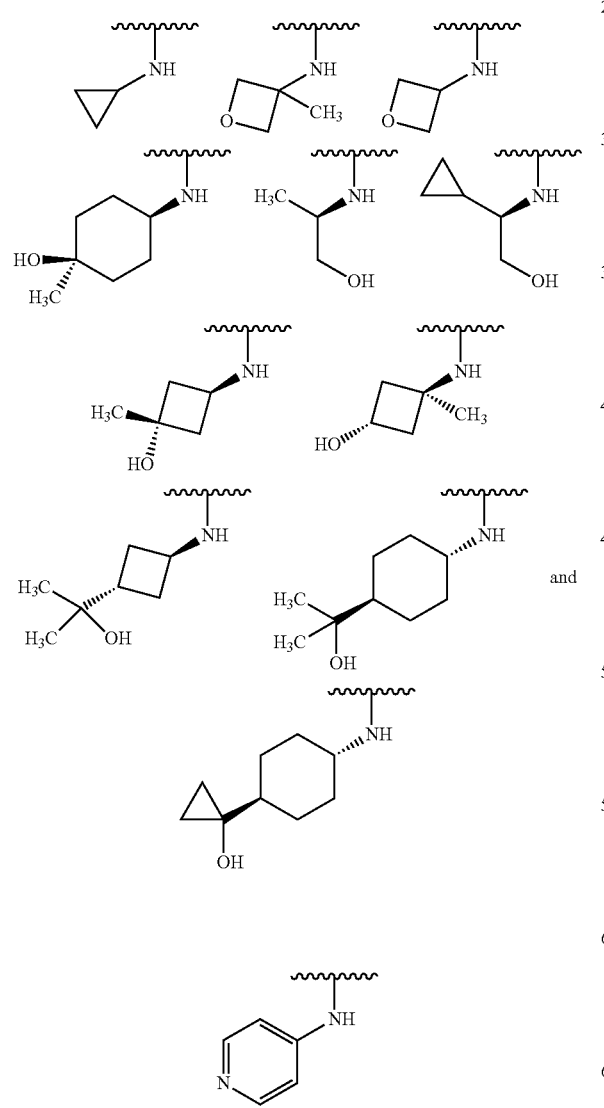
258
-continued
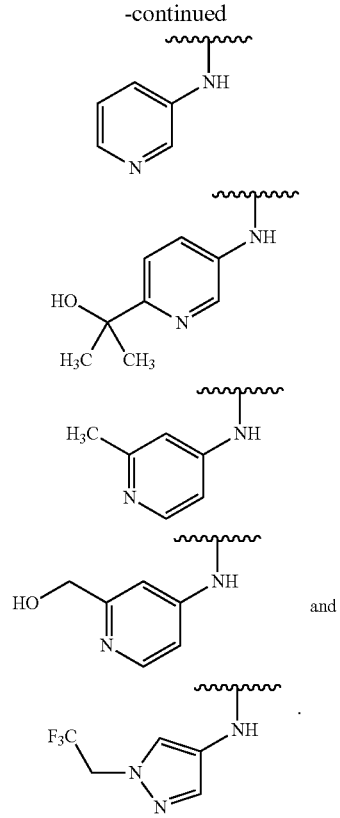
9. The compound of claim 1, selected from the group consisting of:
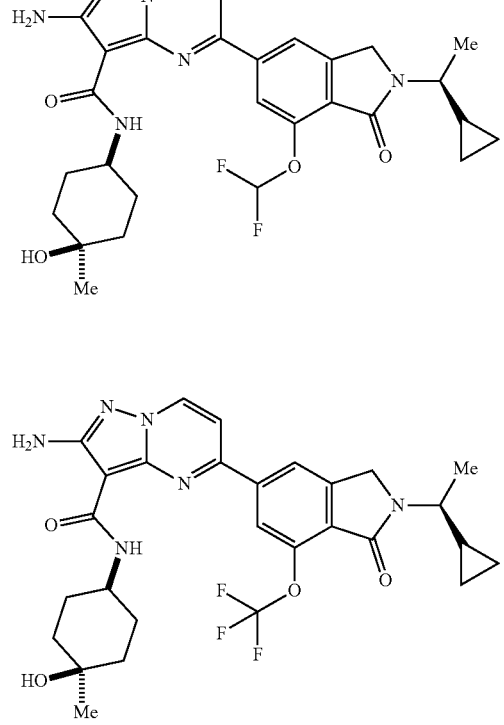

259
-continued
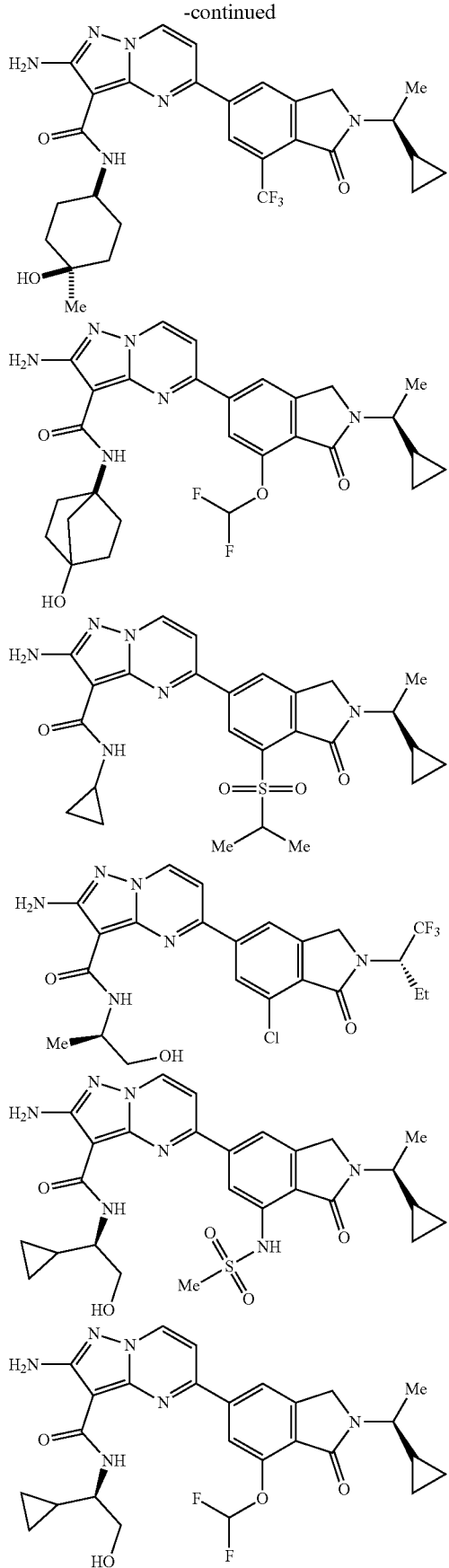
260
-continued
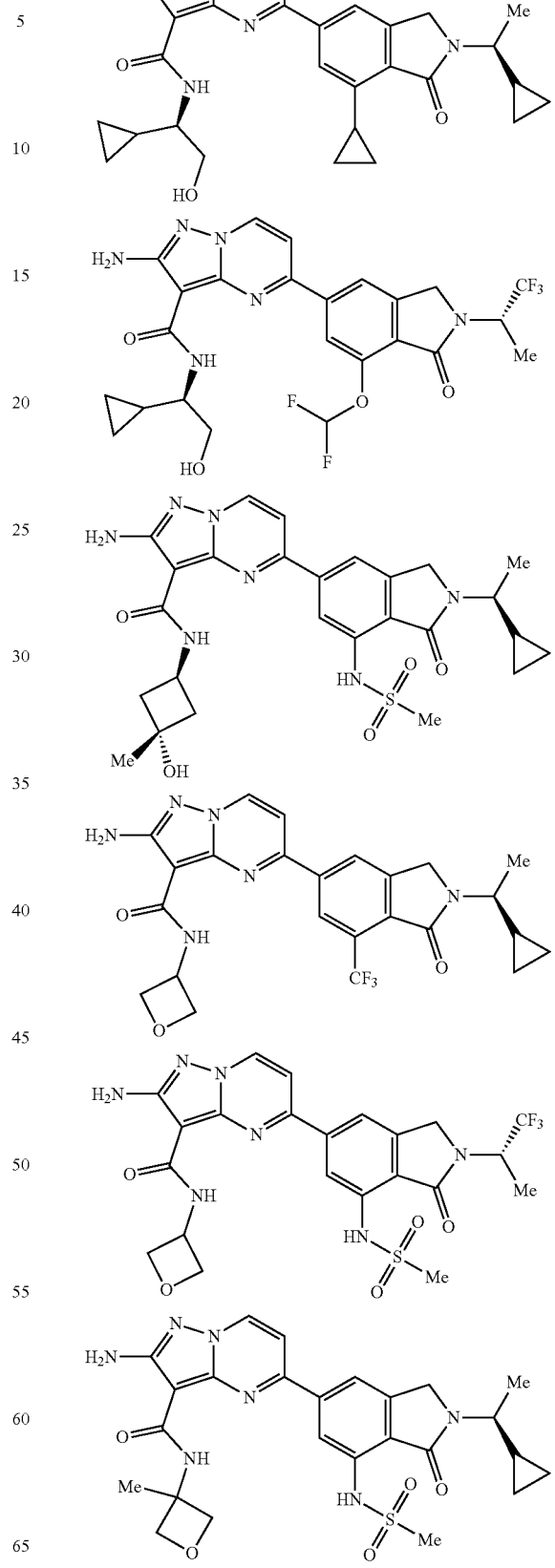

261
-continued
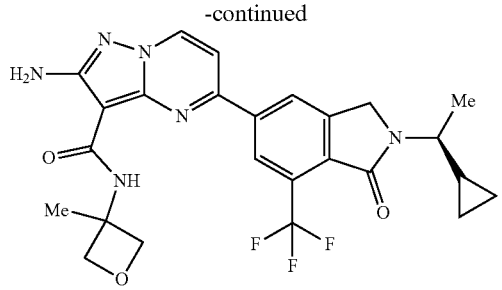
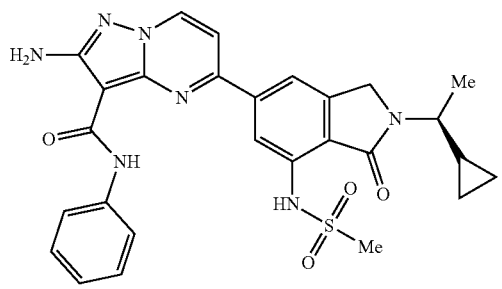
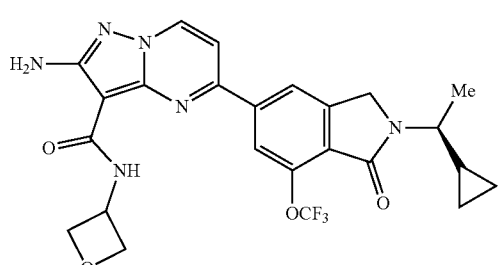
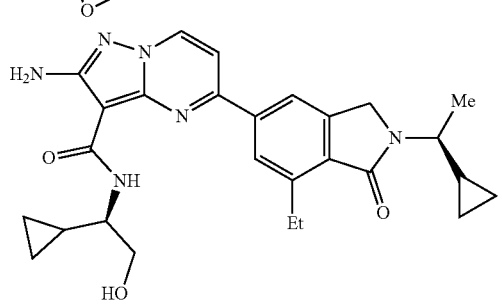
262
-continued
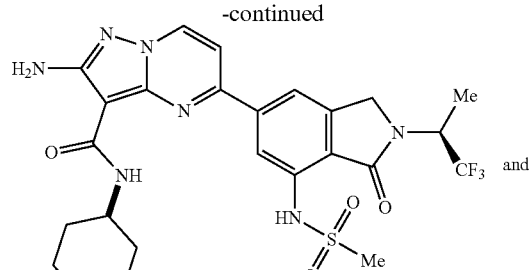
and
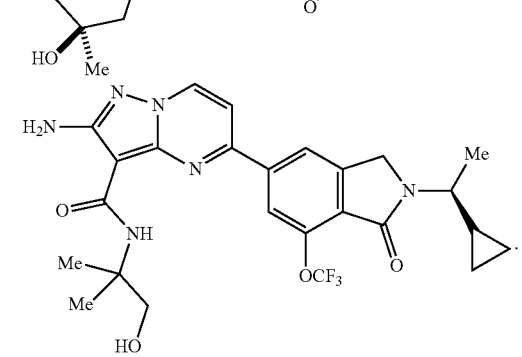
10. A pharmaceutical composition comprising a compound of claim 1 and a pharmaceutically acceptable excipient.
11. The compound of claim 1, which is:
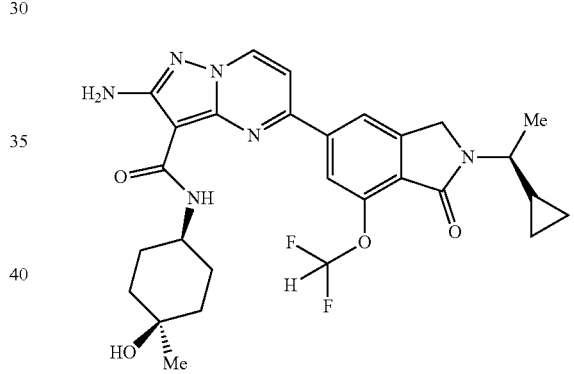
12. A compound selected from the group consisting of:
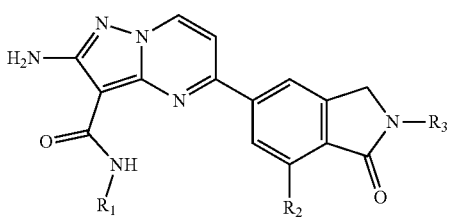
| Compound No. | R₁ | R₂ | R₃ |
|---|---|---|---|
| 1 |  |  | 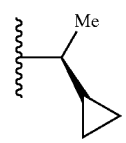 [SMILES: *[C@@H](C)C1CC1] |

-continued

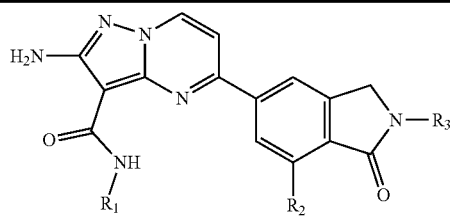

| Compound No. | R₁ | R₂ | R₃ |
|---|---|---|---|
| 2 | 4-hydroxy-4-methylcyclohexyl | Me | (S)-1-cyclopropylethyl |
| 3 | (1S,3R)-3-hydroxycyclopentyl | Me | (S)-1-cyclopropylethyl |
| 4 | (cis)-3-hydroxycyclobutylmethyl | Me | (S)-1-cyclopropylethyl |
| 5 | (cis)-3-hydroxycyclopentyl | Me | (S)-1-cyclopropylethyl |
| 6 | 3-hydroxy-3-methylcyclobutyl | Me | (S)-1-cyclopropylethyl |
| 7 | 4-hydroxy-4-methylcyclohexyl | Me | (S)-1-cyclopropylethyl |
| 8 | (1S,2R)-2-hydroxycyclopentyl | Me | (S)-1-cyclopropylethyl |
| 9 | (1S,3S)-3-hydroxycyclohexyl | Me | (S)-1-cyclopropylethyl |

-continued
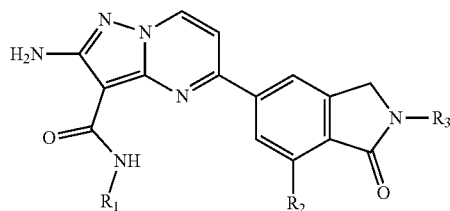
| Compound No. | R₁ | R₂ | R₃ |
|---|---|---|---|
| 10 | 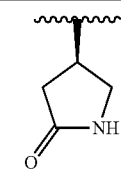 |  Me | 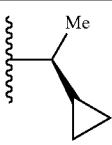 |
| 11 | 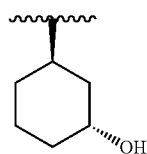 [SMILES: *[C@@H]1CCC[C@@H](O)C1] |  Me | 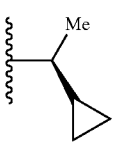 [SMILES: *[C@@H](C)C1CC1] |
| 12 | 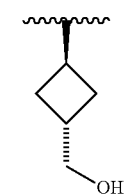 [SMILES: *[C@H]1C[C@H](CO)C1] |  Me | 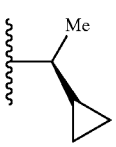 [SMILES: *[C@@H](C)C1CC1] |
| 13 | 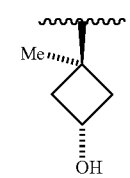 |  Me | 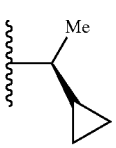 [SMILES: *[C@@H](C)C1CC1] |
| 14 | 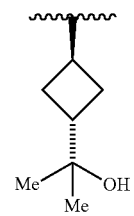 [SMILES: *[C@H]1C[C@H](C(C)(C)O)C1] |  Me | 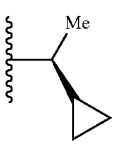 [SMILES: *[C@@H](C)C1CC1] |
| 15 | 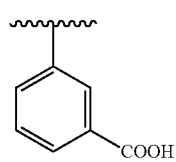 [SMILES: *c1cccc(C(=O)O)c1] |  Me | 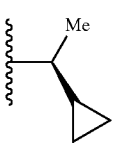 [SMILES: *[C@@H](C)C1CC1] |
| 16 | 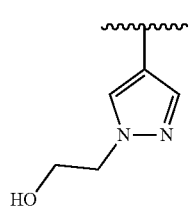 [SMILES: *c1cnn(CCO)c1] |  Me | 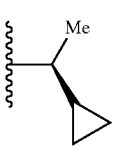 |

-continued

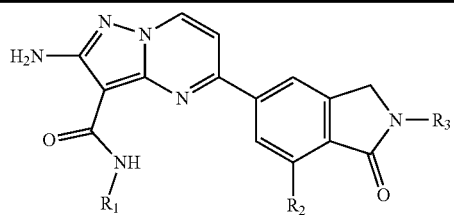

| Compound No. | R₁ | R₂ | R₃ |
|---|---|---|---|
| 17 | 2-hydroxy-2-methylpropyl-pyrazol-4-yl | Me | 1-cyclopropylethyl (Me) |
| 18 | 1-methylpyrazol-4-yl | Me | 1-cyclopropylethyl (Me) |
| 19 | 1,5-dimethylpyrazol-4-yl | Me | 1-cyclopropylethyl (Me) |
| 20 | cyclopropyl | OCF₃ | 1-cyclopropylethyl (Me) |
| 21 | oxetan-3-yl | OCF₃ | 1-cyclopropylethyl (Me) |
| 22 | (S)-2-methyl-3-hydroxypropyl | OCF₃ | 1-cyclopropylethyl (Me) |
| 23 | 3-hydroxy-3-methylcyclobutyl | OCF₃ | 1-cyclopropylethyl (Me) |
| 24 | 4-hydroxy-4-methylcyclohexyl | OCF₃ | 1-cyclopropylethyl (Me) |

-continued

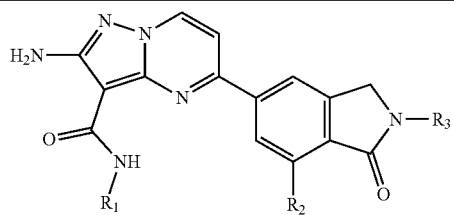

| Compound No. | R₁ | R₂ | R₃ |
|---|---|---|---|
| 25 | Me—CH(Me)—CH—CH₂OH | OCF₃ | CH(Me)—cyclopropyl |
| 26 | cyclopropyl—CH—CH₂OH | OCF₃ | CH(Me)—cyclopropyl |
| 27 | Me—CH—CH₂OH | OCF₃ | CH(Me)—CF₃ |
| 28 | 4-pyrrolidinon-yl | OCF₃ | CH(Me)—cyclopropyl |
| 29 | cis-3-hydroxycyclohexyl | OCF₃ | CH(Me)—cyclopropyl |
| 30 | trans-4-(1-hydroxycyclopropyl)cyclohexyl | OCF₃ | CH(Me)—cyclopropyl |
| 31 | trans-4-aminocyclohexyl | OCF₃ | CH(Me)—cyclopropyl |
| 32 | (3S)-2-oxopyrrolidin-3-yl | OCF₃ | CH(Me)—cyclopropyl |

-continued
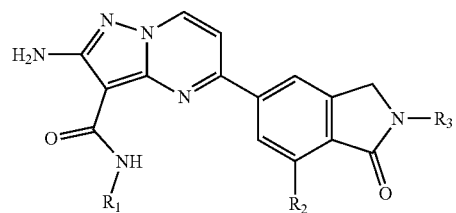
| Compound No. | R₁ | R₂ | R₃ |
|---|---|---|---|
| 33 | 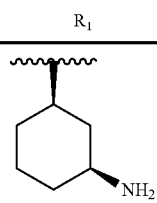 |  OCF₃ | 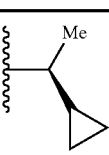 |
| 34 | 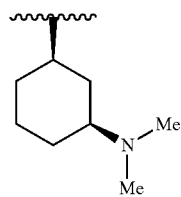 [SMILES: *[C@@H]1CCC[C@H](N(C)C)C1] |  OCF₃ | 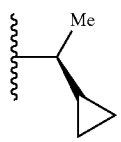 [SMILES: *[C@@H](C)C1CC1] |
| 35 | 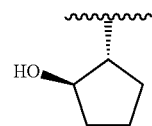 |  OCF₃ | 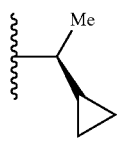 [SMILES: *[C@@H](C)C1CC1] |
| 36 | 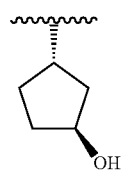 |  OCF₃ | 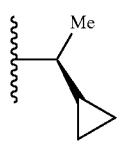 [SMILES: *[C@@H](C)C1CC1] |
| 37 | 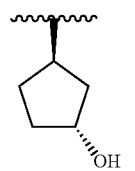 |  OCF₃ | 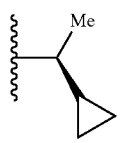 [SMILES: *[C@@H](C)C1CC1] |
| 38 | 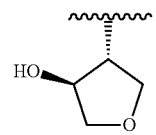 |  OCF₃ | 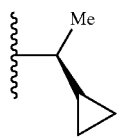 [SMILES: *[C@@H](C)C1CC1] |
| 39 | 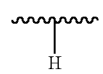 H |  OCF₃ | 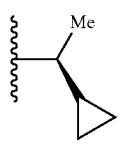 [SMILES: *[C@@H](C)C1CC1] |
| 40 | 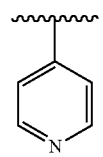 |  OCF₃ | 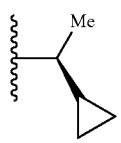 [SMILES: *[C@@H](C)C1CC1] |

-continued

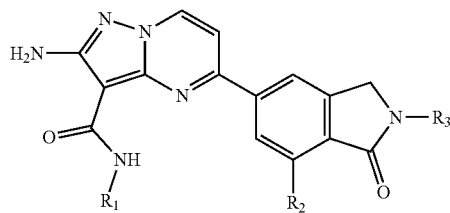

| Compound No. | R₁ | R₂ | R₃ |
|---|---|---|---|
| 41 | 3-pyridyl | OCF₃ | (1-cyclopropyl)ethyl, Me |
| 42 | 5-fluoro-3-pyridyl | OCF₃ | (1-cyclopropyl)ethyl, Me |
| 43 | 5-methoxy-3-pyridyl | OCF₃ | (1-cyclopropyl)ethyl, Me |
| 44 | 2-methyl-3-pyridyl | OCF₃ | (1-cyclopropyl)ethyl, Me |
| 45 | 6-methyl-3-pyridyl | OCF₃ | (1-cyclopropyl)ethyl, Me |
| 46 | 6-amino-3-pyridyl | OCF₃ | (1-cyclopropyl)ethyl, Me |
| 47 | 4-methyl-3-pyridyl | OCF₃ | (1-cyclopropyl)ethyl, Me |
| 48 | 4-methoxy-3-pyridyl | OCF₃ | (1-cyclopropyl)ethyl, Me |

-continued

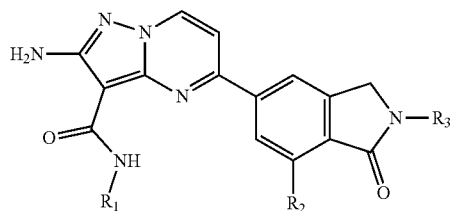

| Compound No. | R₁ | R₂ | R₃ |
|---|---|---|---|
| 49 | 3-oxopyrrolidin-3-yl | CF₃ | 1-cyclopropylethyl (Me) |
| 50 | (S)-2-methyl-3-hydroxypropyl | CF₃ | 1-cyclopropylethyl (Me) |
| 51 | 3-hydroxypropyl | CF₃ | 1-cyclopropylethyl (Me) |
| 52 | 4-hydroxybutyl | CF₃ | 1-cyclopropylethyl (Me) |
| 53 | oxetan-2-ylmethyl | CF₃ | 1-cyclopropylethyl (Me) |
| 54 | trans-4-methyl-4-hydroxycyclohexyl | CF₃ | 1-cyclopropylethyl (Me) |
| 55 | trans-4-trifluoromethyl-4-hydroxycyclohexyl | CF₃ | 1-cyclopropylethyl (Me) |
| 56 | (3-methyloxetan-3-yl)methyl | CF₃ | 1-cyclopropylethyl (Me) |

-continued
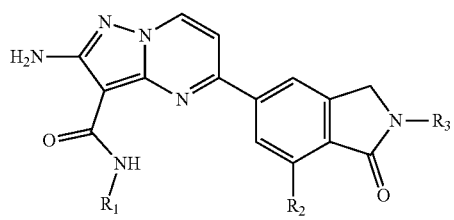
| Compound No. | R₁ | R₂ | R₃ |
|---|---|---|---|
| 57 | 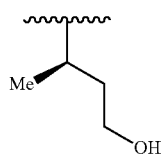 [SMILES: *[C@H](C)CCO] |  | 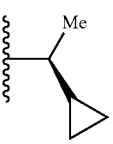 [SMILES: *[C@@H](C)C1CC1] |
| 58 | 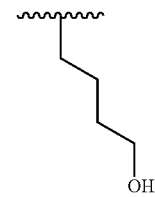 [SMILES: *CCCCO] |  | 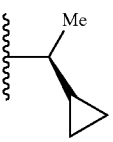 [SMILES: *[C@@H](C)C1CC1] |
| 59 | 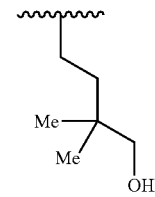 [SMILES: *CCC(C)(C)CO] |  | 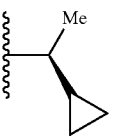 [SMILES: *[C@@H](C)C1CC1] |
| 60 | 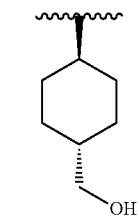 |  | 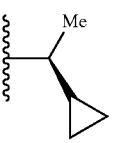 [SMILES: *[C@@H](C)C1CC1] |
| 61 | 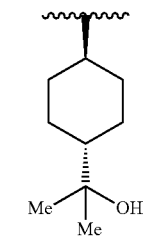 [SMILES: *[C@H]1CC[C@H](C(C)(C)O)CC1] |  | 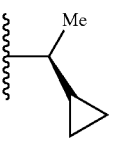 [SMILES: *[C@@H](C)C1CC1] |
| 62 | 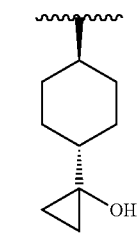 [SMILES: *[C@H]1CC[C@H](C2(O)CC2)CC1] |  | 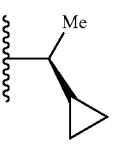 [SMILES: *[C@@H](C)C1CC1] |

-continued
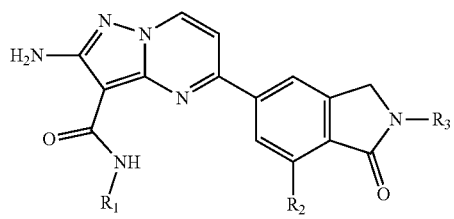
| Compound No. | R₁ | R₂ | R₃ |
|---|---|---|---|
| 63 | 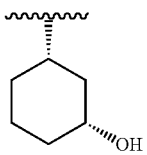 [SMILES: *[C@H]1CCC[C@@H](O)C1] |  | 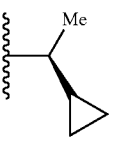 [SMILES: *[C@@H](C)C1CC1] |
| 64 | 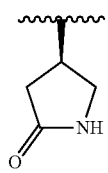 [SMILES: *[C@H]1CNC(=O)C1] |  | 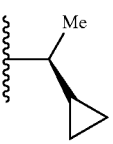 [SMILES: *[C@@H](C)C1CC1] |
| 65 | 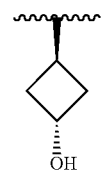 [SMILES: *[C@H]1C[C@H](O)C1] |  | 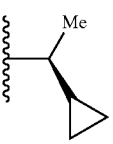 [SMILES: *[C@@H](C)C1CC1] |
| 66 | 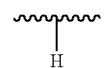 |  | 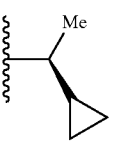 [SMILES: *[C@@H](C)C1CC1] |
| 67 | 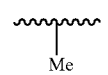 |  | 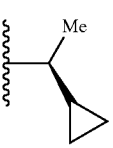 [SMILES: *[C@@H](C)C1CC1] |
| 68 | 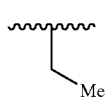 |  | 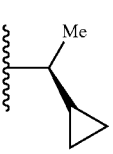 [SMILES: *[C@@H](C)C1CC1] |
| 69 | 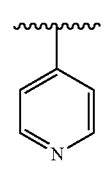 |  | 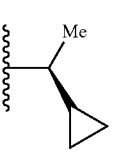 [SMILES: *[C@@H](C)C1CC1] |
| 70 | 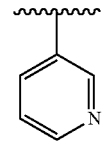 |  | 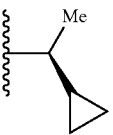 [SMILES: *[C@@H](C)C1CC1] |

-continued

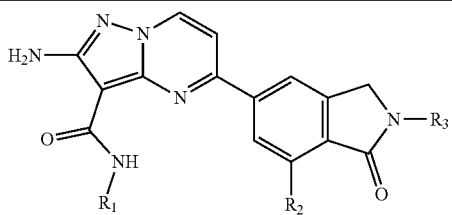

| Compound No. | R₁ | R₂ | R₃ |
|---|---|---|---|
| 71 | -CH₂CH₂-O-CH₂CH₂-O- (bridging to R₂) | | -CH(Me)-cyclopropyl |
| 72 | (1S,2S)-2-hydroxycyclopentyl | NHSO₂Me | -CH(Me)-cyclopropyl |
| 73 | Me | NHSO₂Me | -CH(Me)-cyclopropyl |
| 74 | Et | NHSO₂Me | -CH(Me)-cyclopropyl |
| 75 | iPr | NHSO₂Me | -CH(Me)-cyclopropyl |
| 76 | H | NHSO₂Me | -CH(Me)-cyclopropyl |
| 77 | spiro[2.2]pentyl | NHSO₂Me | -CH(Me)-cyclopropyl |
| 78 | oxetan-3-yl | NHSO₂Me | -CH(Me)-cyclopropyl |
| 79 | 3-methyloxetan-3-yl | NHSO₂Me | -CH(Me)-cyclopropyl |

-continued

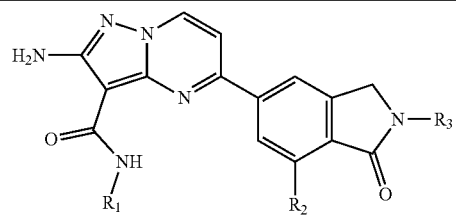

| Compound No. | R₁ | R₂ | R₃ |
|---|---|---|---|
| 80 | 1-cyanooxetan-3-yl | NHSO₂Me | (S)-1-cyclopropylethyl |
| 81 | 1-cyanocyclobutyl | NHSO₂Me | (S)-1-cyclopropylethyl |
| 82 | trans-3-hydroxy-3-methylcyclobutyl | NHSO₂Me | (S)-1-cyclopropylethyl |
| 83 | trans-3-hydroxy-1-methylcyclobutyl | NHSO₂Me | (S)-1-cyclopropylethyl |
| 84 | trans-3-methoxycyclobutyl | NHSO₂Me | (S)-1-cyclopropylethyl |
| 85 | (cis-3-hydroxycyclobutyl)methyl | NHSO₂Me | (S)-1-cyclopropylethyl |
| 86 | trans-3-hydroxycyclopentyl | NHSO₂Me | (S)-1-cyclopropylethyl |
| 87 | cyclopropyl | NHSO₂Me | (S)-1-cyclopropylethyl |

-continued
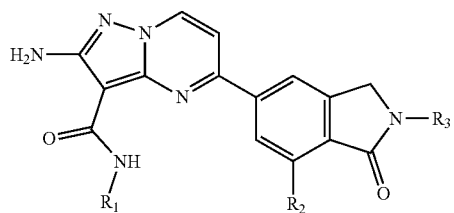
| Compound No. | R₁ | R₂ | R₃ |
|---|---|---|---|
| 88 | 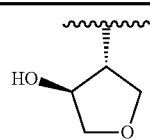 | 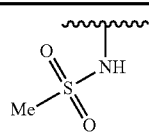 | 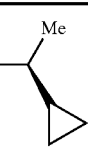 |
| 89 | 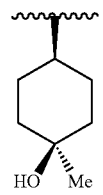 | 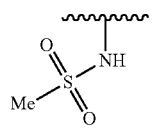 | 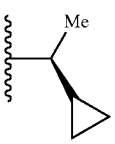 [SMILES: *[C@@H](C)C1CC1] |
| 90 | 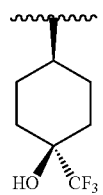 | 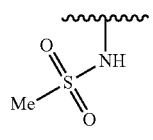 | 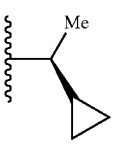 [SMILES: *[C@@H](C)C1CC1] |
| 91 | 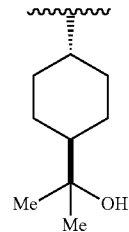 [SMILES: *[C@H]1CC[C@H](C(C)(C)O)CC1] | 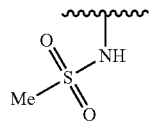 | 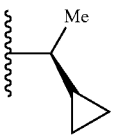 [SMILES: *[C@@H](C)C1CC1] |
| 92 | 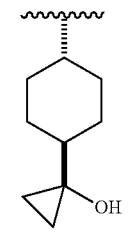 | 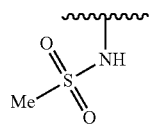 [SMILES: *NS(C)(=O)=O] | 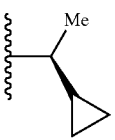 [SMILES: *[C@@H](C)C1CC1] |
| 93 | 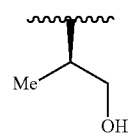 | 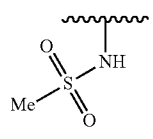 [SMILES: *NS(C)(=O)=O] | 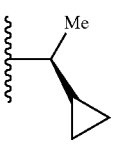 [SMILES: *[C@@H](C)C1CC1] |
| 94 | 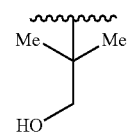 | 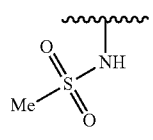 [SMILES: *NS(C)(=O)=O] | 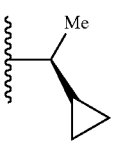 [SMILES: *[C@@H](C)C1CC1] |

-continued

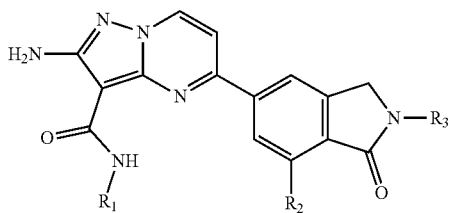

| Compound No. | R₁ | R₂ | R₃ |
|---|---|---|---|
| 95 | Me—C(Me)(OH)—CH₂—CH₂— | MeSO₂NH— | (S)-CH(Me)(cyclopropyl) |
| 96 | iPr-CH(CH₂OH)— | MeSO₂NH— | (S)-CH(Me)(cyclopropyl) |
| 97 | cyclopropyl-CH(CH₂OH)— | MeSO₂NH— | (S)-CH(Me)(cyclopropyl) |
| 98 | (S)-CH(Me)(1-methyl-1H-pyrazol-4-yl) | MeSO₂NH— | (S)-CH(Me)(cyclopropyl) |
| 99 | pyridin-3-yl | MeSO₂NH— | (S)-CH(Me)(cyclopropyl) |
| 100 | pyridin-4-yl | MeSO₂NH— | (S)-CH(Me)(cyclopropyl) |
| 101 | 2-methylpyridin-4-yl | MeSO₂NH— | (S)-CH(Me)(cyclopropyl) |
| 102 | 2,6-dimethylpyridin-4-yl | MeSO₂NH— | (S)-CH(Me)(cyclopropyl) |

-continued

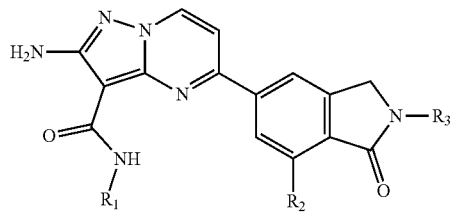

| Compound No. | R₁ | R₂ | R₃ |
|---|---|---|---|
| 103 | 5-(2-(2-hydroxypropan-2-yl)pyridinyl) | MeS(O)₂NH– | 1-cyclopropylethyl |
| 104 | phenyl | MeS(O)₂NH– | 1-cyclopropylethyl |
| 105 | 4-(hydroxymethyl)phenyl | MeS(O)₂NH– | 1-cyclopropylethyl |
| 106 | 1-(2,2,2-trifluoroethyl)-1H-pyrazol-4-yl | MeS(O)₂NH– | 1-cyclopropylethyl |
| 107 | 1,3-dimethyl-1H-pyrazol-4-yl | MeS(O)₂NH– | 1-cyclopropylethyl |
| 108 | 1,5-dimethyl-1H-pyrazol-4-yl | MeS(O)₂NH– | 1-cyclopropylethyl |
| 109 | 1-methyl-1H-1,2,4-triazol-3-yl | MeS(O)₂NH– | 1-cyclopropylethyl |

-continued
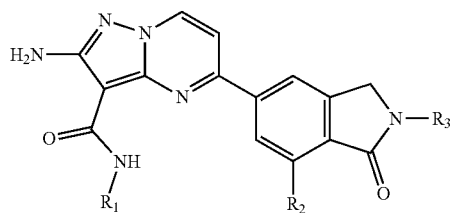
| Compound No. | R₁ | R₂ | R₃ |
|---|---|---|---|
| 110 |  | 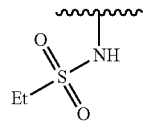 [SMILES: *NS(=O)(=O)CC] | 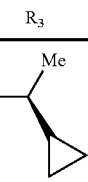 |
| 111 | 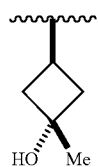 | 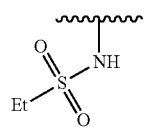 | 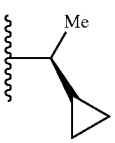 [SMILES: *[C@@H](C)C1CC1] |
| 112 | 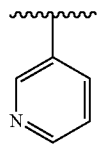 | 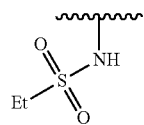 | 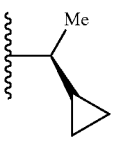 [SMILES: *[C@@H](C)C1CC1] |
| 113 |  | 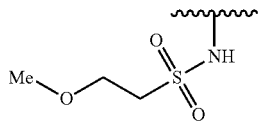 [SMILES: *NS(=O)(=O)CCOC] | 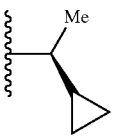 [SMILES: *[C@@H](C)C1CC1] |
| 114 |  | 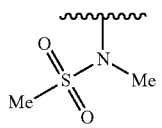 | 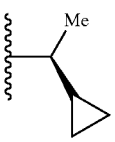 [SMILES: *[C@@H](C)C1CC1] |
| 115 | 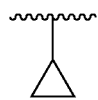 [SMILES: *C1CC1] | 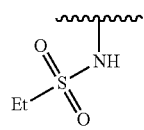 | 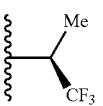 |
| 116 | 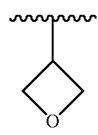 | 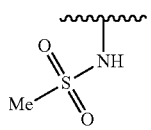 [SMILES: *NS(C)(=O)=O] | 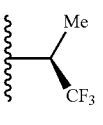 |
| 117 | 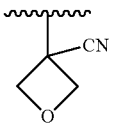 | 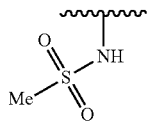 [SMILES: *NS(C)(=O)=O] | 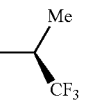 |
| 118 | 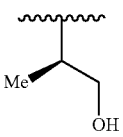 | 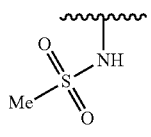 | 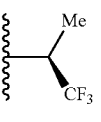 |

-continued
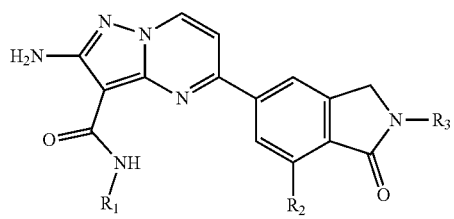
| Compound No. | R₁ | R₂ | R₃ |
|---|---|---|---|
| 119 | -CH(Et)-CH₂OH | -NHS(O)₂Me | -CH(Me)(CF₃) |
| 120 | -CH(cyclopropyl)-CH₂OH | -NHS(O)₂Me | -CH(Me)(CF₃) |
| 121 | trans-3-hydroxycyclobutyl | -NHS(O)₂Me | -CH(Me)(CF₃) |
| 122 | trans-4-hydroxy-4-methylcyclohexyl | -NHS(O)₂Me | -CH(Me)(CF₃) |
| 123 | oxetan-3-yl | -NHS(O)₂Me | -CH(Et)(CF₃) |
| 124 | cyclopropyl | -NHS(O)₂Me | -CH(Et)(CF₃) |
| 125 | 1-methylcyclobutyl | -NHS(O)₂Me | -CH(Et)(CF₃) |
| 126 | trans-3-(2-hydroxypropan-2-yl)cyclobutyl | -NHS(O)₂Me | -CH(Et)(CF₃) |

-continued

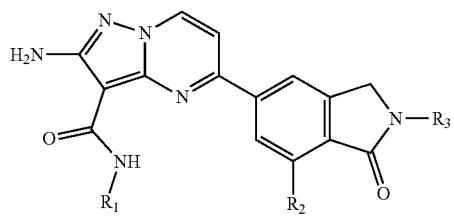

| Compound No. | R₁ | R₂ | R₃ |
|---|---|---|---|
| 127 | trans-4-hydroxy-4-methylcyclohexyl | NHS(O)₂Me | CH(CF₃)Et |
| 128 | cyclopropyl | NHS(O)₂Me | CH(CF₃)(cyclopropyl) |
| 129 | cyclopropyl | NHS(O)₂Me | CH(CF₃)(cyclopropyl) |
| 130 | 1-methylpyrazol-4-yl | S(O)₂Me | CH(Me)(cyclopropyl) |
| 131 | trans-4-hydroxy-4-methylcyclohexyl | S(O)₂Me | CH(Me)(cyclopropyl) |
| 132 | cyclopropyl | S(O)₂Me | CH(Me)(cyclopropyl) |
| 133 | cyclopropyl | S(O)₂CH₂Me | CH(Me)(cyclopropyl) |
| 134 | cyclopropyl | S(O)₂CH(Me)₂ | CH(Me)(cyclopropyl) |

-continued

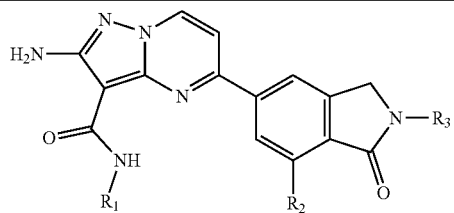

| Compound No. | R₁ | R₂ | R₃ |
|---|---|---|---|
| 135 | cyclopropyl | cyclopropylmethyl-SO₂- | (S)-1-cyclopropylethyl |
| 136 | cyclopropyl | cyclobutyl-SO₂- | (S)-1-cyclopropylethyl |
| 137 | cyclopropyl | cyclopentyl-SO₂- | (S)-1-cyclopropylethyl |
| 138 | cyclopropyl | cyclohexyl-SO₂- | (S)-1-cyclopropylethyl |
| 139 | cyclopropyl | MeNH-SO₂- | 1,1,1-trifluoropropan-2-yl |
| 140 | 1-methyl-1H-pyrazol-4-yl | MeNH-SO₂- | (S)-1-cyclopropylethyl |
| 141 | trans-3-hydroxycyclobutyl | MeNH-SO₂- | (S)-1-cyclopropylethyl |
| 142 | cyclopropyl | MeNH-SO₂- | (S)-1-cyclopropylethyl |

-continued
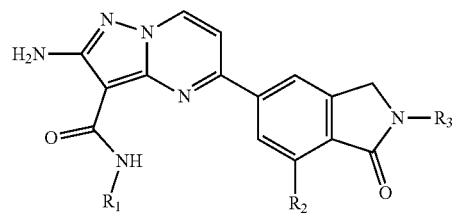
| Compound No. | R₁ | R₂ | R₃ |
|---|---|---|---|
| 143 | 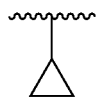 | 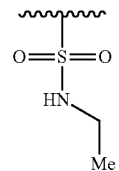 | 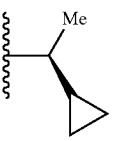 [SMILES: *[C@@H](C)C1CC1] |
| 144 | 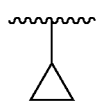 [SMILES: *C1CC1] | 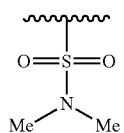 | 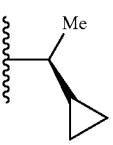 [SMILES: *[C@@H](C)C1CC1] |
| 145 | 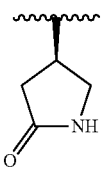 [SMILES: *[C@H]1CNC(=O)C1] | 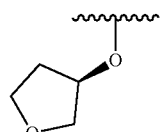 | 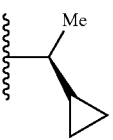 [SMILES: *[C@@H](C)C1CC1] |
| 146 | 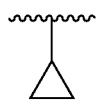 | 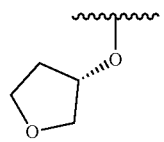 [SMILES: *O[C@H]1CCOC1] | 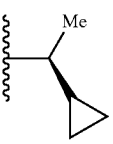 |
| 147 | 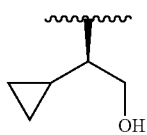 [SMILES: *[C@@H](CO)C1CC1] | 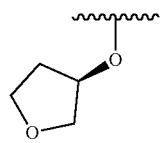 [SMILES: *O[C@@H]1CCOC1] | 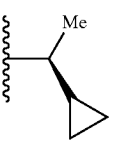 |
| 148 |  | 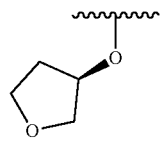 [SMILES: *O[C@@H]1CCOC1] | 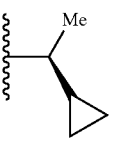 |
| 149 |  | 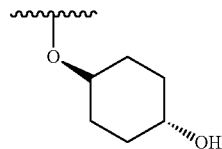 | 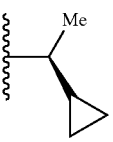 [SMILES: *[C@@H](C)C1CC1] |
| 150 |  | 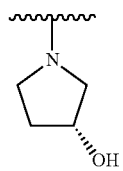 | 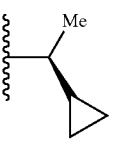 [SMILES: *[C@@H](C)C1CC1] |

-continued

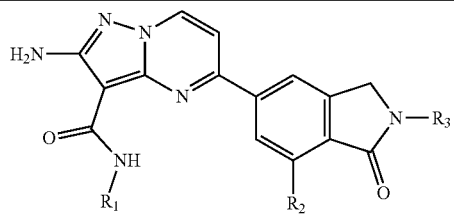

| Compound No. | R₁ | R₂ | R₃ |
|---|---|---|---|
| 151 | 4-hydroxy-4-methylcyclohexyl | 3-hydroxypyrrolidin-1-yl | 1-cyclopropylethyl (Me) |
| 152 | cyclopropyl | 3-hydroxypyrrolidin-1-yl | 1-cyclopropylethyl (Me) |
| 153 | 4-hydroxy-4-(trifluoromethyl)cyclohexyl | 3-hydroxypyrrolidin-1-yl | 1-cyclopropylethyl (Me) |
| 154 | 4-hydroxy-4-methylcyclohexyl | morpholin-4-yl | 1-cyclopropylethyl (Me) |
| 155 | cyclopropyl | 2,2,2-trifluoroethoxy | 1-cyclopropylethyl (Me) |
| 156 | 2-methyl-3-hydroxypropyl | 2,2,2-trifluoroethoxy | 1-cyclopropylethyl (Me) |
| 157 | cyclopropyl | (3,3-difluorocyclobutyl)oxy | 1-cyclopropylethyl (Me) |
| 158 | cyclopropyl | difluoromethoxy | 1-cyclopropylethyl (Me) |

-continued

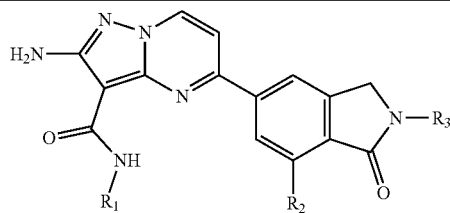

| Compound No. | R₁ | R₂ | R₃ |
|---|---|---|---|
| 159 | cyclopropyl-CH(-)-CH₂OH | OCHF₂ | CH(Me)-cyclopropyl |
| 160 | 4-hydroxy-4-methylcyclohexyl | OCHF₂ | CH(Me)-cyclopropyl |
| 161 | pyridin-3-yl | OCHF₂ | CH(Me)-cyclopropyl |
| 162 | cyclopropyl | Cl | CH(Me)-cyclopropyl |
| 163 | (R)-CH(Me)CH₂OH | Cl | CH(Me)-cyclopropyl |
| 164 | (R)-CH(Me)CH₂OH | Cl | C(Et)(CF₃)H |
| 165 | cyclopropyl | cyclopropyl | CH(Me)-cyclopropyl |
| 166 | (S)-CH(Me)CH₂OH | cyclopropyl | CH(Me)-cyclopropyl |
| 167 | cyclopropyl-CH(-)-CH₂OH | cyclopropyl | CH(Me)-cyclopropyl |

-continued
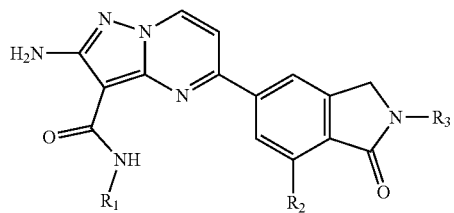
| Compound No. | R₁ | R₂ | R₃ |
|---|---|---|---|
| 168 | 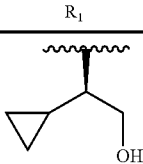 | 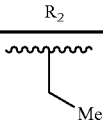 | 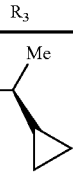 |
| 169 |  | 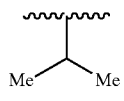 | 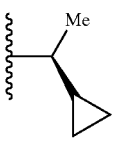 [SMILES: *[C@@H](C)C1CC1] |
| 170 |  | 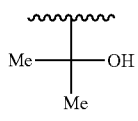 | 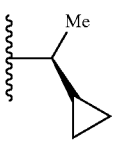 [SMILES: *[C@@H](C)C1CC1] |
| 171 | 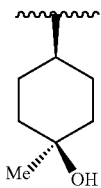 | 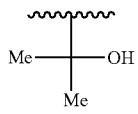 | 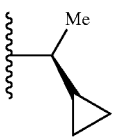 [SMILES: *[C@@H](C)C1CC1] |
| 172 | 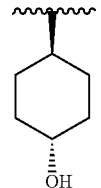 | 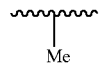 | 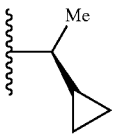 [SMILES: *[C@@H](C)C1CC1] |
| 173 | 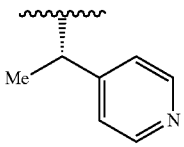 [SMILES: *[C@@H](C)c1ccncc1] | 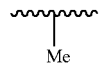 | 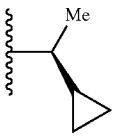 [SMILES: *[C@@H](C)C1CC1] |
| 174 | 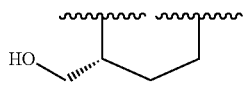 | 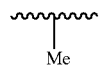 | 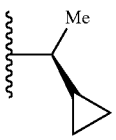 [SMILES: *[C@@H](C)C1CC1] |
| 175 | 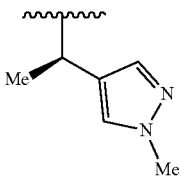 | 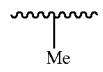 | 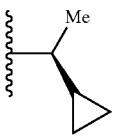 [SMILES: *[C@@H](C)C1CC1] |

-continued

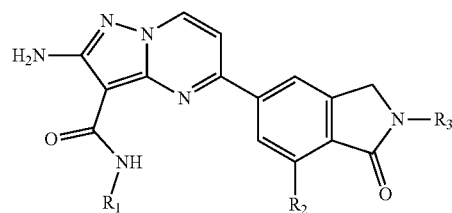

| Compound No. | R₁ | R₂ | R₃ |
|---|---|---|---|
| 176 | tetrahydrofuran-3-yl | Me | 1-cyclopropylethyl (Me) |
| 177 | tetrahydrofuran-3-yl (other stereo) | Me | 1-cyclopropylethyl (Me) |
| 178 | 1-(thiazol-2-yl)ethyl (Me) | Me | 1-cyclopropylethyl (Me) |
| 179 | piperidin-4-yl | Me | 1-cyclopropylethyl (Me) |
| 180 | oxetan-3-yl | Me | 1-cyclopropylethyl (Me) |
| 181 | tetrahydropyran-4-yl | Me | 1-cyclopropylethyl (Me) |
| 182 | 3-methoxycyclobutyl (OMe) | Me | 1-cyclopropylethyl (Me) |
| 183 | 2-(hydroxymethyl)butyl (Me, OH) | Me | 1-cyclopropylethyl (Me) |

-continued

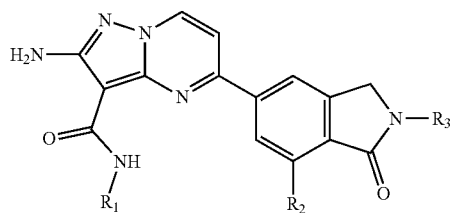

| Compound No. | R₁ | R₂ | R₃ |
|---|---|---|---|
| 184 | 4-aminocyclohexyl | Me | 1-cyclopropylethyl |
| 185 | 3-aminocyclobutyl | Me | 1-cyclopropylethyl |
| 186 | 2-hydroxyethyl-CH₂- (3-hydroxypropyl) | Me | 1-cyclopropylethyl |
| 187 | 4-carboxycyclohexyl | Me | 1-cyclopropylethyl |
| 188 | (1-hydroxycyclopropyl)methyl | Me | 1-cyclopropylethyl |
| 189 | cyclobutyl | Me | 1-cyclopropylethyl |
| 190 | 1-carbamoyl-1-methylethyl (2-methyl-1-amido) | Me | 1-cyclopropylethyl |
| 191 | 2-hydroxymethyl-3-methylbutyl | Me | 1-cyclopropylethyl |

-continued

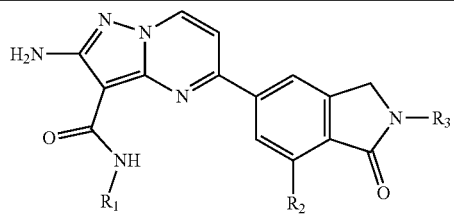

| Compound No. | R₁ | R₂ | R₃ |
|---|---|---|---|
| 192 | [2-phenyl-2-(hydroxymethyl)ethyl] | Me | [(S)-1-cyclopropylethyl] |
| 193 | [trans-4-carboxycyclohexyl] | Me | [(S)-1-cyclopropylethyl] |
| 194 | [1-acetylazetidin-3-yl] | Me | [(S)-1-cyclopropylethyl] |
| 195 | [2-cyclopropyl-2-(hydroxymethyl)ethyl] | Me | [(S)-1-cyclopropylethyl] |
| 196 | [cis-3-hydroxy-3-methylcyclobutyl] | Me | [(S)-1-cyclopropylethyl] |
| 197 | [cis-3-hydroxycyclopentyl] | Me | [(S)-1-cyclopropylethyl] |
| 198 | [(1S,2R)-2-hydroxy-2,3-dihydro-1H-inden-1-yl] | Me | [(S)-1-cyclopropylethyl] |
| 199 | [(3R,4R)-4-hydroxytetrahydrofuran-3-yl] | Me | [(S)-1-cyclopropylethyl] |

-continued

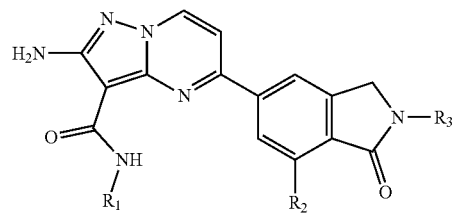

| Compound No. | R₁ | R₂ | R₃ |
|---|---|---|---|
| 200 | (R)-1-(tetrahydro-2H-pyran-4-yl)ethyl | Me | (S)-1-cyclopropylethyl |
| 201 | pyridin-4-ylmethyl | Me | (S)-1-cyclopropylethyl |
| 202 | (S)-5-oxopyrrolidin-3-yl | Me | (S)-1-cyclopropylethyl |
| 203 | 2-hydroxy-2-methylpropyl | Me | (S)-1-cyclopropylethyl |
| 204 | cis-3-hydroxycyclobutyl | Me | (S)-1-cyclopropylethyl |
| 205 | trans-4-hydroxycyclohexyl | Me | (S)-1-cyclopropylethyl |
| 206 | (S)-3-hydroxy-2-methylpropyl | Me | (S)-1-cyclopropylethyl |
| 207 | (1-methyl-1H-pyrazol-3-yl)methyl | Me | (S)-1-cyclopropylethyl |

-continued

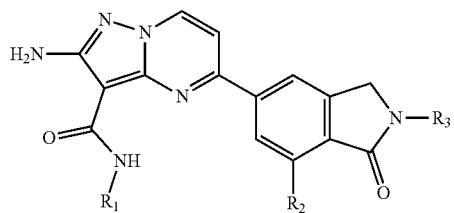

| Compound No. | R₁ | R₂ | R₃ |
|---|---|---|---|
| 208 | cyclopropyl | Me | CH(Me)(cyclopropyl) |
| 209 | 1-methylpiperidin-4-yl | Me | CH(Me)(cyclopropyl) |
| 210 | (1S,2R)-2-hydroxycyclopentyl | Me | CH(Me)(cyclopropyl) |
| 211 | (1S,2R)-2-hydroxycyclobutyl | Me | CH(Me)(cyclopropyl) |
| 212 | (1R)-1-(pyridin-3-yl)ethyl | Me | CH(Me)(cyclopropyl) |
| 213 | cyclopropylmethyl (CH₂-cyclopropyl) | Me | CH(Me)(cyclopropyl) |
| 214 | (1-methyl-1H-pyrazol-4-yl)methyl | Me | CH(Me)(cyclopropyl) |
| 215 | (trans-3-hydroxycyclobutyl)methyl | Me | CH(Me)(cyclopropyl) |

-continued
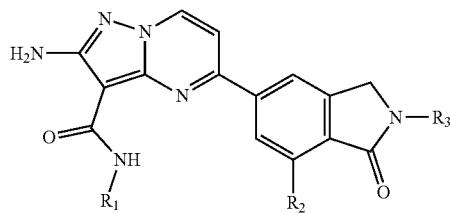
| Compound No. | R₁ | R₂ | R₃ |
|---|---|---|---|
| 216 | 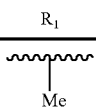 | 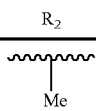 | 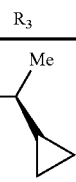 |
| 217 | 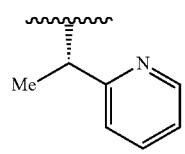 |  | 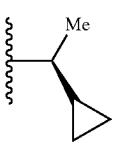 [SMILES: *[C@@H](C)C1CC1] |
| 218 | 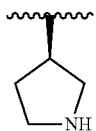 |  | 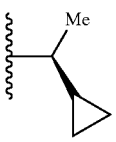 [SMILES: *[C@@H](C)C1CC1] |
| 219 | 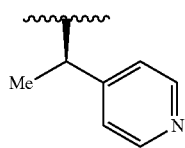 |  | 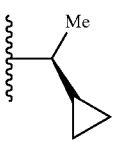 [SMILES: *[C@@H](C)C1CC1] |
| 220 | 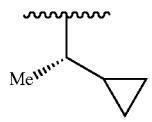 |  | 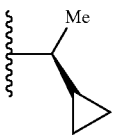 [SMILES: *[C@@H](C)C1CC1] |
| 221 | 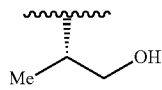 |  | 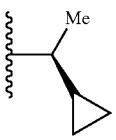 [SMILES: *[C@@H](C)C1CC1] |
| 222 | 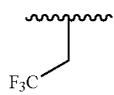 |  | 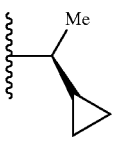 [SMILES: *[C@@H](C)C1CC1] |
| 223 | 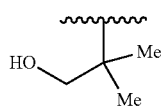 |  | 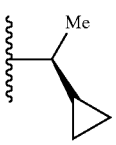 [SMILES: *[C@@H](C)C1CC1] |
| 224 | 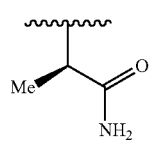 |  | 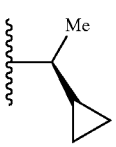 [SMILES: *[C@@H](C)C1CC1] |

-continued
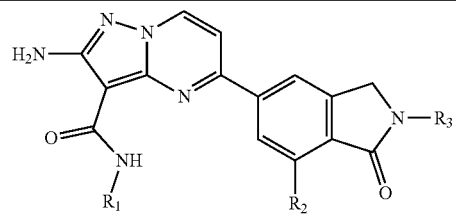
| Compound No. | R₁ | R₂ | R₃ |
|---|---|---|---|
| 225 | 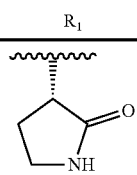 |  Me |  Me |
| 226 | 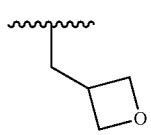 |  Me | 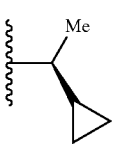 [SMILES: *[C@@H](C)C1CC1] Me |
| 227 | 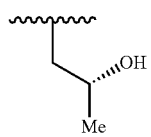 |  Me | 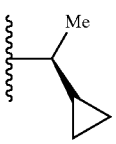 [SMILES: *[C@@H](C)C1CC1] Me |
| 228 | 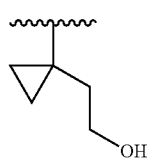 [SMILES: *C1(CCO)CC1] |  Me | 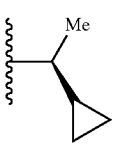 [SMILES: *[C@@H](C)C1CC1] Me |
| 229 | 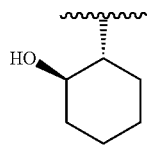 |  Me | 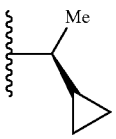 [SMILES: *[C@@H](C)C1CC1] Me |
| 230 | 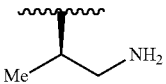 |  Me | 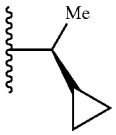 [SMILES: *[C@@H](C)C1CC1] Me |
| 231 | 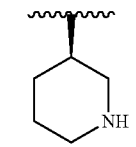 |  Me | 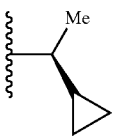 [SMILES: *[C@@H](C)C1CC1] Me |
| 232 | 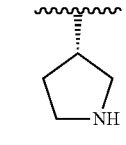 |  Me | 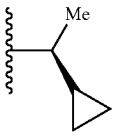 [SMILES: *[C@@H](C)C1CC1] Me |
| 233 | 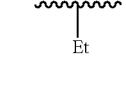 Et |  Me | 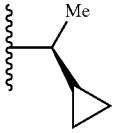 [SMILES: *[C@@H](C)C1CC1] Me |

-continued

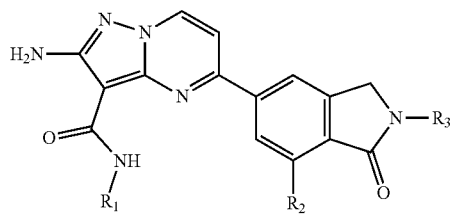

| Compound No. | R₁ | R₂ | R₃ |
|---|---|---|---|
| 234 | (S)-2-hydroxypropyl (CH₂-CH(OH)-Me) | Me | CH(Me)(cyclopropyl) |
| 235 | (R)-1-(1-methyl-1H-pyrazol-4-yl)ethyl | Me | CH(Me)(cyclopropyl) |
| 236 | -CH₂-C(O)NH₂ | Me | CH(Me)(cyclopropyl) |
| 237 | -CH(Me)-C(Me)₂-CH₂OH | Me | CH(Me)(cyclopropyl) |
| 238 | (tetrahydrofuran-3-yl)methyl | Me | CH(Me)(cyclopropyl) |
| 239 | (1R,3S)-3-hydroxycyclopentyl | Me | CH(Me)(cyclopropyl) |
| 240 | (1S,2R)-2-hydroxy-2,3-dihydro-1H-inden-1-yl | Me | CH(Me)(cyclopropyl) |
| 241 | 1,1-dioxidothietan-3-yl | Me | CH(Me)(cyclopropyl) |

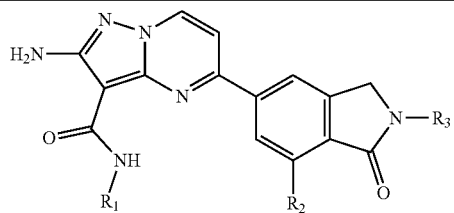

| Compound No. | R₁ | R₂ | R₃ |
|---|---|---|---|
| 242 | 1-methylcyclopropyl | Me | (S)-1-cyclopropylethyl |
| 243 | (R)-piperidin-3-yl | Me | (S)-1-cyclopropylethyl |
| 244 | (1S,3R)-3-hydroxycyclohexyl | Me | (S)-1-cyclopropylethyl |
| 245 | (R)-2-amino-2-oxo-1-phenylethyl | Me | (S)-1-cyclopropylethyl |
| 246 | 1-(hydroxymethyl)cyclopropyl | Me | (S)-1-cyclopropylethyl |
| 247 | 1-carbamoylcyclopropyl | Me | (S)-1-cyclopropylethyl |
| 248 | 2-methyl-2-(pyridin-4-yl)propyl | Me | (S)-1-cyclopropylethyl |
| 249 | (2,2-dimethylcyclopropyl)methyl | Me | (S)-1-cyclopropylethyl |
| 250 | (1-(hydroxymethyl)cyclopropyl)methyl | Me | (S)-1-cyclopropylethyl |

-continued

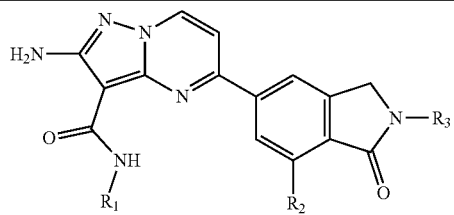

| Compound No. | R₁ | R₂ | R₃ |
|---|---|---|---|
| 251 | cyclopentane with OH | Me | CH(Me)(cyclopropyl) |
| 252 | CH(Me)₂ | Me | CH(Me)(cyclopropyl) |
| 253 | C(cyclopropyl)(Me)(OH) | Me | CH(Me)(cyclopropyl) |
| 254 | trans-2-hydroxycyclohexyl | Me | CH(Me)(cyclopropyl) |
| 255 | 1-cyanocyclobutyl | Me | CH(Me)(cyclopropyl) |
| 256 | CH₂-(1-cyanocyclopropyl) | Me | CH(Me)(cyclopropyl) |
| 257 | CH₂-(tetrahydrofuran-3-yl) | Me | CH(Me)(cyclopropyl) |
| 258 | 3,3-difluorocyclobutyl | Me | CH(Me)(cyclopropyl) |
| 259 | isochroman-4-yl | Me | CH(Me)(cyclopropyl) |

-continued
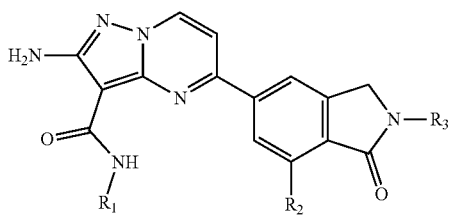
| Compound No. | R₁ | R₂ | R₃ |
|---|---|---|---|
| 260 | 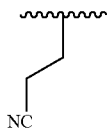 |  Me | 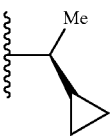 [SMILES: *[C@@H](C)C1CC1] Me |
| 261 | 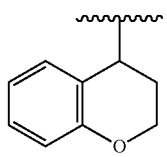 |  Me | 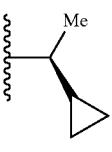 [SMILES: *[C@@H](C)C1CC1] Me |
| 262 | 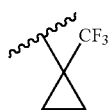 |  Me | 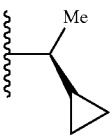 [SMILES: *[C@@H](C)C1CC1] Me |
| 263 | 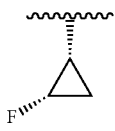 |  Me | 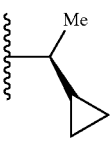 [SMILES: *[C@@H](C)C1CC1] Me |
| 264 | 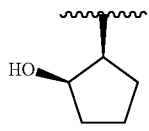 |  Me | 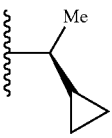 Me |
| 265 | 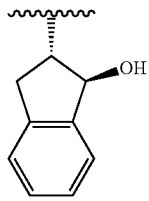 |  Me | 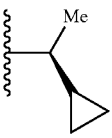 [SMILES: *[C@@H](C)C1CC1] Me |
| 266 | 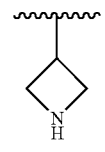 |  Me | 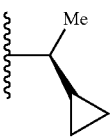 [SMILES: *[C@@H](C)C1CC1] Me |
| 267 | 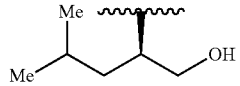 |  Me | 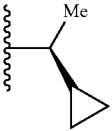 [SMILES: *[C@@H](C)C1CC1] Me |

-continued
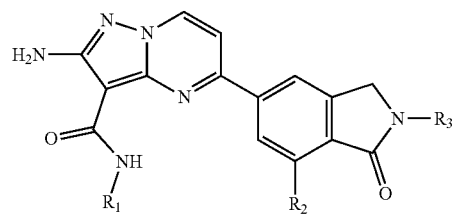
| Compound No. | R₁ | R₂ | R₃ |
|---|---|---|---|
| 268 | 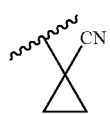 |  Me | 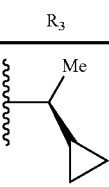 Me |
| 269 | 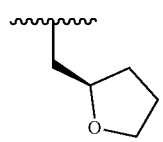 |  Me | 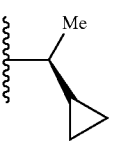 [SMILES: *[C@@H](C)C1CC1] Me |
| 270 | 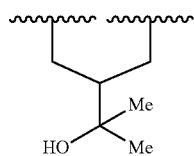 |  Me | 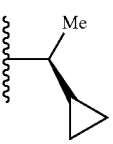 [SMILES: *[C@@H](C)C1CC1] Me |
| 271 | 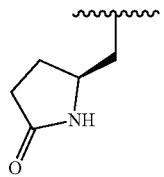 |  Me | 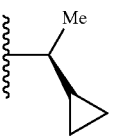 [SMILES: *[C@@H](C)C1CC1] Me |
| 272 | 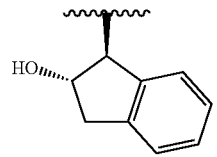 |  Me | 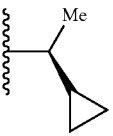 [SMILES: *[C@@H](C)C1CC1] Me |
| 273 | 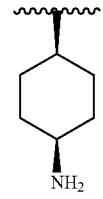 |  Me | 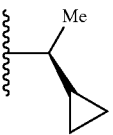 [SMILES: *[C@@H](C)C1CC1] Me |
| 274 | 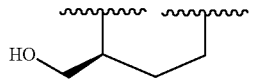 |  Me | 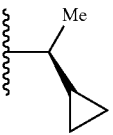 [SMILES: *[C@@H](C)C1CC1] Me |
| 275 | 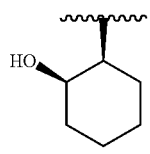 |  Me | 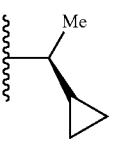 [SMILES: *[C@@H](C)C1CC1] Me |

-continued
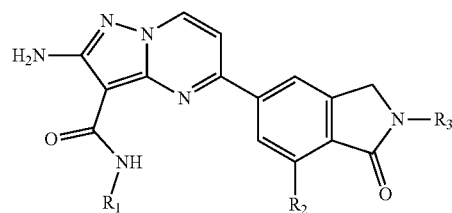
| Compound No. | R₁ | R₂ | R₃ |
|---|---|---|---|
| 276 | 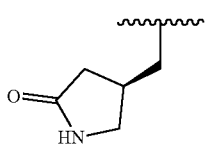 | 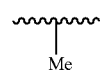 Me | 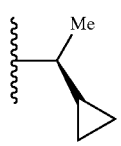 [SMILES: *[C@@H](C)C1CC1] Me |
| 277 | 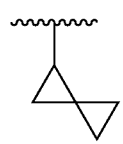 | 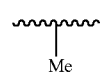 Me | 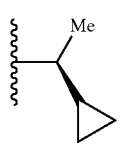 [SMILES: *[C@@H](C)C1CC1] Me |
| 278 | 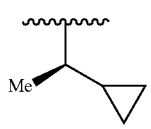 | 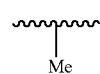 Me | 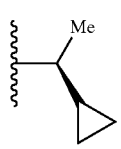 [SMILES: *[C@@H](C)C1CC1] Me |
| 279 | 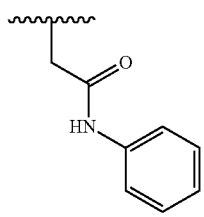 | 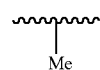 Me | 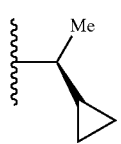 [SMILES: *[C@@H](C)C1CC1] Me |
| 280 | 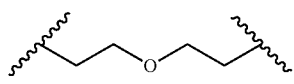 [SMILES: *CCOCC*] | 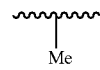 Me | 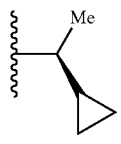 Me |
| 281 | 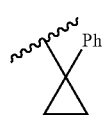 | 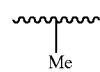 Me | 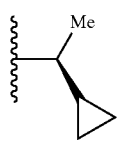 Me |
| 282 | 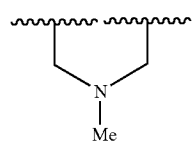 [SMILES: *CN(C)C*] | 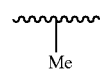 Me | 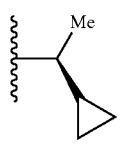 Me |
| 283 | 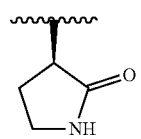 | 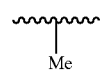 Me | 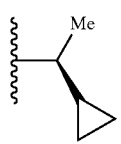 Me |

-continued
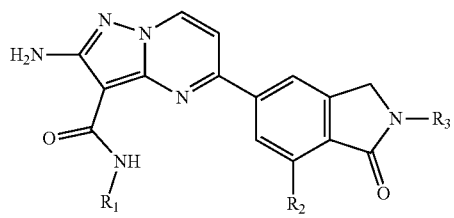
| Compound No. | R₁ | R₂ | R₃ |
| --- | --- | --- | --- |
| 284 | 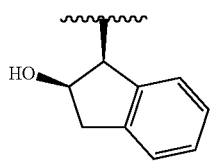 [SMILES: *[C@H]1c2ccccc2C[C@H]1O] |  Me | 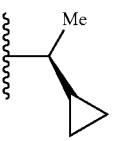 |
| 285 | 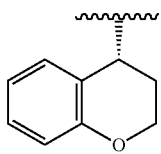 [SMILES: *[C@@H]1CCOc2ccccc21] |  Me | 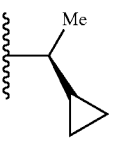 |
| 286 | 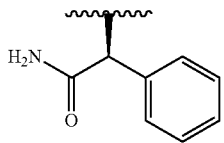 [SMILES: *[C@H](C(N)=O)c1ccccc1] |  Me | 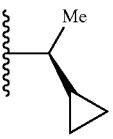 |
| 287 | 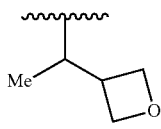 |  Me | 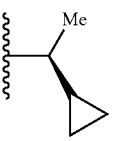 |
| 288 | 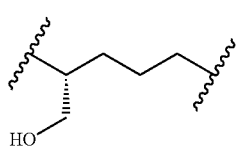 [SMILES: *CCC[C@@H](*)CO] |  Me | 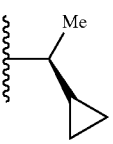 |
| 289 | 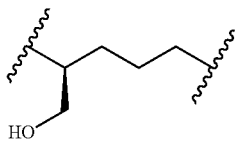 [SMILES: *CCC[C@H](*)CO] |  Me | 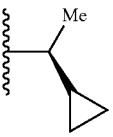 [SMILES: *[C@@H](C)C1CC1] |
| 290 | 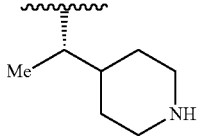 |  Me | 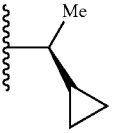 [SMILES: *[C@@H](C)C1CC1] |
| 291 | 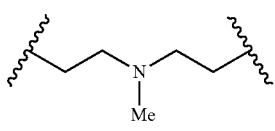 |  Me | 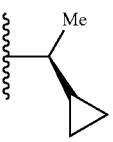 |

-continued
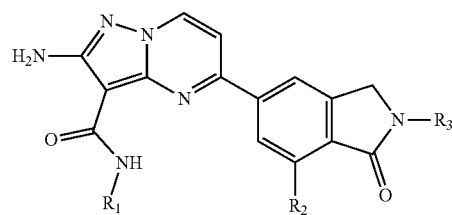
| Compound No. | R₁ | R₂ | R₃ |
|---|---|---|---|
| 292 | 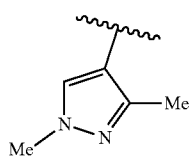 |  Me | 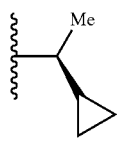 [SMILES: *[C@@H](C)C1CC1] |
| 293 | 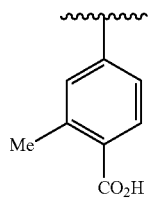 |  Me | 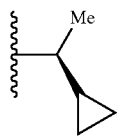 |
| 294 | 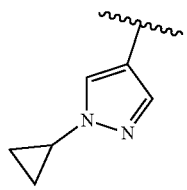 [SMILES: *c1cnn(C2CC2)c1] |  Me | 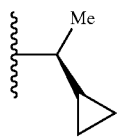 |
| 295 | 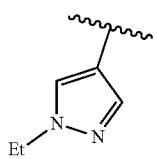 |  Me | 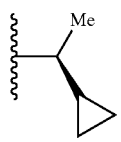 [SMILES: *[C@@H](C)C1CC1] |
| 296 | 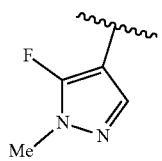 [SMILES: *c1cnn(C)c1F] |  Me | 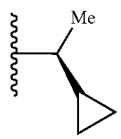 [SMILES: *[C@@H](C)C1CC1] |
| 297 | 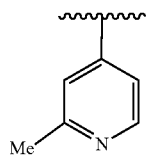 [SMILES: *c1ccnc(C)c1] |  Me | 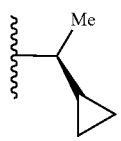 [SMILES: *[C@@H](C)C1CC1] |
| 298 | 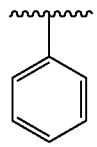 |  Me | 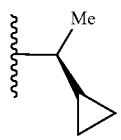 [SMILES: *[C@@H](C)C1CC1] |

-continued
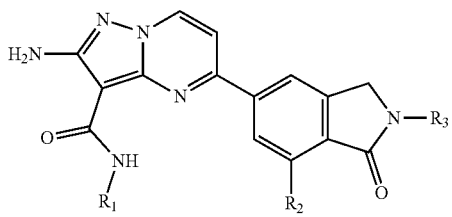
| Compound No. | R₁ | R₂ | R₃ |
|---|---|---|---|
| 299 | 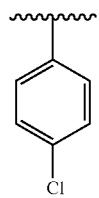 |  Me | 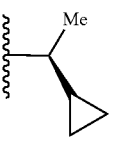 [SMILES: *[C@@H](C)C1CC1] |
| 300 | 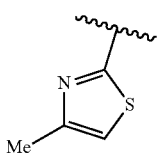 |  Me | 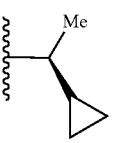 [SMILES: *[C@@H](C)C1CC1] |
| 301 |  |  Me | 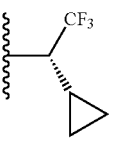 |
| 302 |  |  Me | 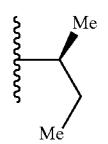 [SMILES: *[C@@H](C)CC] |
| 303 |  |  Me | 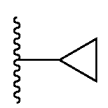 |
| 304 |  |  Me | 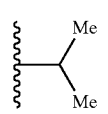 |
| 305 |  |  Me | 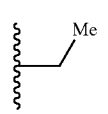 |
| 306 |  |  Me | 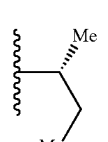 |
| 307 |  |  Me | 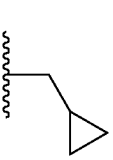 |

-continued
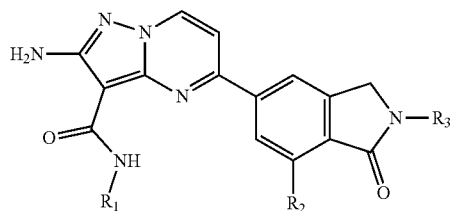
| Compound No. | R₁ | R₂ | R₃ |
|---|---|---|---|
| 308 |  |  Me | 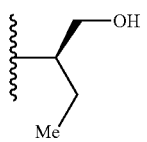 [SMILES: *[C@H](CC)CO] |
| 309 |  |  Me | 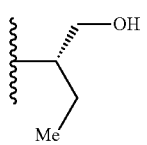 [SMILES: *[C@@H](CC)CO] |
| 310 |  |  Me | 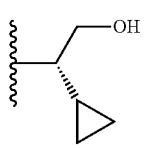 |
| 311 |  |  Me | 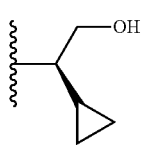 [SMILES: *[C@@H](CO)C1CC1] |
| 312 | 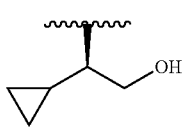 [SMILES: *[C@@H](CO)C1CC1] |  Me | 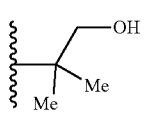 |
| 313 | 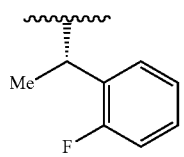 [SMILES: *[C@@H](C)c1ccccc1F] |  Me | 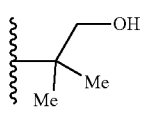 |
| 314 | 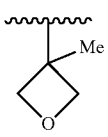 [SMILES: *C1(C)COC1] |  Me | 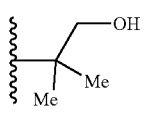 |
| 315 | 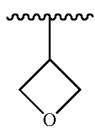 [SMILES: *C1COC1] |  Me | 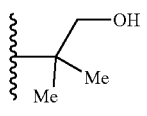 |
| 316 | 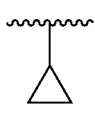 [SMILES: *C1CC1] |  Me | 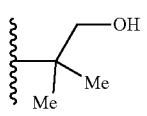 |

-continued

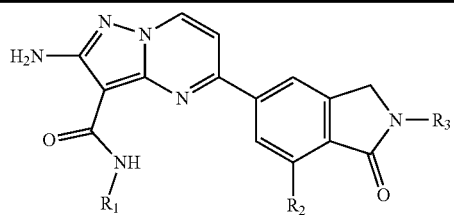

| Compound No. | R₁ | R₂ | R₃ |
|---|---|---|---|
| 317 | (S)-1-(2-fluorophenyl)ethyl | Me | -CH₂-C(Me)₂-OH |
| 318 | 3-methyloxetan-3-yl | Me | -CH₂-C(Me)₂-OH |
| 319 | cyclopropyl | Me | -CH₂-C(Me)₂-OH |
| 320 | oxetan-3-yl | Me | -CH₂-C(Me)₂-OH |
| 321 | (S)-2-cyclopropyl-2-hydroxyethyl | Me | -CH₂-C(Me)₂-OH |
| 322 | cyclopropyl | Me | (1S,3R)-3-hydroxycyclopentyl |
| 323 | cyclopropyl | Me | (1R,3S)-3-hydroxycyclopentyl |
| 324 | cyclopropyl | Me | (1S,3R)-3-hydroxycyclohexyl |
| 325 | (S)-2-hydroxy-1-methylethyl | Me | (1S,3R)-3-hydroxycyclohexyl |
| 326 | (R)-2-hydroxy-1-methylethyl | Me | (1R,3S)-3-hydroxycyclohexyl |

-continued
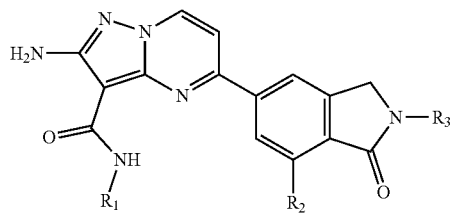
| Compound No. | R₁ | R₂ | R₃ |
|---|---|---|---|
| 327 | cyclopropyl | Me | (1S,3R)-3-hydroxycyclohexyl |
| 328 | cyclopropyl | Me | (1R,3S)-3-hydroxycyclohexyl |
| 329 | (S)-2-methyl-3-hydroxypropyl | Me | (1S,3R)-3-hydroxycyclohexyl |
| 330 | (S)-2-methyl-3-hydroxypropyl | Me | (S)-1-(pyridin-4-yl)ethyl |
| 331 | cyclopropyl | Me | (S)-1-(pyridin-4-yl)ethyl |
| 332 | (S)-2-methyl-3-hydroxypropyl | Me | (S)-1-(pyridin-3-yl)ethyl |
| 333 | cyclopropyl | Me | (S)-1-(pyridin-3-yl)ethyl |
| 334 | 1-acetylazetidin-3-yl | CF₃ | (S)-1-cyclopropylethyl |

-continued

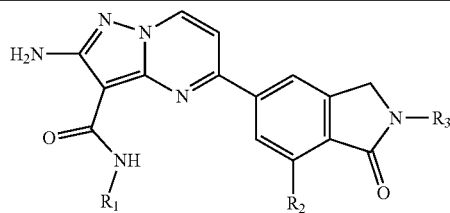

| Compound No. | R₁ | R₂ | R₃ |
|---|---|---|---|
| 335 | ~~~ C(Me)₂CH₂OH | ~~~ CF₃ | ~~~ CH(Me)(cyclopropyl) |
| 336 | ~~~ (CH₂)₄SO₂Me | ~~~ CF₃ | ~~~ CH(Me)(cyclopropyl) |
| 337 | ~~~ (CH₂)₃SO₂Me | ~~~ CF₃ | ~~~ CH(Me)(cyclopropyl) |
| 338 | ~~~ 3-(hydroxymethyl)oxetan-3-yl | ~~~ CF₃ | ~~~ CH(Me)(cyclopropyl) |
| 339 | ~~~ CH(Me)CH₂OMe | ~~~ CF₃ | ~~~ CH(Me)(cyclopropyl) |
| 340 | ~~~ cyclopropyl | ~~~ CF₃ | ~~~ CH(CH₂OH)(cyclopropyl) |
| 341 | ~~~ (CH₂)₃CH(Me)OH | ~~~ CF₃ | ~~~ CH(Me)(cyclopropyl) |
| 342 | ~~~ 1-(hydroxymethyl)cyclopropyl | ~~~ CF₃ | ~~~ CH(Me)(cyclopropyl) |
| 343 | ~~~ CH(Me)CH₂Me | ~~~ CF₃ | ~~~ CH(Me)(cyclopropyl) |

-continued
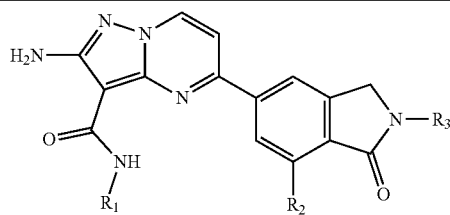
| Compound No. | R₁ | R₂ | R₃ |
|---|---|---|---|
| 344 | CH₂-CH(OH)-CH₂OH (2S) | CF₃ | (S)-CH(Me)-cyclopropyl |
| 345 | 4-(HO,CF₃)-cyclohexyl | CF₃ | (S)-CH(Me)-cyclopropyl |
| 346 | CH₂CH₂-CH(Me)(OH) (R) | CF₃ | (S)-CH(Me)-cyclopropyl |
| 347 | tetrahydrothiopyran-4-yl 1,1-dioxide | CF₃ | (S)-CH(Me)-cyclopropyl |
| 348 | CH₂-CH(OH)-CH₂OH (2R) | CF₃ | (S)-CH(Me)-cyclopropyl |
| 349 | cyclopropyl | CF₃ | (S)-CH(Me)-cyclopropyl |
| 350 | 2-cyano-pyridin-4-yl | CF₃ | (S)-CH(Me)-cyclopropyl |
| 351 | 5-fluoro-pyridin-3-yl | CF₃ | (S)-CH(Me)-cyclopropyl |

-continued

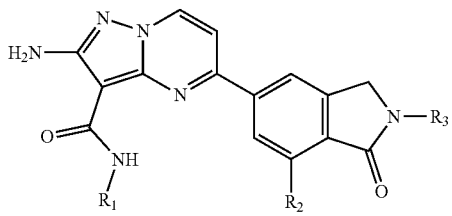

| Compound No. | R₁ | R₂ | R₃ |
|---|---|---|---|
| 352 | CH₂CH₂NHSO₂Me | CF₃ | CH(Me)(cyclopropyl) |
| 353 | CH(cyclopropyl)CH₂OH | CF₃ | CH(Me)(cyclopropyl) |
| 354 | 6-(CF₃CH₂)pyridin-3-yl | CF₃ | CH(Me)(cyclopropyl) |
| 355 | 5-methoxypyridin-3-yl | CF₃ | CH(Me)(cyclopropyl) |
| 356 | piperidin-3-yl | CF₃ | CH(Me)(cyclopropyl) |
| 357 | trans-3-hydroxypyrrolidin-4-yl | CF₃ | CH(Me)(cyclopropyl) |
| 358 | trans-3-aminocyclohexyl | CF₃ | CH(Me)(cyclopropyl) |
| 359 | cis-3-hydroxypyrrolidin-4-yl | CF₃ | CH(Me)(cyclopropyl) |

-continued
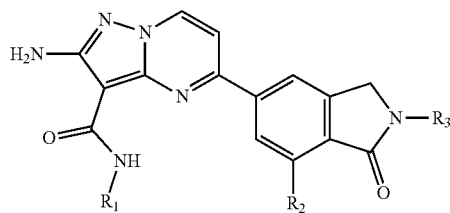
| Compound No. | R₁ | R₂ | R₃ |
|---|---|---|---|
| 360 | 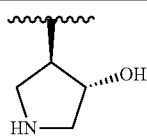 |  | 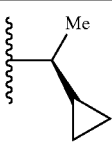 |
| 361 | 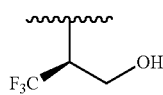 |  | 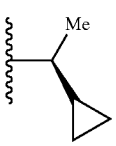 |
| 362 | 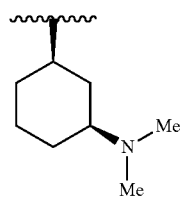 |  | 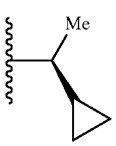 |
| 363 | 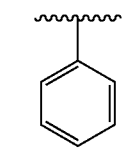 |  | 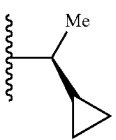 [SMILES: *[C@@H](C)C1CC1] |
| 364 | 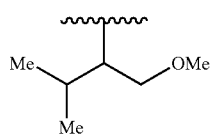 |  | 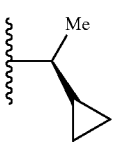 [SMILES: *[C@@H](C)C1CC1] |
| 365 | 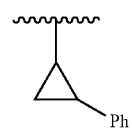 |  | 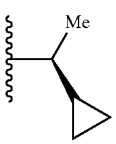 [SMILES: *[C@@H](C)C1CC1] |
| 366 | 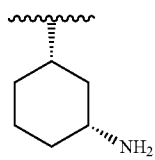 |  | 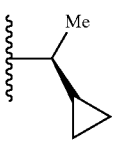 [SMILES: *[C@@H](C)C1CC1] |
| 367 | 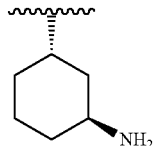 |  | 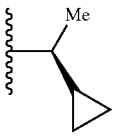 [SMILES: *[C@@H](C)C1CC1] |

-continued

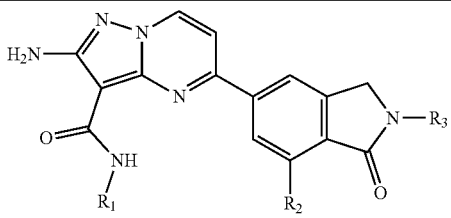

| Compound No. | R₁ | R₂ | R₃ |
|---|---|---|---|
| 368 | cyclohexyl-NH₂ | CF₃ | CH(Me)-cyclopropyl |
| 369 | CH(Me)CH₂OH | F | CH(Me)-cyclopropyl |
| 370 | cyclopropyl | F | CH(Me)-cyclopropyl |
| 371 | +get.2000 | +get.2001 | +get.2002 |
| 372 | +get.2003 | +get.2004 | +get.2005 |
| 373 | +get.2006 | +get.2007 | +get.2008 |
| 374 | +get.2009 | +get.2010 | +get.2011 |
| 375 | +get.2012 | +get.2013 | +get.2014 |
| 376 | +get.2015 | +get.2016 | +get.2017 |
| 377 | +get.2018 | +get.2019 | +get.2020 |
| 378 | +get.2021 | +get.2022 | +get.2023 |
| 379 | +get.2024 | +get.2025 | +get.2026 |
| 380 | +get.2027 | +get.2028 | +get.2029 |
| 381 | +get.2030 | +get.2031 | +get.2032 |
| 382 | +get.2033 | +get.2034 | +get.2035 |
| 383 | +get.2036 | +get.2037 | +get.2038 |
| 384 | +get.2039 | +get.2040 | +get.2041 |
| 385 | +get.2042 | +get.2043 | +get.2044 |
| 386 | +get.2045 | +get.2046 | +get.2047 |
| 387 | +get.2048 | +get.2049 | +get.2050 |
| 388 | +get.2051 | +get.2052 | +get.2053 |
| 389 | +get.2054 | +get.2055 | +get.2056 |
| 390 | +get.2057 | +get.2058 | +get.2059 |
| 391 | +get.2060 | +get.2061 | +get.2062 |

-continued

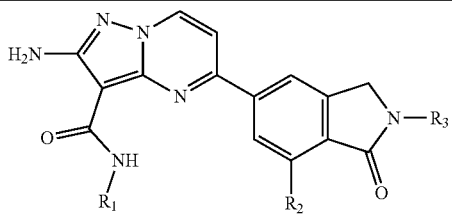

| Compound No. | R₁ | R₂ | R₃ |
|---|---|---|---|
| 392 | +get.2063 | +get.2064 | +get.2065 |
| 393 | +get.2066 | +get.2067 | +get.2068 |
| 394 | +get.2069 | +get.2070 | +get.2071 |
| 395 | +get.2072 | +get.2073 | +get.2074 |
| 396 | +get.2075 | +get.2076 | +get.2077 |
| 397 | +get.2078 | +get.2079 | +get.2080 |
| 398 | +get.2081 | +get.2082 | +get.2083 |
| 399 | +get.2084 | +get.2085 | +get.2086 |
| 400 | +get.2087 | +get.2088 | +get.2089 |
| 401 | +get.2090 | +get.2091 | +get.2092 |
| 402 | +get.2093 | +get.2094 | +get.2095 |
| 403 | +get.2096 | +get.2097 | +get.2098 |
| 408 | +get.2099 | Me-S(O)₂-N(Me)- | 1-methyl-cyclopropyl |
| 409 | cyclopropyl | morpholine-N-S(O)₂-NH- | 1-methyl-cyclopropyl |
| 410 | cyclopropyl | (Me)₂N-S(O)₂-NH- | 1-methyl-cyclopropyl |
| 411 | 4-CO₂H-cyclohexyl | OCF₃ | 1-methyl-cyclopropyl |
| 412 | 2-oxopiperidin-4-yl | OCF₃ | 1-methyl-cyclopropyl |

-continued

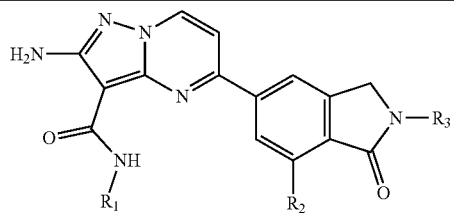

| Compound No. | R₁ | R₂ | R₃ |
|---|---|---|---|
| 413 | 5-oxopiperidin-3-yl | OCF₃ | (S)-1-cyclopropylethyl (Me wedge) |
| 414 | pyridin-3-ylmethyl | OCF₃ | 1-cyclopropylethyl |
| 415 | cyclopropyl | OCF₃ | 1-cyclopropyl-2,2,2-trifluoroethyl (CF₃, Me dashed) |
| 416 | cyclopropyl | OCF₃ | 2-cyclopropyl-2-(hydroxymethyl)ethyl |
| 417 | (3,4-trans)-4-hydroxypyrrolidin-3-yl | OCF₃ | 1-cyclopropylethyl |
| 418 | (3,4-cis)-4-hydroxypyrrolidin-3-yl | OCF₃ | 1-cyclopropylethyl |
| 419 | 4-(2-hydroxypropan-2-yl)phenyl | OCF₃ | 1-cyclopropylethyl |
| 420 | 3-(2-hydroxypropan-2-yl)phenyl | OCF₃ | 1-cyclopropylethyl |

-continued
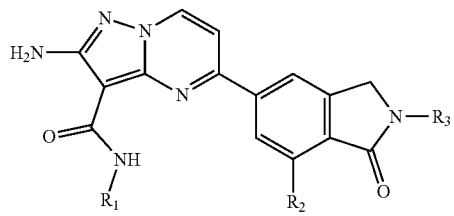
| Compound No. | R₁ | R₂ | R₃ |
|---|---|---|---|
| 421 | 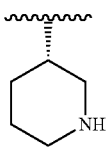 |  OCF₃ | 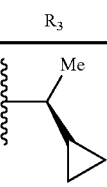 |
| 422 | 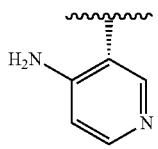 |  OCF₃ | 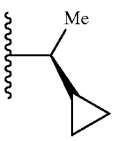 [SMILES: *[C@@H](C)C1CC1] |
| 423 | 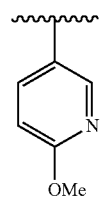 |  OCF₃ | 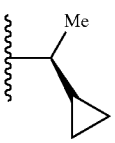 [SMILES: *[C@@H](C)C1CC1] |
| 424 | 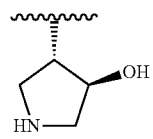 |  OCF₃ | 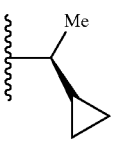 [SMILES: *[C@@H](C)C1CC1] |
| 425 | 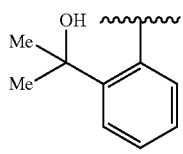 |  OCF₃ | 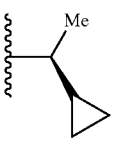 [SMILES: *[C@@H](C)C1CC1] |
| 426 | 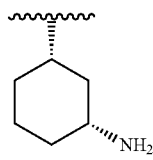 |  OCF₃ | 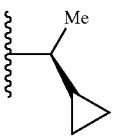 [SMILES: *[C@@H](C)C1CC1] |
| 427 | 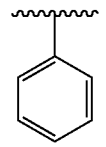 |  OCF₃ | 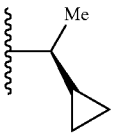 [SMILES: *[C@@H](C)C1CC1] |
| 428 | 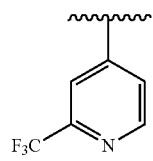 |  OCF₃ | 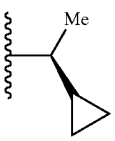 [SMILES: *[C@@H](C)C1CC1] |

-continued

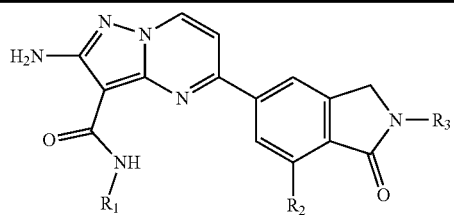

| Compound No. | R₁ | R₂ | R₃ |
|---|---|---|---|
| 429 | 1,3-dimethyl-1H-pyrazol-4-yl | -OCHF₂ | (S)-1-cyclopropylethyl |
| 430 | trans-3-hydroxy-3-methylcyclobutyl | -OCHF₂ | (S)-1-cyclopropylethyl |
| 431 | cyclopropyl | (S)-3-hydroxypyrrolidin-1-yl | (S)-1,1,1-trifluoropropan-2-yl |
| 432 | trans-3-hydroxy-3-methylcyclobutyl | (S)-3-hydroxypyrrolidin-1-yl | (S)-1-cyclopropylethyl |
| 433 | cyclopropyl | 3-hydroxyazetidin-1-yl | (S)-1-cyclopropylethyl |
| 434 | (S)-2-cyclopropyl-1-hydroxyethyl (via CH) | (S)-3-hydroxypyrrolidin-1-yl | (S)-1,1,1-trifluoropropan-2-yl |
| 435 | (S)-1-hydroxy-2-methylpropyl (via CH) | 3,3-difluoroazetidin-1-yl | (S)-1-cyclopropylethyl |
| 436 | cyclopropyl | 3,3-difluoroazetidin-1-yl | (S)-1-cyclopropylethyl |

-continued

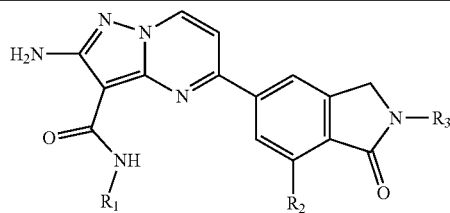

| Compound No. | R₁ | R₂ | R₃ |
|---|---|---|---|
| 437 | 4-hydroxy-4-methylcyclohexyl | 4-methylpiperazin-1-yl | (S)-1-cyclopropylethyl |
| 438 | pyridin-3-yl | (R)-3-hydroxypyrrolidin-1-yl | (S)-1-cyclopropylethyl |
| 439 | (S)-2-methyl-3-hydroxypropyl | 3,3-difluorocyclobutoxy | (S)-1-cyclopropylethyl |
| 440 | (S)-2-methyl-3-hydroxypropyl | (S)-1,1,1-trifluoropropan-2-yloxy | (S)-1-cyclopropylethyl |
| 441 | (S)-2-oxopyrrolidin-3-yl | (S)-tetrahydrofuran-3-yloxy | (S)-1-cyclopropylethyl |
| 442 | cyclopropyl | (S)-1-cyclopropylethyl | (S)-1,1,1-trifluoropropan-2-yloxy |
| 443 | (S)-5-oxopyrrolidin-3-yl | (S)-tetrahydrofuran-3-yloxy | (S)-1-cyclopropylethyl |
| 444 | 3-hydroxy-3-methylcyclobutyl | methanesulfonyl | (S)-1-cyclopropylethyl |

-continued
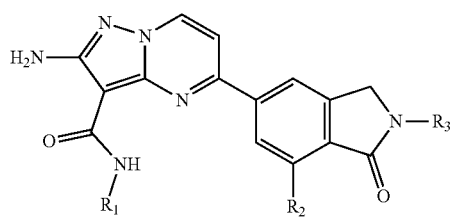
| Compound No. | R₁ | R₂ | R₃ |
|---|---|---|---|
| 445 | 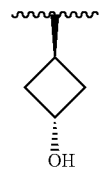 | 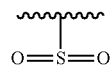 | 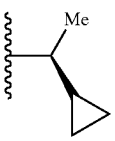 [SMILES: *[C@@H](C)C1CC1] |
| 446 | 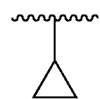 | 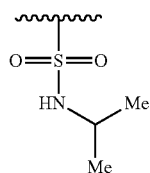 | 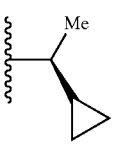 [SMILES: *[C@@H](C)C1CC1] |
| 447 | 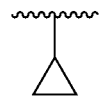 | 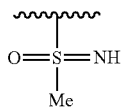 | 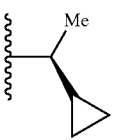 [SMILES: *[C@@H](C)C1CC1] |
| 448 | 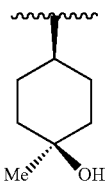 | 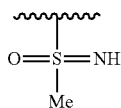 | 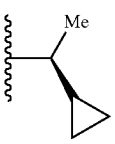 |
| 449 | 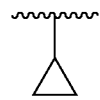 [SMILES: *C1CC1] |  | 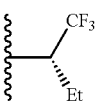 |
| 450 | 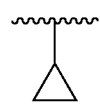 [SMILES: *C1CC1] |  | 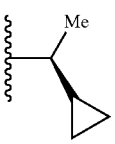 |
| 451 | 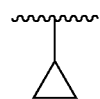 [SMILES: *C1CC1] |  | 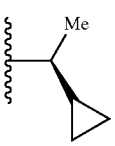 [SMILES: *[C@@H](C)C1CC1] |
| 452 | 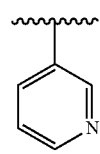 |  | 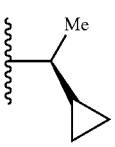 [SMILES: *[C@@H](C)C1CC1] |

-continued
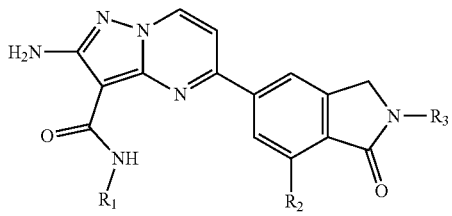
| Compound No. | R₁ | R₂ | R₃ |
|---|---|---|---|
| 453 | 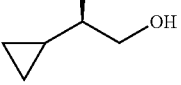 | 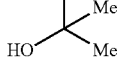 |  |
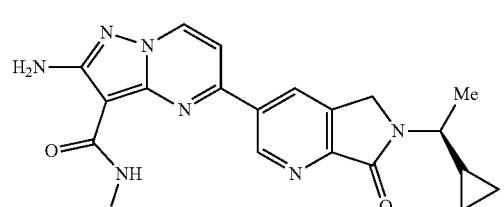
| | R₁ |
|---|---|
| 454 | 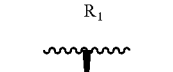 |
| 455 |  |
13. A compound selected from the group consisting of:
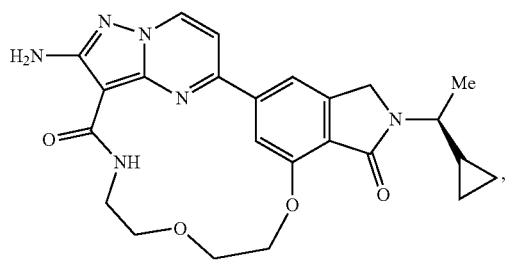
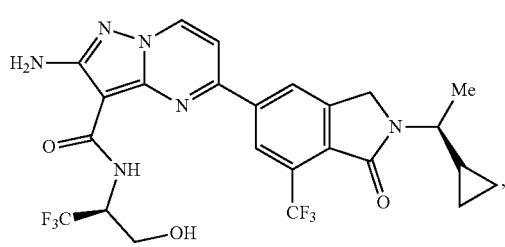
-continued
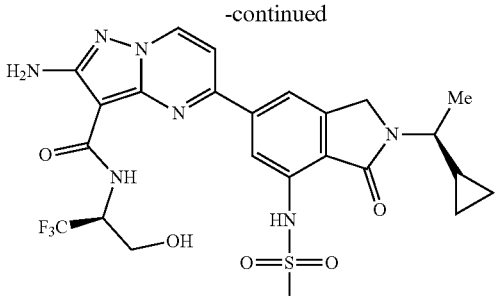
, and
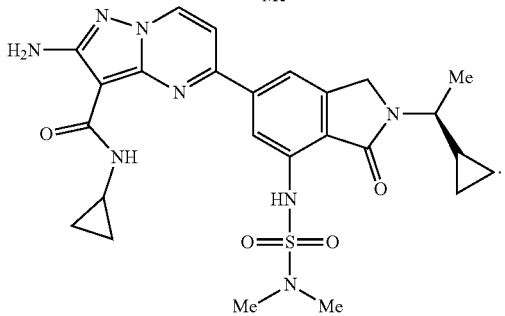
* * * * *